US010745449B2

(12) United States Patent
Blais et al.

(10) Patent No.: US 10,745,449 B2
(45) Date of Patent: Aug. 18, 2020

(54) USPA2 PROTEIN CONSTRUCTS AND USES THEREOF

(71) Applicant: GLAXOSMITHKLINE BIOLOGICALS SA, Rixensart (BE)

(72) Inventors: Normand Blais, Laval (CA); Cindy Castado, Rixensart (BE); Patrick Chomez, Rixensart (BE); Marianne Dewerchin, Rixensart (BE)

(73) Assignee: GlaxoSmithKline, Rixensart (BE)

( * ) Notice: Subject to any disclaimer, the term of this patent is extended or adjusted under 35 U.S.C. 154(b) by 0 days.

(21) Appl. No.: 16/023,164

(22) Filed: Jun. 29, 2018

(65) Prior Publication Data
US 2018/0354996 A1    Dec. 13, 2018

Related U.S. Application Data

(62) Division of application No. 15/119,220, filed as application No. PCT/IB2015/051308 on Feb. 20, 2015, now Pat. No. 10,040,832.

(60) Provisional application No. 61/946,937, filed on Mar. 3, 2014, provisional application No. 61/946,932, filed on Mar. 3, 2014, provisional application No. 61/943,909, filed on Feb. 24, 2014.

(51) Int. Cl.
| *A61K 39/00* | (2006.01) |
| *A61K 39/02* | (2006.01) |
| *A61K 47/00* | (2006.01) |
| *C07K 14/21* | (2006.01) |
| *A61K 39/102* | (2006.01) |
| *A61K 39/104* | (2006.01) |
| *C07K 16/12* | (2006.01) |

(52) U.S. Cl.
CPC ............ *C07K 14/212* (2013.01); *A61K 39/00* (2013.01); *A61K 39/102* (2013.01); *A61K 39/1045* (2013.01); *C07K 16/1217* (2013.01); *A61K 2039/55505* (2013.01); *A61K 2039/55566* (2013.01); *A61K 2039/55572* (2013.01); *A61K 2039/55577* (2013.01); *A61K 2039/70* (2013.01)

(58) Field of Classification Search
CPC ................................ A61K 39/00; A61K 39/02
USPC ...................... 424/184.1, 185.1, 234.1, 251.1
See application file for complete search history.

(56) References Cited

U.S. PATENT DOCUMENTS 8,323,667 B2 * 12/2012 Forsgren ............ A61K 39/1045
                                                   424/251.1

FOREIGN PATENT DOCUMENTS

| WO | 98/28333 A2 | 7/1998 |
| WO | 02/083710 A2 | 10/2002 |
| WO | 2007/018463 A2 | 2/2007 |
| WO | 2007/084053 A1 | 7/2007 |

OTHER PUBLICATIONS

International Search Report for PCT/IB2015/051308 dated Jul. 6, 2015.
Written Opinion for PCT/IB2015/051308.
Nov. 1, 1999 "SubName: Full=Ubiquitous surface protein A2 {ECO:0000313 EMBL:AGH27427.1}; SubName: Full=UspA2 {ECO:0000313 EMBL:AAD43466.1};" XP002739304, retrieved from EBI accession No. UNIPROT:Q9XD55 Database accession No. Q9XD55 sequence.
McMichael, et al., "Isolation and Characterization of Two Proteins from Moraxella catarrhalis That Bear a Common Epitope" Infection and Immunity; 1998; pp. 4374-4381; vol. 66, Issue 9.
Yu-Ching, et al., "Impact of sequence diversity in the Moraxella catarrhalis UspA2/UspA2H head domain on vitronectin binding and antigenic variation"; Microbes & Infection; 2013; pp. 375-387; vol. 15(5).
U.S. Appl. No. 15/119,220, filed Aug. 16, 2016, Publication No. 2017-0008932, Jan. 12, 2017.
U.S. Appl. No. 12/063,408, filed Feb. 8, 2008 now U.S. Pat. No. 8,092,811, Publication No. 2010-0062027, Mar. 10, 2010.
U.S. Appl. No. 13/341,727, filed Dec. 8, 2011 now U.S. Pat. No. 8,323,667, Publication No. 2012-0148614, Jun. 14, 2012.
U.S. Appl. No. 13/666,941, filed Nov. 1, 2012 now U.S. Pat. No. 8,895,030, Publication No. 2013-0129763, May 23, 2013.
U.S. Appl. No. 14/110,857, filed Oct. 9, 2013 now U.S. Pat. No. 8,945,577, Publication No. 2014-0056934, Feb. 27, 2014.
U.S. Appl. No. 14/508,033, filed Oct. 7, 2014 now U.S. Pat. No. 9,255,127, Publication No. 2015-0140026, May 21, 2015.
U.S. Appl. No. 14/571,546, filed Dec. 16, 2014 now U.S. Pat. No. 9,296,794, Publication No. 2015-0166613, Jun. 18, 2015.
U.S. Appl. No. 14/571,807, filed Dec. 16, 2014 now U.S. Pat. No. 9,409,957, Publication No. 2015-0175670, Jun. 25, 2015.
U.S. Appl. No. 14/986,104, filed Dec. 31, 2015 now U.S. Pat. No. 9,657,067, Publication No. 2016-0318979, Nov. 3, 2016.
U.S. Appl. No. 15/046,908, filed Feb. 18, 2016, Publication No. 2016-0250313, Sep. 1, 2016.
U.S. Appl. No. 15/197,952, filed Jun. 30, 2016, Publication No. 2017-0029472, Feb. 2, 2017.
U.S. Appl. No. 15/486,513, filed Apr. 13, 2017, Publication No. 2017-0281746, Oct. 5, 2017.
U.S. Appl. No. 15/861,789, filed Jan. 4, 2018.
Cheng et al., "Effects of His-tag on cholesterol oxidase expression in *Escherichia coli*" Industrial Microbiology, vol. 42, No. 5, pp. 29-34 (2012)—English Abstract on p. 34.
Svensson et al., "Histidine tag fusion increases expression levels of active recombinant amelogenin in *Escherichia coli*", Protein Expression and Purification, vol. 48, pp. 134-141 (2006).

* cited by examiner

*Primary Examiner* — Rodney P Swartz
(74) *Attorney, Agent, or Firm* — Barbara J. Carter

(57) ABSTRACT

The present invention relates to compositions comprising *Moraxella catarrhalis* (*M. catarrhalis*) Ubiquitous surface protein A2 (UspA2). More particularly, the present application relates to UspA2 protein constructs and immunogenic compositions comprising the constructs, vaccines comprising such immunogenic compositions and therapeutic uses of the same. The invention further relates to compositions comprising UspA2 in combination with at least one antigen from *Haemophilus influenzae*, immunogenic compositions comprising the antigens, vaccines comprising such immunogenic compositions and therapeutic uses of the same.

22 Claims, 37 Drawing Sheets

Specification includes a Sequence Listing.

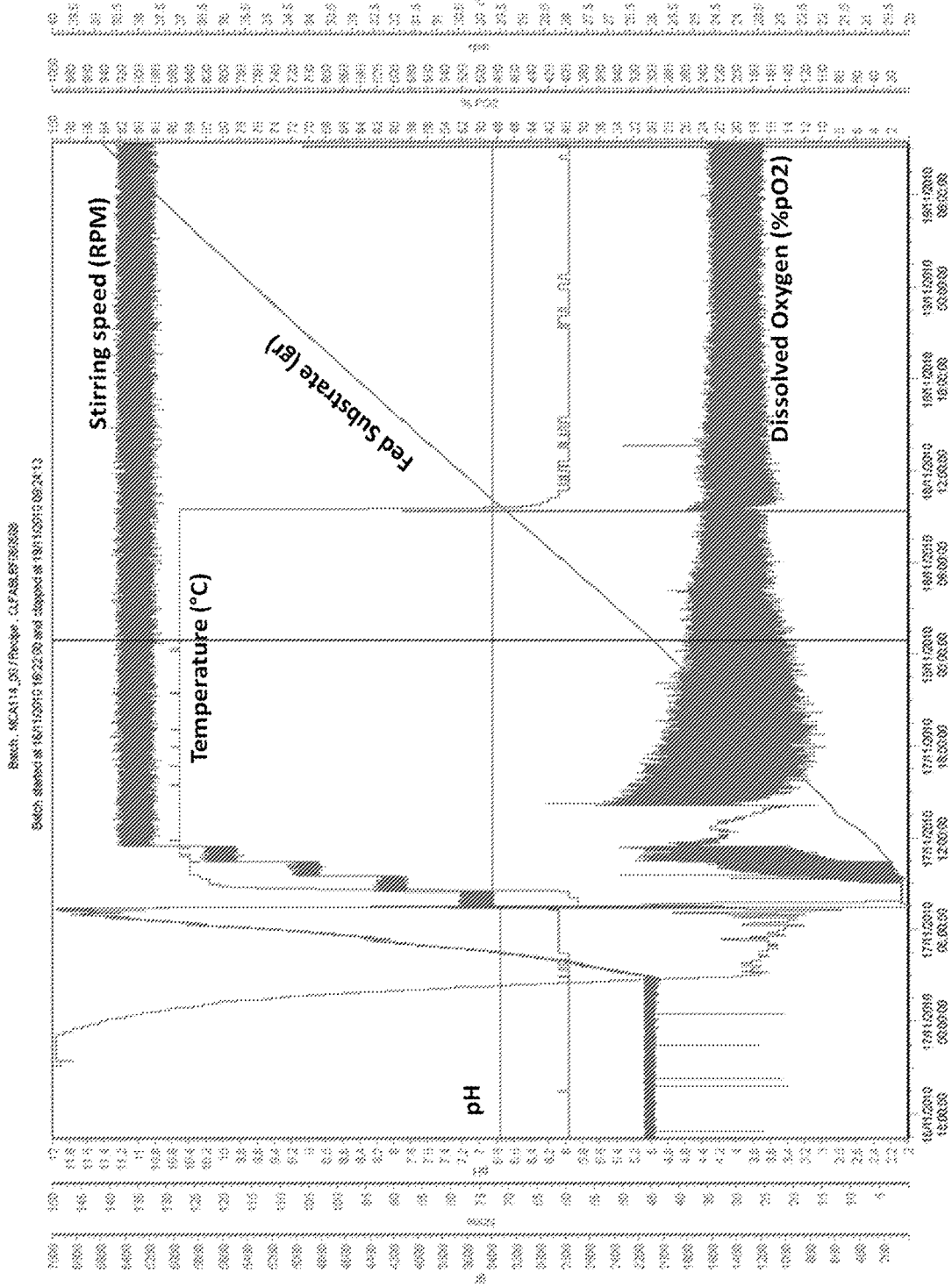
Figure 1: A typical fermentation profile with the High Cell Density Induction (HCDI) processes and the parameters monitored during 20L-scale fed-batch fermentation.

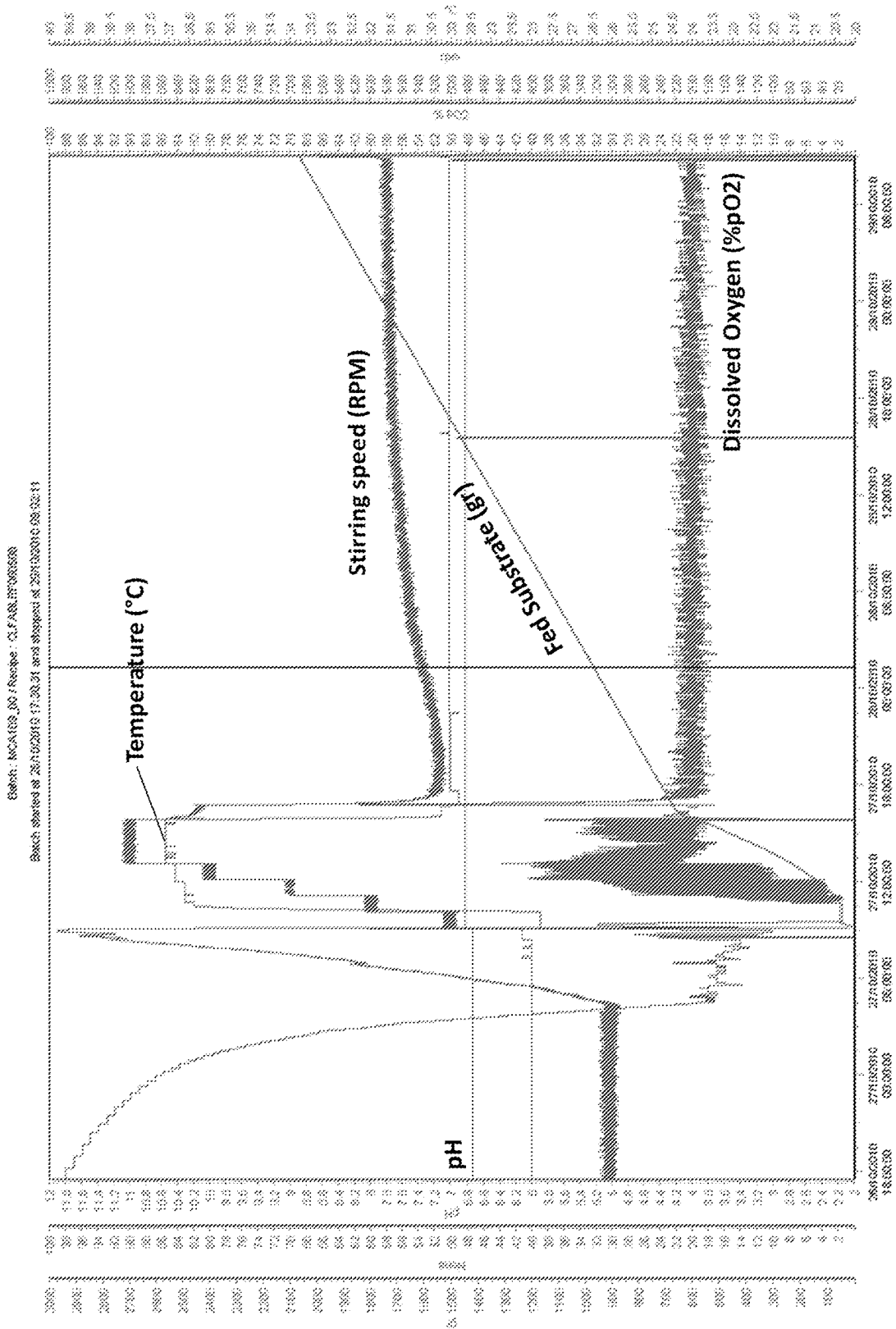
Figure 2: A typical fermentation profile with the Low Cell Density Induction (LCDI) processes and the parameters monitored during 20L-scale fed-batch fermentation.

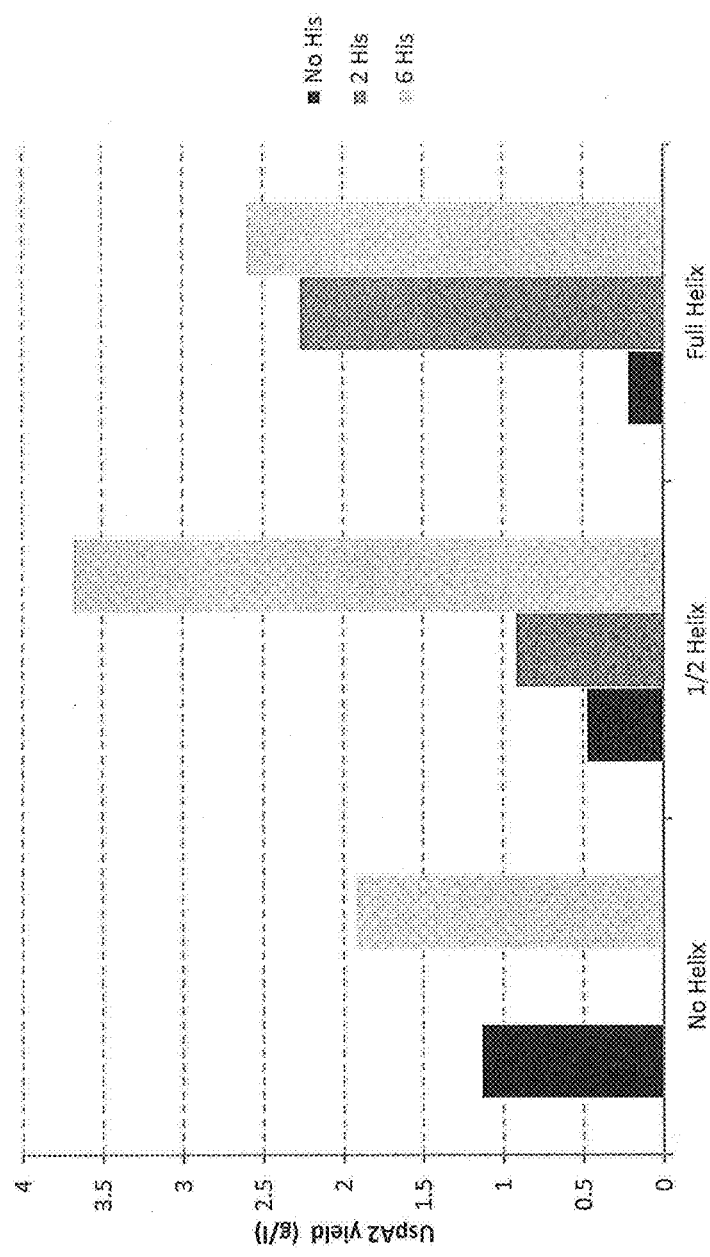

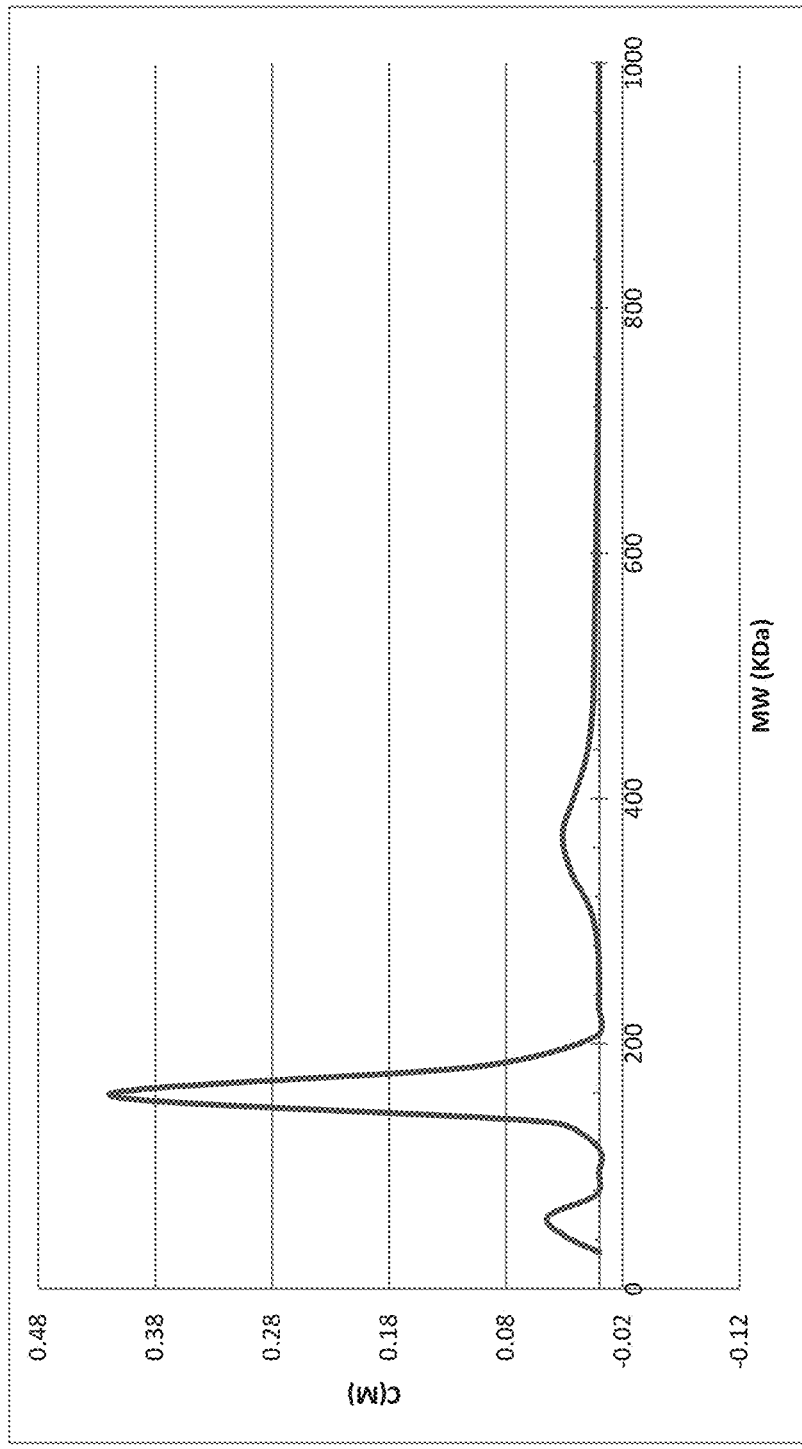

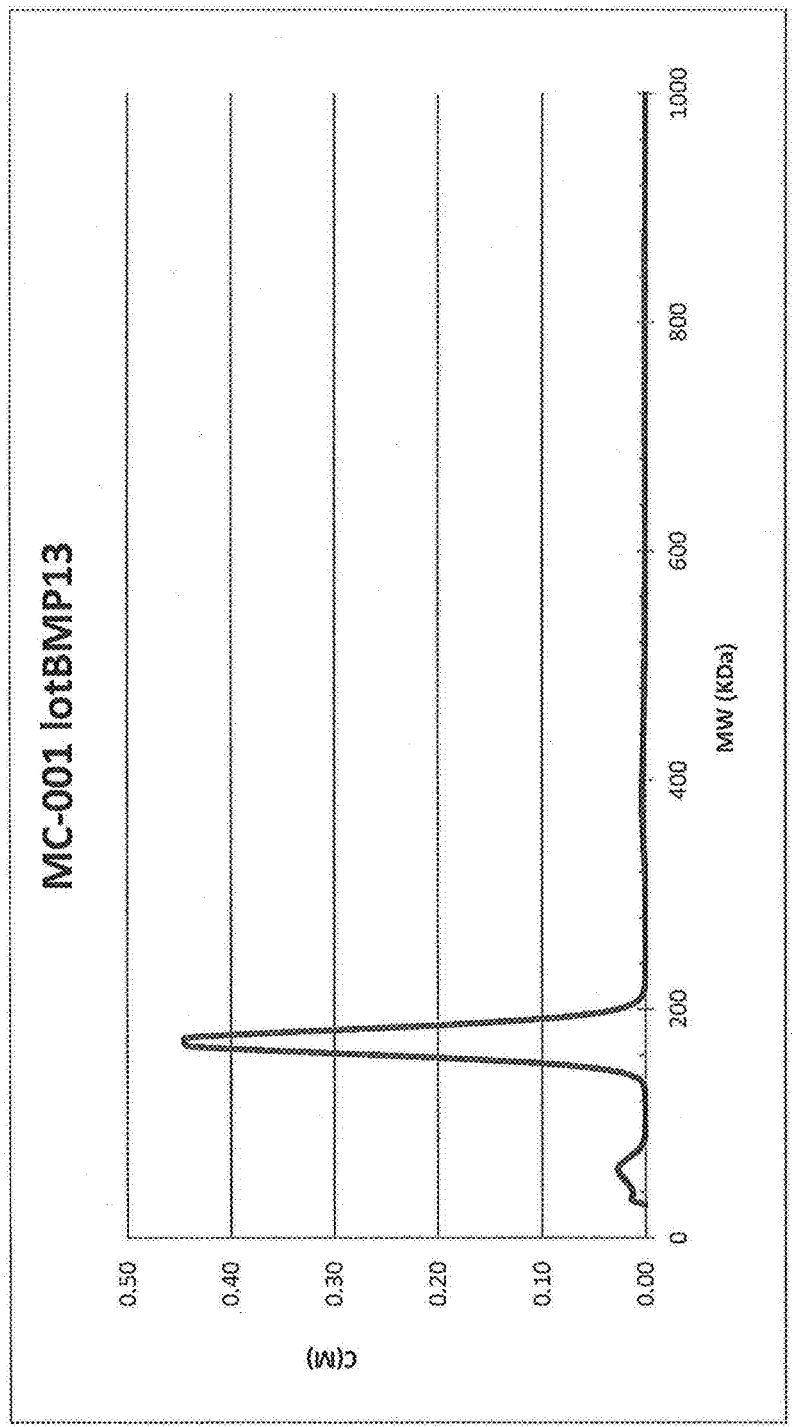
Figure 5: Molecular weight distribution of purified MC-001 determined by sedimentation velocity analytical ultracentrifugation. Majority of protein is found as a trimer.

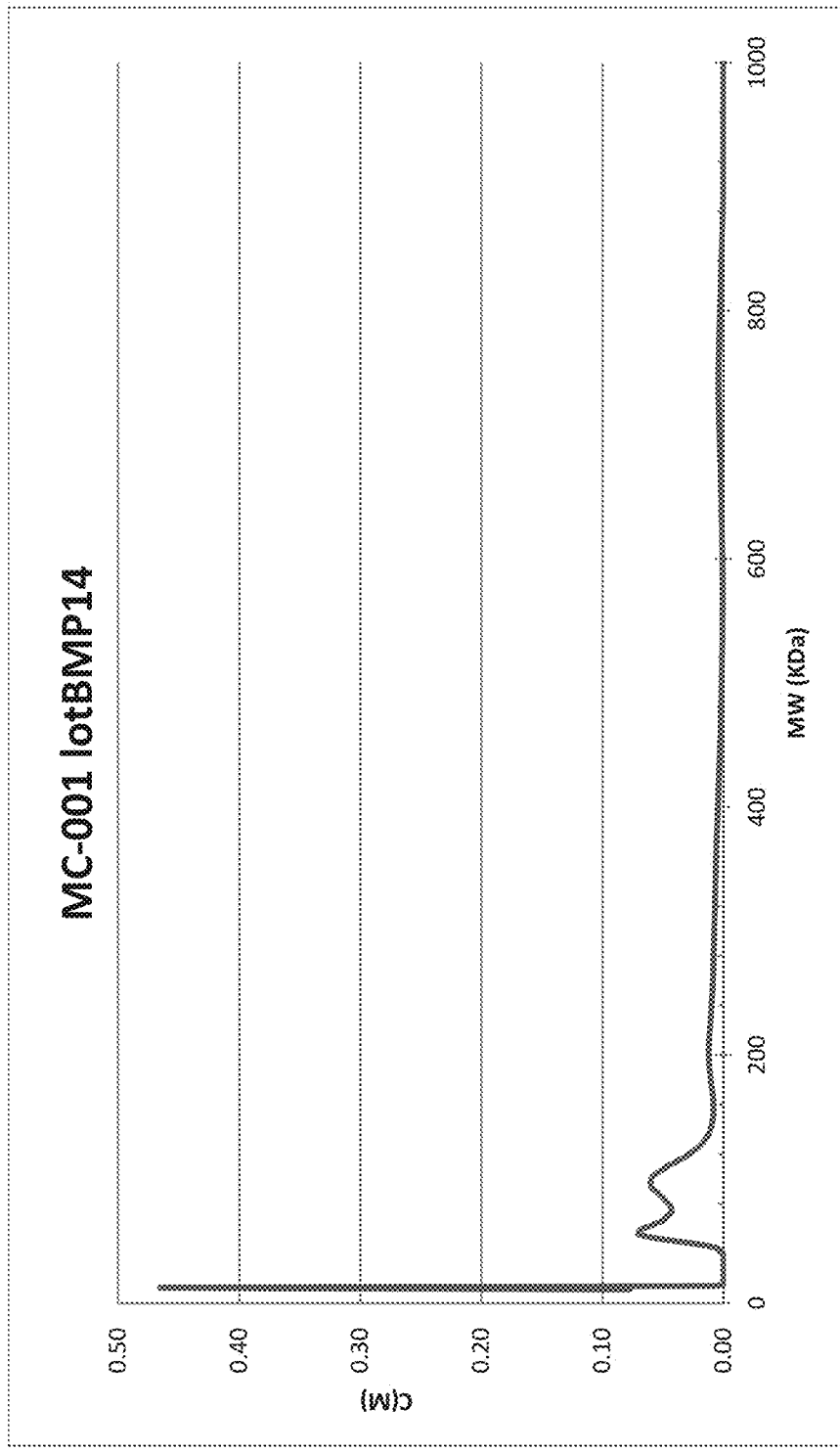
Figure 6: Molecular weight distribution of purified MC-001 determined by sedimentation velocity analytical ultracentrifugation.

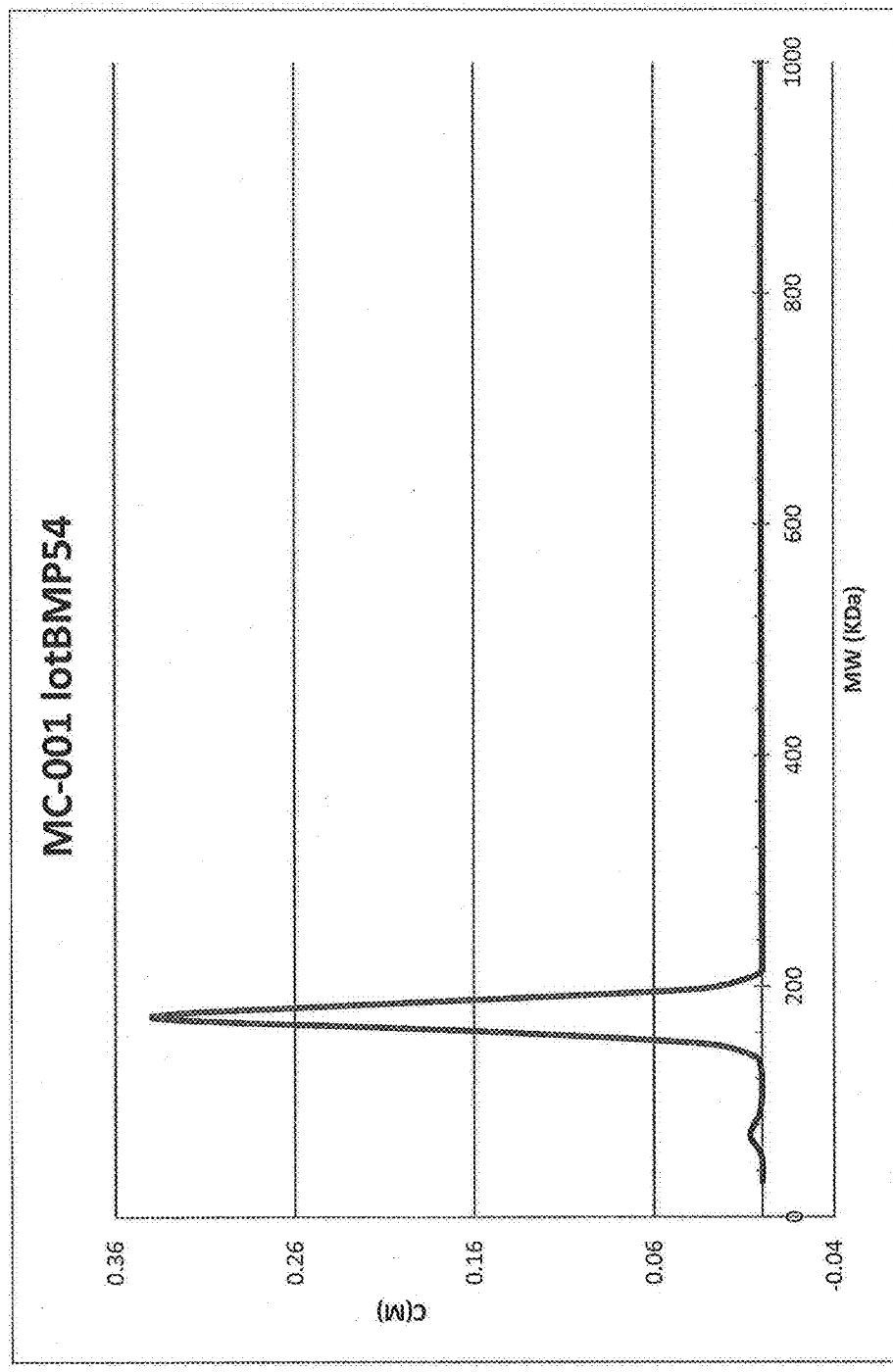
Figure 7: Molecular weight distribution of purified MC-001 determined by sedimentation velocity analytical ultracentrifugation. Majority of protein is found as a trimer.

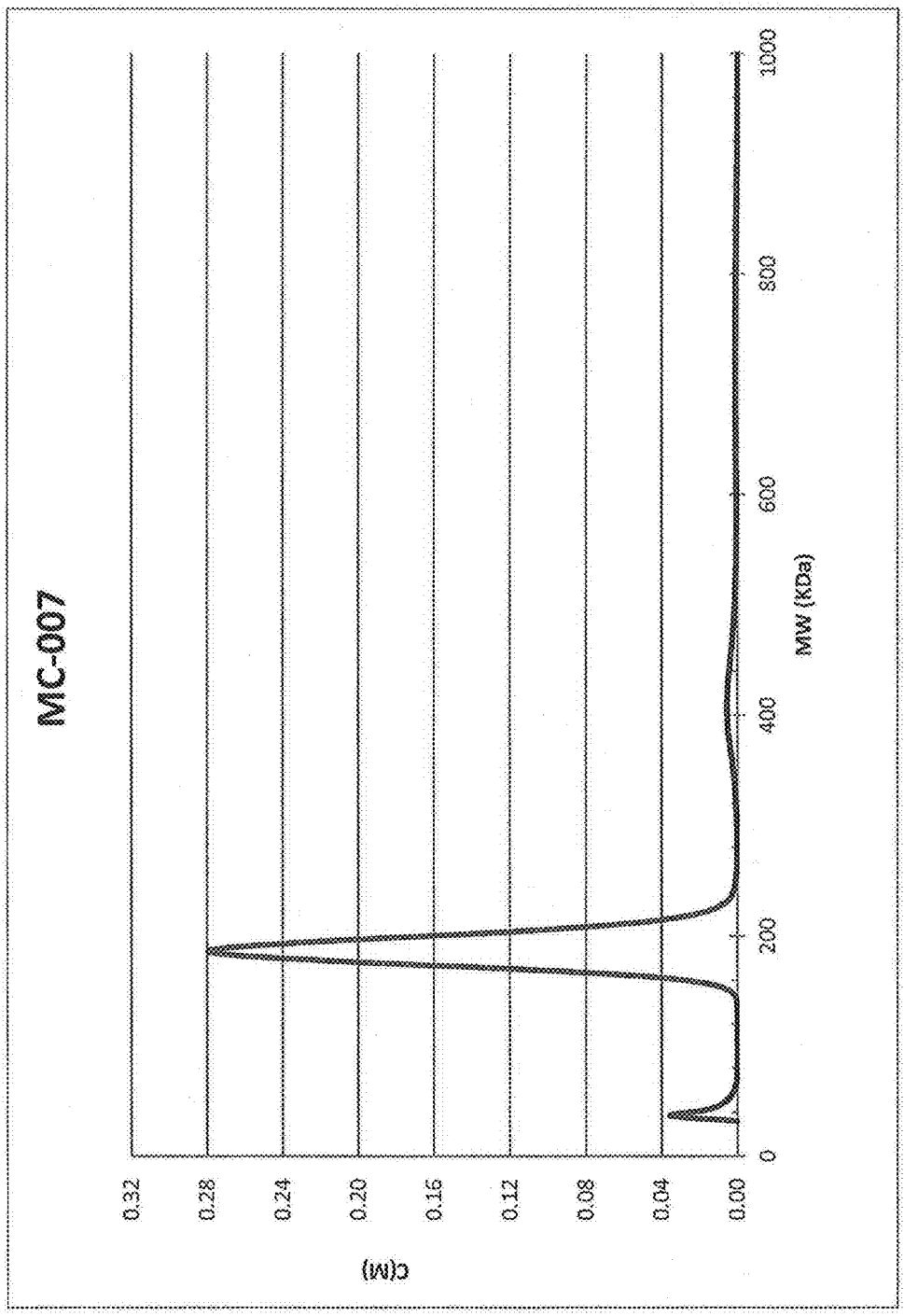
Figure 8: Molecular weight distribution of purified MC-007 determined by sedimentation velocity analytical ultracentrifugation. Majority of protein is found as a trimer.

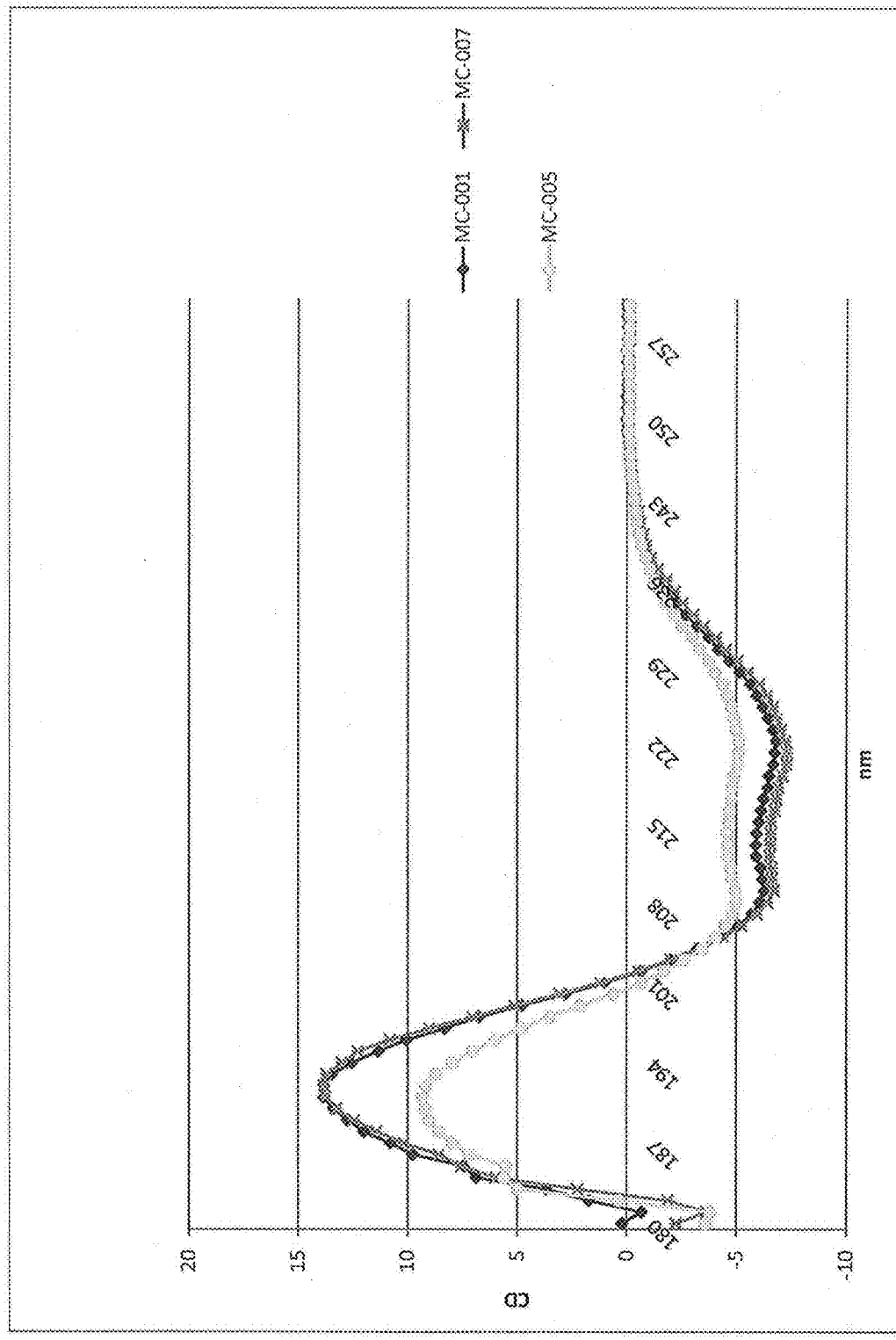

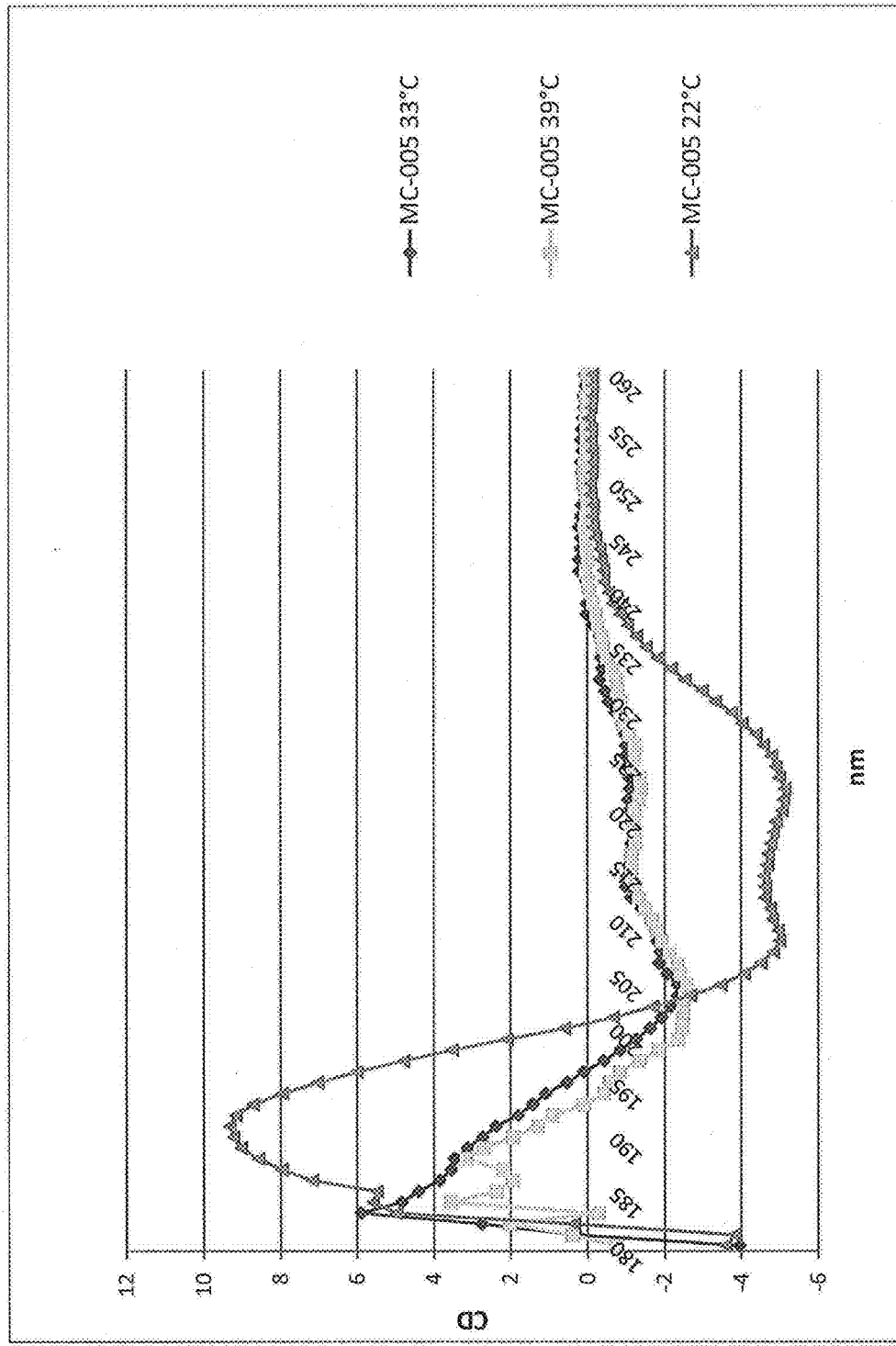
Figure 10: Secondary structures monitoring by circular dichroism (CD) during thermal unfolding of MC-005 (UspA2Δhelix+6His). Visual analysis of the spectra clearly shows that protein loses most of its secondary structures at 33°C.

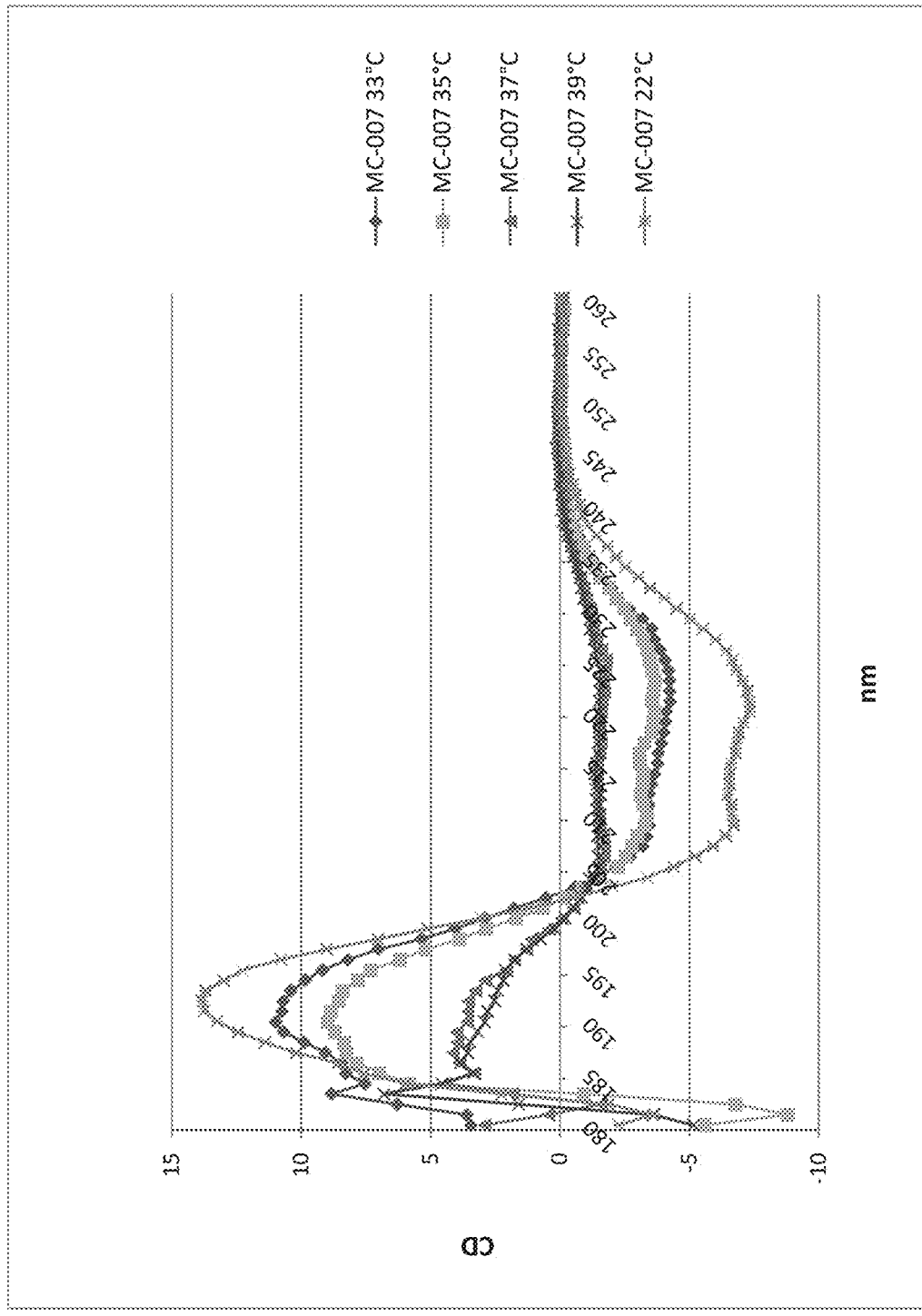
Figure 11: Secondary structures monitoring by circular dichroism (CD) during thermal unfolding of MC-007 (UspA2 full helix + 6His).

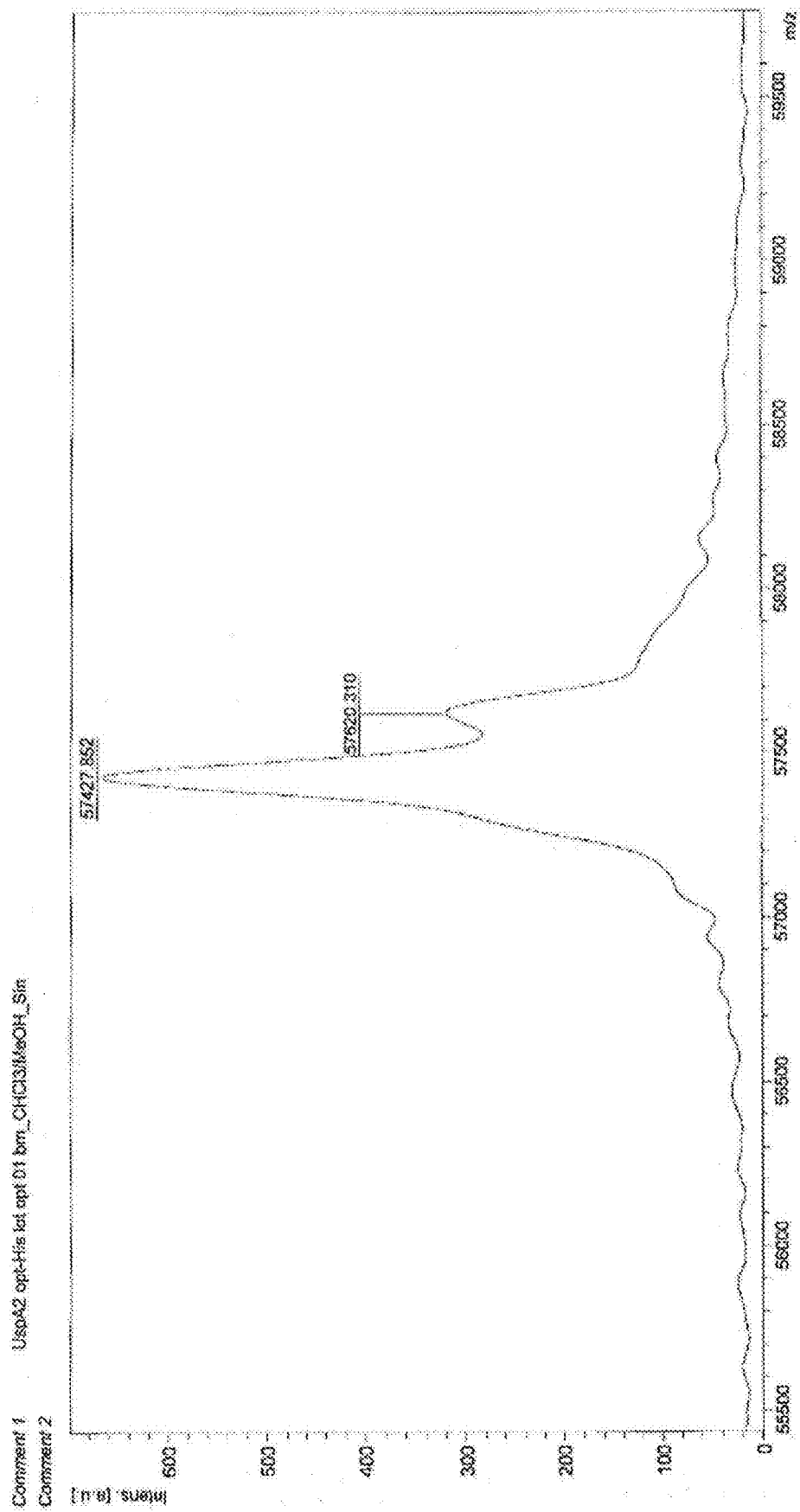
Figure 12: MALDI spectrum of MC-001 lot opt-01. The mass observed at 57427Da may be coherent with the demethionylated protein, while the peak at 57620Da could correspond to the complete protein.

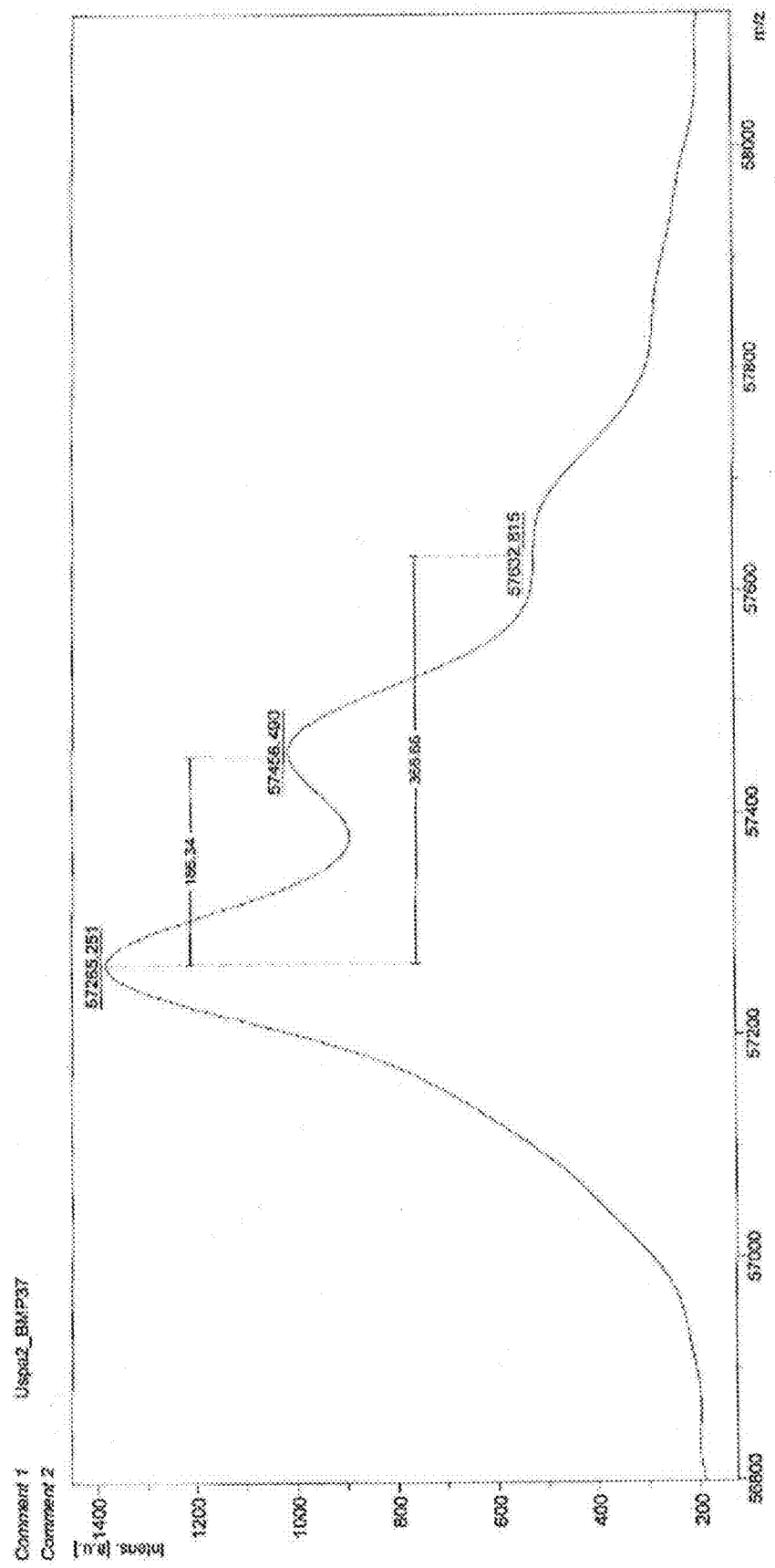
Figure 13: MALDI spectrum of MC-011 lot BMP37. The mass observed may be coherent with the demethionylated protein. The two other peaks at +186Da and +366Da are unidentified.

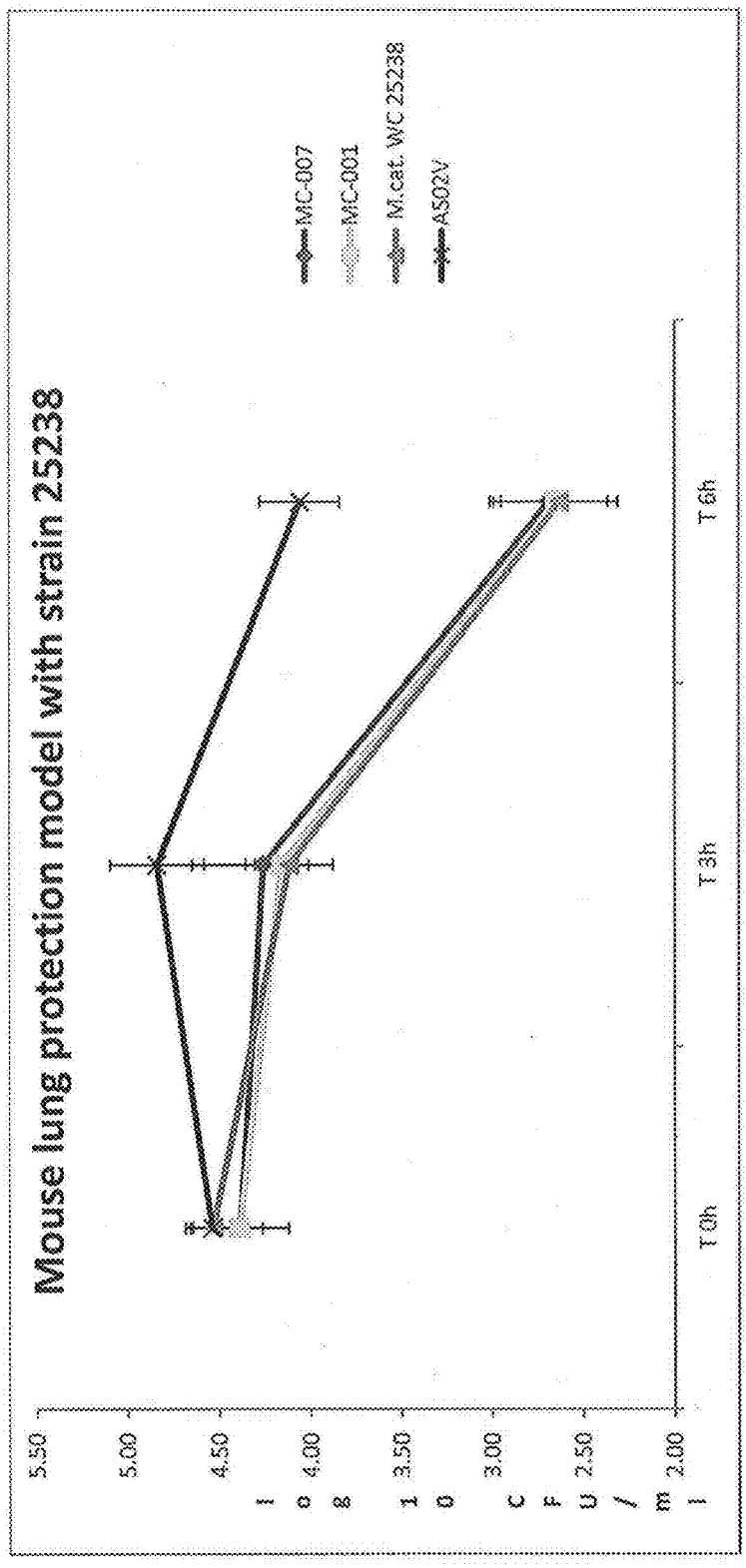
Figure 14: Protective efficacy of MC-001 and MC-007 in a mouse model of lung colonization.

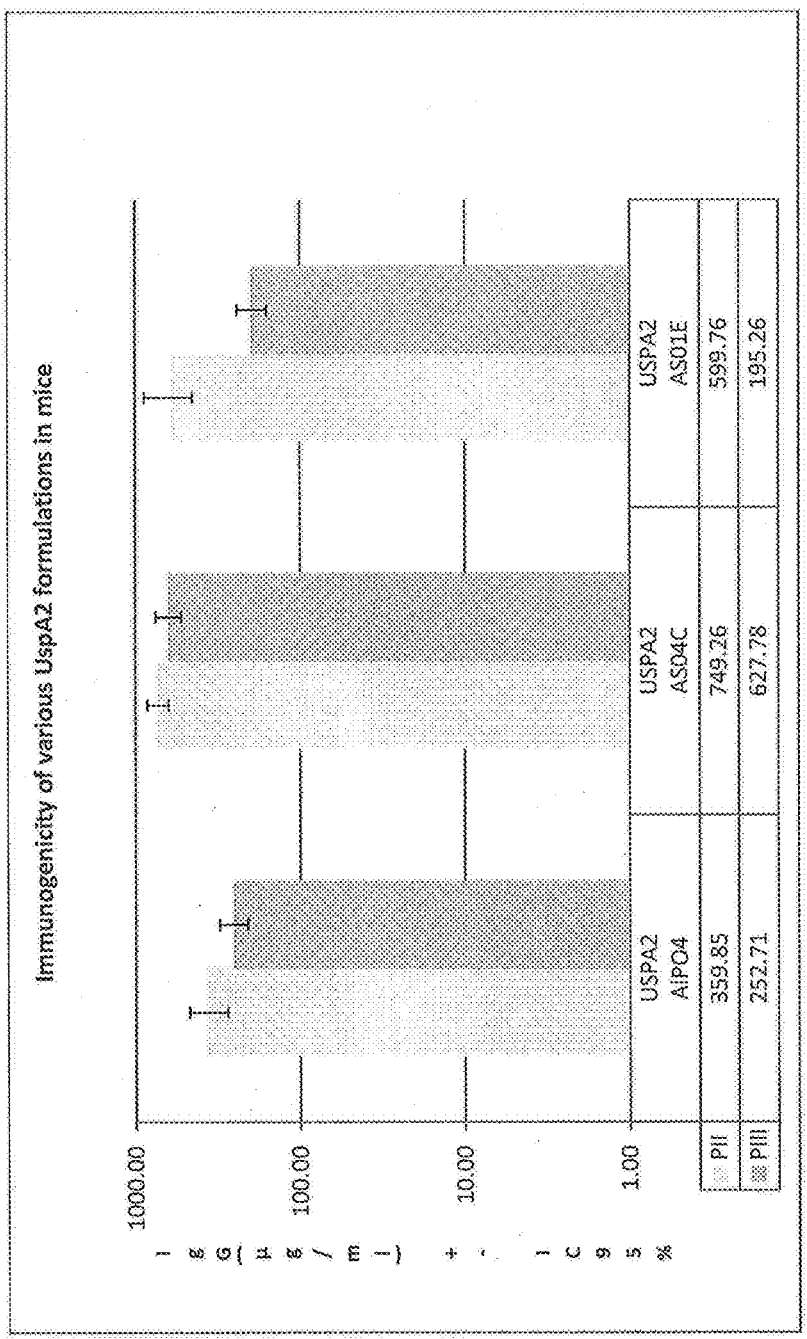
Figure 15: Antibody response directed against UspA2 induced after intramuscular administration in mice, where PII and PIII indicate, respectively, anti-IgG levels in sera collected at day 28 (post II) and day 42 (post III).

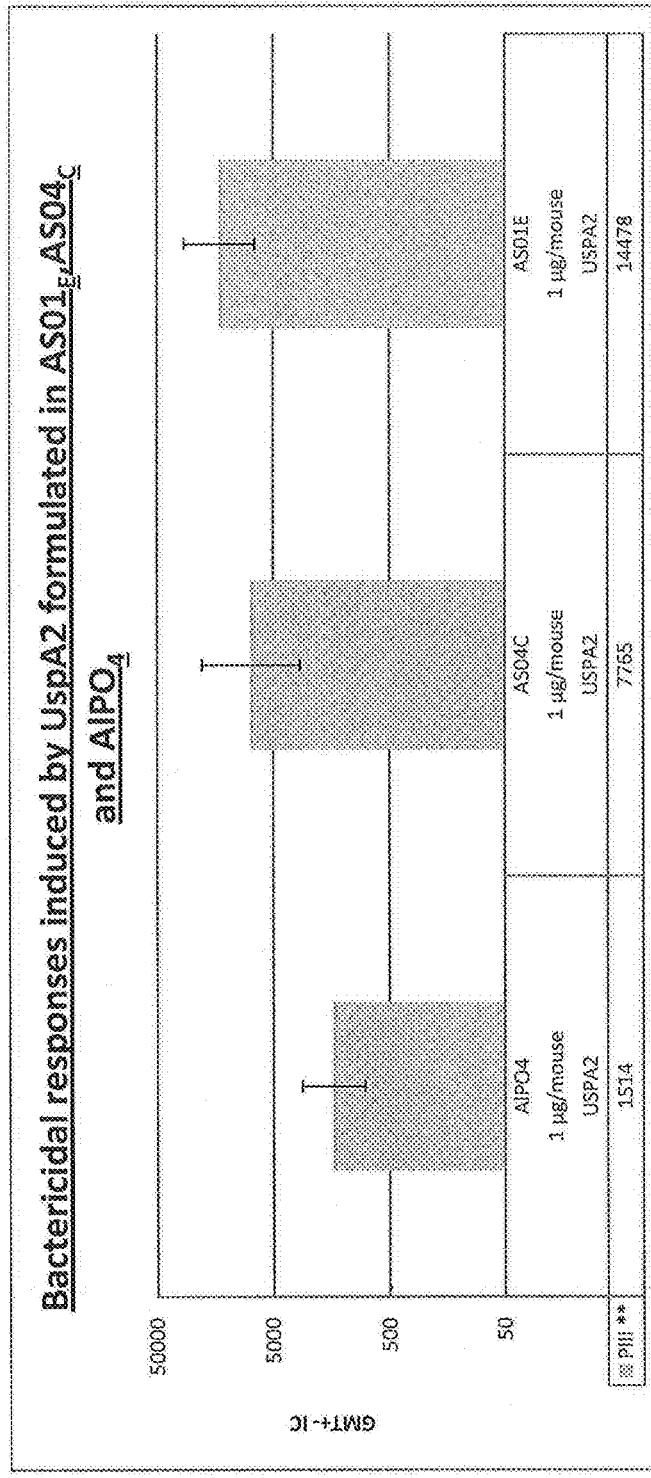
Figure 16: Bactericidal titers induced by UspA2 against a homologous strain, formulated with different adjuvants (AS01$_E$, AS04$_C$ and AlPO$_4$). ** = five pools tested (5 pools of five sera were tested).

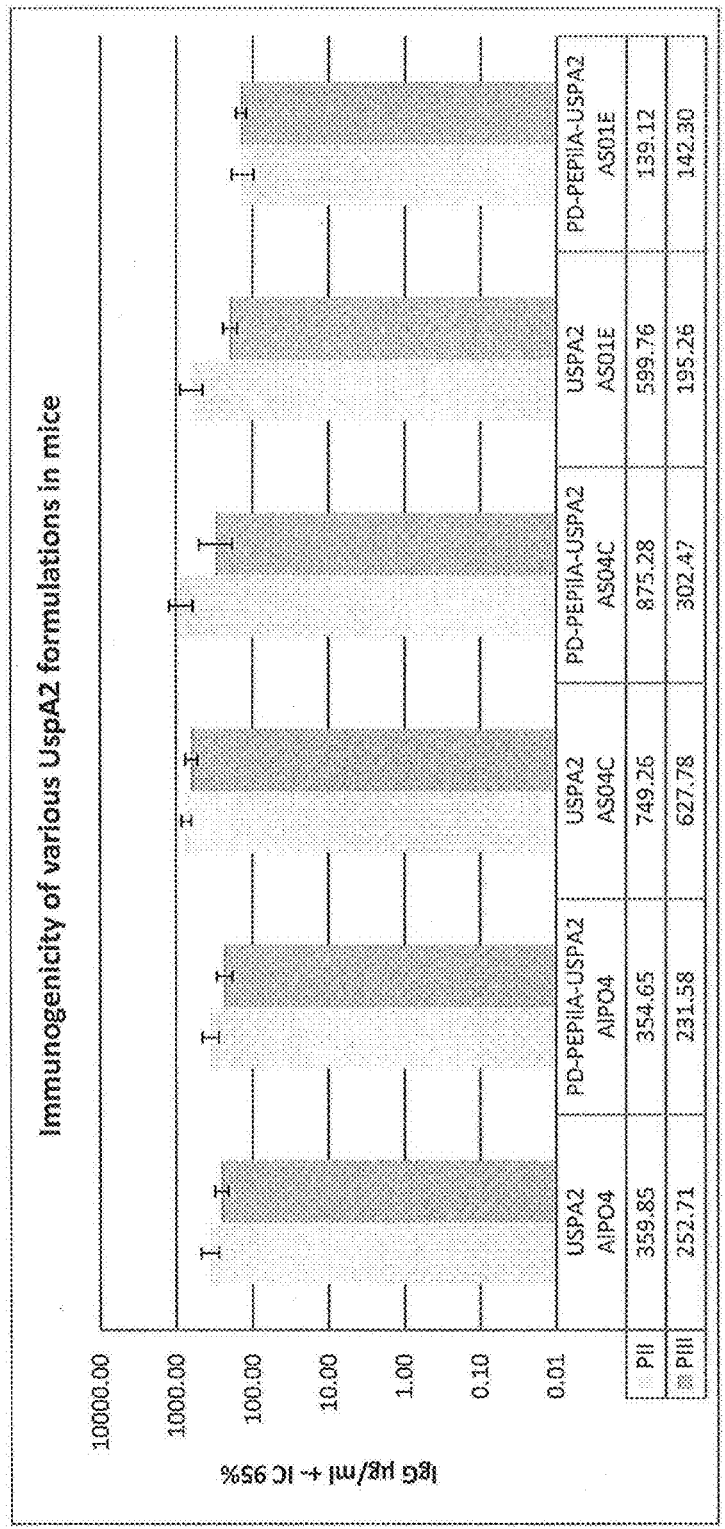
Figure 17: Antibody response directed against UspA2 induced after intramuscular administration in mice, using different formulations of antigens and adjuvants.

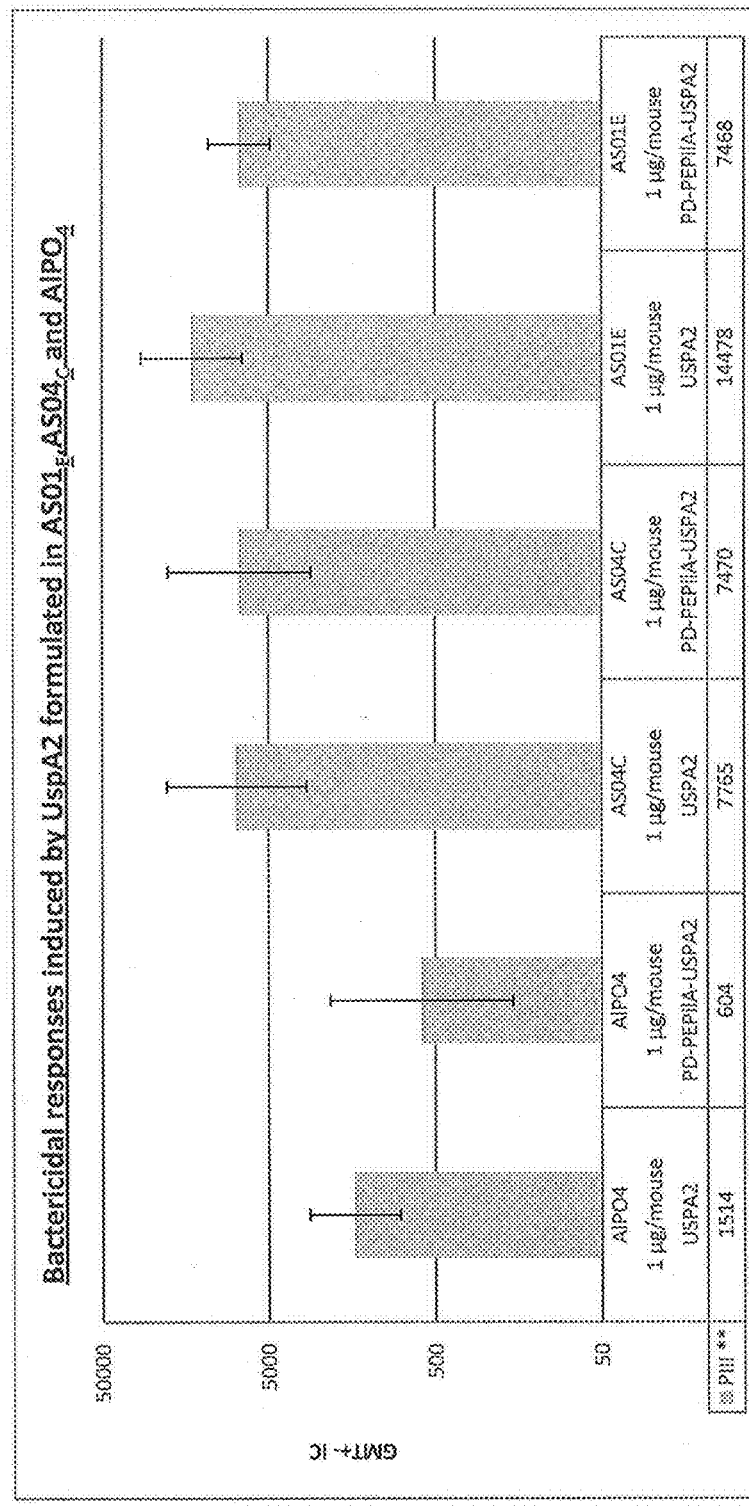
Figure 18: Bactericidal titers induced by UspA2 against a homologous strain, using different formulations of antigens and adjuvants.
** = five pools tested (5 pools of five sera were tested)

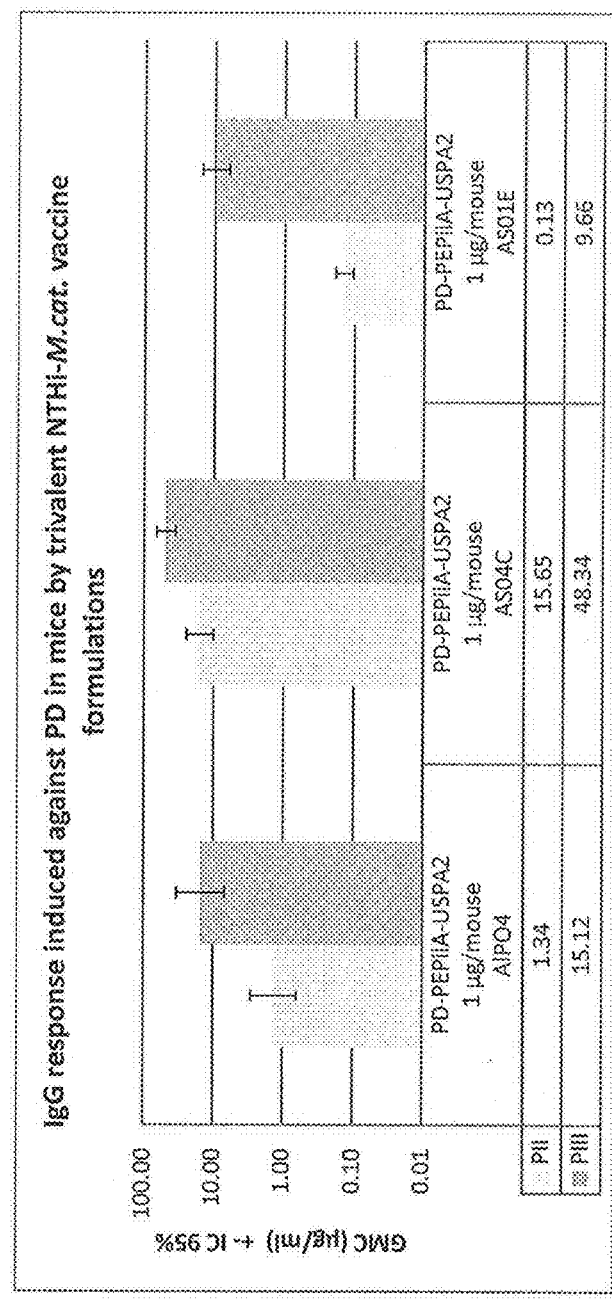
Figure 19: IgG response induced against PD in mice by PD-PEPIIA-UspA2 vaccine (a trivalent NTHi-M.cat. vaccine), formulated with different adjuvants.

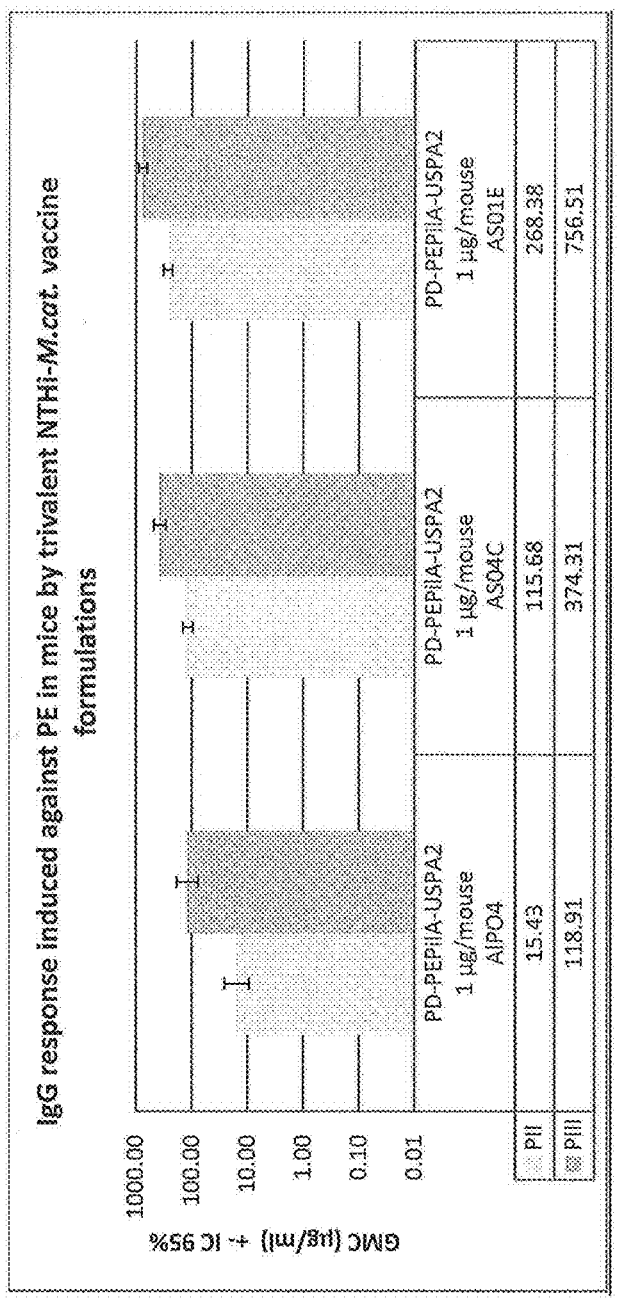
Figure 20: IgG response induced against PE in mice by PD-PEPIIA-UspA2 vaccine, (a trivalent NTHi-*M. cat.* vaccine), formulated with different adjuvants.

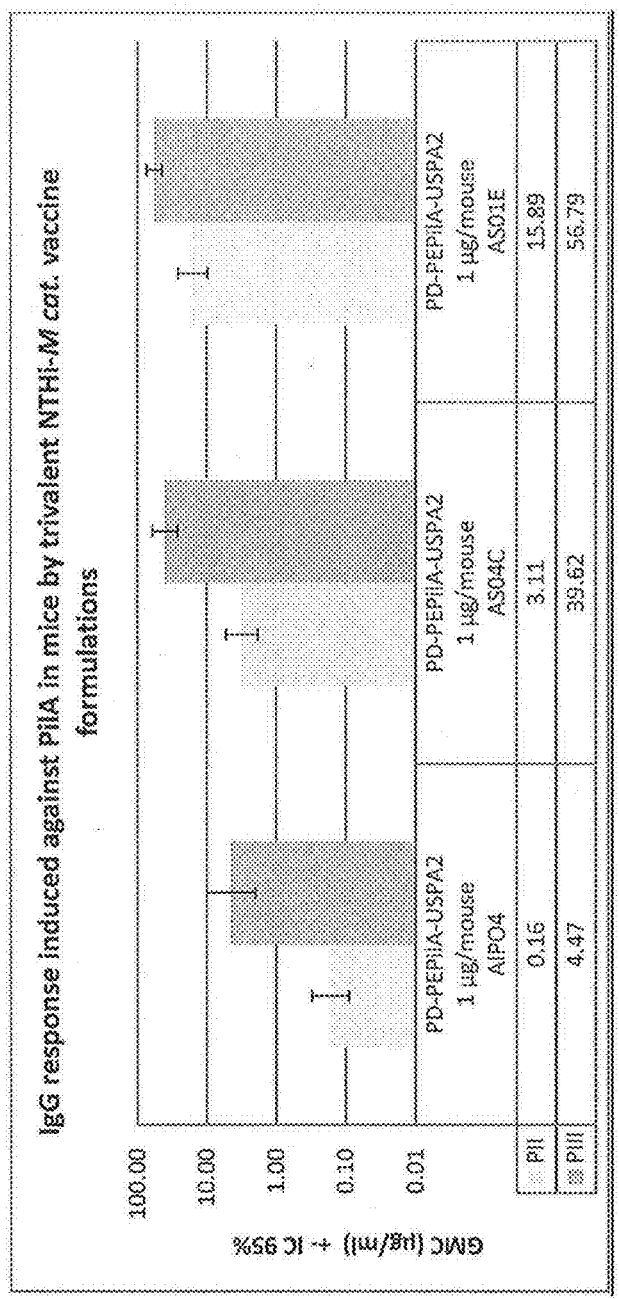
Figure 21: IgG response induced against PilA in mice by PD-PEPilA-UspA2 vaccine (a trivalent NTHi-M. cat. vaccine), formulated with different adjuvants.

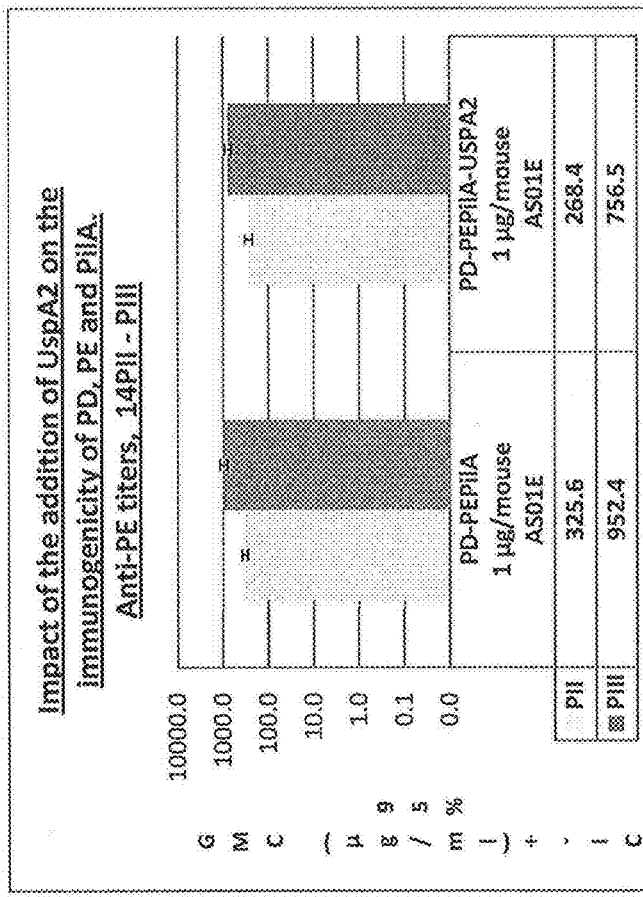
Figure 22: Immunogenicity of PE in the bivalent NTHi PD-PEPilA and trivalent NTHi-M.cat. PD-PEPilA-UspA2 formulations with AS01E.

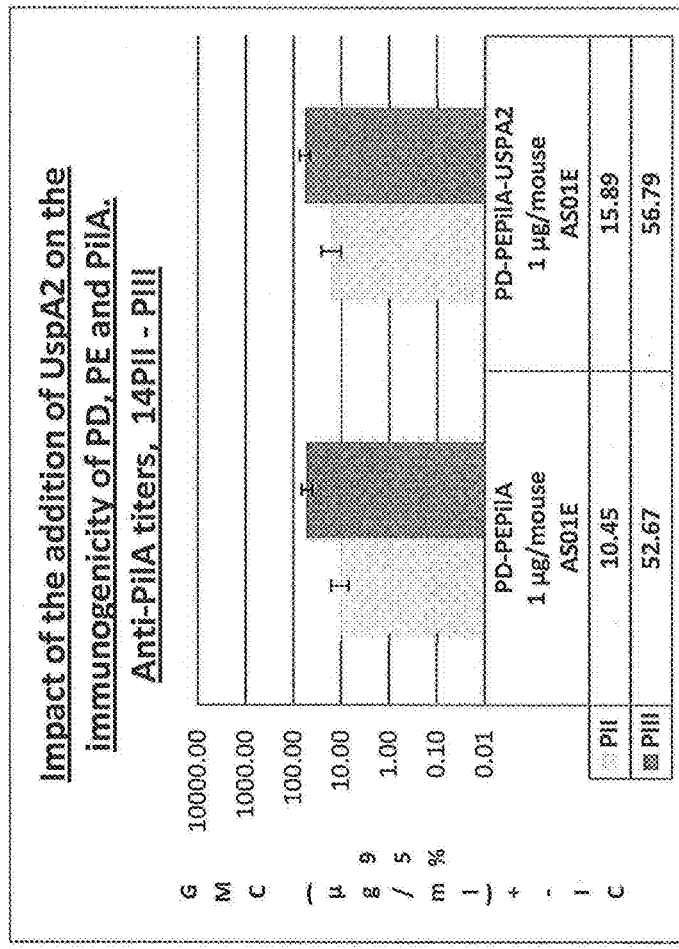
Figure 23: Immunogenicity of PilA in the bivalent NTHi PD-PEPilA and trivalent NTHi-M.cat. PD-PEPilA-UspA2 formulations with AS01E.

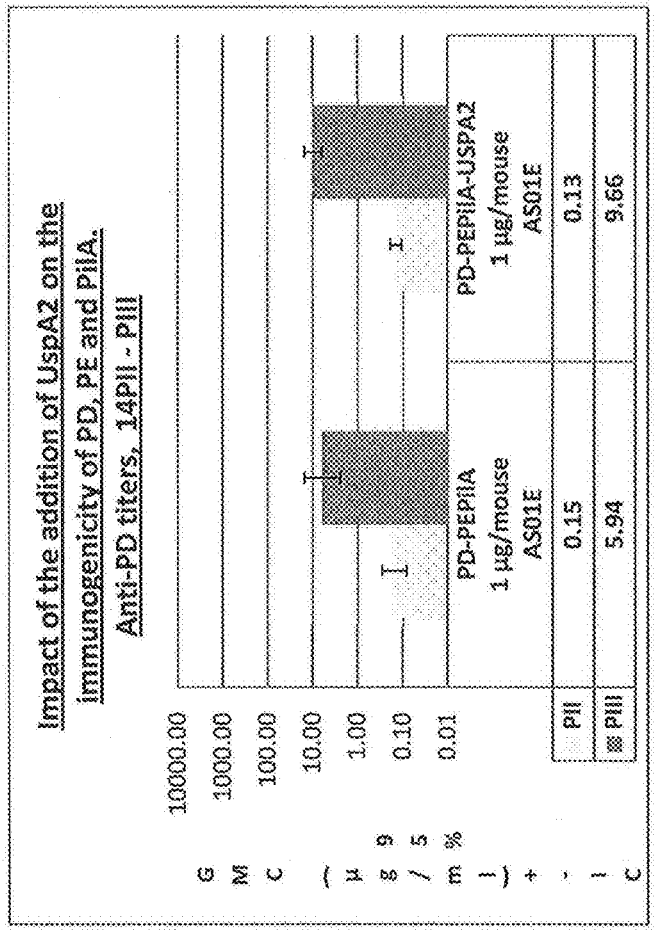
Figure 24: Immunogenicity of PD in the bivalent NTHi PD-PEPilA and trivalent NTHi-M.cat. PD-PEPilA-UspA2 formulations with AS01E.

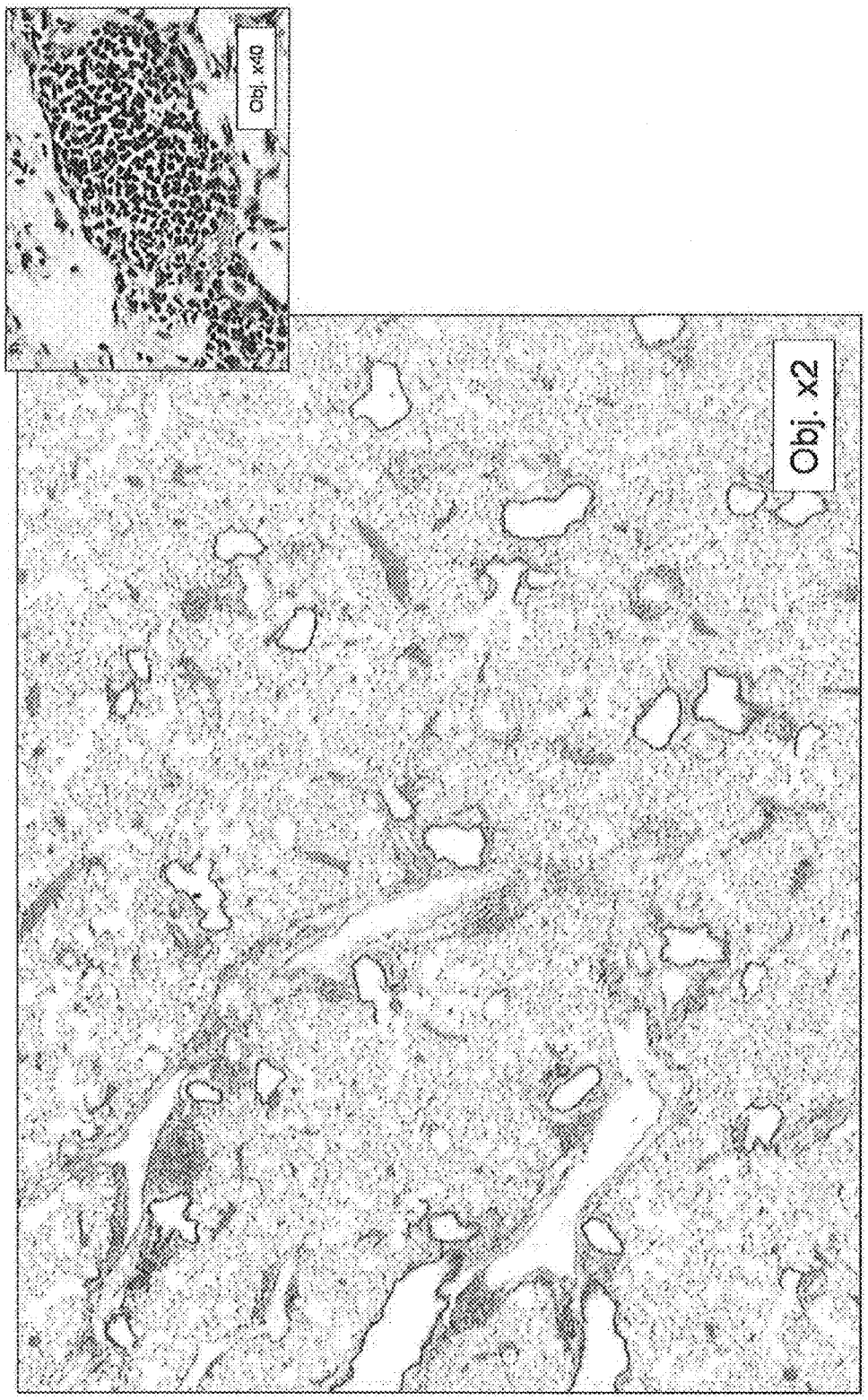
Figure 25 - Effect of the tetravalent PD/ PEPiIA/ UspA2/ AS01$_E$ vaccine formulation on mouse lungs pre-sensitized with heat inactivated M. cat. - Perivascularitis and peribronchiolitis in PBS immunized mice

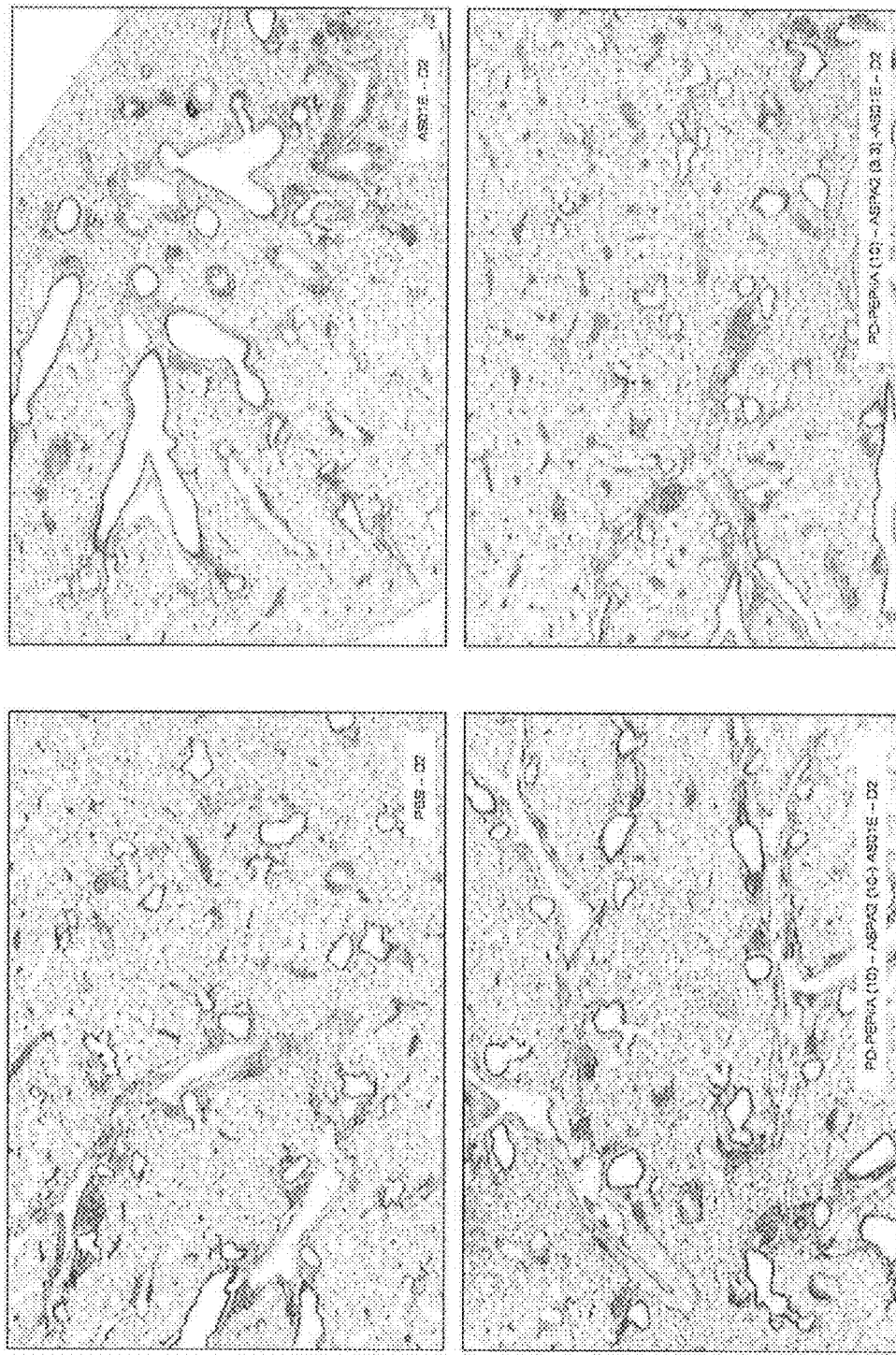
Figure 26 - Effect of the tetravalent PD/ PEPiiA/ UspA2/ AS01$_E$ vaccine formulation on mouse lungs pre-sensitized with heat inactivated M. cat. - Day 2 post-immunization

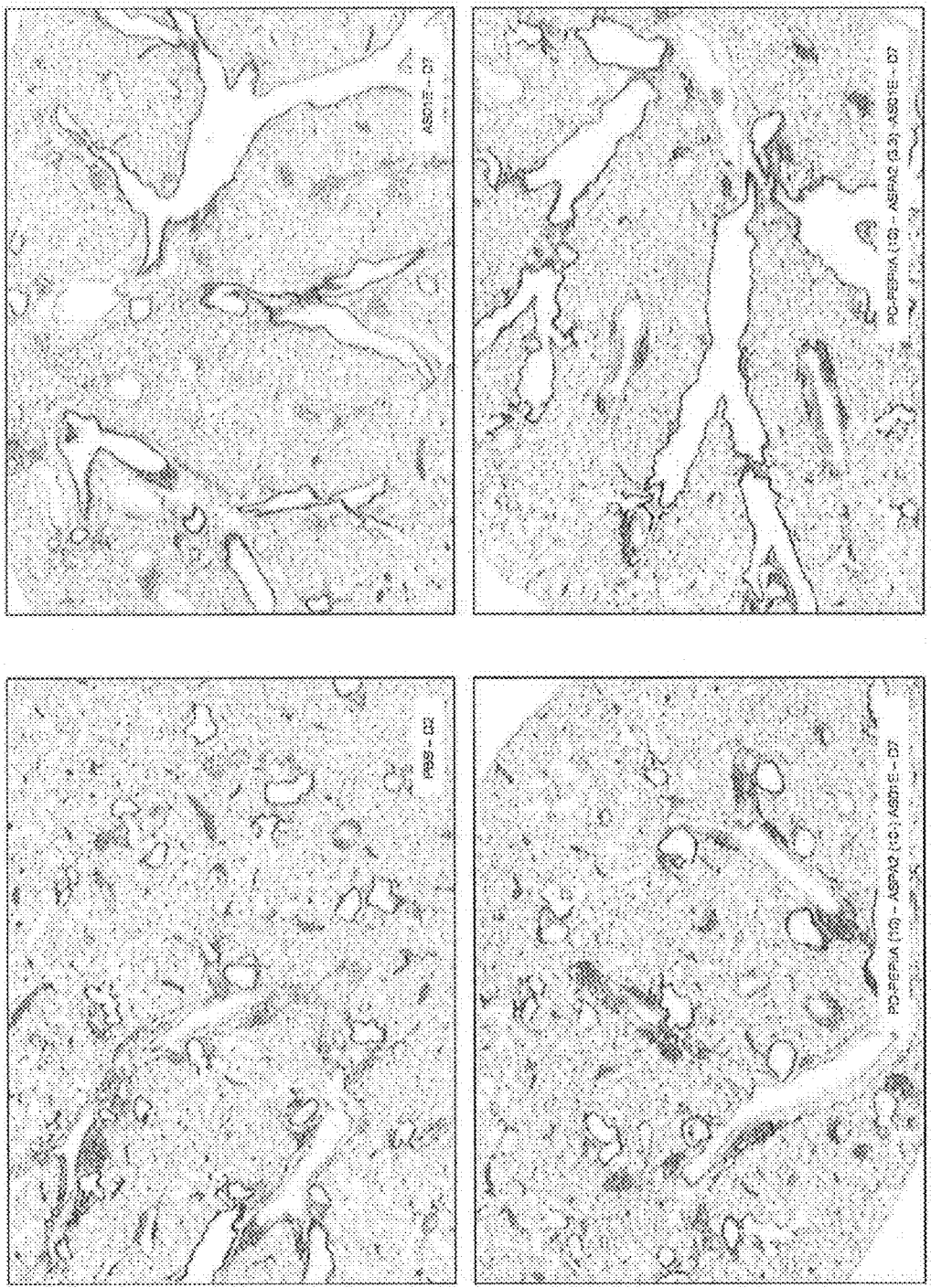
Figure 27 - Effect of the tetravalent PD/ PEPIA/ UspA2/ AS01E vaccine formulation on mouse lungs pre-sensitized with heat inactivated M. cat. - Day 7 post-immunization

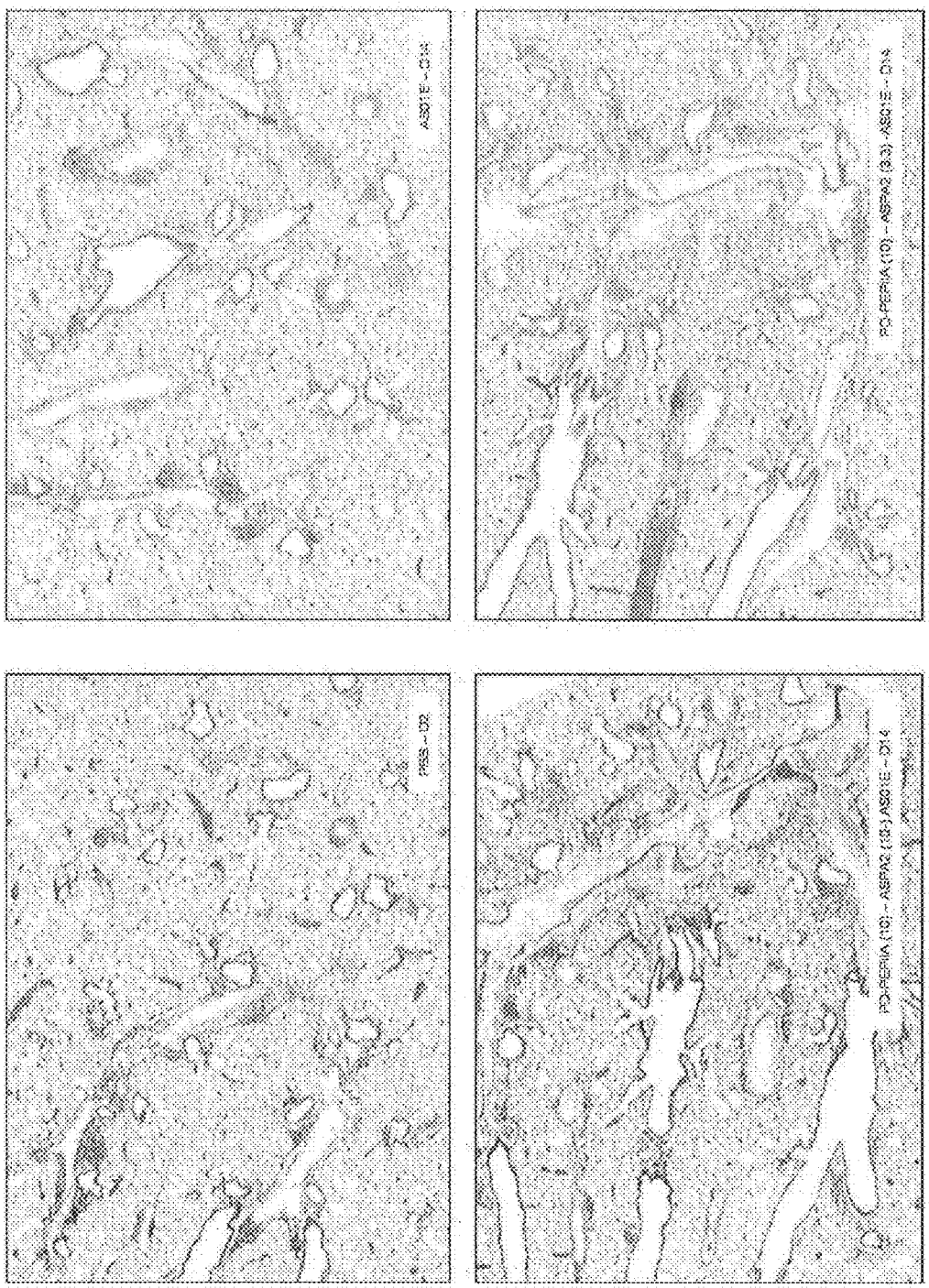
Figure 28- Effect of the tetravalent PD/ PEPIIA/ UspA2/ AS01E vaccine formulation on mouse lungs pre-sensitized with heat inactivated M. cat. - Day 14 post-immunization Figure 29 – Effect of the tetravalent PD/ PEPIIA/ UspA2/ AS01E vaccine formulation on mouse lungs pre-sensitized with heat inactivated M. cat. – Detailed results

| | An. # | Perivasculitis/Peribronchiolitis | | | | |
|---|---|---|---|---|---|---|
| | | 1 | 2 | 3 | 4 | 5 |
| D2 | PBS | 3 F<br>L + M | 3 D<br>L + M | 3 D<br>L + M | 3 D<br>L + M | A |
| | PD:PE-PIIA-USPA2 (10) | 2 D<br>L + M | 2-3 D<br>L + M | 3 D<br>L + M | 2-3 D<br>L + M | 3 D<br>L + M |
| | PD:PE-PIIA-USPA2 (3.3) | 2-3 D<br>L + M | 2-3 D<br>L + M | 2-3 D<br>L + M | 3 D<br>L + M | 3 D<br>L + M |
| | AS01E-3 | 3 D<br>L + M | 3 D<br>L + M | 3 D<br>L + M | 3 D<br>L + M | 3 D<br>L + M |
| D7 | PD:PE-PIIA-USPA2 (10) | 2-3 D<br>L + M | 3 D<br>L + M | 3 D<br>L + M | 2 D<br>L + M | 3 D<br>L + M |
| | PD:PE-PIIA-USPA2 (3.3) | 3 D<br>L + M | 2-3 D<br>L + M | 2-3 D<br>L + M | 2-3 D<br>L + M | 2-3 D<br>L + M |
| | AS01E-3 | 2 D<br>L + M | 2-3 D<br>L + M | 2-3 D<br>L + M | 2-3 D<br>L + M | 2-3 D<br>L + M |
| D14 | PD:PE-PIIA-USPA2 (10) | 2-3 D<br>L + M | 2 D<br>L + M | 2-3 D<br>L + M | 2-3 D<br>L + M | A |
| | PD:PE-PIIA-USPA2 (3.3) | 2-3 D<br>L + M | 2-3 D<br>L + M | 2-3 D<br>L + M | 2-3 D<br>L + M | A |
| | AS01E-3 | 2 D<br>L + M | 2-3 D<br>L + M | 2-3 D<br>L + M | 2-3 D<br>L + M | 2 D<br>L + M |

Legend:
- The first line in each box gives information about the inflammation severity: A = absent; 1 = minimal; 2 = slight; 3 = moderate; 4 = marked; 5 = severe, and the alteration distribution: F = focal; M = multifocal; D = diffuse.
- The second line refers to the nature of the cells observed: L = lymphocytes; M = macrophages.

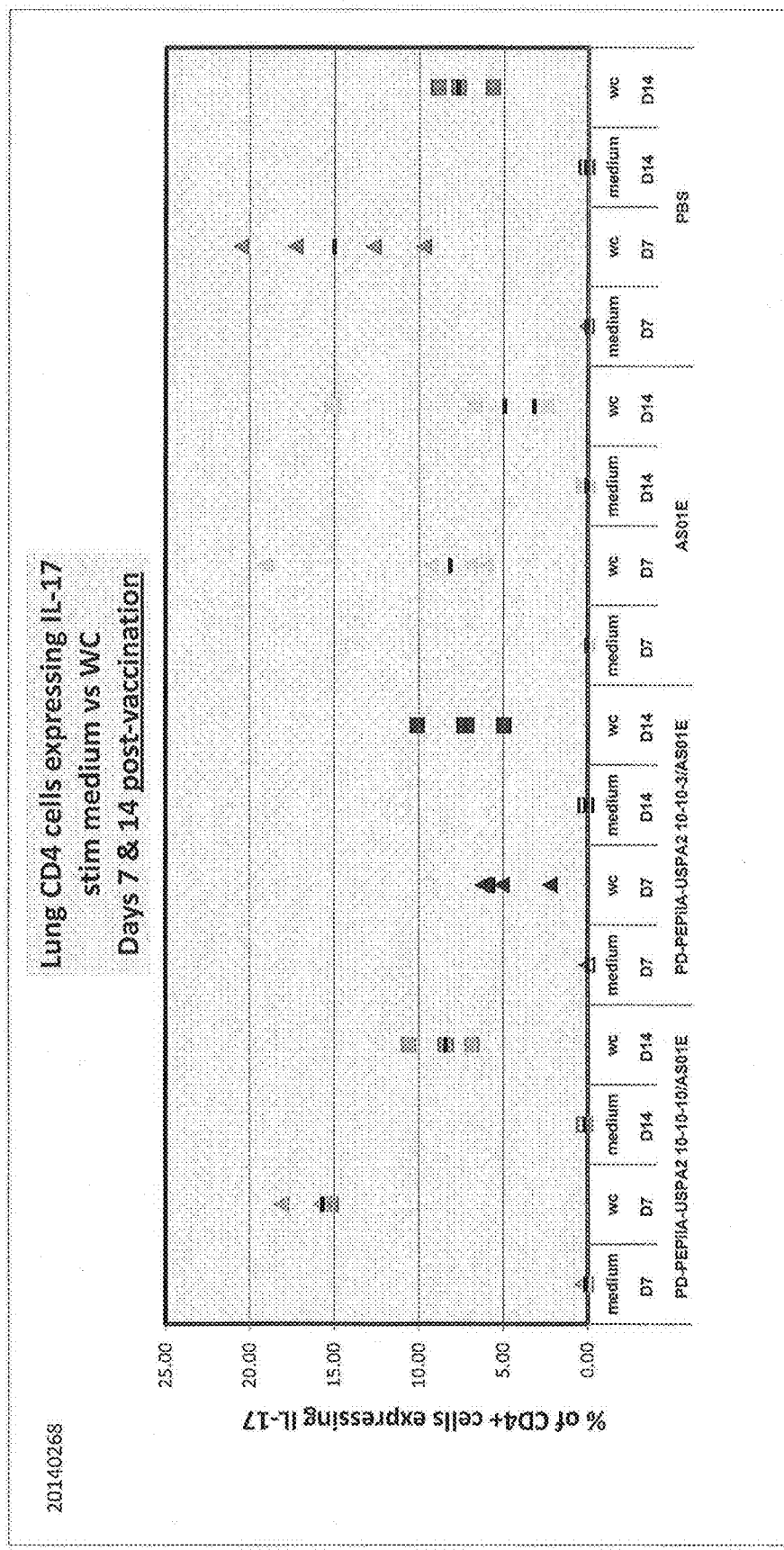
Figure 30: Post-vaccination lung CD4 T cell responses upon *M. cat* WC re-stimulation. Lung CD4 cells expressing IL17. Restimulated with heat-inactivated *M. cat.* whole cells (WC) or medium.

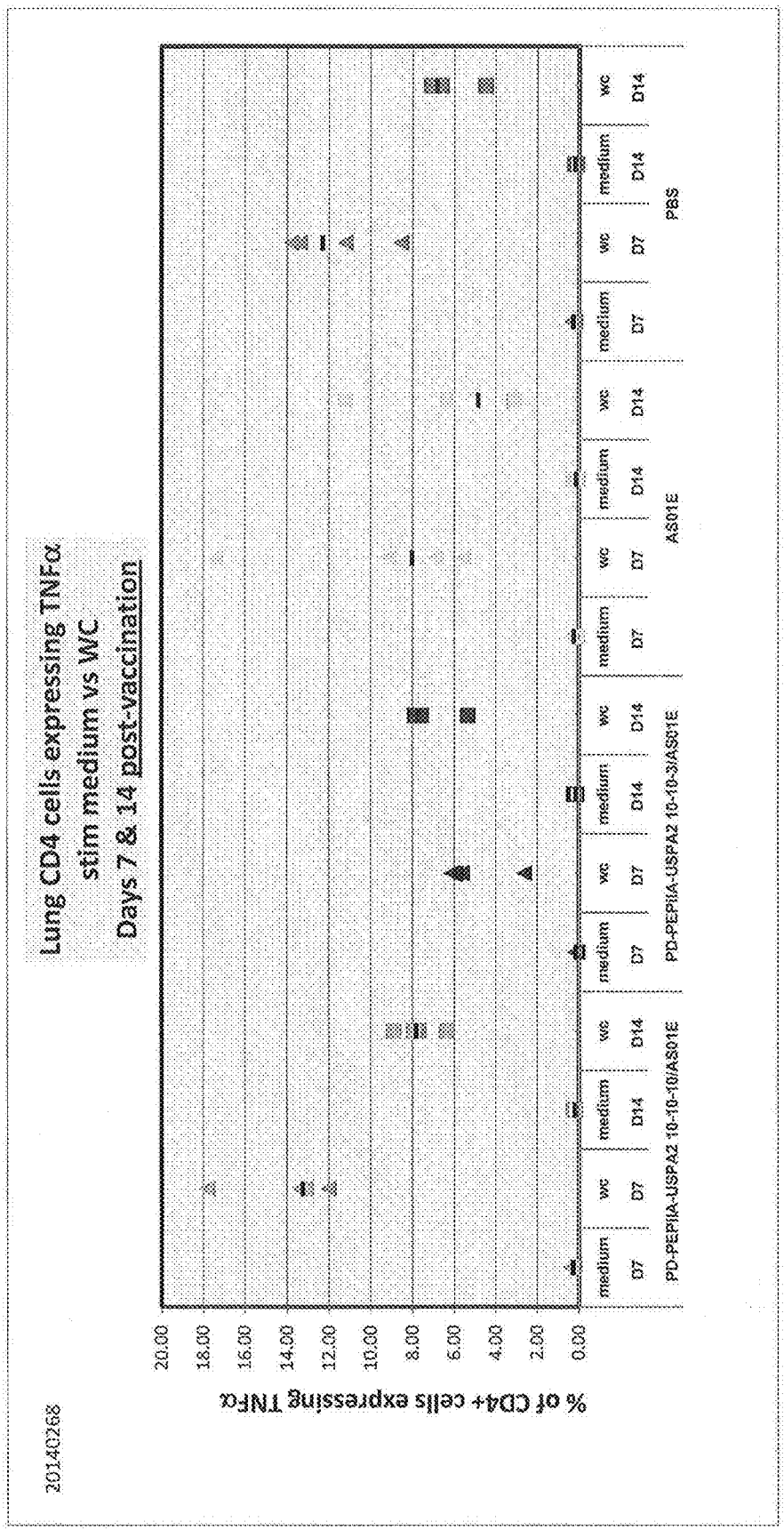
Figure 31: Post-vaccination lung CD4 T cell responses upon *M. cat* WC re-stimulation. Lung CD4 cells expressing TNFα. Restimulated with heat-inactivated *M. cat.* whole cells (WC) or medium.

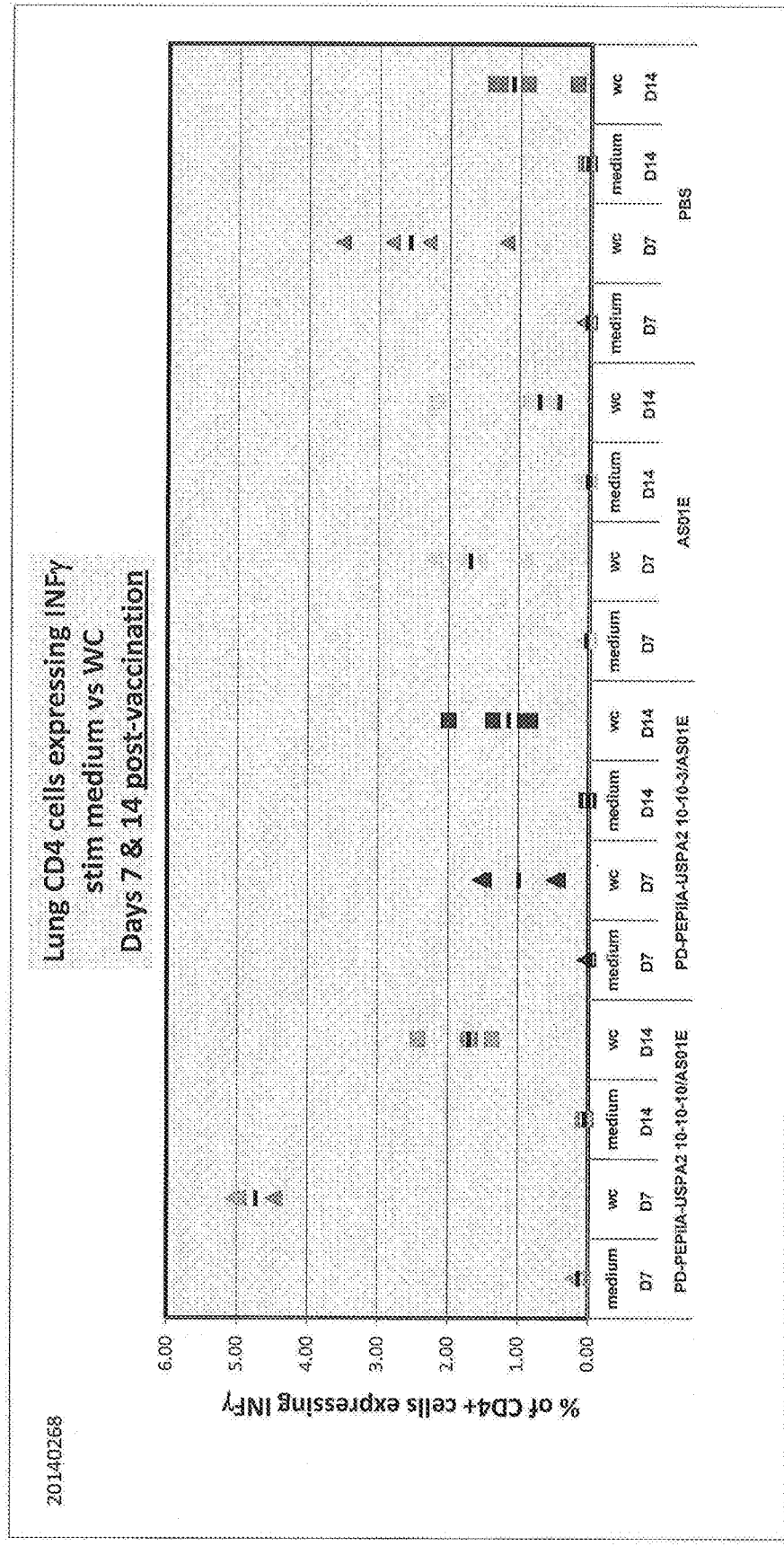
Figure 32: Post-vaccination lung CD4 T cell responses upon *M. cat* WC re-stimulation. Lung CD4 cells expressing IFNγ. Restimulated with heat-inactivated *M. cat.* whole cells (WC) or medium.

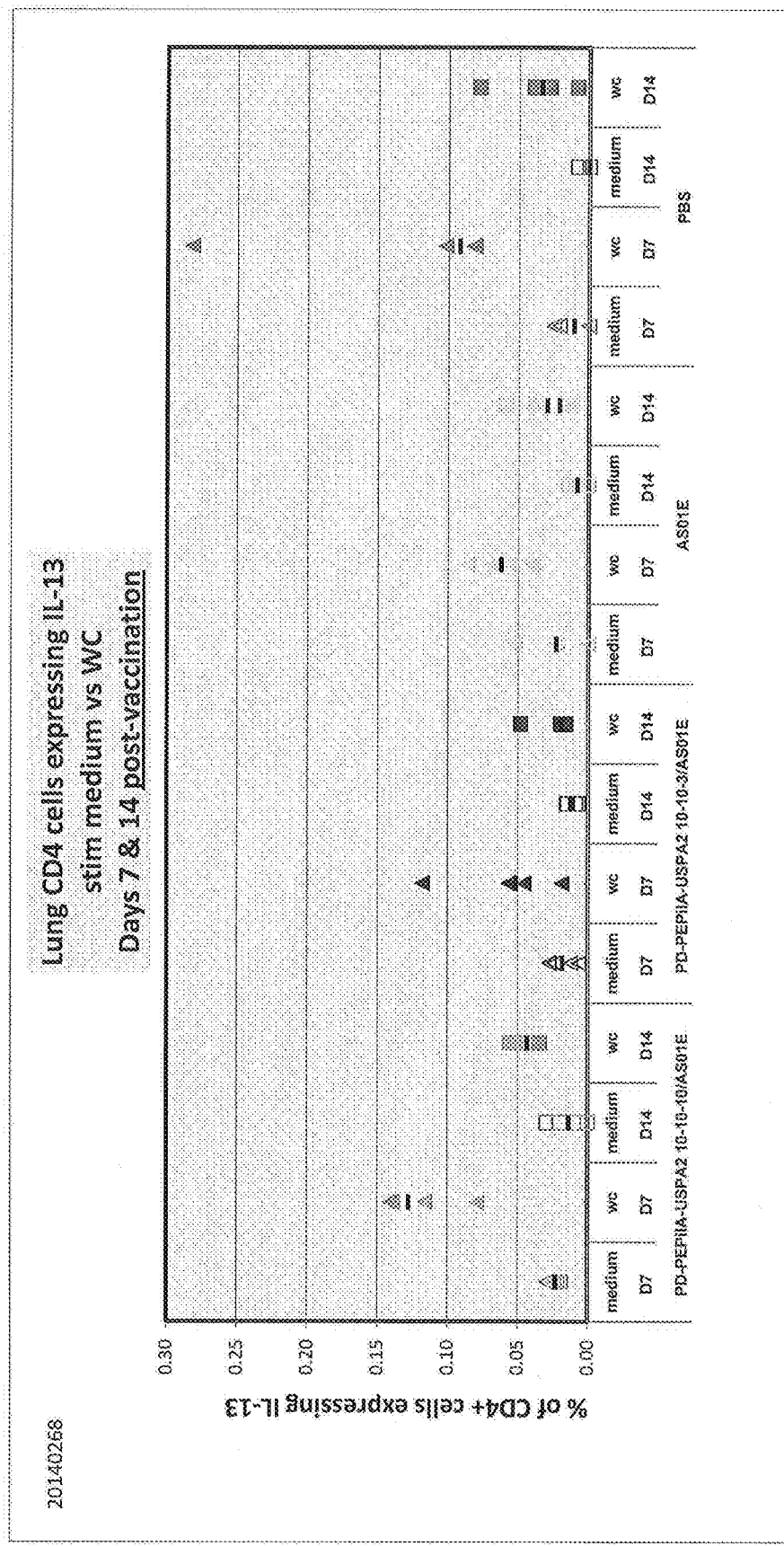
Figure 33: Post-vaccination lung CD4 T cell responses upon *M. cat* WC re-stimulation. L

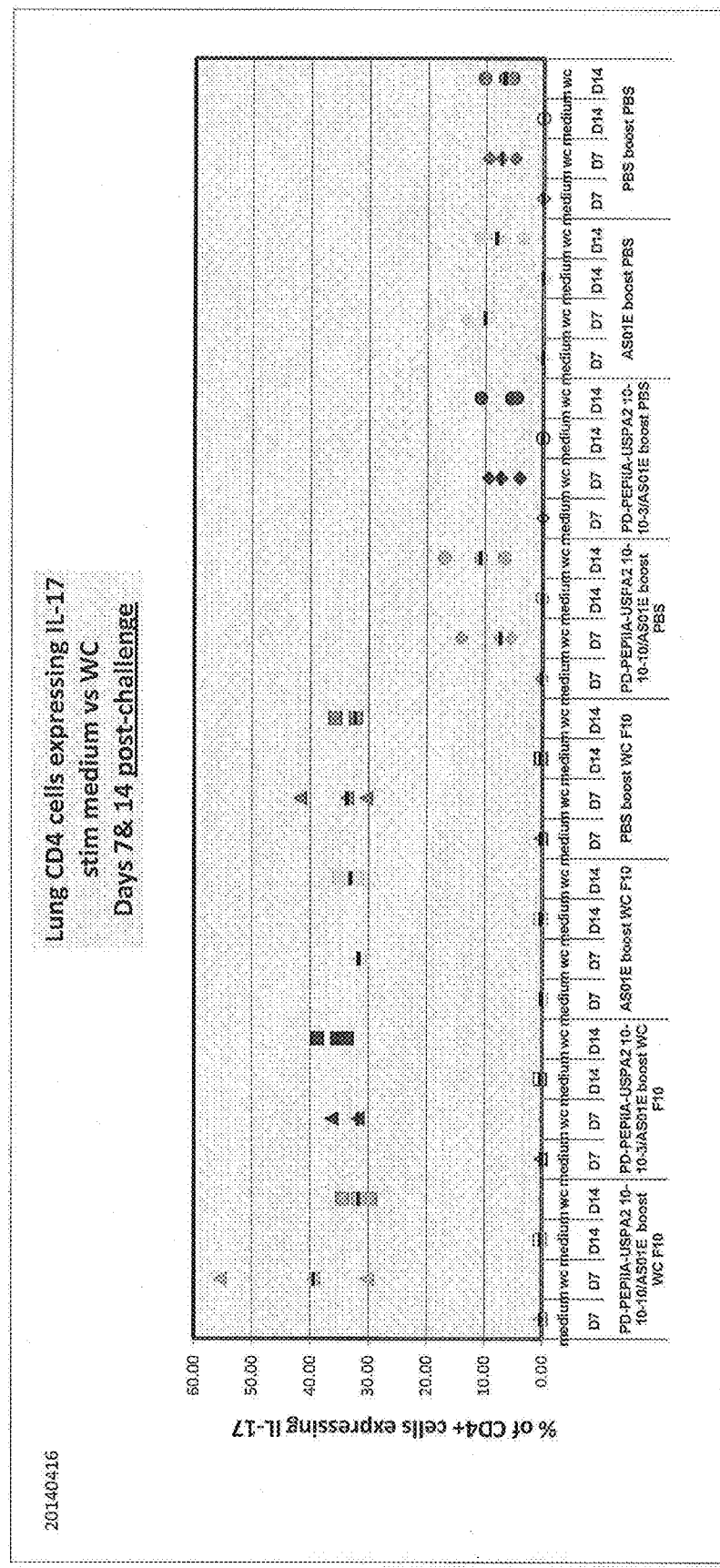
Figure 34: Post-challenge lung CD4 T cell responses upon *M. cat* WC re-stimulation. Lung CD4 cells expressing IL17. Restimulated with heat-inactivated *M. cat.* whole cells (WC) or medium.

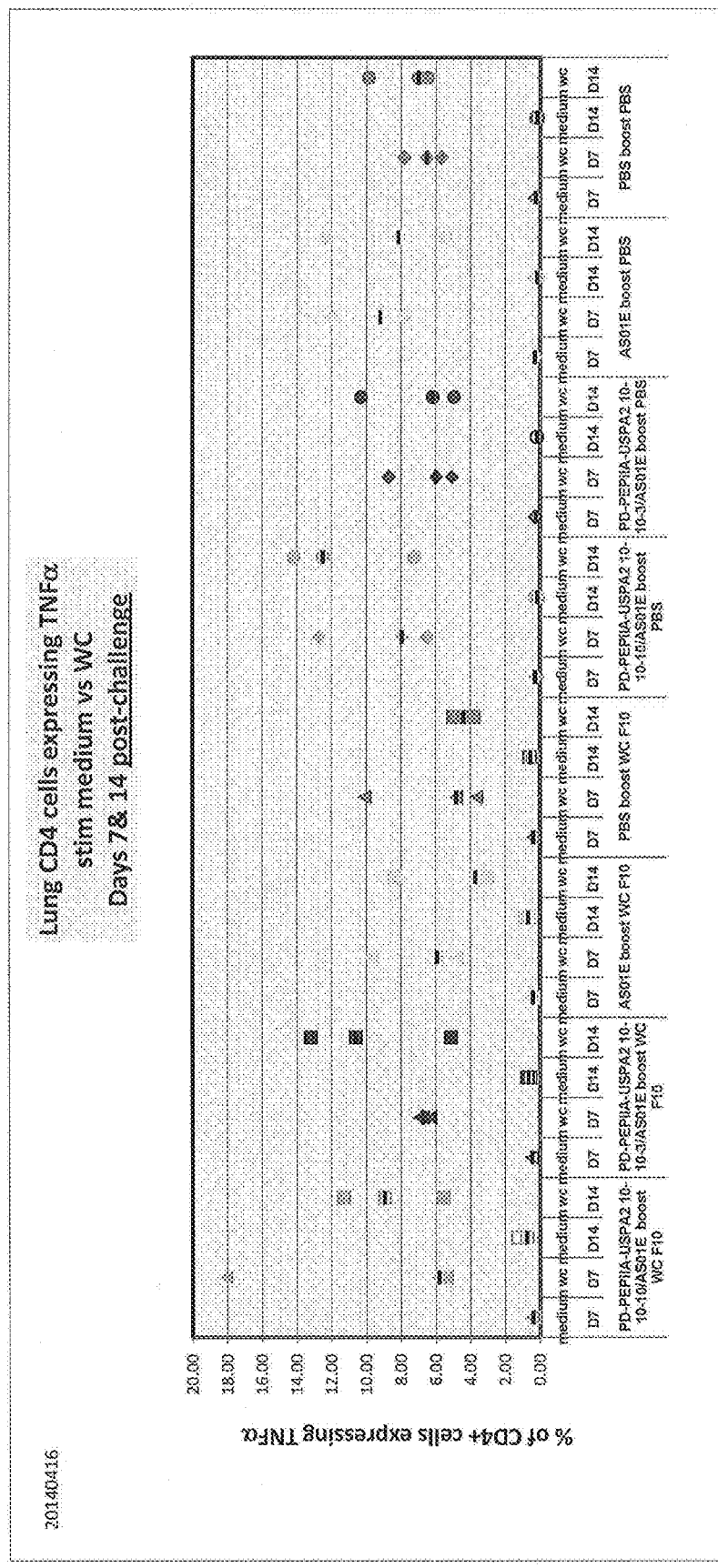
Figure 35: Post-challenge lung CD4 T cell responses upon *M. cat* WC re-stimulation. Lung CD4 cells expressing TNFα. Restimulated with heat-inactivated *M. cat.* whole cells (WC) or medium.

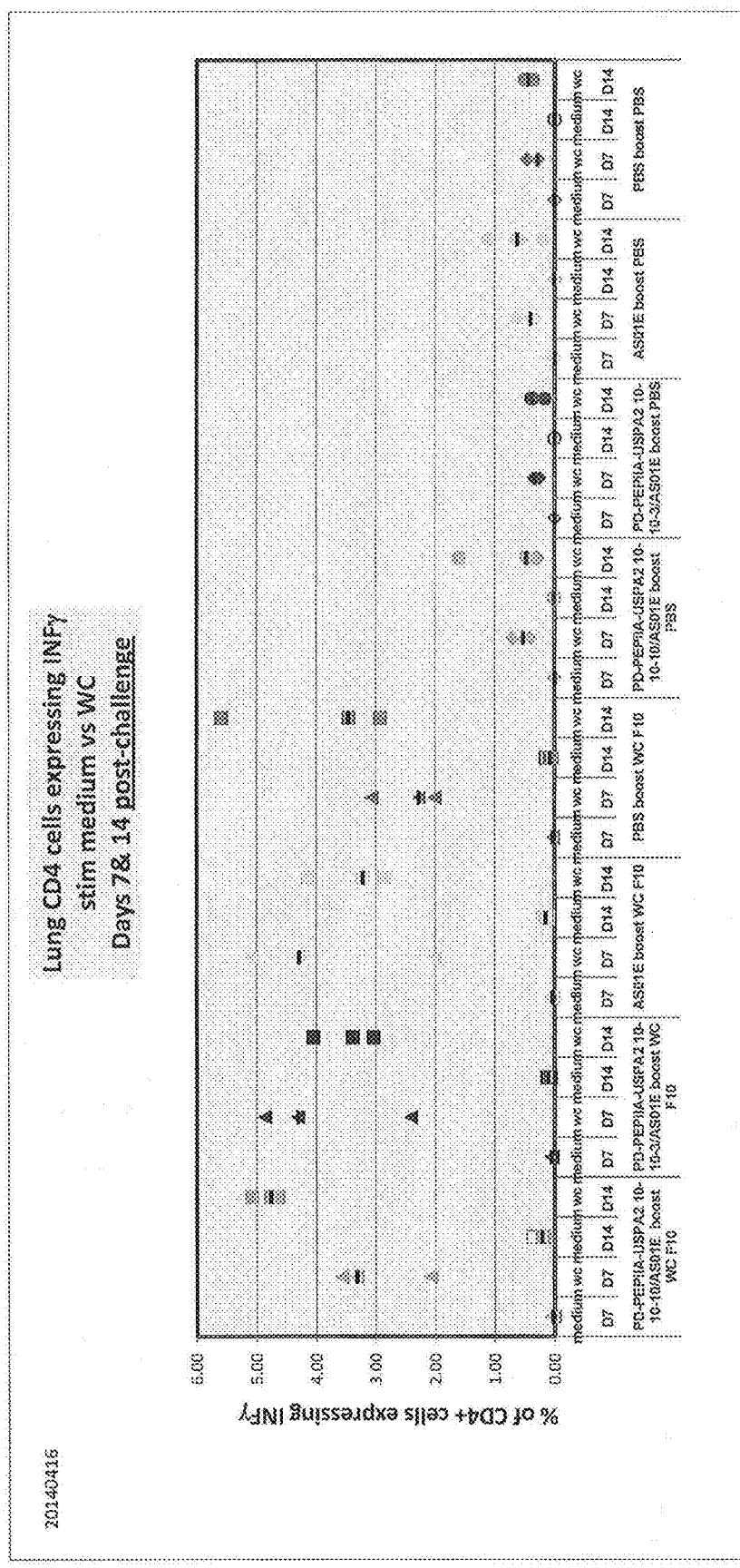
Figure 36: Post-challenge lung CD4 T cell responses upon *M. cat* WC re-stimulation. Lung CD4 cells expressing IFNγ. Restimulated with heat-inactivated *M. cat.* whole cells (WC) or medium.

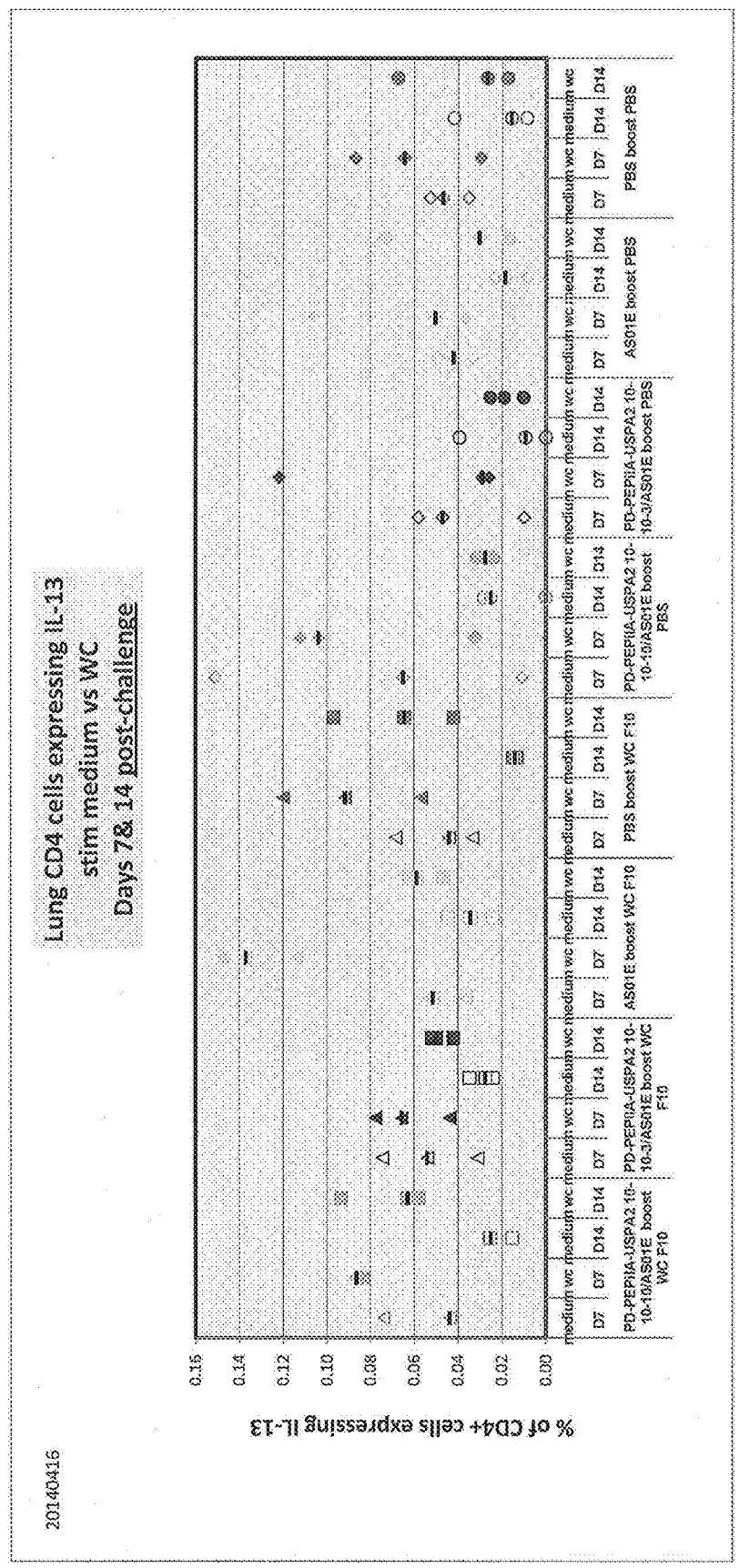
Figure 37: Post-challenge lung CD4 T cell responses upon *M. cat* WC re-stimulation. Lung CD4 cells expressing IL13. Restimulated with heat-inactivated *M. cat.* whole cells (WC) or medium.

USPA2 PROTEIN CONSTRUCTS AND USES THEREOF

FIELD OF THE INVENTION

The present invention relates to compositions comprising *Moraxella catarrhalis* (*M. catarrhalis, M. cat.*) Ubiquitous surface protein A2 (UspA2). More particularly, the present application relates to UspA2 protein constructs and immunogenic compositions comprising the constructs, vaccines comprising such immunogenic compositions and therapeutic uses of the same.

BACKGROUND OF THE INVENTION

Ubiquitous surface protein A2 (UspA2) is a trimeric autotransporter that appears as a lollipop-shared structure in electron micrographs (Hoiczyk et al. EMBO J. 19: 5989-5999 (2000)). It is composed of a N-terminal head, followed by a stalk which ends by an amphipathic helix and a C-terminal membrane domain. (Hoiczyk et al. EMBO J. 19: 5989-5999 (2000)). UspA2 contains a very well conserved domain (Aebi et al., Infection & Immunity 65(11) 4367-4377 (1997)), which is recognized by a monoclonal antibody that was shown protective upon passive transfer in a mouse *Moraxella catarrhalis* challenge model (Helminnen et al. J Infect Dis. 170(4): 867-72 (1994)).

UspA2 has been shown to interact with host structures and extracellular matrix proteins like fibronectin (Tan et al., J Infect Dis. 192(6): 1029-38 (2005)) and laminin (Tan et al., J Infect Dis. 194(4): 493-7 (2006)), suggesting it can play a role at an early stage of *Moraxella catarrhalis* infection.

UspA2 also seems to be involved in the ability of *Moraxella catarrhalis* to resist the bactericidal activity of normal human serum. (Attia A S et al. Infect Immun 73(4): 2400-2410 (2005)). It (i) binds the complement inhibitor C4bp, enabling *Moraxella catarrhalis* to inhibit the classical complement system, (ii) prevents activation of the alternative complement pathway by absorbing C3 from serum and (iii) interferes with the terminal stages of the complement system, the Membrane Attack Complex (MAC), by binding the complement regulator protein vitronectin. (de Vries et al., Microbiol Mol Biol Rev. 73(3): 389-406 (2009)).

*Moraxella catarrhalis* is an important and common respiratory pathogen that has been associated with increased risk of exacerbations in chronic obstructive pulmonary disease (COPD) in adults. (Sateesh et al., Journal of Chronic Obstructive Pulmonary Disease 3:109-115 (2006)).

A need for vaccines for *Moraxella catarrhalis* exists.

BRIEF SUMMARY OF THE INVENTION

As a first aspect, the present invention provides the proteins of formula (I).

$$A\text{-}(R_1)_m\text{---}(B)_n \quad \text{(formula I)}$$

wherein:
A is UspA2 from *Moraxella catarrhalis* or an immunogenic fragment thereof;
$R_1$ is an amino acid;
m is 0, 1 or 2;
B is histidine; and
n is 0, 1, 2, 3, 4, 5 or 6.

As a second aspect, the present invention provides immunogenic compositions comprising proteins of formula (I) and proteins of the invention. The composition may further comprise a pharmaceutically acceptable adjuvant. The composition may comprise an excipient.

In a third aspect, the present invention provides a method for the treatment or prevention of a condition or disease caused wholly or in part by *Moraxella catarrhalis*. The method comprises administering to a subject in need thereof a therapeutically effective amount of a protein of formula (I) or a protein of the invention.

In a fourth aspect, the present invention provides a method for the treatment or prevention of otitis media. The method comprises administering to a subject in need thereof a therapeutically effective amount of a protein of formula (I) or a protein of the invention.

In a fifth aspect, the present invention provides a method for the treatment or prevention of exacerbations in chronic obstructive pulmonary disease. The method comprises administering to a subject in need thereof a therapeutically effective amount of a protein of formula (I) or a protein of the invention.

In a sixth aspect, the present invention provides a method for the treatment or prevention of pneumonia. The method comprises administering to a subject in need thereof a therapeutically effective amount of a protein of formula (I) or a protein of the invention.

In a seventh aspect, the present invention provides a pharmaceutical composition comprising a protein of formula (I) or a protein of the invention for use in the treatment or prevention of a condition or disease caused wholly or in part by *Moraxella catarrhalis*. Pharmaceutical compositions may further comprise a pharmaceutically acceptable adjuvant.

In an eighth aspect, the present invention provides nucleic acids encoding the proteins of the invention.

In a ninth aspect, the present invention provides a process of producing nucleic acids of the invention.

In a tenth aspect, the present invention provides a composition comprising at least one antigen from *Moraxella catarrhalis* and at least one antigen from *Haemophilus influenzae*. The composition may further comprise a pharmaceutically acceptable adjuvant. The composition may comprise an excipient.

In an additional aspect, the present invention provides a method for the treatment or prevention of a condition or disease caused wholly or in part by *Moraxella catarrhalis* and/or *Haemophilus influenzae*. The method comprises administering to a subject in need thereof a therapeutically effective amount of a protein of formula (I) or a protein of the invention.

In a further aspect, the present invention provides a method for the treatment or prevention of exacerbations in chronic obstructive pulmonary disease. The method comprises administering to a subject in need thereof a therapeutically effective amount of a protein of formula (I) or a protein of the invention and a therapeutically effective amount of at least one antigen from *Haemophilus influenzae*.

The present invention also provides a pharmaceutical composition comprising a protein of formula (I) or a protein of the invention for use in the treatment or prevention of a condition or disease caused wholly or in part by *Moraxella catarrhalis* in combination with at least one antigen from *Haemophilus influenzae*. Pharmaceutical compositions may further comprise a pharmaceutically acceptable adjuvant.

Further aspects of the present invention are described in the detailed description of particular embodiments, examples and claims which follow.

BRIEF DESCRIPTION OF THE DRAWINGS

FIG. 1: A typical fermentation profile with the High Cell Density Induction (HCDI) processes and the parameters monitored during 20 L-scale fed-batch fermentation.

FIG. 2: A typical fermentation profile with the Low Cell Density Induction (LCDI) processes and the parameters monitored during 20 L-scale fed-batch fermentation.

FIG. 3: UspA2 yield from protein constructs MC-001, MC-002, MC-004, MC-005, MC-006, MC-007, MC-008 and MC-010 evaluated in fermenter; data from Table 4.

FIG. 4: Molecular weight distribution of purified MC-005 determined by sedimentation velocity analytical ultracentrifugation. The majority of protein is found as a trimer, with a small proportion of a higher molecular weight oligomer that may correspond to dimer of trimer. MW=molecular weight. kDa=kilodalton.

FIG. 5: Molecular weight distribution of purified MC-001 determined by sedimentation velocity analytical ultracentrifugation. Majority of protein is found as a trimer.

FIG. 6: Molecular weight distribution of purified MC-001 determined by sedimentation velocity analytical ultracentrifugation. The sample presents multiple species and is highly polydisperse. The sedimentation coefficient of the major species detected doesn't correspond to the one of the trimers normally detected in the other lots.

FIG. 7: Molecular weight distribution of purified MC-001 determined by sedimentation velocity analytical ultracentrifugation. Majority of protein is found as a trimer.

FIG. 8: Molecular weight distribution of purified MC-007 determined by sedimentation velocity analytical ultracentrifugation. Majority of protein is found as a trimer.

FIG. 9: Far-UV circular dichroism (CD) spectra of UspA2 constructs giving an indication of protein secondary structures.

FIG. 10: Secondary structures monitoring by circular dichroism (CD) during thermal unfolding of MC-005 (UspA2Δhelix+6His). Visual analysis of the spectra clearly shows that protein loses most of its secondary structures at 33° C.

FIG. 11: Secondary structures monitoring by circular dichroism (CD) during thermal unfolding of MC-007 (UspA2 full helix+6His). Visual analysis of the spectra shows that loss of secondary structure is slower compared to the construct without helix. Structural changes are detectable upon heating to 33° C., but complete unfolding seems to occur between 35° C. and 37° C.

FIG. 12: MALDI spectrum of MC-001 lot opt-01. The mass observed at 57427 Da may be coherent with the demethionylated protein, while the peak at 57620 Da could correspond to the complete protein.

FIG. 13: MALDI spectrum of MC-011 lot BMP37. The mass observed may be coherent with the demethionylated protein. The two other peaks at +186 Da and +366 Da are unidentified.

FIG. 14: Protective efficacy of MC-001 and MC-007 in a mouse model of lung colonization.

FIG. 15: Antibody response directed against UspA2 induced after intramuscular administration in mice, where PII and PIII indicate, respectively, anti-IgG levels in sera collected at day 28 (post II) and day 42 (post III).

FIG. 16: Bactericidal titers induced by UspA2 against a homologous strain formulated with different adjuvants ($AS01_E$, $AS04_C$ and $AlPO_4$).

FIG. 17: Antibody response directed against UspA2 induced after intramuscular administration in mice, using different formulations of antigens and adjuvants.

FIG. 18: Bactericidal titers induced by UspA2 against a homologous strain, using different formulations of antigens and adjuvants.

FIG. 19: IgG response induced against PD in mice by PD-PEPilA-UspA2 vaccine (a trivalent NTHi-M. cat. vaccine), formulated with different adjuvants.

FIG. 20: IgG response induced against PE in mice by PD-PEPilA-UspA2 vaccine (a trivalent NTHi-M. cat. vaccine), formulated with different adjuvants.

FIG. 21: IgG response induced against PilA in mice by PD-PEPilA-UspA2 vaccine (a trivalent NTHi-M. cat. vaccine), formulated with different adjuvants.

FIG. 22: Immunogenicity of PE in the bivalent PD-PEPilA and trivalent PD-PEPilA-UspA2 formulations with AS01E.

FIG. 23: Immunogenicity of PilA in the bivalent PD-PEPilA and trivalent PE-PilA-UspA2 formulations with AS01E.

FIG. 24: Immunogenicity of PD in the bivalent PD-PEPilA and trivalent PE-PilA-UspA2 formulations with AS01E.

FIG. 25: Effect of the tetravalent PD/PEPilA/UspA2/$AS01_E$ vaccine formulation on mouse lungs pre-sensitized with heat inactivated M. cat.—Perivascularitis and peribronchiolitis in PBS immunized mice.

FIG. 26: Effect of the tetravalent PD/PEPilA/UspA2/$AS01_E$ vaccine formulation on mouse lungs pre-sensitized with heat inactivated M. cat.—Day 2 post-immunization.

FIG. 27: Effect of the tetravalent PD/PEPilA/UspA2/$AS01_E$ vaccine formulation on mouse lungs pre-sensitized with heat inactivated M. cat.—Day 7 post-immunization.

FIG. 28: Effect of the tetravalent PD/PEPilA/UspA2/$AS01_E$ vaccine formulation on mouse lungs pre-sensitized with heat inactivated M. cat.—Day 14 post-immunization.

FIG. 29: Effect of the tetravalent PD/PEPilA/UspA2/$AS01_E$ vaccine formulation on mouse lungs pre-sensitized with heat inactivated M. cat.—Detailed results.

FIG. 30: Post-vaccination lung CD4 T cell responses upon M. cat. WC re-stimulation. Lung CD4 cells expressing IL17. Restimulated with heat-inactivated M. cat. whole cells (WC) or medium.

FIG. 31: Post-vaccination lung CD4 T cell responses upon M. cat. WC re-stimulation. Lung CD4 cells expressing TNFα. Restimulated with heat-inactivated M. cat. whole cells (WC) or medium.

FIG. 32: Post-vaccination lung CD4 T cell responses upon M. cat. WC re-stimulation. Lung CD4 cells expressing IFNγ. Restimulated with heat-inactivated M. cat. whole cells (WC) or medium.

FIG. 33: Post-vaccination lung CD4 T cell responses upon M. cat. WC re-stimulation. Lung CD4 cells expressing IL13. Restimulated with heat-inactivated M. cat. whole cells (WC) or medium.

FIG. 34: Post-challenge lung CD4 T cell responses upon M. cat. WC re-stimulation. Lung CD4 cells expressing IL17. Restimulated with heat-inactivated M. cat. whole cells (WC) or medium.

FIG. 35: Post-challenge lung CD4 T cell responses upon M. cat. WC re-stimulation. Lung CD4 cells expressing TNFα. Restimulated with heat-inactivated M. cat. whole cells (WC) or medium.

FIG. 36: Post-challenge lung CD4 T cell responses upon M. cat. WC re-stimulation. Lung CD4 cells expressing IFNα. Restimulated with heat-inactivated M. cat. whole cells (WC) or medium.

FIG. 37: Post-challenge lung CD4 T cell responses upon *M. cat*. WC re-stimulation. Lung CD4 cells expressing IL13. Restimulated with heat-inactivated *M. cat*. whole cells (WC) or medium.

DETAILED DESCRIPTION OF THE INVENTION

Unless otherwise explained or defined herein, all technical and scientific terms used herein have the same meaning as commonly understood by one of ordinary skill in the art to which this disclosure belongs. For example, definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen may be approximate. Thus, where a concentration is indicated to be (for example) approximately 200 pg, it is intended that the concentration includes values slightly more or slightly less than ("about" or "~") 200 pg.

Although methods and materials similar or equivalent to those described herein can be used in the practice or testing of this disclosure, suitable methods and materials are described below.

The term "comprises" means "includes". Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

In order to facilitate review of the various embodiments of this disclosure, the following explanations of terms are provided. Additional terms and explanations are provided in the context of this disclosure.

A "subject" as used herein is a mammal, including humans, non-human primates, and non-primate mammals such as members of the rodent genus (including but not limited to mice and rats) and members of the order Lagomorpha (including but not limited to rabbits).

As used herein "UspA2" means Ubiquitous surface protein A2 from *Moraxella catarrhalis*. UspA2 may consist of or comprise the amino acid sequence of SEQ ID NO: 1 from ATCC 25238.

(SEQ ID NO: 1)
MKTMKLLPLKIAVTSAMIIGLGAASTANAQAKNDITLEDLPYLIKKIDQN

ELEADIGDITALEKYLALSQYGNILALEELNKALEELDEDVGWNQMDIAN

LEDDVETLTKNQNALAEQGEAIKEDLQGLADFVEGQEGKILQNETSIKKN

-continued
TQRNLVNGFEIEKNKDAIAKNNESIEDLYDFGHEVAESIGEIHAHNEAQN

ETLKGLITNSIENTNNITKNKADIQALENNVVEELFNLSGRLIDQKADID

NNINNIYELAQQQDQHSSDIKTLKKNVEEGLLELSGHLIDQKTDIAQNQA

NIQDLATYNELQDQYAQKQTEAIDALNKASSENTQNIEDLAAYNELQDAY

AKQQTEAIDALNKASSENTQNIEDLAAYNELQDAYAKQQTEAIDALNKAS

SENTQNIAKNQADIANNINNIYELAQQQDQHSSDIKTLAKASAANTDRIA

KNKADADASFETLTKNQNTLIEKDKEHDKLITANKTAIDANKASADTKFA

ATADAITKNGNAITKNAKSITDLGTKVDGFDSRVTALDTKVNAFDGRITA

LDSKVENGMAAQAALSGLFQPYSVGKFNATAALGGYGSKSAVAIGAGYRV

NPNLAFKAGAAINTSGNKKGSYNIGVNYEF as well as sequences with at least or exactly 63%, 66%, 70%, 72%, 74%, 75%, 77%, 80%, 84%, 85%, 90%, 95%, 96%, 97%, 98%, 99% or 100% identity, over the entire length, to SEQ ID NO: 1. Comparison of 38 sequences of UspA2 from *Moraxella catarrhalis* (Table 1, SEQ ID NO: 1-SEQ ID NO: 38) demonstrated approximately 63% to approximately 100% identity to UspA2 as set forth in SEQ ID NO. 1.

UspA2 as described in SEQ ID NO: 1 contains a signal peptide (for example, amino acids 1 to 29 of SEQ ID NO: 1), a laminin binding domain (for example, amino acids 30 to 177 of SEQ ID NO: 1), a fibronectin binding domain (for example, amino acids 165 to 318 of SEQ ID NO: 1) (Tan et al. JID 192: 1029-38 (2005)), a C3 binding domain (for example, amino acids 30 to 539 of SEQ ID NO: 1 (WO2007/018463), or a fragment of amino acids 30 to 539 of SEQ ID NO: 1, for example, amino acids 165 to 318 of SEQ ID NO: 1 (Hallström T et al. J. Immunol. 186: 3120-3129 (2011)), an amphipathic helix (for example, amino acids 519 to 564 of SEQ ID NO: 1 or amino acids 520-559 of SEQ ID NO:1, identified using different prediction methods) and a C terminal anchor domain (for example, amino acids 576 to 630 amino acids of SEQ ID NO: 1 (Brooks et al., Infection & Immunity, 76(11), 5330-5340 (2008)).

UspA2 amino acid differences have been described for various *Moraxella catarrhalis* species. See for example, J Bacteriology 181(13):4026-34 (1999), Infection and Immunity 76(11):5330-40 (2008) and PLoS One 7(9):e45452 (2012).

UspA2 may consist of or comprise an amino acid sequence that differs from SEQ ID NO. 1 at any one or more amino acid selected from the group consisting of: AA (amino acid) 30 to 298, AA 299 to 302, AA 303 to 333, AA 334 to 339, AA 349, AA 352 to 354, AA 368 to 403, AA 441, AA 451 to 471, AA 472, AA474 to 483, AA 487, AA 490, AA 493, AA 529, AA 532 or AA 543. UspA2 may consist of or comprise an amino acid sequence that differs from SEQ ID NO: 1 in that it contains at least one amino acid insertion in comparison to SEQ ID NO. 1. UspA2 may consists of or comprise an amino acid sequence that differs from SEQ ID NO. 1 at any one of the amino acid differences in SEQ ID NO: 2 through SEQ ID NO: 38. For example, SEQ ID NO. 1 may contain K instead of Q at amino acid 70, Q instead of G at amino acid 135 and/or D instead of N at amino acid 216.

TABLE 1

UspA2 amino acid sequences from 38 strains of *Moraxalla catarrhalis* (SEQ ID NO: 1 - SEQ ID NO: 38).

| Strain | UspA2 sequences |
|---|---|
| ATCC 25238 (SEQ ID NO: 1) | MKTMKLLPLKIAVISAMIIGLGAASTANAQAKNDITLEDLPYLIKKIDQNELEADIGDITALEK YLALSQYGNILALEELNKALEELDEDVGWNQNDIANLEDDVETLTKNQNALAEQGEAIKEDLQG LADFVEGQEGKILQNETSIKKNTQRNLVNGFEIEKNKDAIAKNNESIEDLYDFGHEVAESIGEI HAHNEAQNETLKGLITNSIENTNNITKNKADIQALENNVVEELFNLSGRLIDQKADIDNNINNI YELAQQQDQHSSDIKTLKKNVEEGLLELSGHLIDQKTDIAQNQANIQDLATYNELQDQYAQKQT EAIDALNKASSENTQNIEDLAAYNELQDAYAKQQTEAIDALNKASSENTQNIEDLAAYNELQDA YAKQQTEAIDALNKASSENTQNIAKNQADIANNINNIYELAQQQDQHSSDIKTLAKASAANTDR IAKNKADADASFETLTKNQNTLIEKDKEHDKLITANKTAIDANKASADTKFAATADAITKNGNA ITKNAKSITDLGTKVDGFDSRVTALDTKVNAFDGRITALDSKVENGMAAQAALSGLFQPYSVGK FNATAALGGYGSKSAVAIGAGYRVNPNLAFKAGAAINTSGNKKGSYNIGVNYEF (630 aa) |
| American 2933 (SEQ ID NO: 2) | MKTMKLLPLKIAVISAMIIGLGAASTANAQSRDRSLEDIQDSISKLVQDDINTLKQDQQKMNKY LLLNQLANTLITDELNNNVIKNTNSIEALGDEIGWLENDIADLEEGVEELTKNQNTLIEKDEEH DRLIAQNQADIQTLENNVVEELFNLSGRLIDQEADIAKNNASIEELYDFDNEVAERIGEIHAYT EEVNKTLENLITNSVKNTDNIDKNKADIDNNINHIYELAQQQDQHSSDIKTLKNNVEEGLLELS GHLIDQKADLTKDIKALESNVEEGLLDLSGRLLDQKADLTKDIKALESNVEEGLLDLSGRLLDQ KADIAQNQTDIQDLAAYNELQDQYAQKQTEAIDALNKASSENTQNIEDLAAYNELQDAYAKQQT EAIDALNKASSENTQNIAKNQADIANNINNIYELAQQQDQHSSDIKTLAKASAANTNRIATAEL GIAENKKDAQIAKAQANANKTAIDENKASADTKFAATADAITKNGNAITKNAKSITDLGTKVDG FDGRVTALDTKVNAFDGRITALDSKVENGMAAQAALSGLFQPYSVGKFNATAALGGYGSKSAVA IGAGYRVNPNLAFKAGAAINTSGNKKGSYNIGVNYEF (613 aa) |
| American 2912 (SEQ ID NO: 3) | MKTMKLLPLKIAVTSALIIGLGAASTANAQQQLQTETFLPNFLSNDNYDLTDPFYHNMILGDTA LLDKQDGSQPQLKFYSNDKDSVPDSLLFSKLLHEQQLNGFKKGDTIIPLDKDGKPVYQVDYKLD GKGKKQKRRQVYSVTTKTATDDDVNSAYSRGILGKVDDLDDEMNFLNHDITSLYDVTANQQDAI KDLKKGVKGLNKELKELDKEVGVLSRDIGSLNDDVAQNNESIEDLYDFSQEVADSIGEIHAHNK AQNETLQDLITNSVENTNNITKNKADIQALENNVVEELFNLSGRLIDQKADLTKDIKTLESNVE EGLLELSGHLIDQKADIAKNQADIAQNQANIQDLAAYNELQDAYAKQQTEAIDALNKASSENTQ NIEDLAAYNELQDAYAKQQTEAIDALNKASSENTQNIAKNQADIANNINNIYELAQQQDQHSSD IKTLAKASAANTDRIAKNKADADASFETLTKNQNTLIEKDKEHDKLITANKTAIDENKASADTK FAATADAITKNGNAITKNAKSITDLGTKVDGFDSRVTALDTKVNAFDGRITALDSKVENGMAAQ AALSGLFQPYSVGKFNATAALGGYGSKSAVAIGAGYRVNPNLAFKAGAAINTSGNKKGSYNIGV NYEF (644 aa) |
| American 2908 (SEQ ID NO: 4) | MKTMKLLPLKIAVTSALIVGLGAASTANAQLVERFFPNIFLDKPLAKQHYHNVVVGDTSIVSDL QSNSDQLKFYSDDEGLVPDSLLFNKMLHEQLLNGFKEGDTIIPLDENGKPVYKVDYKLDGKEPR KVYSVTTKIATAEDVATSSYANGIQKDIDDLYDFDHQVTERLTQNLGFKTIYRNGERILANEESVQ YLNKEVQNNIEHIYELAQQQDQHSSDIKTLESNVEKGLLELSGHLIDQKADLTKDIKTLESNVE EGLLDLSGRLIDQKADLTKDIKTLESNVEEGLLDLSGRLIDQKADIAQNQANIQDLAAYNELQD QYAQKQTEAIDALNKASSENTQNIEDLAAYNELQDAYAKQQTEAIDALNKASSENTQNIAKNQA DIANNINNIYELAQQQDQHSSDIKTLAKASAANTNRIATAELGIAENKKDAQIAKAQANANKTA IDENKASADTKFAATADAITKNGNAITKNAKSITDLGTKVDGFDSRVTALDTKVNAFDGRITAL DSKVENGMAAQAALSGLFQPYSVGKFNATAALGGYGSKSAVAIGAGYRVNPNLAFKAGAAINTS GNKKGSYNIGVNYEF (591 aa) |
| Finnish 307 (SEQ ID NO: 5) | MKTMKLLPLKIAVTSAMIIGLGAASTANAQQQQQQQQQQQSRTEIFFPNIFFNENHDELDDAYH NIILGDTALLDKQDGSQPQLKFYSNDKDSVPDSLLFSKLLHEQQLNGFKKGDTIIPLDKDGKPV YQVDYKLDGKGKKQKRRQVYSVTTKTATDDDVNSAYSRGILGKVDDLDDEMNFLNHDITSLYDV TANQQDAIKGLKKGVKGLNKELKELDKEVGVLSRDIGSLNDDVAQNNESIEDLYDFSQEVADSI GEIHAHNKAQNETLQDLITNSVENTNNITKNKADIQALENNVVEELFNLSGRLIDQKADLTKDI KTLESNVEEGLLELSGHLIDQKADIAKNQADIAQNQANIQDLAAYNELQDAYAKQQTEAIDALN KASSENTQNIEDLAAYNELQDAYAKQQTEAIDALNKASSENTQNIEDLAAYNELQDAYAKQQTE AIDALNKASSENTQNIAKNQADIANNINNIYELAQQQDQHSSDIKTLAKASAANTDRIAKNKAD ADASFETLTKNQNTLIEKDKEHDKLITANKTAIDENKASADTKFAATADAITKNGNAITKNAKS ITDLGTKVDAFDGRVTALDTKVNAFDGRITALDSKVENGMAAQAALSGLFQPYSVGKFNATAAL GGYGSKSAVAIGAGYRVNPNLAFKAGAAINTSGNKKGSYNIGVNYEF (687 aa) |
| Finnish 353 (SEQ ID NO: 6) | MKTMKLLPLKIAVTSAMIVGLGMASTANAQQQKSPKTETFLPNIFFNEYADDLDTLYHNMILGD TAITHDDQYKFYADDATEVPDSLFFNKILHDQLLYGFKEGDKIIPLDENGKPVYKLDKRLENGV QKTVYSVTTKTATADDVNSAYSRGIQGDIDDLYEANKENVNRLIEHGDKIFANEESVQYLNREV QNNIENIHELAQQQDQHSSDIKTLKKNVEKDLLDLSGRLIAQKEDIAQNQTDIQDLATYNELQD QYAQKQTEAIDALNKASSENTQNIAKNSNHIKTLENNIEEGLLELSGHLIDQKADLTKDIKALE SNVEEGLLDLSGRLIDQKADIAQNQANIQDLAAYNELQDAYAKQQTEAIDALNKASSENTQNIE DLAAYNELQDAYAKQQTEAIDALNKASSENTQNIEDLAAYNELQDAYAKQQTEAIDALNKASSE NTQNIAKNQADIANNINNIYELAQQQDQHSSDIKTLAKASAANTDRIAKNKADADASFETLTKN QNTLIEKDKEHDKLITANKTAIDANKASADTKFAATADAITKNGNAITKNAKSITDLGTKVDGF DGRVTALDTKVNALDTKVNAFDGRITALDSKVENGMAAQAALSGLFQPYSVGKFNATAALGGYG SKSAVAIGAGYRVNPNLAFKAGAAINTSGNKKGSYNIGVNYEF (683 amino acids) |
| Finnish 358 (SEQ ID NO: 7) | MKTMKLLPLKIAVTSAMMVGLGMASTANAQQQKSPKTEIFLPNLFDNDNTELTDPLYHNMILGN TALLTQENQYKFYADDGNGVPDSLLFNKILHDQLLHGFKEGGTIIPLDENGKPVYKLDSIVEQG KTKTVYSVTTKTATADDVNSAYSRGIQGDIDDLYEANKENVNRLIEHGDKIFANEESVQYLNRE VQNNIENIHELAQQQDQHSSDIKTLKKNVEKDLLDLSGRLIAQKEDIAQNQTDIQDLATYNELQ DQYAQKQTEAIDALNKASSENTQNIAKNSNHIKTLENNIEEGLLELSGHLIDQKADLTKDIKAL ESNVEEGLLDLSGRLIDQKADIAQNQANIQDLAAYNELQDAYAKQQTEAIDALNKASSENTQNI |

TABLE 1-continued

UspA2 amino acid sequences from 38 strains of *Moraxalla catarrhalis* (SEQ ID NO: 1 - SEQ ID NO: 38).

| Strain | UspA2 sequences |
|---|---|
| | EDLAAYNELQDAYAKQQTEAIDALNKASSENTQNIEDLAAYNELQDAYAKQQTEAIDALNKASS ENTQNIAKNQADIANNINNIYELAQQQDQHSSDIKTLAKASAANTDRIAKNKADADASFETLTK NQNTLIEKDKEHDKLITANKTAIDANKASADTKFAATADAIKNGNAITKNAKSITDLGTKVDG FDGRVTALDTKVNALDTKVNAFDGRITALDSKVENGMAAQAALSGLFQPYSVGKFNATAALGGY GSKSAVAIGAGYRVNPNLAFKAGAAINTSGNKKGSYNIGVNYEF (684 amino acids) |
| Finnish 216 (SEQ ID NO: 8) | MKTMKLLPLKIAVTSAMIIGLGAASTANAQQQKTKTEVFLPNLFDNDYYDLTDPLYHSMILGD TATLFDQQDNSKSQLKFYSNDKDSVPDSLLFSKLLHEQQLNGFKAGDTIIPLDKDGKPVYTQDT RTKDGKVETVYSVTTKIATQDDVEQSAYSRGIQGDIDDLYDINREVNEYLKATHDYNERQTEAI DALNKASSANTDRIDTAEERIDKNEYDIKALESNVGKDLLDLSGRLIAQKEDIDNNINHIYELA QQQDQHSSDIKTLKNNVEEGLLELSGHLIDQKADLTKDIKTLENNIEEGLLELSGHLIDQKADL TKDIKTLENNIEEGLLELSGHLIDQKADIAQNQANIQDLAAYNELQDQYAQKQTEAIDALNKAS SENTQNIEDLAAYNELQDAYAKQQTEAIDALNKASSENTQNIEDLAAYNELQDAYAKQQTEAID ALNKASSENTQNIAKNQADIANNINNIYELAQQQDQHSSDIKTLAKVSAANTDRIAKNKADADA SFETLTKNQNTLIEKDKEHDKLITANKTAIDANKASADTKFAATADAITKNGNAITKNAKSITD LGTKVDGFDGRVTALDTKVNALDTKVNAFDGRITALDSKVENGMAAQAALSGLFQPYSVGKFNATAALGGY GSKSAVAIGAGYRVNPNLAFKAGAAINTSGNKKGSYNIGVNYEF (684 amino acids) |
| Dutch H2 (SEQ ID NO: 9) | MKTMKLLPLKIAVTSAMMVGLGMASTANAQQQKSPKTEIFLPNLFDNDNTELTDPLYHNMILGN TALLTQENQYKFYADDGNGVPDSLLFNKILHDQLLHGFKKGDTIIPLDENGKPVYKLDSIVEQG KIKTVYSVTTKTATADDVNSAYSRGIQGDIDDLYEANKENVNRLIEHGDKIFANEESVQYLNRE VQNNIENIYELVQQQDQHSSDIKTLKKNVEKDLLDLSGRLIAQKEDIAQNQTDIQDLATYNELQ DQYAQKQTEAIDALNKASSENTQNIAKNSNHIKTLENNIEEGLLELSGHLIDQKADLTKDIKAL ESNVEEGLLDLSGRLIDQKADIAQNQANIQDLAAYNELQDAYAKQQTEAIDALNKASSENTQNI EDLAAYNELQDAYAKQQTEAIDALNKASSENTQNIEDLAAYNELQDAYAKQQTEAIDALNKASS ENTQNIAKNQADIANNINNIYELAQQQDQHSSDIKTLAKASAANTDRIAKNKADADASFETLTK NQNTLIEKDKEHDKLITANKTAIDANKASADTKFAATADAITKNGNAITKNAKSITDLGTKVDG FDGRVTALDTKVNALDTKVNAFDGRITALDSKVENGMAAQAALSGLFQPYSVGKFNATAALGGY GSKSAVAIGAGYRVNPNLAFKAGAAINTSGNKKGSYNIGVNYEF (684 amino acids) |
| Dutch F10 (SEQ ID NO: 10) | MKTMKLLPLKIAVTSAMIIGLGAASTANAQLAEQFFPNIFSNHAPVKQHYHNVVVGDTSIVENL QDSDDTQLKFYSNDEYSVPDSLLFNKMLHEQQLNGFKKGDTIIPLDENGKPVYKVDYKLDGQEP RRVYSVTTKIATQDDVDNSPYSRGIQGDIDDLYEANKENVNRLIEHGDKIFANEESVQYLNRE QNNIENIYELAQQQDQHSSDIKTLKKNVEEGLLELSGHLIDQKADLTKDIKTLESNVEEGLLEL SGHLIDQKADIAKNQADIAQNQANIQDLAAYNELQDAYAKQQTEAIDALNKASSENTQNIEDLA AYNELQDAYAKQQTEAIDALNKASSENTQNIAKNQADIANNINNIYELAQQQDQHSSDIKTLAK ASAANTDRIAKNKADADASFETLIKNQNTLIEKDKEHDKLITANKTAIDANKASADTKFAATAD AITKNGNAITKNAKSITDLGTKVDAFDGRVTALDTKVNALDTKVNAFDGRITALDSKVENGMAAQAALSGL FQPYSVGKFNATAALGGYGSKSAVAIGAGYRVNPNLAFKAGAAINTSGNKKGSYNIGVNYEF (574 amino acids) |
| Norwegian 1 (SEQ ID NO: 11) | MKTMKLLPLKIAVTSALIVGLGAASTANAQQQPQTETFFPNIFFNENHDALDDVYHNMILGDTA ITQDNQYKFYADAISEVPDSLLFNKILHDQQLNGFKEGDTIIPLDENGKPVYKLDEKVENGVKK SVYSVTTKTATRADVEQSAYSRGIQGDIDDLYEANKENVNRLIEHGDKIFANEESVQYLNKEVQ NNIENIHELAQQQDQHSSDIKTLKKNVEEGLLELSGHLIDQKADLTKDIKTLESNVEEGLLDLS GRLLDQKADIAQNQANIQDLAAYNELQDAYAKQQTEAIDALNKASSENTQNIEDLAAYNELQDA YAKQQTEAIDALNKASSENTQNIEDLAAYNELQDAYAKQQTEAIDALNKASSENTQNIEDLAAY NELQDAYAKQQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLIKNQNTLI EKDKEHDKLITANKTAIDANKASADTKFAATADAITKNGNAITKNAKSITDLGTKVDAFDGRVT ALDTKVNALDTKVNAFDGRITALDSKVENGMAAQAALSGLFQPYSVGKFNATAALGGYGSKSAV AIGAGYRVNPNLAFKAGAAINTSGNKKGSYNIGVNYEF (678 amino acids) |
| Norwegian 13 (SEQ ID NO: 12) | MKTMKLLPLKIAVTSAMIVGLGAASTANAQQQQQPRTETFFPNIFFNENHDALDDVYHNMILGD TAITQDNQYKFYADAISEVPDSLLFNKILHDQQLNGFKEGDTIIPLDENGKPVYKLDEKVENGV KKSVYSVTTKTATRADVEQSAYSRGIQGDIDDLYEANKENVNRLIEHGDKIFANEESVQYLNRE VQNNIENIHELAQQQDQHSSDIKTLKKNVEKDLLDLSGRLIAQKEDIAQNQTDIQDLATYNELQ DQYAQKQTEAIDALNKASSENTQNIAKNSNHIKTLENNIEEGLLELSGHLIDQKADLTKDIKTL ENNIEEGLLELSGHLIDQKADLTKDIKALESNVEEGLLDLSGRLLDQKADIAQNQANIQDLAAY NELQDQYAQKQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLTKNQNTLI EKDKEHDKLITANKTAIDTNKASADTKFAATADAITKNGNAITKNAKSITDLGTKVDGFDGRVT ALDTKVNALDTKVNAFDGRITALDSKVENGMAAQAALSGLFQPYSVGKFNATAALGGYGSKSAV AIGAGYRVNPNLAFKAGAAINTSGNKKGSYNIGVNYEF (678 amino acids) |
| Norwegian 20 (SEQ ID NO: 13) | MKTMKLLPLKIAVTSALIVGLGAASTANAQLVERFFPNIFLDKPLAKQHYHNVVVGDTSIVSDL QSNSDQLKFYSDDEGLVPDSLLFNKMLHEQLLNGFKEGDTIIPLDENGKPVYKVDYKLDGKEPR KVYSVTTKIATAEDVATSSYANGIQKDIDDLYDFDHQVTERLTQHGKTIYRNGERILANEESVQ YLNKEVQNNIEHIYELAQQQDQHSSDIKTLESNVEKGLLELSGHLIDQKADLTKDIKTLENNVE EGLLDLSGRLIDQKADIAQNQANIQDLAAYNELQDQYAQKQTEAIDALNKASSENTQNIEDLAA YNELQDAYAKQQTEAIDALNKASSENTQNIAKNQADIANNINNIYELAQQQDQHSSDIKTLAKA SAANTDRIAKNKADADASFETLTKNQNTLIEKDKEHDKLITANKTAIDNKASADTKFAATADA ITKNGNAITKNAKSITDLGTKVDGFDSRVTALDTKVNALDTKVNALDTKVNAFDGRITALDSKV ENGMAAQAALSGLFQPYSVGKFNATAALGGYGSKSAVAIGAGYRVNPNLAFKAGAAINTSGNKK GSYNIGVNYEF (587 amino acids) |

TABLE 1-continued

UspA2 amino acid sequences from 38 strains of *Moraxalla catarrhalis* (SEQ ID NO: 1 - SEQ ID NO: 38).

| Strain | UspA2 sequences |
|---|---|
| Norwegian 25 (SEQ ID NO: 14) | MKTMKLLPLKIAVTSAMIVGLGAASTANAQQQQQPRTETFFPNIFFNENHDALDDVYHNMILGD TAITQDNQYKFYADAISEVPDSLLFNKILHDQQLNGFKEGDTIIPLDENGKPVYKLDEKVENGV KKSVYSVTTKTATRADVEQSAYSRGIQGDIDDLYEANKENVNRLIEHGDKIFANEESVQYLNRE VQNNIENIHELAQQQDQHSSDIKTLKKKNVEKDLLDLSGRLIAQKEDIAQNQTDIQDLATYNELQ DQYAQKQTEAIDALNKASSENTQNIAKNSNHIKTLENNIEEGLLELSGHLIDQKADLTKDIKTL ENNIEEGLLELSGHLIDQKADLTKDIKALESNVEEGLLDLSGRLLDQKADIAQNQANIQDLAAY NELQDQYAQKQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLIKNQNTLI EKDKEHDKLITANKTAIDQNKASADTKFAATADAITKNGNAITKNAKSITDLGTKVDGFDGRVT ALDTKVNALDTKVNAFDGRITALDSKVENGMAAQAALSGLFQPYSVGKFNATAALGGYGSKSAV AIGAGYRVNPNLAFKAGAAINTSGNKKGSYNIGVNYEF (678 amino acids) |
| Norwegian 27 (SEQ ID NO: 15) | MKTMKLLPLKIAVTSALIVGLGAASTANAQVRDKSLEDIEALLGKIDISKLEKEKKQQTELQKY LLLSQYANVLTMEELNKNVEKNTNSIEALGYEIGWLENDIADLEEGVEELTKNQNTLIEKDEEH DRLIAQNQADIKTLENNVVEELFNLSDRLIDQEADIAKNNASIEELYDFDNEVAERIGEIHAYT EEVNKTLEKLITNSVKNTDNIDKNKADIQALENNVEEGLLELSGHLIDQKADLTKDIKALESNV EEGLLDLSGRLLDQKADIAKNQADIAQNQTDIQDLAAYNELQDQYAQKQTEAIDALNKASSENT QNIEDLAAYNELQDAYAKQQTEAIDALNKASSENTQNIEDLAAYNELQDAYAKQQTEAIDALNK ASSENTQNIAKNQADIANNINNIYELAQQQDQHSSDIKTLAKVSAANTDRIAKNKADADASFET LTKNQNTLIEKDKEHDKLITANKTAIDANKASADTKFAATADAITKNGNAITKNAKSITDLGTK VDGFDSRVTALDTKVNAFDGRITALDSKVENGMAAQAALSGLFQPYSVGKFNATAALGGYGSKS AVAIGAGYRVNPNLAFKAGAAINTSGNKKGSYNIGVNYEF (616 amino acids) |
| Norwegian 36 (SEQ ID NO: 16) | MKTMKLLPLKIAVTSALIVGLGAASTANAQATETFLPNLFDNDYTETTDPLYHGMILGNTAITQ DTQYKFYAENGNEVPDSLFFNKILHDQQLNGFKEGDTIIPLDENGKPVYKLDEITENGVKRKVY SVTTKTATREDVEQSAYSRGIQGDIDDLYEANKENVNRLIEHGDKIFANEESVQYLNKEVQNNI ENIHELAQQQDQHSSDIKTLKKNVEEGLLELSGHLIDQKADLTKDIKALESNVEEGLLDLSGHL IDQKADLTKDIKALESNVEEGLLDLSGRLLDQKADIAKNQADIAQNQTDIQDLAAYNELQDQYA QKQTEAIDALNKASSENTQNIEDLAAYNELQDAYAKQQTEAIDALNKASSENTQNIEDLAAYNE LQDQYAQKQTEAIDALNKASSENTQNIEDLAAYNELQDAYAKQQTEAIDALNKASSENTQNIAK NQADIANNINNIYELAQQQDQHSSDIKTLAKASAANTDRIAKNKADADASFETLTKNQNTLIEK DKEHDKLITANKTAIDANKASADTKFAATADAITKNGNAITKNAKSITDLGTKVDGFDGRVTAL DTKVNALDTKVNAFDGRITALDSKVENGMAAQAALSGLFQPYSVGKFNATAALGGYGSKSAVAI GAGYRVNPNLAFKAGAAINTSGNKKGSYNIGVNYEF (676 amino acids) |
| BC5SV (SEQ ID NO: 17) | MKTMKLLPLKIAVTSALIVGLGAASTANAQNGTSTKLKNLKEYAQYLDNYAQYLDDDIDDL DKEVGELSQNIAKNQANIKDLNKKLSRDIDSLREDVYDNQYEIVNNQADIEKNQDDIKELE NNVGKELLNLSGRLLDQKADIDNNINNIYELAQQQDQHSSDIKTLKKNVEEGLLELSGHLI DQKSDIAQNQTDIQDLATYNELQDQYAQKQTEAIDALNKASSENTQNIEDLAAYNELQDAY AKQQTEAIDALNKASSENTQNIQDLAAYNELQDAYAKQQTEAIDALNKASSENTQNIEDLA AYNELQDAYAKQQTEAIDALNKASSENTQNIEDLAAYNELQDAYAKQQTEAIDALNKASSE NTQNIEDLAAYNELQDAYAKQQTEAIDALNKASSENTQNIAKNQADIANNINNIYELAQQQ DQHSSDIKTLAKASAANTDRIAKNKADADASFETLTKNQNTLIEKDKEHDKLITANKTAID ANKASADTKFAATADAITKNGNAITKNAKSITDLGTKVDAFDGRVTALDTKVNAFDGRITA LDSKVENGMAAQAALSGLFQPYSVGKFNATAALGGYGSKSAVAIGAGYRVNPNLAFKAGAA INTSGNKKGSYNIGVNYEF (629 amino acids) |
| Norwegian 14 (SEQ ID NO: 18) | MKTMKLLPLKIAVTSAMIVGLGMASTANAQQQRSPKTETFLPNIFFNEYADDLDTLYHNMI LGDTAITHDDQYKFYADDATEVPDSLFFNKILHDQLLYGFKEGDKIIPLDENGKPVYKLDK RLDNGVQKTVYSVTTKTATADDVNSAYSRGIQGDIDDLYEANKENVNRLIEHGDKIFANEE SVQYLNKEVQNNIENIHELAQQQDQHSSDIKTLKKNVEEGLLELSGHLIDQKTDIAQNQTD IQDLATYNELQDQYAQKQTEAIDALNKASSENTQNIAKNSNRIKALENNIEEGLLELSGHL IDQKADLTKDIKALESNVEEGLLDLSGRLIDQKADIAQNQANIQDLAAYNELQDAYAKQQT EAIDALNKASSENTQNIEDLAAYNELQDAYAKQQTEAIDALNKASSENTQNIEDLAAYNEL QDAYAKQQTEAIDALNKASSENTQNIAKNQADIANNINNIYELAQQQDQHSSDIKTLAKAS AANTDRIAKNKADADASFETLTKNQNTLIEKDKEHDKLITANKTAIDANKASADTKFAATA DAITKNGNAITKNAKSITDLGTKVDGFDGRVTALDTKVNALDTKVNAFDGRITALDSKVEN GMAAQAALSGLFQPYSVGKFNATAALGGYGSKSAVAIGAGYRVNPNLAFKAGAAINTSGNK KGSYNIGVNYEF (683 amino acids) |
| Norwegian 3 (SEQ ID NO: 19) | MKTMKLLPLKIAVTSAMIVGLGAASTANAQAQSNRSLDQVQALLRGIDETKIKKEIQQSQQ PELNKYLTFNQLANALNIEELNNNVQKNTQRLDSAATLYGDLSKTVPKSIKENKESIKENK ESIKENKESIKENKESIKENKESITTLTRKSFQNQVDIVRNNASIEDLYAYGQE VAKSIGEIHAYTEEVNKTLENLITNSVENTNNITKNKADIQALENNVVEELFNLSGRLIDQ KADIDNNINNIYELAQQQDQHSSDIKTLKKNVEEGLLELSGHLIDQKADLTKDIKTLESNV EEGLLDLSGRLLDQKADIAQNQANIQDLAAYNELQDAYAKQQTEAIDALNKASSENTQNIE DLAAYNELQDAYAKQQTEAIDALNKASSENTQNIEDLAAYNELQDAYAKQQTEAIDALNKA SSENTQNIEDLAAYNELQDAYAKQQTEAIDALNKASSENTQNIAKNQADIANNINNIYELA QQQDQHSSDIKTLAKASAANTDRIAKNKADADASFETLTKNQNTLIEKDKEHDKLITANKT VIDANKASADTKFAATADAITKNGNAITKNAKSITDLGTKVDGFDGRVTALDTKVNALDTK VNAFDGRITALDSKVENGMAAQAALSGLFQPYSVGKFNATAALGGYGSKSAVAIGAGYRVN PNLAFKAGAAINTSGNKKGSYNIGVNYEF (700 amino acids) |

TABLE 1-continued

UspA2 amino acid sequences from 38 strains of *Moraxalla catarrhalis* (SEQ ID NO: 1 - SEQ ID NO: 38).

| Strain | UspA2 sequences |
|---|---|
| Finnish 414 (SEQ ID NO: 20) | MKTMKLLPLKIAVTSALIVGLGAASTANAQATETFLPNLFDNDYIETTDPLYHGMILGNTA ITQDTQYKFYAENGNEVPDSLFFNKILHDQQLNGFKEGDTIIPLDENGKPVYKLDEITENG VKRKVYSVTTKTATREDVEQSAYSRGIQGDIDDLYEANKENVNRLIEHGDKIFANEESVQY LNKEVQNNIENIHELAQQQDQHSSDIKTLKKNVEEGLLELSGHLIDQKADLTKDIKTLENN VEEGLLELSGHLIDQKADLTKDIKALESNVEEGLLDLSGRLLDQKADIAKNQADIAQNQTD IQDLAAYNELQDQYAQKQTEAIDALNKASSENTQNIEDLAAYNELQDQYAQKQTEAIDALN KASSENTQNIEDLAAYNELQDQYAQKQTEAIDALNKASSENTQNIEDLAAYNELQDQYAQK QTEAIDALNKASSENTQNIAKNQADIANNINNIYELAQQQDQHSSDIKTLAKASAANTDRI AKNKADADASFETLTKNQNTLIEKDKEHDKLITANKTAIDANKASADTKFAATADAITKNG NAITKNAKSITDLGTKVDGFDGRVTALDTKVNALDTKVNAFDGRITALDSKVENGMAAQAA LSGLFQPYSVGKFNATAALGGYGSKSAVAIGAGYRVNPNLAFKAGAAINTSGNKKGSYNIG VNYEF (676 amino acids) |
| Japanese Z7476 (SEQ ID NO: 21) | MKTMKLLPLKIAVTSAMIIGLGAASTANAQLAEQFFPNIFSNHAPVKQHYHNVVVGDTSIV ENLQDSDDTQLKFYSNDEYSVPDSLFFNKMLHEQQLNGFKKGDTIIPLDENGKPVYKVDYK LDGQEPRRVYSVTTKIATQDDVDNSPYSRGIQGDIDDLYEANKENVNRLIEHGDKIFANEE SVQYLNKEVQNNIENIYELAQQQDQHSSDIKTLKKNVEEGLLELSGRLIDQKADIAQNQAN IQDLAAYNELQDQYAQKQTEAIDALNKASSENTQNIEDLAAYNELQDAYAKQQTEAIDALN KASSENTQNIEDLAAYNELQDAYAKQQTEAIDALNKASSENTQNIEDLAAYNELQDAYAKQ QTEAIDALNKASSENTQNIEDLAAYNELQDAYAKQQTEAIDALNKASSENTQNIEDLAAYN ELQDAYAKQQTEAIDALNKASSENTQNIAKNQADIANNINNIYELAQQQDQHSSDIKTLAK VSAANTDRIAKNKADADASFETLTKNQNTLIEKDKEHDKLITANKTAIDANKASADTKFAA TADAITKNGNAITKNAKSITDLGTKVDGFDGRVTALDTKVNAFDGRITALDSKVENGMAAQ AALSGLFQPYSVGKFNATAALGGYGSKSAVAIGAGYRVNPNLAFKAGAAINTSGNKKGSYN IGVNYEF (678 amino acids) |
| Belgian Z7530 (SEQ ID NO: 22) | MKTMKLLPLKIAVTSAMIIGLGAASTANAQSRDRSLEDIQDSISKLVQDDINTLKQDQQKM NKYLLLNQLANTLITDELNNNVIKNTNSIEALGDEIGWLENDIADLEEGVEELTKNQNTLI EKDEEHDRLIAQNQADIQTLENNVVEELFNLSGRLIDQEADIAKNNASIEELYDFDNEVAE RIGEIHAYTEEVNKTLENLITNSVKNTDNIDKNKADIDNNINHIYELAQQQDQHSSDIKTL KKNVEEGLLELSGHLIDQKADLTKDIKALESNVEEGLLDLSGRLLDQKADLTKDIKALESN VEEGLLDLSGRLLDQKADIAQNQTDIQDLAAYNELQDQYAQKQTEAIDALNKASSENTQNI EDLAAYNELQDAYAKQQTEAIDALNKASSENTQNIAKNQADIANNINNIYELAQQQDQHSS DIKTLAKASAANTNRIATAELGIAENKKDAQIAKAQANANKTAIDENKASADTKFAATADA ITKNGNAITKNAKSITDLGTKVDGFDGRVTALDTKVNAFDGRITALDSKVENGMAAQAALS GLFQPYSVGKFNATAALGGYGSKSAVAIGAGYRVNPNLAFKAGAAINTSGNKKGSYNIGVN YEF (613 amino acids) |
| German Z8063 (SEQ ID NO: 23) | MKTMKLLPLKIAVTSALIVGLGAASTANAQATNKDITLEDVLKSIEEIDPYELRDYIEYPT AIERFLLLSQYGNTLTLEEFDNDIELLDQDVEDLEESVTELAKNQNSLIEQGEAIKEDLQG LADFVERQEDKILQNETSIKKNTQRNLVNGFEIEKNKDAIAKNNESIEDLYDFDNEVAKSI GEIHAHNEAQNETLKDLITNSVKNTDNITKNKADIQALESNVEKGLLELSGHLIDQKADID NNINNIHELAQQQDQHSSDIKTLKKNVEEGLLELSGHLIDQKSDIAQNQANIQDLATYNEL QDQYAQKQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLTKNQN TLIEKDKEHDKLITANKTAIDANKASADTKFAATADAITKNGNAITKNAKSITDLGTKVDG FDSRVTALDTKVNAFDGRITALDSKVENGMAAQAALSGLFQPYSVGKFNATAALGGYGSKS AVAIGAGYRVNPNLAFKAGAAINTSGNKKGSYNIGVNYEF (589 amino acids) |
| American O12E (SEQ ID NO: 24) | MKTMKLLPLKIAVTSAMMVGLGMASTANAQQQKSPKTEIFLPNLFDNDNTELTDPLYHNMI LGNTALLTQENQYKFYADDGNGVPDSLLFNKILHDQLLHGFKEGDTIIPLDENGKPVYKLD SIVEQGKTKTVYSVTTKTATADDVNSAYSRGIQGDIDDLYEANKENVNRLIEHGDKIFANE ESVQYLNREVQNNIENIHELAQQQDQHSSDIKTLKKNVEKDLLDLSGRLIAQKEDIAQNQT DIQDLATYNELQDQYAQKQTEAIDALNKASSENTQNIAKNSNHIKTLENNIEEGLLELSGH LIDQKADLTKDIKALESNVEEGLLDLSGRLIDQKADIAQNQANIQDLAAYNELQDAYAKQQ TEAIDALNKASSENTQNIEDLAAYNELQDAYAKQQTEAIDALNKASSENTQNIEDLAAYNE LQDAYAKQQTEAIDALNKASSENTQNIAKNQADIANNINNIYELAQQQDQHSSDIKTLAKA SAANTDRIAKNKADADASFETLTKNQNTLIEKDKEHDKLITANKTAIDANKASADTKFAAT ADAITKNGNAITKNAKSITDLGTKVDGFDGRVTALDTKVNALDTKVNAFDGRITALDSKVE NGMAAQAALSGLFQPYSVGKFNATAALGGYGSKSAVAIGAGYRVNPNLAFKAGAAINTSGN KKGSYNIGVNYEF (684 amino acids) |
| Greek MC317 (SEQ ID NO: 25) | MKTMKLLPLKIAVTSALIVGLGAASTANAQQQKTKTEVFLPNLFYNDYIEETDLLYHNMI LGDTAALVDRQNYSNSQLKFYSNDEESVPDSLLFSKMLNNQQLNGFKAGDIIIPVDANGQV IYQKDTRVEGGKTRTVLSVTTKIATQQDVDSAYSRGIQGKVNDLDDEMNFLNHDITSLYDV TANQQDDIKGLKKGVKDLKKGVKGLNKELKELDKEVGVLSRDIGSLNDDVAQNNESIEDLY DFSQEVADSIGEIHAHNKAQNETLQDLITNSVENTNNITKNKADIQALENNVVEELFNLSG RLIDQKADLTKDIKTLESNVEEGLLELSGHLIDQKADIAKNQADIAQNQANIQDLAAYNEL QDAYAKQQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLTKNQN TLIEKDKEHDKLITANKTAIDENKASADTKFAATADAITKNGNAITKNAKSITDLGTKVDG FDGRVTALDTKVNAFDGRITALDSKVENGMAAQAALSGLFQPYSVGKFNATAALGGYGSKS AVAIGAGYRVNPNLAFKAGAAINTSGNKKGSYNIGVNYEF (650 amino acids) |

TABLE 1-continued

UspA2 amino acid sequences from 38 strains of *Moraxalla catarrhalis* (SEQ ID NO: 1 - SEQ ID NO: 38).

| Strain | UspA2 sequences |
|---|---|
| American V1122 (SEQ ID NO: 26) | MKTMKLLPLKIAVTSALIVGLGAVSTTNAQAQSRSLDQIQTKLADLAGKIAAGKNGGGQNN QNNQNDINKYLFLSQYANILTMEELNNNVVKNSSSIETLETDFGWLENDVADLEDGVEELT KNQNTLIEKDEEHDRLIAQNQADIQTLENNVVEELFNLSDRLIDQKADIAKNQADIAQNNE SIEELYDFDNEVAEKIGEIHAYTEEVNKTLQDLITNSVKNTDNIDKNKADIDNNINHIYEL AQQQDQHSSDIKTLKNNVEEGLLELSGHLIDQKADLTKDIKTLENNVEEGLLDLSGRLIDQ KADIAKNQADIAQNQTDIQDLAAYNELQDYAQKQTEAIDALNKASSENTQNIEDLAAYNE LQDAYAKQQTEAIDALNKASSENTQNIAKNQADIANNINNIYELAQQQDQHSSDIKTLAKA SAANTDRIAKNKADADASFETLTKNQNTLIEKDKEHDKLITANKTAIDENKASADTKFAAT ADAITKNGNAITKNAKSITDLGTKVDGFDGRVTALDTKVNAFDGRITALDSKVENGMAAQA ALSGLFQPYSVGKFNATAALGGYGSKSAVAIGAGYRVNPNLAFKAGAAINTSGNKKGSYNI GVNYEF (616 amino acids) |
| American P44 (SEQ ID NO: 27) | MKTMKLLPLKIAVTSALIVGLGTASTANAQVASPANQKIQQKIKKVRKELRQDIKSLRNDI DSNTADIGSLNDDVADNQDDILDNQADIAKNQDDIEKNQADIKELDKEVGVLSREIGSLND DIADNYTDIIDNYTDIIDNQANIAKNQDDIEKNQADIKELDKEVGVLSREIGSLNDDVADN QDDIAKNQADIQTLENNVEEGLLELSGHLLDQKADIDNNINNIYELAQQQDQHSSDIKTLK KNVEEGLLELSGHLIDQKTDIAQNQANIQDLATYNELQDYAQEQTEAIDALNKASSENTQ NIAKNSNRIKALESNVEEGLLELSGHLIDQKADLTKDIKALESNVEEGLLELSGHLIDQKA DIAQNQANIQDLAAYNELQDYAQKQTEAIDALNKASSENTQNIEDLAAYNELQDAYAKQQ TEAIDALNKASSENTQNIAKNQADIANNINNIYELAQQQDQHSSDIKTLAKASAANTDRIA KNKADADASFETLTKNQNTLIEKDKEHDKLITANKTAIDANKVSADTKFAATADAITKNGN AITKNAKSITDLGTKVDAFDSRVTALDTKVNAFDGRITALDSKVENGMAAQAALSGLFQPY SVGKFNATAALGGYGSKSAVAIGAGYRVNPNLAFKAGAAINTSGNKKGSYNIGVNYEF (668 amino acids) |
| American V1171 (SEQ ID NO: 28) | MKTMKLLPLKIAVTSAMIVGLGATSTVNAQVVEQFFPNIFFNENHDELDDAYHNMILGDTA IVSNSQDNSTQLKFYSNDEDSVPDSLLFSKLLHEQQLNGFKAGDTIIPLDKDGKPVYTKDT RTKDGKVETVYSVTTKIATQDDVEQSAYSRGIQGDIDDLYDINREVNEYLKATHDYNERQT EAIDALNKASSANTDRIDTAEERIDKNEYDIKALESNVEEGLLELSGHLIDQKADLTKDIK ALESNVEEGLLELSGHLIDQKADLTKDIKALESNVEEGLLDLSGRLIDQKADIAQNQANIQ DLAAYNELQDAYAKQQTEAIDALNKASSENTQNIEDLAAYNELQDAYAKQQTEAIDALNKA SSENTQNIEDLAAYNELQDAYAKQQTEAIDALNKASSENTQNIEDLAAYNELQDAYAKQQT EAIDALNKASSENTQNIAKNQADIANNINNIYELAQQQDQHSSDIKTLAKASAANTDRIAK NKADADASFETLTKNQNTLIEKDKEHDKLITANKTAIDANKASADTKFAATADAITKNGNA ITKNAKSITDLGTKVDGFDGRVTALDTKVNALDTKVNAFDGRITALDSKVENGMAAQAALS GLFQPYSVGKFNATAALGGYGSKSAVAIGAGYRVNPNLAFKAGAAINTSGNKKGSYNIGVN YEF (674 amino acids) |
| American TTA24 (SEQ ID NO: 29) | MKTMKLLPLKIAVTSAMIIGLGAASTANAQSRDRSLEDIQDSISKLVQDDIDTLKQDQQKM NKYLLLNQLANTLITDELNNNVIKNTNSIEALGDEIGWLENDIADLEEGVEELTKNQNTLI EKDEEHDRLIAQNQADIQTLENNVVEELFNLSGRLIDQEADIAKNNASIEELYDFDNEVAE RIGEIHAYTEEVNKTLENLITNSVKNTDNIDKNKADIDNNINHIYELAQQQDQHSSDIKTL KNNVEEGLLELSGHLIDQKADLTKDIKALESNVEEGLLDLSGRLLDQKADLTKDIKALESN VEEGLLDLSGRLLDQKADIAQNQTDIQDLAAYNELQDYAQKQTEAIDALNKASSENTQNI EDLAAYNELQDAYAKQQTEAIDALNKASSENTQNIAKNQADIANNINNIYELAQQQDQHSS DIKTLAKASAANTNRIATAELGIAENKKDAQIAKAQANANKTAIDENKASADTKFAATADA ITKNGNAITKNAKSITDLGTKVDGFDGRVTALDTKVNAFDGRITALDSKVENGMAAQAALS GLFQPYSVGKFNATAALGGYGSKSAVAIGAGYRVNPNLAFKAGAAINTSGNKKGSYNIGVN YEF (613 amino acids) |
| American O5E (SEQ ID NO: 30) | MKTMKLLPLKIAVTSAMIVGLGATSTVNAQVVEQFFPNIFFNENHDELDDAYHNMILGDTA IVSNSQDNSTQLKFYSNDEDSVPDSLLFSKLLHEQQLNGFKAGDTIIPLDKDGKPVYTKDT RTKDGKVETVYSVTTKIATQDDVEQSAYSRGIQGDIDDLYDINREVNEYLKATHDYNERQT EAIDALNKASSANTDRIDTAEERIDKNEYDIKALESNVEEGLLELSGHLIDQKADLTKDIK ALESNVEEGLLELSGHLIDQKADLTKDIKALESNVEEGLLDLSGRLLDQKADIAKNQADIA QNQTDIQDLAAYNELQDAYAKQQTEAIDALNKASSENTQNIAKNQADIANNINNIYELAQQ QDQHSSDIKTLAKASAANTDRIAKNKADADASFETLTKNQNTLIEKDKEHDKLITANKTAI DANKASADTKFAATADAITKNGNAITKNAKSITDLGTKVDGFDGRVTALDTKVNALDTKVN AFDGRITALDSKVENGMAAQAALSGLFQPYSVGKFNATAALGGYGSKSAVAIGAGYRVNPN LAFKAGAAINTSGNKKGSYNIGVNYEF (576 amino acids) |
| American SP12-6 (SEQ ID NO: 31) | MKTMKLLPLKIAVTSAMMVGLGMASTANAQQQKSPKTEIFLPNLFDNDNTELTDPLYHNMI LGNTALLTQENQYKFYADDGNGVPDSLLFNKILHDQLLHGFKEGDTIIPLDENGKPVYKLD SIVEQGKTKTVYSVTTKTATADDVNSAYSRGIQGDIDDLYEANKENVNRLIEHGDKIFANE ESVQYLNREVQNNIENIHELAQQQDQHSSDIKTLKKNVEKDLLDLSGRLIAQKEDIAQNQT DIQDLATYNELQDYAQKQTEAIDALNKASSENTQNIAKNSNHIKTLENNIEEGLLELSGH LIDQKADLTKDIKALESNVEEGLLDLSGRLIDQKADIAQNQANIQDLAAYNELQDAYAKQQ TEAIDALNKASSENTQNIEDLAAYNELQDAYAKQQTEAIDALNKASSENTQNIEDLAAYNE LQDAYAKQQTEAIDALNKASSENTQNIAKNQADIANNINNIYELAQQQDQHSSDIKTLAKA SAANTDRIAKNKADADASFETLTKNQNTLIEKDKEHDKLITANKTAIDANKASADTKFAAT ADAITKNGNAITKNAKSITDLGTKVDGFDGRVTALDTKVNALDTKVNAFDGRITALDSKVE NGMAAQAALSGLFQPYSVGKFNATAALGGYGSKSAVAIGAGYRVNPNLAFKAGAAINTSGN KKGSYNIGVNYEF (684 amino acids) |

TABLE 1-continued

UspA2 amino acid sequences from 38 strains of *Moraxalla catarrhalis* (SEQ ID NO: 1 - SEQ ID NO: 38).

| Strain | UspA2 sequences |
|---|---|
| American SP12-5 (SEQ ID NO: 32) | MKTMKLLPLKIAVTSAMIIGLGAASTANAQATETFLPNLFDNDYTETTDPLYHGMILGNTA ITQDTQYKFYAENGNEVPDSLFFNKILHDQQLNGFKEGDTIIPLDENGKPVYKLDEITENG VKRKVYSVTTKTATREDVEQSAYSRGIQGDIDDLYEANKENVNRLIEHGDKIFANEESVQY LNKEVQNNIENIHELAQQQDQHSSDIKTLKKNVEEGLLELSGRLIAQKEDIAQNQTDIQDL ATYNELQDQYAQKQTEAIDALNKASSENTQNIAKNSNHIKTLENNIEEGLLELSGHLIDQK ADLTKDIKALESNVEEGLLDLSGRLLDQKADIAKNQADIAQNQTDIQDLAAYNELQDQYAQ KQTEAIDALNKASSENTQNIEDLAAYNELQDAYAKQQTEAIDALNKASSENTQNIEDLAAY NELQDAYAKQQTEAIDALNKASSENTQNIAKNQADIANNINNIYELAQQQDQHSSDIKTLA KASAANTDRIAKNKADADASFETLTKNQNTLIEKDKEHDKLITANKTAIDANKASADTKFA ATADAITKNGNAITKNAKSITDLGTKVDGFDGRVTALDTKVNALDTKVNAFDGRITALDSK VENGMAAQAALSGLFQPYSVGKFNATAALGGYGSKSAVAIGAGYRVNPNLAFKAGAAINTS GNKKGSYNIGVNYEF (686 amino acids) |
| Swedish BC5 (SEQ ID NO: 33) | MKTMKLLPLKIAVTSAMIIGLGAASTANAQAKNDITLEDLPYLIKKIDQNELEADIGDITALEK YLALSQYGNILALEELNKALEELDEDVGWNQNDIANLEDDVETLTKNQNALAEQGEAIKEDLQG LADFVEGQEGKILQNETSIKKNTQRNLVNGFEIEKNKDAIAKNNESIEDLYDFGHEVAESIGEI HAHNEAQNETLKGLITNSIENTNNITKNKADIQALENNVVEELFNLSGRLIDQKADIDNNINNI YELAQQQDQHSSDIKTLKKNVEEGLLELSGHLIDQKTDIAQNQANIQDLATYNELQDQYAQKQT EAIDALNKASSENTQNIEDLAAYNELQDAYAKQQTEAIDALNKASSENTQNIEDLAAYNELQDA YAKQQTEAIDALNKASSENTQNIAKNQADIANNINNIYELAQQQDQHSSDIKTLAKASAANTDR IAKNKADADASFETLTKNQNTLIEKDKEHDKLITANKTAIDANKASADTKFAATADAITKNGNA ITKNAKSITDLGTKVDGFDSRVTALDTKVNAFDGRITALDSKVENGMAAQAALSGLFQPYSVGK FNATAALGGYGSKSAVAIGAGYRVNPNLAFKAGAAINTSGNKKGSYNIGVNYEF (630 amino acids) |
| American 7169 (SEQ ID NO: 34) | MKTMKLLPLKIAVTSALIVGLGAASTANAQAQDRSLEQIQDKLANLVEKIEQAKSQNGQSQ KDINQYLLLSQYANVLTMEELNNNVVKNSSSIETLDNDIAWLNDDLIDLDKEVGVLSRDIG SLHDDVAQNQADIKTLKNNVVEELFNLSDRLIDQEADIAQNNNESIEDLYDFGREVAESIGE IHAHNEAQNETLKDLITNSVKNTDNITKNKADIQALENDVGKELLNLSGRLIDQKADIDNN INHIYELAQQQDQHSSDIKTLKNNVEEGLLELSGHLIDQKADLTKDIKALESNVEEGLLDL SGRLLDQKADIAQNQANIQDLAAYNELQDAYAKQQTEAIDALNKASSENTQNIEDLAAYNE LQDAYAKQQTEAIDALNKASSENTQNIAKNQADIANNINNIYELAQQQDQHSSDIKTLAKA SAANTDRIAKNKADADASFETLTKNQNTLIEKDKEHDKLITANKTAIDANKASADTKFAAT ADAITKNGNAITKNAKSITDLGTKVDGFDSRVTALDTKVNAFDGRITALDSKVENGMAAQA ALSGLFQPYSVGKFNATAALGGYGSKSAVAIGAGYRVNPNLAFKAGAAINTSGNKKGSYNI GVNYEF (616 amino acids) |
| Finnish FIN2344 (SEQ ID NO: 35) | MKTMKLLPLKIAVTSAMIIGLGATSTVNAQVVEQFFPNIFFNENHDELDDAYHNMILGDTA IVSNSQDNSTQLKFYSNDEDSVPDSLLFSKLLHEQQLNGFKAGDTIIPLDKDGKPVYTKDT RTKDGKVETVYSVTTKIATQDDVEQSAYSRGIQGDIDDLYDINREVNEYLKATHDYNERQT EAIDALNKASSANTDRIDTAEERIDKNEYDIKALESNVGKDLLDLSGRLIAQKEDIDNNIN HIYELAQQQDQHSSDIKTLKNNVEEGLLELSGHLIDQKADLTKDIKTLESNVEEGLLDLSG RLIDQKADIAQNQANIQDLAAYNELQDQYAQKQTEAIDALNKASSENTQNIEDLAAYNELQ DAYAKQQTEAIDALNKASSENTQNIAKNQADIANNINNIYELAQQQDQHSSDIKTLAKVSA ANTDRIAKNKADADASFETLTKNQNTLIEKDKEHDKLITANKTAIDANKASADTKFAATAD AITKNGNAITKNAKSITDLGTKVDGFDGRVTALDTKVNAFDGRITALDSKVENGMAAQAAL SGLFQPYSVGKFNATAALGGYGSKSAVAIGAGYRVNPNLAFKAGAAINTSGNKKGSYNIGV NYEF (614 amino acids) |
| American V1118 (SEQ ID NO: 36) | MKTMKLPPLKIAVTSAMIIGLGAASTANAQTTETFLPNLFDNDYTETTDPLYHGMILGDTA ITQDTQYKFYAENGNEVPDSLFFNKILHDQLLNGFKAGDTIIPLDENGKPVYKLDERTENG VKRKVYSVTTKTATQADVEQSAYSRGIQGDIDDLYEANKENVNRLIEHGDKIFANEESVQY LNREVQNNIENIHELAQQQDQHSSDIKTLKKNVEKDLLDLSGRLIAQKEDIAQNQTDIQDL ATYNELQDQYAQKQTEAIDALNKASSENTQNIAKNSNHIKTLENNIEECLLELSGHLIDQK ADLTKDIKALESNVEEGLLDLSGRLIDQKADIAQNQANIQDLAAYNELQDAYAKQQTEAID ALNKASSENTQNIEDLAAYNELQDAYAKQQTEAIDALNKASSENTQNIEDLAAYNELQDAY AKQQTEAIDALNKASSENTQNIAKNQADIANNINNIYELAQQQDQHSSDIKTLAKASAANT DRIAKNKADADASFETLTKNQNTLIEKDKEHDKLITANKTAIDANKASADTKFAATADAIT KNGNAITKNAKSITDLGTKVDGFDGRVTALDTKVNALDTKVNAFDGRITALDSKVENGMAA QAALSGLFQPYSVGKFNATAALGGYGSKSAVAIGAGYRVNPNLAFKAGAAINTSGNKKGSY NIGVNYEF (679 amino acids) |
| American V1145 (SEQ ID NO: 37) | MKTMKLLPLKIAVTSALIVGLGAASTANAQETLEEVLESIKQINEQDLQDDIGYNSALDRY LVLSQYGNLLIAKELNENVEKNSNSIAKNSNSIADLEADVGYLAENQNTLIEQNETINQEL EGITHELESFIAYAHAQDQKNLVNEFEIEKNKDAIAKNNESIEDLYDFGHEVAESIGEIHA YTEEVNKTLENLITNSVKNTDNITKNKADIQALESNVEKELLNLSGRLIDQKADIDNNINH IYELAQQQDQHSSDIKTLKKNVEEGLLELSGHLIDQKSDIAQNQTDIQDLATYNELQDQYA QKQTEAIDALNKASSENTQNIEDLAAYNELQDAYAKQQTEAIDALNKASSENTQNIEDLAA YNELQDAYAKQQTEAIDALNKASSENTQNIEDLAAYNELQDAYAKQQTEAIDALNKASSEN TQNIEDLAAYNELQDAYAKQQTEAIDALNKASSENTQNIEDLAAYNELQDAYAKQQTEAID ALNKASSENTQNIAKNQADIANNINNIYELAQQQDQHSSDIKTLAKASAANTDRIAKNKAD ADASFETLTKNQNTLIEKDKEHDKLITANKTAIDANKASADTKFAATADAITKNGNAITKN AKSITDLGTKVDGFDSRVTALDTKVNAFDGRITALDSKVENGMAAQAALSGLFQPYSVGKF NATAALGGYGSKSAVAIGAGYRVNPNLAFKAGAAINTSGNKKGSYNIGVNYEF (724 amino acids) |

TABLE 1-continued

UspA2 amino acid sequences from 38 strains of *Moraxalla catarrhalis* (SEQ ID NO: 1 - SEQ ID NO: 38).

| Strain | UspA2 sequences |
|---|---|
| American V1156 (SEQ ID NO: 38) | MKTMKLLPLKIAVTSALIVGLGAASTANAQAQARDRSLEDIQALIGNIDVDKIRSQKQKNP<br>EIFQYLLLNQLSNTLITDELNNNVIKNTNSIETLDNDIAWLNDDLIDLDKEVGVLSRDIGS<br>LHDDVAQNQADIKTLENNVVEELFNLSDRLIDQEAEIAQNNESIEDLYDFGREVAESIGEI<br>HAHNEAQNETLKDLITNSVKNTDNIDKNKADIQALENNVEEGLLELSGHLIDQKADLTKDI<br>KALESNVEEGLLDLSGRLLDQKADIAKNQADIAQNQTDIQDLAAYNELQDQYAQKQTEAID<br>ALNKASSENTQNIEDLAAYNELQDAYAKQQTEAIDALNKASSENTQNIEDLAAYNELQDAY<br>AKQQTEAIDALNKASSENTQNIAKNQADIANNINNIYELAQQQDQHSSDIKTLAKVSAANT<br>DRIAKNKADADASFETLTKNQNTLIEKDKEHDKLITANKTAIDANKASADTKFAATADAIT<br>KNGNAITKNAKSITDLGTKVDGFDSRVTALDTKVNAFDGRITALDSKVENGMAAQAALSGL<br>FQPYSVGKFNATAALGGYGSKSAVAIGAGYRVNPNLAFKAGAAINTSGNKKGSYNIGVNYE<br>F (611 amino acids) |

UspA2 may be UspA2 from *M. catarrhalis* strain ATCC (a US registered trademark) 25238™, American 2933. American 2912, American 2908, Finnish 307, Finnish 353, Finnish 358, Finnish 216, Dutch H2, Dutch F10, Norwegian 1, Norwegian 13, Norwegian 20, Norwegian 25, Norwegian 27, Norwegian 36, BC5SV, Norwegian 14, Norwegian 3, Finish 414, Japanese Z7476, Belgium Z7530, German Z8063, American O12E, Greek MC317, American V1122, American P44, American V1171, American TTA24, American 035E, American SP12-6, American SP12-5, Swedish BC5, American 7169, Finnish FIN2344, American V1118, American V1145 or American V1156. UspA2 may be UspA2 as set forth in any of SEQ ID NO: 1-SEQ ID NO: 38. UspA2 may be UspA2 from another source which corresponds to the sequence of UspA2 in any one of SEQ ID NO: 1-SEQ ID NO: 38. Corresponding UspA2 sequences may be determined by one skilled in the art using various algorithms. For example, the Gap program or the Needle program may be used to determine UspA2 sequences corresponding to any one of SEQ ID NO: 1-SEQ ID NO: 38.

UspA2 may be a sequence with at least 95% identity, over the entire length, to any of SEQ ID NO: 1-SEQ ID NO: 38.

Immunogenic fragments of UspA2 comprise immunogenic fragments of at least 450 contiguous amino acids of SEQ ID NO: 1, 490 contiguous amino acids of SEQ ID NO: 1 (for example, the UspA2 fragment of MC-004 or MC-005), 511 contiguous amino acids of SEQ ID NO: 1 (for example, the UspA2 fragment of construct MC-001, MC-002, MC-003 or MC-004), 534 contiguous amino acids of SEQ ID NO: 1 (for example, the UspA2 fragment of MC-009 or MC-011) or 535 contiguous amino acids of SEQ ID NO: 1 (for example, the UspA2 fragment of MC-007, MC-008 or MC-010). The immunogenic fragments may elicit antibodies which can bind SEQ ID NO: 1.

Immunogenic fragments of UspA2 may comprise immunogenic fragments of at least 450, 490, 511, 534 or 535 contiguous amino acids of any of SEQ ID NO: 1-SEQ ID NO: 38. Immunogenic fragments of UspA2 may comprise immunogenic fragments of UspA2 from any of SEQ ID NO: 2-SEQ ID NO: 38 which correspond to the UspA2 fragment of SEQ ID NO: 1 in any of the UspA2 constructs MC-001, MC-002, MC-003, MC-004, MC-005, MC-006, MC-007, MC-008, MC-009, MC-010 or MC-011. The immunogenic fragments may elicit antibodies which can bind the full length sequence from which the fragment is derived.

Alignments between polypeptides pairs may be calculated by various programs. For example, the Needle program from the EMBOSS package (Free software; EMBOSS: The European Molecular Biology Open Software Suite (2000). Trends in Genetics 16(6): 276-277) and the Gap program from the GCG (a US registered trademark) package (Accelrys Inc.) may be used.

The Gap and Needle programs are an implementation of the Needleman-Wunsch algorithm described in: Needleman, S. B. and Wunsch, C. D. (1970) J. Mol. Biol. 48, 443-453. These programs are using frequently the BLOSUM62 scoring matrix (Steven Henikoft and Jorja G. Henikoft (1992), "Amino acid substitution matrices from protein blocks"), Proc. Natl. Acad. Sci. USA 89 (Biochemistry): 10915-10919) with gap open and extension penalties of, respectively, 8 and 2. Sometimes, the PAM250 scoring matrix (Dayhoft et al., (1978), "A model of evolutionary changes in proteins", In "Atlas of Protein sequence and structure" 5(3) M. O. Dayhoft (ed.), 345-352, National Biomedical Research Foundation, Washington) is also used.

Scoring matrices are describing by numbers the tendency of each amino acid to mutate in another, or to be conserved. These numbers are generally computed from statistics of mutations observed in faithful pairwise or multiple alignments, or even in fragments of multiple alignments. Generally, in these tables, if a high positive number is associated with a pair of identical amino acids, it is indicating that this residue has a low tendency for mutation. At the opposite, a high positive number associated with a pair of different amino acids is indicating a high tendency of mutation between these two. And this is called a "conservative substitution".

Looking at a pairwise alignment, aligned identical residues ("identities") between the two sequences can be observed. A percentage of identity can be computed by multiplying by 100 (1) the quotient between the number of identities and the length of the alignment (for example, in the Needle program output), or (2) the quotient between the number of identities and the length of the longest sequence, or (3) the quotient between the number of identities and the length of the shortest sequence, or (4) the quotient between the number of identities and the number of aligned residues (for example, in the Gap program output).

The percentage of identities of Table 8 have been calculated according the definition (3) of the previous paragraph, using the pairwise alignments computed by the Gap software.

As used herein, "adjuvant" means a compound or substance that, when administered to a subject in conjunction with a vaccine, immunotherapeutic, or other antigen- or immunogen-containing composition, increases or enhances the subject's immune response to the administered antigen or immunogen (as compared to the immune response that would be obtained in the absence of adjuvant). This is to be distinguished from "adjuvant therapy", defined by the National Cancer Institute of the United States Institutes of Health in the context of cancer treatment as additional treatment given after the primary treatment, to lower the risk that the cancer will recur.

The invention further provides proteins of formula (I) containing conservative amino acid substitutions. For example, the proteins of formula (I) may contain a conservative substitution of any amino acid from UspA2 of *Moraxella catarrahlis* as described in any of the sequences set forth herein (for example, any UspA2 sequence set forth in SEQ ID NO. 1-SEQ ID NO. 38).

As used herein "signal peptide" refers to a short (less than 60 amino acids, for example, 3 to 60 amino acids) polypeptide present on precursor proteins (typically at the N terminus), and which is typically absent from the mature protein. The signal peptide (sp) is typically rich in hydrophobic amino acids. The signal peptide directs the transport and/or secretion of the translated protein through the membrane. Signal peptides may also be called targeting signals, transit peptides, localization signals, or signal sequences. For example, the signal sequence may be a co-translational or post-translational signal peptide.

A heterologous signal peptide may be cleaved from a protein construct by signal peptide peptidases during or after protein transportation or secretion. For example, the signal peptide peptidase is signal peptide peptidase I. A "heterologous" signal peptide is one which is not associated with the protein as it exists in nature.

As used herein "treatment" means the prevention of occurrence of symptoms of the condition or disease in a subject, the prevention of recurrence of symptoms of the condition or disease in a subject, the delay of recurrence of symptoms of the condition or disease in a subject, the decrease in severity or frequency of symptoms of the condition or disease in a subject, slowing or eliminating the progression of the condition and the partial or total elimination of symptoms of the disease or condition in a subject.

As used herein, "optionally" means that the subsequently described event(s) may or may not occur, and includes both event(s) that occur and events that do not occur.

Otitis media is a major cause of morbidity in 80% of all children less than 3 years of age. (Expert Rev. Vaccines 5:517-534 (2006)). More than 90% of children develop otitis media before age 7 (Current Opinion in Investigational Drugs 4:953-958 (2003)). In 2000, there were 16 million visits made to office-based physicians for otitis media in the United States and approximately 13 million antibacterial prescriptions dispensed. (Pediatrics 113:1451-1465 (2004)). In European countries, the reported acute otitis media rates range between 0.125 to 1.24 per child-year. (Expert Review of Vaccines 8:1479-1500 (2009)). Otitis media is a costly infection and the most common reason children receive antibiotics. (Current Infectious Disease Reports 11:177-182 (2009)). Bacteria are responsible for approximately 70% of cases of acute otitis media, with *Streptococcus pneumoniae*, non-typeable *Haemophilus influenzae* (NTHi), and *Moraxella catarrhalis* predominating as the causative agents (Expert Review of Vaccines 5:517-534 (2006)). A subset of children experience recurrent and chronic otitis media and these otitis prone children have protracted middle-ear effusions that are associated with hearing loss and delays in speech and language development. (Current Infectious Disease Reports 11:177-182 (2009)). Recent antibiotic pressure and vaccination with the pneumococcal conjugate vaccine have resulted in the emergence of 13-lactamase-producing *Haemophilus influenzae* and *Moraxella catarrhalis* as the leading organisms causing acute otitis media in North America, followed by *Streptococcus pneumoniae* (Pediatr Clin N Am 60 (2013) 391-407).

Since otitis media is a multifactorial disease, the feasibility of preventing otitis media using a vaccination strategy has been questioned. (Current Infectious Disease Reports 11:177-182 (2009)).

The chinchilla model is a robust and validated animal model of otitis media and its prevention (Expert Review of Vaccines 8:1063-1082 (2009)). While the chinchilla model may mimic the natural course of human infection, others have suggested that results in the chinchilla model may vary from one laboratory to the next. (Current Opinion in Investigational Drugs 4:953-958 (2003)).

Various other rodents have also been used for the induction of otitis media and are summarized in Vaccine 26:1501-1524 (2008). The murine animal model is often studied in otitis media research.

The presence of bactericidal antibody is associated with protection from otitis media due to non-typeable *H. influenzae*. (Current Opinion in Infectious Disease 16:129-134 (2003)). However, an immune response need not be bactericidal to be effective against NTHi. Antibodies that merely react with NTHi surface adhesins can reduce or eliminate otitis media in the chinchilla. (Current Opinion in Investigational Drugs 4:953-958 (2003)).

Chronic obstructive pulmonary disease is a chronic inflammatory disease of the lungs and a major cause of morbidity and mortality worldwide. Approximately one in 20 deaths in 2005 in the US had COPD as the underlying cause. (Drugs and Aging 26:985-999 (2009)). It is projected that in 2020 COPD will rise to the fifth leading cause of disability adjusted life years, chronic invalidating diseases, and to the third most important cause of mortality (Lancet 349:1498-1504 (1997)).

The course of COPD is characterized by progressive worsening of airflow limitation and a decline in pulmonary function. COPD may be complicated by frequent and recurrent acute exacerbations (AE), which are associated with enormous health care expenditure and high morbidity. (Proceedings of the American Thoracic Society 4:554-564 (2007)). One study suggests that approximately 50% of acute exacerbations of symptoms in COPD are caused by non-typeable *Haemophilus influenzae*, *Moraxella catarrhalis*, *Streptococcus pneumoniae*, and *Pseudomonas aeruginosa*. (Drugs and Aging 26:985-999 (2009)). *Haemophilus influenzae* (*H. influenzae*) is found in 20-30% of exacerbations of COPD; *Streptococcus pneumoniae*, in 10-15% of exacerbations of COPD; and *Moraxella catarrhalis*, in 10-15% of exacerbations of COPD. (New England Journal of Medicine 359:2355-2365 (2008)). *Haemophilus influenzae*, *Streptococcus pneumoniae*, and *Moraxella catarrhalis* have been shown to be the primary pathogens in acute exacerbations of bronchitis in Hong Kong, South Korea, and the Phillipines, while *Klebsiella* spp., *Pseudomonas aeruginosa* and *Acinetobacter* spp. constitute a large proportion of pathogens in other Asian countries/regions including Indonesia, Thailand, Malaysia and Taiwan (Respirology, (2011) 16, 532-539; doi:10.1111/j.1440.1843.2011.01943.x). In Bangladesh, 20% of patients with COPD showed positive sputum culture for *Pseudomonas*, *Klebsiella*, *Streptococcus pneumoniae* and *Haemophilus influenzae*, while 65% of patients with AECOPD (acute exacerbation of COPD) showed positive cultures for *Pseudomonas*, *Klebsiella*, *Acinetobacter*, *Enterobacter*, *Moraxella catarrhalis* and combinations thereof. (Mymensingh Medical Journal 19:576-585 (2010)). However, it has been suggested that the two most important measures to prevent COPD exacerbation are active immunizations and chronic maintenance of pharmacotherapy. (Proceedings of the American Thoracic Society 4:554-564 (2007)).

Community-acquired pneumonia (CAP) has been described as the leading cause of death from infectious disease and the six-ranked cause of death overall in the United States. *Moraxella catarrhalis* is one of the pathogens associated with CAP in North America (Clin Chest Med 26 (2005) 37-55) and is one of the pathogens associated with moderate to severe community acquired pneumonia in Japan (J Infect Chemother. 2014 Nov. 20. pii: S1341-321X(14) 00396-1. doi: 10.1016/j.jiac.2014.11.006. [Epub ahead of print]).

There is a need for effective vaccines against *M. catarrhalis*.

The present invention relates to proteins of formula (I).

$$A\text{-}(R_1)_m\text{—}(B)_n \quad \text{(formula I)}$$

wherein:
A is UspA2 from *Moraxella catarrhalis* or an immunogenic fragment thereof;
$R_1$ is an amino acid;
m is 0 or 2;
B is histidine; and
n is 0, 1, 2, 3, 4, 5 or 6.

In one particular embodiment, $R_1$ and m are defined wherein $(R_1)_m$ is AS (alanine serine). In another embodiment, $R_1$ is non-native amino acids.

In one embodiment, the proteins of formula (I) and proteins of the invention are defined wherein m is 0. In one embodiment, when m is 0, n is 2. In another embodiment of the invention, when m is 0, n is not 0.

In one embodiment, m is 2.

In one particular embodiment, n is selected from the group consisting of 1, 2 and 6. In another embodiment, n is selected from the group consisting of 2 and 6. In one particular embodiment, n is 2. In another embodiment, n is 6.

In one embodiment, n is selected from the group consisting of 0, 1, 2, and 6, or any subset thereof.

In one embodiment n is 0. In another embodiment, when n is 0, m is 2.

In one embodiment, n is 1. In one embodiment, n is 3. In one embodiment, n is 4. In one embodiment, n is 5.

In one embodiment, the proteins of formula (I) further contain a methionine (M) at the amino terminus; a protein with the following formula: methionine-A-$(R_1)_m$—$(B)_n$. These are included within proteins of the invention. In one particular embodiment, when m is 0 and n is 0, the proteins of formula (I) and proteins of the invention are non-native proteins.

In one embodiment, the proteins of formula (I) and proteins of the invention are non-native proteins.

In one embodiment, the proteins of formula (I) are defined wherein A is UspA2 from *M. catarrhalis*. In another embodiment, the proteins of formula (I) are defined wherein A is UspA2 as set forth in an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37 and SEQ ID NO: 38 or any subset of SEQ ID NO: 1 through SEQ ID NO:38. In another embodiment, the proteins of formula (I) are defined wherein A is UspA2, wherein UspA2 is at least 63%, 66%, 70%, 72%, 74%, 75%, 77%, 80%, 84%, 85%, 90%, 95%, 96%, 97%, 98%, 99% or 100% identical, over the entire length, to SEQ ID NO: 1. In another embodiment, the proteins of formula (I) are defined wherein A is UspA2, wherein UspA2 is approximately 75% to 100% identical to the UspA2 amino acid sequence set forth in SEQ ID NO: 1. In another embodiment, A is UspA2 wherein UspA2 is approximately 90% to 100% identical to the UspA2 amino acid sequence set forth in SEQ ID NO: 1. In another embodiment, A is UspA2 wherein UspA2 is at least 95% identical to the UspA2 amino acid sequence set forth in SEQ ID NO: 1. In another embodiment, the proteins of formula (I) are defined wherein A is UspA2, wherein UspA2 is approximately 75% to 100% identical to the UspA2 amino acid sequence set forth in any one of SEQ ID NO: 1-SEQ ID NO: 38. In another embodiment, A is UspA2 wherein UspA2 is approximately 90% to 100% identical to the UspA2 amino acid sequence set forth in any one of SEQ ID NO: 1-SEQ ID NO: 38. In additional embodiment, A is UspA2 wherein UspA2 is at least 95% identical to UspA2 as set forth in any of SEQ ID NO: 1-SEQ ID NO: 38. In a particular embodiment, A is UspA2 having the amino acid sequence set forth in SEQ ID NO. 1.

In another embodiment, the proteins of formula (I) are defined wherein A is an immunogenic fragment of UspA2 from *M. catarrhalis*. In another embodiment, A is an immunogenic fragment of UspA2 wherein UspA2 has an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37 and SEQ ID NO: 38 or any subset of SEQ ID NO: 1 through SEQ ID NO: 38. In another embodiment, A is an immunogenic fragment of UspA2, wherein UspA2 is approximately 75% to 100% identical to the amino acid sequence set forth in SEQ ID NO: 1. In another embodiment, A is an immunogenic fragment of UspA2, wherein UspA2 is approximately 90% to 100% identical to SEQ ID NO. 1. In an another embodiment, A is an immunogenic fragment of UspA2, wherein UspA2 is at least 95% identical to SEQ ID NO: 1. In another embodiment, A is an immunogenic fragment of UspA2, wherein UspA2 is approximately 75% to 100% identical to the amino acid sequence set forth in any one of SEQ ID NO: 1-SEQ ID NO: 38. In another embodiment, A is an immunogenic fragment of UspA2, wherein UspA2 is approximately 90% to 100% identical to any one of SEQ ID NO: 1-SEQ ID NO: 38. In an additional embodiment, A is an immunogenic fragment of UspA2, wherein UspA2 is at least 95% identical to any of SEQ ID NO: 1-SEQ ID NO: 38. In a particular embodiment, A is an immunogenic fragment of UspA2 wherein UspA2 has the amino acid sequence set forth in SEQ ID NO: 1.

In another embodiment, A is an immunogenic fragment of UspA2 from *M. catarrhalis* selected from the group consisting of amino acids 30-540 of SEQ ID NO. 1 (SEQ ID NO: 39), amino acids 31-540 of SEQ ID NO: 1 (SEQ ID NO: 40), amino acids 30-519 of SEQ ID NO: 1 (SEQ ID NO: 41), amino acids 30-564 of SEQ ID NO: 1 (SEQ ID NO: 42) and amino acids 31-564 of SEQ ID NO: 1 (SEQ ID NO: 43). More specifically, in one embodiment, A is SEQ ID NO: 43, amino acids 31-564 of SEQ ID NO: 1. In an additional embodiment, A is SEQ ID NO: 42, amino acids 30-564 of SEQ ID NO: 1. In another embodiment, A is an immunogenic fragment of UspA2 from *M. catarrhalis* selected from the group consisting of amino acids 30-540 of SEQ ID NO. 1 (SEQ ID NO:39), amino acids 31-540 of SEQ ID NO. 1 (SEQ ID NO: 40) and amino acids 30-519 of SEQ ID NO. 1 (SEQ ID NO: 41). In another embodiment, A is an immunogenic fragment of UspA2 with at least 52% (American 2908), 55% (Norwegian 25), 57% (Japanese Z7476), 62% (Finnish FIN2344), 64% (American 2912), 69% (American P44), 73% (American 7169), 76% (Norwegian 27), 81% (American V1145), 88% (German Z8063) or 100% (Swedish BC5) identity to SEQ ID NO. 39. In another embodiment, A is an immunogenic fragment of UspA2 with at least 52% (American 2908), 57% (Dutch F10), 62% (American 2933), 65% (Greek MC317), 67% (American V1122), 70% (American P44), 73% (American 7169), 76% (Norwegian 3), 81% (German Z8063), 100% (Swedish BC5) identical to SEQ ID NO. 43.

In another embodiment, A is an immunogenic fragment of UspA2 from *M. catarrhalis* from SEQ ID NO: 2 through SEQ ID NO: 38 where the fragment comprises the amino acids that align with amino acids 30-540 of SEQ ID NO. 1 (SEQ ID NO: 39), amino acids 31-540 of SEQ ID NO: 1 (SEQ ID NO: 40), amino acids 30-519 of SEQ ID NO: 1 (SEQ ID NO: 41), amino acids 30-564 of SEQ ID NO: 1 (SEQ ID NO: 42) or amino acids 31-564 of SEQ ID NO: 1 (SEQ ID NO: 43). In one embodiment, the Gap program (from the GCG package), or the Needle program (from the EMBOSS package), implementing the Needleman-Wunsch algorithm, may be used to align the sequences.

```
UspA2-
                                                    SEQ ID NO: 1
MKTMKLLPLKIAVTSAMIIGLGAASTANAQAKNDITLEDLPYLIKKIDQNELEADIGDIT

ALEKYLALSQYGNILALEELNKALEELDEDVGWNQNDIANLEDDVETLTKNQNALAEQGE

AIKEDLQGLADFVEGQEGKILQNETSIKKNTQRNLVNGFEIEKNKDAIAKNNESIEDLYD

FGHEVAESIGEIHAHNEAQNETLKGLITNSIENTNNITKNKADIQALENNVVEELFNLSG

RLIDQKADIDNNINNIYELAQQQDQHSSDIKTLKKNVEEGLLELSGHLIDQKTDIAQNQA

NIQDLATYNELQDQYAQKQTEAIDALNKASSENTQNIEDLAAYNELQDAYAKQQTEAIDA

LNKASSENTQNIEDLAAYNELQDAYAKQQTEAIDALNKASSENTQNIAKNQADIANNINN

IYELAQQQDQHSSDIKTLAKASAANTDRIAKNKADADASFETLTKNQNTLIEKDKEHDKL

ITANKTAIDANKASADTKFAATADAITKNGNAITKNAKSITDLGTKVDGFDSRVTALDTK

VNAFDGRITALDSKVENGMAAQAALSGLFQPYSVGKFNATAALGGYGSKSAVAIGAGYRV

NPNLAFKAGAAINTSGNKKGSYNIGVNYEF

Amino acides 30-540 of UspA2 from SEQ ID NO: 1,
                                                    SEQ ID NO: 39
QAKNDITLEDLPYLIKKIDQNELEADIGDIT

ALEKYLALSQYGNILALEELNKALEELDEDVGWNQNDIANLEDDVETLTKNQNALAEQGE

AIKEDLQGLADFVEGQEGKILQNETSIKKNTQRNLVNGFEIEKNKDAIAKNNESIEDLYD

FGHEVAESIGEIHAHNEAQNETLKGLITNSIENTNNITKNKADIQALENNVVEELFNLSG

RLIDQKADIDNNINNIYELAQQQDQHSSDIKTLKKNVEEGLLELSGHLIDQKTDIAQNQA

NIQDLATYNELQDQYAQKQTEAIDALNKASSENTQNIEDLAAYNELQDAYAKQQTEAIDA

LNKASSENTQNIEDLAAYNELQDAYAKQQTEAIDALNKASSENTQNIAKNQADIANNINN

IYELAQQQDQHSSDIKTLAKASAANTDRIAKNKADADASFETLTKNQNTLIEKDKEHDKL

ITANKTAIDANKASADTKFAATADAITKNGNAITKNAKSITDLGTKVDGFDSRVTALDTK

Amino acids 31-540 of UspA2 from SEQ ID NO: 1,
                                                    SEQ ID NO: 40
AKNDITLEDLPYLIKKIDQNELEADIGDIT

ALEKYLALSQYGNILALEELNKALEELDEDVGWNQNDIANLEDDVETLTKNQNALAEQGE

AIKEDLQGLADFVEGQEGKILQNETSIKKNTQRNLVNGFEIEKNKDAIAKNNESIEDLYD

FGHEVAESIGEIHAHNEAQNETLKGLITNSIENTNNITKNKADIQALENNVVEELFNLSG

RLIDQKADIDNNINNIYELAQQQDQHSSDIKTLKKNVEEGLLELSGHLIDQKTDIAQNQA

NIQDLATYNELQDQYAQKQTEAIDALNKASSENTQNIEDLAAYNELQDAYAKQQTEAIDA
```

```
LNKASSENTQNIEDLAAYNELQDAYAKQQTEAIDALNKASSENTQNIAKNQADIANNINN

IYELAQQQDQHSSDIKTLAKASAANTDRIAKNKADADASFETLTKNQNTLIEKDKEHDKL

ITANKTAIDANKASADTKFAATADAITKNGNAITKNAKSITDLGTKVDGFDSRVTALDTK

Amino acids 30-519 of UspA2 from SEQ ID NO: 1,
                                                SEQ ID NO: 41
QAKNDITLEDLPYLIKKIDQNELEADIGDIT

ALEKYLALSQYGNILALEELNKALEELDEDVGWNQNDIANLEDDVETLTKNQNALAEQGE

AIKEDLQGLADFVEGQEGKILQNETSIKKNTQRNLVNGFEIEKNKDAIAKNNESIEDLYD

FGHEVAESIGEIHAHNEAQNETLKGLITNSIENTNNITKNKADIQALENNVVEELFNLSG

RLIDQKADIDNNINNIYELAQQQDQHSSDIKTLKKNVEEGLLELSGHLIDQKTDIAQNQA

NIQDLATYNELQDQYAQKQTEAIDALNKASSENTQNIEDLAAYNELQDAYAKQQTEAIDA

LNKASSENTQNIEDLAAYNELQDAYAKQQTEAIDALNKASSENTQNIAKNQADIANNINN

IYELAQQQDQHSSDIKTLAKASAANTDRIAKNKADADASFETLTKNQNTLIEKDKEHDKL

ITANKTAIDANKASADTKFAATADAITKNGNAITKNAKS

Amino acids 30-564 of UspA2 from SEQ ID NO: 1,
                                                SEQ ID NO: 42
QAKNDITLEDLPYLIKKIDQNELEADIGDIT

ALEKYLALSQYGNILALEELNKALEELDEDVGWNQNDIANLEDDVETLTKNQNALAEQGE

AIKEDLQGLADFVEGQEGKILQNETSIKKNTQRNLVNGFEIEKNKDAIAKNNESIEDLYD

FGHEVAESIGEIHAHNEAQNETLKGLITNSIENTNNITKNKADIQALENNVVEELFNLSG

RLIDQKADIDNNINNIYELAQQQDQHSSDIKTLKKNVEEGLLELSGHLIDQKTDIAQNQA

NIQDLATYNELQDQYAQKQTEAIDALNKASSENTQNIEDLAAYNELQDAYAKQQTEAIDA

LNKASSENTQNIEDLAAYNELQDAYAKQQTEAIDALNKASSENTQNIAKNQADIANNINN

IYELAQQQDQHSSDIKTLAKASAANTDRIAKNKADADASFETLTKNQNTLIEKDKEHDKL

ITANKTAIDANKASADTKFAATADAITKNGNAITKNAKSITDLGTKVDGFDSRVTALDTK

VNAFDGRITALDSKVENGMAAQAA

Amino acids 31-564 of UspA2 from SEQ ID NO: 1,
                                                SEQ ID NO: 43
AKNDITLEDLPYLIKKIDQNELEADIGDIT

ALEKYLALSQYGNILALEELNKALEELDEDVGWNQNDIANLEDDVETLTKNQNALAEQGE

AIKEDLQGLADFVEGQEGKILQNETSIKKNTQRNLVNGFEIEKNKDAIAKNNESIEDLYD

FGHEVAESIGEIHAHNEAQNETLKGLITNSIENTNNITKNKADIQALENNVVEELFNLSG

RLIDQKADIDNNINNIYELAQQQDQHSSDIKTLKKNVEEGLLELSGHLIDQKTDIAQNQA

NIQDLATYNELQDQYAQKQTEAIDALNKASSENTQNIEDLAAYNELQDAYAKQQTEAIDA

LNKASSENTQNIEDLAAYNELQDAYAKQQTEAIDALNKASSENTQNIAKNQADIANNINN

IYELAQQQDQHSSDIKTLAKASAANTDRIAKNKADADASFETLTKNQNTLIEKDKEHDKL

ITANKTAIDANKASADTKFAATADAITKNGNAITKNAKSITDLGTKVDGFDSRVTALDTK

VNAFDGRITALDSKVENGMAAQAA
```

In another embodiment, A is an immunogenic fragment of UspA2 from *M. catarrhalis* that differs from SEQ ID NO: 1 in one or more of the following amino acids: AA (amino acid) 30 to 298, AA 299 to 302, AA 303 to 333, AA 334 to 339, AA 349, AA 352 to 354, AA 368 to 403, AA 441, AA 451 to 471, AA 472, AA 474 to 483, AA 487, AA 490, AA 493, AA 529, AA 532 or AA 543. In another embodiment, A is an immunogenic fragment of UspA2 from *M. catarrhalis* that differs from SEQ ID NO: 1 in that it contains at least one amino acid insertion in comparison to SEQ ID NO. 1.

In another embodiment, A is an immunogenic fragment of UspA2 that contains a laminin binding domain and a fibronectin binding domain.

In an additional embodiment, A is an immunogenic fragment of UspA2 that contains a laminin binding domain, a fibronectin binding domain and a C3 binding domain.

In a further embodiment, A is an immunogenic fragment of UspA2 that contains a laminin binding domain, a fibronectin binding domain, a C3 binding domain and an amphipathic helix.

The laminin binding domain, fibronectin binding domain, C3 binding domain or amphipathic helix may be as defined for SEQ ID NO: 1 or may be the corresponding sequence in any one of SEQ ID NO: 2 through SEQ ID NO: 38.

Proteins of formula (I) and proteins of the invention are useful as immunogens in subjects such as mammals, particularly humans. In particular, the proteins of formula (I) and proteins of the invention are useful in inducing an immune response against *M. catarrhalis* in subjects, particularly humans. The proteins of formula (I) and proteins of the invention are useful in the treatment or prevention of *M. catarrhalis* infection or disease. More specifically, the proteins of formula (I) and proteins of the invention are useful in the treatment or prevention of otitis media and/or COPD and/or AECOPD and/or pneumonia.

The present invention relates to immunogenic compositions comprising UspA2 from *M. catarrhalis* or an immunogenic fragment thereof. The present invention also relates to vaccines comprising such immunogenic compositions and therapeutic uses of the same. Immunogenic compositions and vaccines of the present invention are useful in the treatment or prevention of *M. catarrhalis* infection or disease. More specifically, immunogenic compositions and vaccines described herein are useful in the treatment or prevention of otitis media and/or COPD and/or AECOPD and/or pneumonia.

In one embodiment, the immunogenic composition comprises UspA2 from *M. catarrhalis*. UspA2 may be any one of SEQ ID NO: 1 through SEQ ID NO: 38 or a UspA2 sequence at least 75%, 80%, 85%, 90%, 95%, 96%, 97%, 98% or 99% identical to any one of SEQ ID NO: 1 through SEQ ID NO: 38. UspA2 may also be a UspA2 sequence at least 63% (American 2908), 66% (Japanese Z7476), 70% (Dutch F10), 72% (Finnish 358), 74% (American P44), 77% (Finnish 307), 80% (Norwegian 3), 84% (American V1145), 90% (German Z8063) or 100% (Swedish BC5) identical to that of SEQ ID NO. 1.

In another embodiment, the immunogenic composition comprises an immunogenic fragment of UspA2. The immunogenic fragment of UspA2 may be SEQ ID NO: 39, SEQ ID NO: 40, SEQ ID NO: 41, SEQ ID NO: 42 or SEQ ID NO.43, or a sequence having at least 90%, 95%, 96%, 97%, 98%, 99% sequence identity to any one of SEQ ID NO: 39, SEQ ID NO: 40, SEQ ID NO: 41, SEQ ID NO: 42 or SEQ ID NO.43. The immunogenic fragment of UspA2 may be a UspA2 sequence at least 52% (American 2908), 55% (Norwegian 25), 57% (Japanese Z7476), 62% (Finnish FIN2344), 64% (American 2912), 69% (American P44), 73% (American 7169), 76% (Norwegian 27), 81% (American V1145), 88% (German Z8063) or 100% (Swedish BC5) identical to SEQ ID NO. 39. The immunogenic fragment of UspA2 may also be a UspA2 sequence at least 52% (American 2908), 57% (Dutch F10), 62% (American 2933), 65% (Greek MC317), 67% (American V1122), 70% (American P44), 73% (American 7169), 76% (Norwegian 3), 81% (German Z8063), 100% (Swedish BC5) identical to SEQ ID NO. 43. Amino acid differences have been described in UspA2 from various *Moraxella catarrhalis* species.

UspA2 contains a laminin binding domain (for example, amino acids 30-177 of SEQ ID NO: 1, SEQ ID NO: 44). In one embodiment, the fragment of UspA2 comprises the laminin binding region of SEQ ID NO: 1. In an additional embodiment, the fragment of UspA2 comprises the laminin binding region of any one of SEQ ID NO: 2-SEQ ID NO: 38.

```
Amino acids 30-177 of SEQ ID NO: 1, SEQ ID
NO: 44:
QAKNDITLEDLPYLIKKIDQNELEADIGDITALEKYLALSQYGNILALE

ELNKALEELDEDVGWNQNDIANLEDDVETLTKNQNALAEQGEAIKEDLQ

GLADFVEGQEGKILQNETSIKKNTQRNLVNGFEIEKNKDAIAKNNESIE

D.
```

UspA2 contains a fibronectin binding domain (for example, amino acids 165-318 of SEQ ID NO: 1, SEQ ID NO: 45). In one embodiment, the fragment of UspA2 comprises the fibronectin binding region of SEQ ID NO: 1. In an additional embodiment, the fragment of UspA2 comprises the fibronectin binding region of any one of SEQ ID NO: 2-SEQ ID NO:38. The fibronectin binding domain of SEQ ID NO: 45 also has C3 binding properties.

```
Amino acids 165-318 of SEQ ID NO: 1, SEQ ID
NO: 45:
KDAIAKNNESIEDLYD

FGHEVAESIGEIHAHNEAQNETLKGLITNSIENTNNITKNKADIQALEN

NVVEELFNLSGRLIDQKADIDNNINNIYELAQQQDQHSSDIKTLKKNVE

EGLLELSGHLIDQKTDIAQNQANIQDLATYNELQDQYAQK.
```

UspA2 contains a complement component 3 (C3) binding domain (for example, amino acids 30-539 of SEQ ID NO: 1, SEQ ID NO: 46, or amino acids 165-318 of SEQ ID NO: 1, SEQ ID NO: 45). In one embodiment, the fragment of UspA2 comprises the C3 binding region of SEQ ID NO: 1. In an additional embodiment, the fragment of UspA2 comprises a C3 binding domain of any one of SEQ ID NO: 2-SEQ ID NO: 38.

```
Amino acids of 30-539 of SEQ ID NO: 1, SEQ ID
NO: 46:
QAKNDITLEDLPYLIKKIDQNELEADIGDIT

ALEKYLALSQYGNILALEELNKALEELDEDVGWNQNDIANLEDDVETLT

KNQNALAEQGEAIKEDLQGLADFVEGQEGKILQNETSIKKNTQRNLVNG

FEIEKNKDAIAKNNESIEDLYDFGHEVAESIGEIHAHNEAQNETLKGLI

TNSIENTNNITKNKADIQALENNVVEELFNLSGRLIDQKADIDNNINNI

YELAQQQDQHSSDIKTLKKNVEEGLLELSGHLIDQKTDIAQNQANIQDL

ATYNELQDQYAQKQTEAIDALNKASSENTQNIEDLAAYNELQDAYAKQQ

TEAIDALNKASSENTQNIEDLAAYNELQDAYAKQQTEAIDALNKASSEN

TQNIAKNQADIANNINNIYELAQQQDQHSSDIKTLAKASAANTDRIAKN

KADADASFETLTKNQNTLIEKDKEHDKLITANKTAIDANKASADTKFAA

TADAITKNGNAITKNAKSITDLGTKVDGFDSRVTALDT
```

UspA2 contains an amphipathic helix (for example, amino acids 519-564 of SEQ ID NO: 1 or or amino acids 520-559 of SEQ ID NO:1). In one embodiment, the fragment of UspA2 comprises amino acids 519-564 of SEQ ID NO: 1. In another embodiment, the fragment of UspA2 comprises amino acids 520-559 of SEQ ID NO:1. In an additional embodiment, the fragment of UspA2 comprises an amphipathic helix of any one of SEQ ID NO: 2-SEQ ID NO:38.

In one embodiment, the immunogenic composition comprises a protein of formula (I) wherein A is an immunogenic fragment of UspA2 that comprises a laminin binding domain and a fibronectin binding domain.

In an additional embodiment, the immunogenic composition comprises a protein of formula (I) wherein A is an immunogenic fragment of UspA2 that comprises a laminin binding domain, a fibronectin binding domain and a C3 binding domain.

In a further embodiment, the immunogenic composition comprises a protein of formula (I) wherein A is an immunogenic fragment of UspA2 that comprises a laminin binding domain, a fibronectin binding domain, a C3 binding domain and an amphipathic helix.

In another embodiment, the immunogenic composition comprises a protein as defined by formula (I). The immunogenic composition may contain, for example, a protein of formula (I) with an additional methionine at the amino terminus.

In one embodiment, the present immunogenic compositions may be administered with other antigens. For example, the present immunogenic composition may be administered with antigens from *H. influenzae*. For example, the protein of formula (I) may be administered with Protein D (PD) from *H. influenzae*. Protein D may be as described in WO91/18926. The present immunogenic composition may be administered with Protein E (PE) and Pilin A (PilA) from H. *Influenzae*. Protein E and Pilin A may be as described in WO2012/139225; the contents of which are incorporated herein by reference. Protein E and Pilin A may be presented as a fusion protein.

In another embodiment, the immunogenic compositions of the invention may be administered with additional antigens from other bacterial species also known to cause otitis media, COPD, AECOPD or pneumonia.

The amount of the immunogenic composition which is required to achieve the desired therapeutic or biological effect will depend on a number of factors such as the use for which it is intended, the means of administration, the recipient and the type and severity of the condition being treated, and will be ultimately at the discretion of the attendant physician or veterinarian. In general, a typical dose for the treatment of a condition caused in whole or in part by *M. catarrhalis* in a human, for instance, may be expected to lie in the range of from about 0.001 mg-0.120 mg. More specifically, a typical dose for the treatment of a condition caused wholly or in part by *M. catarrhalis* in a human may lie in the range of from about 0.003 mg to about 0.03 mg of protein. The present invention provides an immunogenic composition comprising a protein of formula (I) or a protein of the invention for use in the treatment or prevention of a condition or disease caused wholly or in part by *M. catarrhalis*. The immunogenic composition may contain additional antigens; a typical dose for the treatment of a condition caused wholly or in part by *H. influenzae* in a human may lie in the range of from about 0.005 mg to about 0.05 mg for each additional antigen. This dose may be administered as a single unit dose. Several separate unit doses may also be administered. For example, separate unit doses may be administered as separate priming doses within the first year of life or as separate booster doses given at regular intervals (for example, every 1, 5 or 10 years). The present invention also provides an immunogenic composition comprising a protein of formula (I) or a protein of the invention for use in the treatment or prevention of a condition or disease caused wholly or in part by *Moraxella catarrhalis* in combination with at least one antigen from *Haemophilus influenzae*.

Formulations comprising the immunogenic compositions of the invention may be adapted for administration by an appropriate route, for example, by the intramuscular, sublingual, transcutaneous, intradermal or intranasal route. Such formulations may be prepared by any method known in the art.

The immunogenic compositions of the present invention may additionally comprise an adjuvant. When the term "adjuvant" is used in this specification, it refers to a substance that is administered in conjunction with the immunogenic composition to boost the patient's immune response to the immunogenic component of the composition.

Suitable adjuvants include an aluminum salt such as aluminum hydroxide gel or aluminum phosphate or alum, but may also be a salt of calcium, magnesium, iron or zinc, or may be an insoluble suspension of acylated tyrosine, or acylated sugars, cationically or anionically derivatized saccharides, or polyphosphazenes. In one embodiment, the protein may be adsorbed onto aluminium phosphate. In another embodiment, the protein may be adsorbed onto aluminium hydroxide. In a third embodiment, alum may be used as an adjuvant.

Suitable adjuvant systems which promote a predominantly Th1 response include: non-toxic derivatives of lipid A, Monophosphoryl lipid A (MPL) or a derivative thereof, particularly 3-de-O-acylated monophosphoryl lipid A (3D-MPL) (for its preparation see GB 2220211 A); and a combination of monophosphoryl lipid A, preferably 3-de-O-acylated monophosphoryl lipid A, together with either an aluminum salt (for instance aluminum phosphate or aluminum hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen (Thoelen et al. Vaccine (1998) 16:708-14; EP 689454-B1).

AS01 is an Adjuvant System containing MPL (3-O-desacyl-4'-monophosphoryl lipid A), QS21 ((Quillaja *saponaria* Molina, fraction 21) Antigenics, New York, N.Y., USA) and liposomes. AS01B is an Adjuvant System containing MPL, QS21 and liposomes (50 μg MPL and 50 μg QS21). AS01E is an Adjuvant System containing MPL, QS21 and liposomes (25 μg MPL and 25 μg QS21). In one embodiment, the immunogenic composition or vaccine comprises AS01. In another embodiment, the immunogenic composition or vaccine comprises AS01B or AS01E. In a particular embodiment, the immunogenic composition or vaccine comprises AS01E.

AS02 is an Adjuvant System containing MPL and QS21 in an oil/water emulsion. AS02V is an Adjuvant System containing MPL and QS21 in an oil/water emulsion (50 μg MPL and 50 μg Q521).

AS03 is an Adjuvant System containing α-Tocopherol and squalene in an oil/water (o/w) emulsion. $AS03_A$ is an Adjuvant System containing α-Tocopherol and squalene in an o/w emulsion (11.86 mg tocopherol). $AS03_B$ is an Adjuvant System containing α-Tocopherol and squalene in an o/w emulsion (5.93 mg tocopherol). AS03c is an Adjuvant System containing α-Tocopherol and squalene in an o/w emulsion (2.97 mg tocopherol). In one embodiment, the immunogenic composition or vaccine comprises AS03.

AS04 is an Adjuvant System containing MPL (50 μg MPL) adsorbed on an aluminum salt (500 μg $Al^{3+}$). In one embodiment, the immunogenic composition or vaccine comprises AS04.

A system involving the use of QS21 and 3D-MPL is disclosed in WO 94/00153. A composition wherein the QS21 is quenched with cholesterol is disclosed in WO 96/33739. An additional adjuvant formulation involving QS21, 3D-MPL and tocopherol in an oil in water emulsion is described in WO 95/17210. In one embodiment the immunogenic composition additionally comprises a saponin, which may be QS21. The formulation may also comprise an oil in water emulsion and tocopherol (WO 95/17210). Unmethylated CpG containing oligonucleotides (WO 96/02555) and other immunomodulatory oligonucleotides (WO 0226757 and WO 03507822) are also preferential inducers of a TH1 response and are suitable for use in the present invention.

Additional adjuvants are those selected from the group of metal salts, oil in water emulsions, Toll like receptor agonists, (in particular Toll like receptor 2 agonist, Toll like receptor 3 agonist, Toll like receptor 4 agonist, Toll like receptor 7 agonist, Toll like receptor 8 agonist and Toll like receptor 9 agonist), saponins or combinations thereof.

The present invention provides a process for preparing an immunogenic composition comprising combining a protein of formula (I) or a protein of the invention with an adjuvant.

The present invention further provides a vaccine containing an immunogenic composition of the invention and a pharmaceutically acceptable adjuvant.

Possible excipients include arginine, pluronic acid and/or polysorbate. In a preferred embodiment, polysorbate 80 (for example, TWEEN (a US registered trademark) 80) is used. In a further embodiment, a final concentration of about 0.03% to about 0.06% is used. Specifically, a final concentration of about 0.03%, 0.04%, 0.05% or 0.06% polysorbate 80 (w/v) may be used.

The present invention provides a process for preparing an immunogenic composition or vaccine comprising combining a protein of formula (I) or protein of the invention with a pharmaceutically acceptable excipient.

The present invention also provides nucleic acids encoding the proteins of the invention. The term "nucleic acid" refers to a polymeric form of nucleotides. Nucleotides can be ribonucleotides, deoxyribonucleotides, or modified forms of either ribonucleotides or deoxyribonucleotides. The term includes single and double forms of DNA. The nucleic acids are preferably substantially free from other nucleic acids.

The present invention provides a process of producing nucleic acids of the invention. Nucleic acids of the invention may be prepared by methods known by those skilled in the art. For example, the nucleic acids of the invention may be synthesized in part or in whole. The nucleic acids may be prepared by digesting longer amino acids or joining shorter amino acids.

The present invention provides a method for the treatment or prevention of otitis media. The method comprises administering to a subject in need thereof a therapeutically effective amount of a protein of formula (I) or a protein of the invention.

The present invention provides a method for the treatment or prevention of exacerbations in chronic obstructive pulmonary disease. The exacerbation of COPD may be an acute exacerbation. The method comprises administering to a subject in need thereof a therapeutically effective amount of the protein of formula (I) or a protein of the invention.

The present invention provides a method for the treatment or prevention of pneumonia. The method comprises administering to a subject in need thereof a therapeutically effective amount of the protein of formula (I) or a protein of the invention.

The present invention provides a pharmaceutical composition comprising a protein of formula (I) or a protein of the invention for use in the treatment or prevention of a condition or disease caused wholly or in part by *Moraxella catarrhalis*. Pharmaceutical compositions may further comprise a pharmaceutically acceptable adjuvant.

The present invention provides use of (a) proteins of formula (I) and proteins of the invention, (b) an immunogenic composition comprising a protein of formula (I) or protein of the invention or (c) a vaccine comprising (c1) a protein of formula (I) or protein of the invention or (c2) immunogenic composition comprising a protein of formula (I) or protein of the invention for the manufacture of a medicament for treating or preventing *M. catarrhalis* infection or disease.

The present invention provides use of (a) proteins of formula (I) and proteins of the invention, (b) an immunogenic composition comprising a protein of formula (I) or protein of the invention or (c) a vaccine comprising (c1) a protein of formula (I) or protein of the invention or (c2) immunogenic composition comprising a protein of formula (I) or protein of the invention for the manufacture of a medicament for treating or preventing otitis media.

The present invention provides use of (a) proteins of formula (I) and proteins of the invention, (b) an immunogenic composition comprising a protein of formula (I) or protein of the invention or (c) a vaccine comprising (c1) a protein of formula (I) or protein of the invention or (c2) immunogenic composition comprising a protein of formula (I) or protein of the invention for the manufacture of a medicament for treating or preventing acute exacerbations of chronic obstructive pulmonary disease (AECOPD).

The present invention provides a use of (a) proteins of formula (I) and proteins of the invention, (b) an immunogenic composition comprising a protein of formula (I) or protein of the invention or (c) a vaccine comprising (c1) a protein of formula (I) or protein of the invention or (c2) immunogenic composition comprising a protein of formula (I) or protein of the invention for the manufacture of a medicament for treating or preventing pneumonia.

The following examples are intended for illustration only and are not intended to limit the scope of the invention in any way.

In the examples, the following terms have the designated meaning:
6×his=six histidines;
xg=centrifugal force (number gravities)
AS=alanine serine
BSA=bovine serum albumin;
° C.=degrees Celsius;
$CaCl_2$)=calcium chloride;
CD=circular dichroism;
$CHCl_3$=chloroform;
$CH_3CN$=acetonitrile;
$CO_2$=carbon dioxide;
Da=dalton;
DNA=deoxyribonucleic acid;
DO=dissolved oxygen;
DSC=differential scanning calorimetry;
EDTA=ethylenediaminetetraacetic acid;
h=hour;
$H_2O$=water;
$H_2O_2$=hydrogen peroxide;
HCDI=high cell density induction;
HCl=hydrogen chloride;
His=his=histidine;
IMAC=immobilized metal affinity chromatography;

IPTG=isopropyl β-D-1-thiogalactopyranoside;
kVolts=kilovolts
L=liter;
LB=Luria-Bertani;
LCD=low cell density induction;
MeOH=methanol;
ml=milliliter;
NaCl=sodium chloride;
RPM=rpm=revolutions per minute;
min=minute;
mM=millimolar;
μg=microgram;
μL=microliter;
MW=molecular weight;
m/z=mass/charge;
NaCl=sodium chloride;
NaPO$_4$=sodium phosphate;
ng=nanogram;
NH$_4$OH=ammonium hydroxide;
nm=nanometer;
O.D.=optical density;
PBS=phosphate buffered saline;
PCR=polymerase chain reaction;
psi=pounds per square inch;
PVDF=polyvinylidence diluoride;
SDS-PAGE=sodium dodecyl sulphate polyacrylamide gel electrophoresis;
TFA=trifluoroacetic acid
Tm=melting point;
Tm$_1$=first melting point;
Tm$_2$=second melting point;
w/v=weight/volume.

EXAMPLES

Example 1: Protein Constructs

Protein constructs were produced with different fragments of UspA2 with and without additional amino acids. The following table describes protein constructs made.

TABLE 2

Protein constructs containing UspA2 protein.

| Construct ID | Description | N-terminal | | C-Terminal |
|---|---|---|---|---|
| MC-001 | UspA2 + 1/2 helix + 6His | UspA2 fragment (A.A.: 30-540 of SEQ ID NO: 1, SEQ ID NO: 47) | | ASHHHHHH |
| | A.A. | 30 | 540 | 541    548 |
| MC-002 | UspA2 + 1/2 helix | UspA2 fragment (A.A.: 30-540 of SEQ ID NO: 1, SEQ ID NO: 47) | | |
| | A.A. | 30 | 540 | |
| MC-003 | UspA2 + 1/2 helix + 1His | UspA2 fragment (A.A.: 30-540 of SEQ ID NO:. 1, SEQ ID NO: 47) | | H |
| | A.A. | 30 | 540 | 541 |
| MC-004 | UspA2 + 1/2 helix + 2His | UspA2 fragment (A.A.: 30-540 of SEQ ID NO: 1, SEQ ID NO: 47) | | HH |
| | A.A. | 30 | 540 | 541 542 |
| MC-005 | UspA2 Δhelix + 6His | UspA2 fragment (A.A.: 30-519 of SEQ ID NO: 1, SEQ ID NO: 48) | | ASHHHHHH |
| | A.A. | 30 | 519 | 520    527 |
| MC-006 | UspA2 Δhelix | UspA2 fragment (A.A.: 30-519 of SEQ ID NO: 1, SEQ ID NO: 48) | | |
| | A.A. | 30 | 519 | |
| MC-007 | UspA2 + helix + 6His | UspA2 fragment (A.A.: 30-564 of SEQ ID NO: 1, SEQ ID NO: 49) | | ASHHHHHH |
| | A.A. | 30 | 564 | 565    572 |
| MC-008 | UspA2 + helix + 2His | UspA2 fragment (A.A.: 30-564 of SEQ ID NO: 1, SEQ ID NO: 49) | | HH |
| | A.A. | 30 | | 564 565 566 |
| MC-009 | UspA2 + helix + 2His ΔQ | UspA2 fragment (A.A.: 31-564 of SEQ ID NO: 1, SEQ ID NO: 50) | | HH |
| | A.A. | 31 | | 564 565 566 |
| MC-010 | UspA2 + helix | UspA2 fragment (A.A.: 30-564 of SEQ ID NO: 1, SEQ ID NO: 49) | | |
| | A.A. | 30 | 564 | |
| MC-011 | UspA2 + 1/2 helix + 6His ΔQ | UspA2 fragment (A.A.: 31-540 of SEQ ID NO: 1, SEQ ID NO: 51) | | ASHHHHHH |
| | A.A. | 31 | 540 | 541    548 |

A.A. = amino acid

The DNA and amino acid sequences for each protein constructs listed in Table 2 are set forth below.

PROTEIN CONSTRUCT SEQUENCES:

MC-001(DNA)-SEQ ID NO: 52
ATGCAGGCCAAAAATGATATTACCCTGGAAGATCTGCCGTATCTGATCAAAAAAATCGATCAG
AACGAACTGGAAGCCGATATTGGTGATATTACCGCACTGGAAAAATATCTGGCACTGAGCCAG
TATGGAAATATTCTGGCCCTGGAAGAACTGAATAAAGCTCTGGAAGAGCTGGATGAAGATGTG
GGTTGGAATCAGAATGATATCGCCAATCTGGAAGATGATGTTGAAACCCTGACCAAAAATCAG
AATGCACTGGCAGAACAGGGTGAAGCAATTAAAGAAGATCTGCAGGGTCTGGCAGATTTTGTT
GAAGGTCAGGAAGGCAAATTCTGCAGAACGAAACCAGCATCAAAAAAAACACCCAGCGTAAT

PROTEIN CONSTRUCT SEQUENCES:

CTGGTGAATGGCTTTGAAATTGAAAAAAACAAAGATGCCATTGCCAAAAACAACGAAAGCATT
GAAGATCTGTATGATTTTGGTCATGAAGTTGCCGAAAGCATTGGTGAAATTCATGCACATAAC
GAAGCACAGAATGAAACCCTGAAAGGTCTGATTACCAACAGCATCAAAAATACCAATAACATT
ACCAAAAACAAAGCAGATATTCAGGCGCTGGAAAATAATGTTGTGGAAGAACTGTTTAATCTG
AGCGGTCGTCTGATTGATCAGAAAGCCGATATCGATAATAACATTAACAACATTTATGAACTG
GCACAGCAGCAGGATCAGCATAGCAGCGATATCAAAACCCTGAAAAAAAACGTTGAAGAAGGT
CTGCTGGAACTGTCTGGTCACCTGATCGATCAGAAAACTGATATTGCCCAGAATCAGGCAAAT
ATTCAGGATCTGGCCACCTATAATGAACTGCAGGATCAGTATGCACAGAAACAGACCGAAGCA
ATTGATGCCCTGAATAAAGCGAGCAGCGAAAACACCCAGAATATCGAAGATCTGGCAGCATAC
AACGAACTGCAGGATGCCTATGCAAAACAGCAGACTGAAGCCATCGACGCACTGAACAAGGCA
AGCTCTGAAAACACGCAGAACATTGAAGATCTGGCTGCCTATAATGAATTACAGGATGCGTAT
GCCAAACAGCAGACCGAAGCGATTGATGCGCTGAACAAAGCCTCTTCTGAAAATACACAGAAT
ATCGCCAAAAATCAGGCCGATATTGCCAACAATATCAATAATATCTATGAACTGGCCCAGCAG
CAGGATCAGCACTCTTCTGATATCAAAACACTGGCAAAGCAAGCGCAGCAAATACCGATCGT
ATTGCGAAAAACAAAGCCGATGCAGATGCAAGCTTTGAAACACTGACGAAAAACCAGAACACC
CTGATTGAAAAAGATAAAGAACATGATAAACTGATCACCGCCAATAAAACCGCAATTGATGCA
AATAAAGCCAGCGCAGATACCAAATTTGCAGCAACCGCAGATGCAATTACCAAAAATGGCAAT
GCCATCACCAAAAATGCCAAAAGCATTACCGATCTGGGCACCAAAGTTGATGGTTTTGATAGC
CGTGTGACCGCACTGGATACCAAAGCAAGCCATCATCATCACCACCACTAA

MC-001 (protein)-(M)(UspA2 amino acids 30-540)(ASHHHHHH) SEQ ID NO: 53
MQAKNDITLEDLPYLIKKIDQNELEADIGDITALEKYLALSQYGNILALEELNKALEELDEDV
GWNQNDIANLEDDVETLTKNQNALAEQGEAIKEDLQGLADFVEGQEGKILQNETSIKKNTQRN
LVNGFEIEKNKDAIAKNNESIEDLYDFGHEVAESIGEIHAHNEAQNETLKGLITNSIENTNNI
TKNKADIQALENNVVEELFNLSGRLIDQKADIDNNINNIYELAQQQDQHSSDIKTLKKNVEEG
LLELSGHLIDQKTDIAQNQANIQDLATYNELQDQYAQKQTEAIDALNKASSENTQNIEDLAAY
NELQDAYAKQQTEAIDALNKASSENTQNIEDLAAYNELQDAYAKQQTEAIDALNKASSENTQN
IAKNQADIANNINNIYELAQQQDQHSSDIKTLAKASAANTDRIAKNKADADASFETLTKNQNT
LIEKDKEHDKLITANKTAIDANKASADTKFAATADAITKNGNAITKNAKSITDLGTKVDGFDS
RVTALDTKASHHHHHH MC-002 (DNA)-SEQ ID NO: 54
ATGCAGGCCAAAAATGATATTACCCTGGAAGATCTGCCGTATCTGATCAAAAAAATCGATCAG
AACGAACTGGAAGCCGATATTGGTGATATTACCGCACTGGAAAAATATCTGGCACTGAGCCAG
TATGGAAATATTCTGGCCCTGGAAGAACTGAATAAAGCTCTGGAAGAGCTGGATGAAGATGTG
GGTTGGAATCAGAATGATATCGCCAATCTGGAAGATGATGTTGAAACCCTGACCAAAAATCAG
AATGCACTGGCAGAACAGGGTGAAGCAATTAAAGAAGATCTGCAGGGTCTGGCAGATTTTGTT
GAAGGTCAGGAAGGCAAAATTCTGCAGAACGAAACCAGCATCAAAAAAAACACCCAGCGTAAT
CTGGTGAATGGCTTTGAAATTGAAAAAAACAAAGATGCCATTGCCAAAAACAACGAAAGCATT
GAAGATCTGTATGATTTTGGTCATGAAGTTGCCGAAAGCATTGGTGAAATTCATGCACATAAC
GAAGCACAGAATGAAACCCTGAAAGGTCTGATTACCAACAGCATCAAAAATACCAATAACATT
ACCAAAAACAAAGCAGATATTCAGGCGCTGGAAAATAATGTTGTGGAAGAACTGTTTAATCTG
AGCGGTCGTCTGATTGATCAGAAAGCCGATATCGATAATAACATTAACAACATTTATGAACTG
GCACAGCAGCAGGATCAGCATAGCAGCGATATCAAAACCCTGAAAAAAAACGTTGAAGAAGGT
CTGCTGGAACTGTCTGGTCACCTGATCGATCAGAAAACTGATATTGCCCAGAATCAGGCAAAT
ATTCAGGATCTGGCCACCTATAATGAACTGCAGGATCAGTATGCACAGAAACAGACCGAAGCA
ATTGATGCCCTGAATAAAGCGAGCAGCGAAAACACCCAGAATATCGAAGATCTGGCAGCATAC
AACGAACTGCAGGATGCCTATGCAAAACAGCAGACTGAAGCCATCGACGCACTGAACAAGGCA
AGCTCTGAAAACACGCAGAACATTGAAGATCTGGCTGCCTATAATGAATTACAGGATGCGTAT
GCCAAACAGCAGACCGAAGCGATTGATGCGCTGAACAAAGCCTCTTCTGAAAATACACAGAAT
ATCGCCAAAAATCAGGCCGATATTGCCAACAATATCAATAATATCTATGAACTGGCCCAGCAG
CAGGATCAGCACTCTTCTGATATCAAAACACTGGCAAAGCAAGCGCAGCAAATACCGATCGT
ATTGCGAAAAACAAAGCCGATGCAGATGCAAGCTTTGAAACACTGACGAAAAACCAGAACACC
CTGATTGAAAAAGATAAAGAACATGATAAACTGATCACCGCCAATAAAACCGCAATTGATGCA
AATAAAGCCAGCGCAGATACCAAATTTGCAGCAACCGCAGATGCAATTACCAAAAATGGCAAT
GCCATCACCAAAAATGCCAAAAGCATTACCGATCTGGGCACCAAAGTTGATGGTTTTGATAGC
CGTGTGACCGCACTGGATACCAAATAA MC-002 (Protein)-(M)(UspA2 amino acids 30-540) SEQ ID NO: 55
MQAKNDITLEDLPYLIKKIDQNELEADIGDITALEKYLALSQYGNILALEELNKALEELDEDV
GWNQNDIANLEDDVETLTKNQNALAEQGEAIKEDLQGLADFVEGQEGKILQNETSIKKNTQRN
LVNGFEIEKNKDAIAKNNESIEDLYDFGHEVAESIGEIHAHNEAQNETLKGLITNSIENTNNI
TKNKADIQALENNVVEELFNLSGRLIDQKADIDNNINNIYELAQQQDQHSSDIKTLKKNVEEG
LLELSGHLIDQKTDIAQNQANIQDLATYNELQDQYAQKQTEAIDALNKASSENTQNIEDLAAY
NELQD
AYAKQQTEAIDALNKASSENTQNIEDLAAYNELQDAYAKQQTEAIDALNKASSENTQNIAKNQ
ADIANNINNIYELAQQQDQHSSDIKTLAKASAANTDRIAKNKADADASFETLTKNQNTLIEKD
KEHDKLITANKTAIDANKASADTKFAATADAITKNGNAITKNAKSITDLGTKVDGFDSRVTAL
DTK SEQ ID NO: 56
ATGCAGGCCAAAAATGATATTACCCTGGAAGATCTGCCGTATCTGATCAAAAAAATCGATCAG
AACGAACTGGAAGCCGATATTGGTGATATTACCGCACTGGAAAAATATCTGGCACTGAGCCAG
TATGGAAATATTCTGGCCCTGGAAGAACTGAATAAAGCTCTGGAAGAGCTGGATGAAGATGTG
GGTTGGAATCAGAATGATATCGCCAATCTGGAAGATGATGTTGAAACCCTGACCAAAAATCAG
AATGCACTGGCAGAACAGGGTGAAGCAATTAAAGAAGATCTGCAGGGTCTGGCAGATTTTGTT
GAAGGTCAGGAAGGCAAAATTCTGCAGAACGAAACCAGCATCAAAAAAAACACCCAGCGTAAT

PROTEIN CONSTRUCT SEQUENCES:

```
CTGGTGAATGGCTTTGAAATTGAAAAAAACAAAGATGCCATTGCCAAAAACAACGAAAGCATT
GAAGATCTGTATGATTTTGGTCATGAAGTTGCCGAAAGCATTGGTGAAATTCATGCACATAAC
GAAGCACAGAATGAAACCCTGAAAGGTCTGATTACCAACAGCATCGAAAATACCAATAACATT
ACCAAAAACAAAGCAGATATTCAGGCGCTGGAAAATAATGTTGTGGAAGAACTGTTTAATCTG
AGCGGTCGTCTGATTGATCAGAAAGCCGATATCGATAATAACATTAACAACATTTATGAACTG
GCACAGCAGCAGGATCAGCATAGCAGCGATATCAAAACCCTGAAAAAAAACGTTGAAGAAGGT
CTGCTGGAACTGTCTGGTCACCTGATCGATCAGAAAACTGATATTGCCCAGAATCAGGCAAAT
ATTCAGGATCTGGCCACCTATAATGAACTGCAGGATCAGTATGCACAGAAACAGACCGAAGCA
ATTGATGCCCTGAATAAAGCGAGCAGCGAAAACACCCAGAATATCGAAGATCTGGCAGCATAC
AACGAACTGCAGGATGCCTATGCAAAACAGCAGACTGAAGCCATCGACGCACTGAACAAGGCA
AGCTCTGAAAACACGCAGAACATTGAAGATCTGGCTGCCTATAATGAATTACAGGATGCGTAT
GCCAAACAGCAGACCGAAGCGATTGATGCGCTGAACAAAGCCTCTTCTGAAAATACACAGAAT
ATCGCCAAAAATCAGGCCGATATTGCCAACAATATCAATAATATCTATGAACTGGCCCAGCAG
CAGGATCAGCACTCTTCTGATATCAAAACACTGGCAAAGCAAGCGCAGCAAATACCGATCGT
ATTGCGAAAACAAAGCCGATGCAGATGCAAGCTTTGAAACACTGACGAAAAACCAGAACACC
CTGATTGAAAAAGATAAAGAACATGATAAACTGATCACCGCCAATAAAACCGCAATTGATGCA
AATAAAGCCAGCGCAGATACCAAATTTGCAGCAACCGCAGATGCAATTACCAAAAATGGCAAT
GCCATCACCAAAAATGCCAAAGCATTACCGATCTGGGCACCAAAGTTGATGGTTTTGATAGC
CGTGTGACCGCACTGGATACCAAAGTTAATGCATTTGATGGTCGTATTACCGCTCTGGATAGT
AAAGTTGAAAATGGAATGGCAGCACAAGCAGCACACTAA

SEQ ID NO: 57
MQAKNDITLEDLPYLIKKIDQNELEADIGDITALEKYLALSQYGNILALEELNKALEELDEDV
GWNQNDIANLEDDVETLTKNQNALAEQGEAIKEDLQGLADFVEGQEGKILQNETSIKKNTQRN
LVNGFEIEKNKDAIAKNNESIEDLYDFGHEVAESIGEIHAHNEAQNETLKGLITNSIENTNNI
TKNKADIQALENNVVEELFNLSGRLIDQKADIDNNINNIYELAQQQDQHSSDIKTLKKNVEEG
LLELSGHLIDQKTDIAQNQANIQDLATYNELQDQYAQKQTEAIDALNKASSENTQNIEDLAAY
NELQDAYAKQQTEAIDALNKASSENTQNIEDLAAYNELQDAYAKQQTEAIDALNKASSENTQN
IAKNQADIANNINNIYELAQQQDQHSSDIKTLAKASAANTDRIAKNKADADASFETLTKNQNT
LIEKDKEHDKLITANKTAIDANKASADTKFAATADAITKNGNAITKNAKSITDLGTKVDGFDS
RVTALDTKVNAFDGRITALDSKVENGMAAQAAH

MC-003 (DNA)-SEQ ID NO: 87
ATGCAGGCCAAAAATGATATTACCCTGGAAGATCTGCCGTATCTGATCAAAAAAATCGATCAG
AACGAACTGGAAGCCGATATTGGTGATATTACCGCACTGGAAAAATATCTGGCACTGAGCCAG
TATGGAAATATTCTGGCCCTGGAAGAACTGAATAAAGCTCTGGAAGAGCTGGATGAAGATGTG
GGTTGGAATCAGAATGATATCGCCAATCTGGAAGATGATGTTGAAACCCTGACCAAAAATCAG
AATGCACTGGCAGAACAGGGTGAAGCAATTAAAGAAGATCTGCAGGGTCTGGCAGATTTTGTT
GAAGGTCAGGAAGGCAAAATTCTGCAGAACGAAACCAGCATCAAAAAAAACACCCAGCGTAAT
CTGGTGAATGGCTTTGAAATTGAAAAAAACAAAGATGCCATTGCCAAAAACAACGAAAGCATT
GAAGATCTGTATGATTTTGGTCATGAAGTTGCCGAAAGCATTGGTGAAATTCATGCACATAAC
GAAGCACAGAATGAAACCCTGAAAGGTCTGATTACCAACAGCATCGAAAATACCAATAACATT
ACCAAAAACAAAGCAGATATTCAGGCGCTGGAAAATAATGTTGTGGAAGAACTGTTTAATCTG
AGCGGTCGTCTGATTGATCAGAAAGCCGATATCGATAATAACATTAACAACATTTATGAACTG
GCACAGCAGCAGGATCAGCATAGCAGCGATATCAAAACCCTGAAAAAAAACGTTGAAGAAGGT
CTGCTGGAACTGTCTGGTCACCTGATCGATCAGAAAACTGATATTGCCCAGAATCAGGCAAAT
ATTCAGGATCTGGCCACCTATAATGAACTGCAGGATCAGTATGCACAGAAACAGACCGAAGCA
ATTGATGCCCTGAATAAAGCGAGCAGCGAAAACACCCAGAATATCGAAGATCTGGCAGCATAC
AACGAACTGCAGGATGCCTATGCAAAACAGCAGACTGAAGCCATCGACGCACTGAACAAGGCA
AGCTCTGAAAACACGCAGAACATTGAAGATCTGGCTGCCTATAATGAATTACAGGATGCGTAT
GCCAAACAGCAGACCGAAGCGATTGATGCGCTGAACAAAGCCTCTTCTGAAAATACACAGAAT
ATCGCCAAAAATCAGGCCGATATTGCCAACAATATCAATAATATCTATGAACTGGCCCAGCAG
CAGGATCAGCACTCTTCTGATATCAAAACACTGGCAAAGCAAGCGCAGCAAATACCGATCGT
ATTGCGAAAACAAAGCCGATGCAGATGCAAGCTTTGAAACACTGACGAAAAACCAGAACACC
CTGATTGAAAAAGATAAAGAACATGATAAACTGATCACCGCCAATAAAACCGCAATTGATGCA
AATAAAGCCAGCGCAGATACCAAATTTGCAGCAACCGCAGATGCAATTACCAAAAATGGCAAT
GCCATCACCAAAAATGCCAAAGCATTACCGATCTGGGCACCAAAGTTGATGGTTTTGATAGC
CGTGTGACCGCACTGGATACCAAACACTAA

MC-003 (Protein)-(M)(UspA2 amino acids 30-540)(H)-SEQ ID NO: 88
MQAKNDITLEDLPYLIKKIDQNELEADIGDITALEKYLALSQYGNILALEELNKALEELDEDV
GWNQNDIANLEDDVETLTKNQNALAEQGEAIKEDLQGLADFVEGQEGKILQNETSIKKNTQRN
LVNGFEIEKNKDAIAKNNESIEDLYDFGHEVAESIGEIHAHNEAQNETLKGLITNSIENTNNI
TKNKADIQALENNVVEELFNLSGRLIDQKADIDNNINNIYELAQQQDQHSSDIKTLKKNVEEG
LLELSGHLIDQKTDIAQNQANIQDLATYNELQDQYAQKQTEAIDALNKASSENTQNIEDLAAY
NELQDAYAKQQTEAIDALNKASSENTQNIEDLAAYNELQDAYAKQQTEAIDALNKASSENTQN
IAKNQADIANNINNIYELAQQQDQHSSDIKTLAKASAANTDRIAKNKADADASFETLTKNQNT
LIEKDKEHDKLITANKTAIDANKASADTKFAATADAITKNGNAITKNAKSITDLGTKVDGFDS
RVTALDTKH MC-004 (DNA)-SEQ ID NO: 58
ATGCAGGCCAAAAATGATATTACCCTGGAAGATCTGCCGTATCTGATCAAAAAAATCGATCAG
AACGAACTGGAAGCCGATATTGGTGATATTACCGCACTGGAAAAATATCTGGCACTGAGCCAG
TATGGAAATATTCTGGCCCTGGAAGAACTGAATAAAGCTCTGGAAGAGCTGGATGAAGATGTG
GGTTGGAATCAGAATGATATCGCCAATCTGGAAGATGATGTTGAAACCCTGACCAAAAATCAG
AATGCACTGGCAGAACAGGGTGAAGCAATTAAAGAAGATCTGCAGGGTCTGGCAGATTTTGTT
GAAGGTCAGGAAGGCAAAATTCTGCAGAACGAAACCAGCATCAAAAAAAACACCCAGCGTAAT
```

| PROTEIN CONSTRUCT SEQUENCES: |
|---|
| CTGGTGAATGGCTTTGAAATTGAAAAAAACAAAGATGCCATTGCCAAAAACAACGAAAGCATT<br>GAAGATCTGTATGATTTTGGTCATGAAGTTGCCGAAAGCATTGGTGAAATTCATGCACATAAC<br>GAAGCACAGAATGAAACCCTGAAAGGTCTGATTACCAACAGCATCGAAAATACCAATAACATT<br>ACCAAAAACAAAGCAGATATTCAGGCGCTGGAAAATAATGTTGTGGAAGAACTGTTTAATCTG<br>AGCGGTCGTCTGATTGATCAGAAAGCCGATATCGATAATAACATTAACAACATTTATGAACTG<br>GCACAGCAGCAGGATCAGCATAGCAGCGATATCAAAACCCTGAAAAAAAACGTTGAAGAAGGT<br>CTGCTGGAACTGTCTGGTCACCTGATCGATCAGAAAACTGATATTGCCCAGATCAGGCAAAT<br>ATTCAGGATCTGGCCACCTATAATGAACTGCAGGATCAGTATGCACAGAAACAGACCGAAGCA<br>ATTGATGCCCTGAATAAAGCGAGCAGCGAAAACACCCAGAATATCGAAGATCTGGCAGCATAC<br>AACGAACTGCAGGATGCCTATGCAAAACAGCAGACTGAAGCCATCGACGCACTGAACAAGGCA<br>AGCTCTGAAAACACGCAGAACATTGAAGATCTGGCTGCCTATAATGAATTACAGGATGCGTAT<br>GCCAAACAGCAGACCGAAGCGATTGATGCGCTGAACAAAGCCTCTTCTGAAAATACACAGAAT<br>ATCGCCAAAAATCAGGCCGATATTGCCAACAATATCAATAATATCTATGAACTGGCCCAGCAG<br>CAGGATCAGCACTCTTCTGATATCAAAACACTGGCAAAAGCAAGCGCAGCAAATACCGATCGT<br>ATTGCGAAAAACAAAGCCGATGCAGATGCAAGCTTTGAAACACTGACGAAAAACCAGAACACC<br>CTGATTGAAAAAGATAAAGAACATGATAAACTGATCACCGCCAATAAAACCGCAATTGATGCA<br>AATAAAGCCAGCGCAGATACCAAATTTGCAGCAACCGCAGATGCAATTACCAAAAATGGCAAT<br>GCCATCACCAAAAATGCCAAAAGCATTACCGATCTGGGCACCAAAGTTGATGGTTTTGATAGC<br>CGTGTGACCGCACTGGATACCAAACATCATTAA |

MC-004 (Protein)-(M)(UspA2 amino acids 30-540)(HH) SEQ ID NO: 59
MQAKNDITLEDLPYLIKKIDQNELEADIGDITALEKYLALSQYGNILALEELNKALEELDEDV
GWNQNDIANLEDDVETLTKNQNALAEQGEAIKEDLQGLADFVEGQEGKILQNETSIKKNTQRN
LVNGFEIEKNKDAIAKNNESIEDLYDFGHEVAESIGEIHAHNEAQNETLKGLITNSIENTNNI
TKNKADIQALENNVVEELFNLSGRLIDQKADIDNNINNIYELAQQQDQHSSDIKTLKKNVEEG
LLELSGHLIDQKTDIAQNQANIQDLATYNELQDQYAQKQTEAIDALNKASSENTQNIEDLAAY
NELQDAYAKQQTEAIDALNKASSENTQNIEDLAAYNELQDAYAKQQTEAIDALNKASSENTQN
IAKNQADIANNINNIYELAQQQDQHSSDIKTLAKASAANTDRIAKNKADADASFETLTKNQNT
LIEKDKEHDKLITANKTAIDANKASADTKFAATADAITKNGNAITKNAKSITDLGTKVDGFDS
RVTALDTKHH MC-005 (DNA)-SEQ ID NO: 60
ATGCAGGCCAAAAATGATATTACCCTGGAAGATCTGCCGTATCTGATCAAAAAAATCGATCAG
AACGAACTGGAAGCCGATATTGGTGATATTACCGCACTGGAAAAATATCTGGCACTGAGCCAG
TATGGAAATATTCTGGCCCTGGAAGAACTGAATAAAGCTCTGGAAGAGCTGGATGAAGATGTG
GGTTGGAATCAGAATGATATCGCCAATCTGGAAGATGATGTTGAAACCCTGACCAAAAATCAG
AATGCACTGGCAGAACAGGGTGAAGCAATTAAAGAAGATCTGCAGGGTCTGGCAGATTTTGTT
GAAGGTCAGGAAGGCAAATTCTGCAGAACGAAACCAGCATCAAAAAAAACACCCAGCGTAAT
CTGGTGAATGGCTTTGAAATTGAAAAAAACAAAGATGCCATTGCCAAAAACAACGAAAGCATT
GAAGATCTGTATGATTTTGGTCATGAAGTTGCCGAAAGCATTGGTGAAATTCATGCACATAAC
GAAGCACAGAATGAAACCCTGAAAGGTCTGATTACCAACAGCATCGAAAATACCAATAACATT
ACCAAAAACAAAGCAGATATTCAGGCGCTGGAAAATAATGTTGTGGAAGAACTGTTTAATCTG
AGCGGTCGTCTGATTGATCAGAAAGCCGATATCGATAATAACATTAACAACATTTATGAACTG
GCACAGCAGCAGGATCAGCATAGCAGCGATATCAAAACCCTGAAAAAAAACGTTGAAGAAGGT
CTGCTGGAACTGTCTGGTCACCTGATCGATCAGAAAACTGATATTGCCCAGATCAGGCAAAT
ATTCAGGATCTGGCCACCTATAATGAACTGCAGGATCAGTATGCACAGAAACAGACCGAAGCA
ATTGATGCCCTGAATAAAGCGAGCAGCGAAAACACCCAGAATATCGAAGATCTGGCAGCATAC
AACGAACTGCAGGATGCCTATGCAAAACAGCAGACTGAAGCCATCGACGCACTGAACAAGGCA
AGCTCTGAAAACACGCAGAACATTGAAGATCTGGCTGCCTATAATGAATTACAGGATGCGTAT
GCCAAACAGCAGACCGAAGCGATTGATGCGCTGAACAAAGCCTCTTCTGAAAATACACAGAAT
ATCGCCAAAAATCAGGCCGATATTGCCAACAATATCAATAATATCTATGAACTGGCCCAGCAG
CAGGATCAGCACTCTTCTGATATCAAAACACTGGCAAAAGCAAGCGCAGCAAATACCGATCGT
ATTGCGAAAAACAAAGCCGATGCAGATGCAAGCTTTGAAACACTGACGAAAAACCAGAACACC
CTGATTGAAAAAGATAAAGAACATGATAAACTGATCACCGCCAATAAAACCGCAATTGATGCA
AATAAAGCCAGCGCAGATACCAAATTTGCAGCAACCGCAGATGCAATTACCAAAAATGGCAAT
GCCATCACCAAAAATGCCAAAAGCGCAAGCCATCATCATCACCACCACTAA MC-005 (Protein)-(M)(UspA2 amino acids 30-519)(ASHHHHHH) SEQ ID NO: 61
MQAKNDITLEDLPYLIKKIDQNELEADIGDITALEKYLALSQYGNILALEELNKALEELDEDV
GWNQNDIANLEDDVETLTKNQNALAEQGEAIKEDLQGLADFVEGQEGKILQNETSIKKNTQRN
LVNGFEIEKNKDAIAKNNESIEDLYDFGHEVAESIGEIHAHNEAQNETLKGLITNSIENTNNI
TKNKADIQALENNVVEELFNLSGRLIDQKADIDNNINNIYELAQQQDQHSSDIKTLKKNVEEG
LLELSGHLIDQKTDIAQNQANIQDLATYNELQDQYAQKQTEAIDALNKASSENTQNIEDLAAY
NELQDAYAKQQTEAIDALNKASSENTQNIEDLAAYNELQDAYAKQQTEAIDALNKASSENTQN
IAKNQADIANNINNIYELAQQQDQHSSDIKTLAKASAANTDRIAKNKADADASFETLTKNQNT
LIEKDKEHDKLITANKTAIDANKASADTKFAATADAITKNGNAITKNAKSASHHHHHH MC-006 (DNA)-SEQ ID NO: 62
ATGCAGGCCAAAAATGATATTACCCTGGAAGATCTGCCGTATCTGATCAAAAAAATCGATCAG
AACGAACTGGAAGCCGATATTGGTGATATTACCGCACTGGAAAAATATCTGGCACTGAGCCAG
TATGGAAATATTCTGGCCCTGGAAGAACTGAATAAAGCTCTGGAAGAGCTGGATGAAGATGTG
GGTTGGAATCAGAATGATATCGCCAATCTGGAAGATGATGTTGAAACCCTGACCAAAAATCAG
AATGCACTGGCAGAACAGGGTGAAGCAATTAAAGAAGATCTGCAGGGTCTGGCAGATTTTGTT
GAAGGTCAGGAAGGCAAATTCTGCAGAACGAAACCAGCATCAAAAAAAACACCCAGCGTAAT
CTGGTGAATGGCTTTGAAATTGAAAAAAACAAAGATGCCATTGCCAAAAACAACGAAAGCATT
GAAGATCTGTATGATTTTGGTCATGAAGTTGCCGAAAGCATTGGTGAAATTCATGCACATAAC
GAAGCACAGAATGAAACCCTGAAAGGTCTGATTACCAACAGCATCGAAAATACCAATAACATT -continued

| PROTEIN CONSTRUCT SEQUENCES: |
|---|
| ACCAAAAACAAAGCAGATATTCAGGCGCTGGAAAATAATGTTGTGGAAGAACTGTTTAATCTG |
| AGCGGTCGTCTGATTGATCAGAAAGCCGATATCGATAATAACATTAACAACATTTATGAACTG |
| GCACAGCAGCAGGATCAGCATAGCAGCGATATCAAAACCCTGAAAAAAACGTTGAAGAAGGT |
| CTGCTGGAACTGTCTGGTCACCTGATCGATCAGAAAACTGATATTGCCCAGAATCAGGCAAAT |
| ATTCAGGATCTGGCCACCTATAATGAACTGCAGGATCAGTATGCACAGAAACAGACCGAAGCA |
| ATTGATGCCCTGAATAAAGCGAGCAGCGAAAACACCCAGAATATCGAAGATCTGGCAGCATAC |
| AACGAACTGCAGGATGCCTATGCAAAACAGCAGACTGAAGCCATCGACGCACTGAACAAGGCA |
| AGCTCTGAAAACACGCAGAACATTGAAGATCTGGCTGCCTATAATGAATTACAGGATGCGTAT |
| GCCAAACAGCAGACCGAAGCGATTGATGCGCTGAACAAAGCCTCTTCTGAAAATACACAGAAT |
| ATCGCCAAAAATCAGGCCGATATTGCCAACAATATCAATAATATCTATGAACTGGCCCAGCAG |
| CAGGATCAGCACTCTTCTGATATCAAAACACTGGCAAAAGCAAGCGCAGCAAATACCGATCGT |
| ATTGCGAAAAACAAAGCCGATGCAGATGCAAGCTTTGAAACACTGACGAAAAACCAGAACACC |
| CTGATTGAAAAAGATAAAGAACATGATAAACTGATCACCGCCAATAAAACCGCAATTGATGCA |
| AATAAAGCCAGCGCAGATACCAAATTTGCAGCAACCGCAGATGCAATTACCAAAAATGGCAAT |
| GCCATCACCAAAAATGCCAAAAGCTAA |

MC-006 (Protein)-(M)(UspA2 amino acids 30-519) SEQ ID NO: 63
MQAKNDITLEDLPYLIKKIDQNELEADIGDITALEKYLALSQYGNILALEELNKALEELDEDV
GWNQNDIANLEDDVETLTKNQNALAEQGEAIKEDLQGLADFVEGQEGKILQNETSIKKNTQRN
LVNGFEIEKNKDAIAKNNESIEDLYDFGHEVAESIGEIHAHNEAQNETLKGLITNSIENTNNI
TKNKADIQALENNVVEELFNLSGRLIDQKADIDNNINNIYELAQQQDQHSSDIKTLKKNVEEG
LLELSGHLIDQKTDIAQNQANIQDLATYNELQDQYAQKQTEAIDALNKASSENTQNIEDLAAY
NELQDAYAKQQTEAIDALNKASSENTQNIEDLAAYNELQDAYAKQQTEAIDALNKASSENTQN
IAKNQADIANNINNIYELAQQQDQHSSDIKTLAKASAANTDRIAKNKADADASFETLTKNQNT
LIEKDKEHDKLITANKTAIDANKASADTKFAATADAITKNGNAITKNAKS MC-007 (DNA)-SEQ ID NO: 64
ATGCAGGCCAAAAATGATATTACCCTGGAAGATCTGCCGTATCTGATCAAAAAAATCGATCAG
AACGAACTGGAAGCCGATATTGGTGATATTACCGCACTGGAAAAATATCTGGCACTGAGCCAG
TATGGAAATATTCTGGCCCTGGAAGAACTGAATAAAGCTCTGGAAGAGCTGGATGAAGATGTG
GGTTGGAATCAGAATGATATCGCCAATCTGGAAGATGATGTTGAAACCCTGACCAAAAATCAG
AATGCACTGGCAGAACAGGGTGAAGCAATTAAAGAAGATCTGCAGGGTCTGGCAGATTTTGTT
GAAGGTCAGGAAGGCAAAATTCTGCAGAACGAAACCAGCATCAAAAAAAACACCCAGCGTAAT
CTGGTGAATGGCTTTGAAATTGAAAAAAACAAAGATGCCATTGCCAAAAACAACGAAAGCATT
GAAGATCTGTATGATTTTGGTCATGAAGTTGCCGAAAGCATTGGTGAAATTCATGCACATAAC
GAAGCACAGAATGAAACCCTGAAAGGTCTGATTACCAACAGCATCGAAAATACCAATAACATT
ACCAAAAACAAAGCAGATATTCAGGCGCTGGAAAATAATGTTGTGGAAGAACTGTTTAATCTG
AGCGGTCGTCTGATTGATCAGAAAGCCGATATCGATAATAACATTAACAACATTTATGAACTG
GCACAGCAGCAGGATCAGCATAGCAGCGATATCAAAACCCTGAAAAAAACGTTGAAGAAGGT
CTGCTGGAACTGTCTGGTCACCTGATCGATCAGAAAACTGATATTGCCCAGAATCAGGCAAAT
ATTCAGGATCTGGCCACCTATAATGAACTGCAGGATCAGTATGCACAGAAACAGACCGAAGCA
ATTGATGCCCTGAATAAAGCGAGCAGCGAAAACACCCAGAATATCGAAGATCTGGCAGCATAC
AACGAACTGCAGGATGCCTATGCAAAACAGCAGACTGAAGCCATCGACGCACTGAACAAGGCA
AGCTCTGAAAACACGCAGAACATTGAAGATCTGGCTGCCTATAATGAATTACAGGATGCGTAT
GCCAAACAGCAGACCGAAGCGATTGATGCGCTGAACAAAGCCTCTTCTGAAAATACACAGAAT
ATCGCCAAAAATCAGGCCGATATTGCCAACAATATCAATAATATCTATGAACTGGCCCAGCAG
CAGGATCAGCACTCTTCTGATATCAAAACACTGGCAAAAGCAAGCGCAGCAAATACCGATCGT
ATTGCGAAAAACAAAGCCGATGCAGATGCAAGCTTTGAAACACTGACGAAAAACCAGAACACC
CTGATTGAAAAAGATAAAGAACATGATAAACTGATCACCGCCAATAAAACCGCAATTGATGCA
AATAAAGCCAGCGCAGATACCAAATTTGCAGCAACCGCAGATGCAATTACCAAAAATGGCAAT
GCCATCACCAAAAATGCCAAAAGCATTACCGATCTGGGCACCAAAGTTGATGGTTTTGATAGC
CGTGTGACCGCACTGGATACCAAAGTTAATGCATTTGATGGTCGTATTACCGCTCTGGATAGT
AAAGTTGAAAATGGTATGGCAGCACAGGCAGCAGCAAGCCATCATCATCACCACCACTAA MC-007 (Protein)-(M)(UspA2 amino acids 30-564)(ASHHHHHH) SEQ ID NO: 65
MQAKNDITLEDLPYLIKKIDQNELEADIGDITALEKYLALSQYGNILALEELNKALEELDEDV
GWNQNDIANLEDDVETLTKNQNALAEQGEAIKEDLQGLADFVEGQEGKILQNETSIKKNTQRN
LVNGFEIEKNKDAIAKNNESIEDLYDFGHEVAESIGEIHAHNEAQNETLKGLITNSIENTNNI
TKNKADIQALENNVVEELFNLSGRLIDQKADIDNNINNIYELAQQQDQHSSDIKTLKKNVEEG
LLELSGHLIDQKTDIAQNQANIQDLATYNELQDQYAQKQTEAIDALNKASSENTQNIEDLAAY
NELQDAYAKQQTEAIDALNKASSENTQNIEDLAAYNELQDAYAKQQTEAIDALNKASSENTQN
IAKNQADIANNINNIYELAQQQDQHSSDIKTLAKASAANTDRIAKNKADADASFETLTKNQNT
LIEKDKEHDKLITANKTAIDANKASADTKFAATADAITKNGNAITKNAKSITDLGTKVDGFDS
RVTALDTKVNAFDGRITALDSKVENGMAAQAAASHHHHHH MC-008 (DNA)-SEQ ID NO: 66
ATGCAGGCCAAAAATGATATTACCCTGGAAGATCTGCCGTATCTGATCAAAAAAATCGATCAG
AACGAACTGGAAGCCGATATTGGTGATATTACCGCACTGGAAAAATATCTGGCACTGAGCCAG
TATGGAAATATTCTGGCCCTGGAAGAACTGAATAAAGCTCTGGAAGAGCTGGATGAAGATGTG
GGTTGGAATCAGAATGATATCGCCAATCTGGAAGATGATGTTGAAACCCTGACCAAAAATCAG
AATGCACTGGCAGAACAGGGTGAAGCAATTAAAGAAGATCTGCAGGGTCTGGCAGATTTTGTT
GAAGGTCAGGAAGGCAAAATTCTGCAGAACGAAACCAGCATCAAAAAAAACACCCAGCGTAAT
CTGGTGAATGGCTTTGAAATTGAAAAAAACAAAGATGCCATTGCCAAAAACAACGAAAGCATT
GAAGATCTGTATGATTTTGGTCATGAAGTTGCCGAAAGCATTGGTGAAATTCATGCACATAAC
GAAGCACAGAATGAAACCCTGAAAGGTCTGATTACCAACAGCATCGAAAATACCAATAACATT
ACCAAAAACAAAGCAGATATTCAGGCGCTGGAAAATAATGTTGTGGAAGAACTGTTTAATCTG
AGCGGTCGTCTGATTGATCAGAAAGCCGATATCGATAATAACATTAACAACATTTATGAACTG

PROTEIN CONSTRUCT SEQUENCES:

GCACAGCAGCAGGATCAGCATAGCAGCGATATCAAAACCCTGAAAAAAAACGTTGAAGAAGGT
CTGCTGGAACTGTCTGGTCACCTGATCGATCAGAAAACTGATATTGCCCAGAATCAGGCAAAT
ATTCAGGATCTGGCCACCTATAATGAACTGCAGGATCAGTATGCACAGAAACAGACCGAAGCA
ATTGATGCCCTGAATAAAGCGAGCAGCGAAAACACCCAGAATATCGAAGATCTGGCAGCATAC
AACGAACTGCAGGATGCCTATGCAAAACAGCAGACTGAAGCCATCGACGCACTGAACAAGGCA
AGCTCTGAAAACACGCAGAACATTGAAGATCTGGCTGCCTATAATGAATTACAGGATGCGTAT
GCCAAACAGCAGACCGAAGCGATTGATGCGCTGAACAAAGCCTCTTCTGAAAATACACAGAAT
ATCGCCAAAAATCAGGCCGATATTGCCAACAATATCAATAATATCTATGAACTGGCCCAGCAG
CAGGATCAGCACTCTTCTGATATCAAAACACTGGCAAAAGCAAGCGCAGCAAATACCGATCGT
ATTGCGAAAAACAAGCCGATGCAGATGCAAGCTTTGAAACACTGACGAAAAACCAGAACACC
CTGATTGAAAAAGATAAAGAACATGATAAACTGATCACCGCCAATAAAACCGCAATTGATGCA
AATAAAGCCAGCGCAGATACCAAATTTGCAGCAACCGCAGATGCAATTACCAAAAATGGCAAT
GCCATCACCAAAAATGCCAAAAGCATTACCGATCTGGGCACCAAAGTTGATGGTTTTGATAGC
CGTGTGACCGCACTGGATACCAAAGTTAATGCATTTGATGGTCGTATTACCGCTCTGGATAGT
AAAGTTGAAAATGGTATGGCAGCACAGGCAGCACACCACTAA

MC-008 (Protein)-(M)(UspA2 30-564)(HH) SEQ ID NO: 67
MQAKNDITLEDLPYLIKKIDQNELEADIGDITALEKYLALSQYGNILALEELNKALEELDEDV
GWNQNDIANLEDDVETLTKNQNALAEQGEAIKEDLQGLADFVEGQEGKILQNETSIKKNTQRN
LVNGFEIEKNKDAIAKNNESIEDLYDFGHEVAESIGEIHAHNEAQNETLKGLITNSIENTNNI
TKNKADIQALENNVVEELFNLSGRLIDQKADIDNNINNIYELAQQQDQHSSDIKTLKKNVEEG
LLELSGHLIDQKTDIAQNQANIQDLATYNELQDQYAQKQTEAIDALNKASSENTQNIEDLAAY
NELQDAYAKQQTEAIDALNKASSENTQNIEDLAAYNELQDAYAKQQTEAIDALNKASSENTQN
IAKNQADIANNINNIYELAQQQDQHSSDIKTLAKASAANTDRIAKNKADADASFETLTKNQNT
LIEKDKEHDKLITANKTAIDANKASADTKFAATADAITKNGNAITKNAKSITDLGTKVDGFDS
RVTALDTKVNAFDGRITALDSKVENGMAAQAAHH MC-009 (DNA)-SEQ ID NO: 68
ATGGCGAAAAATGATATTACCCTGGAAGATCTGCCGTATCTGATCAAAAAAATCGATCAGAAC
GAACTGGAAGCCGATATTGGTGATATTACCGCACTGGAAAAATATCTGGCACTGAGCCAGTAT
GGAAATATTCTGGCCCTGGAAGAACTGAATAAAGCTCTGGAAGAGCTGGATGAAGATGTGGGT
TGGAATCAGAATGATATCGCCAATCTGGAAGATGATGTTGAAACCCTGACCAAAAATCAGAAT
GCACTGGCAGAACAGGGTGAAGCAATTAAAGAAGATCTGCAGGGTCTGGCAGATTTTGTTGAA
GGTCAGGAAGGCAAATTCTGCAGAACGAAACCAGCATCAAAAAAAACACCCAGCGTAATCTG
GTGAATGGCTTTGAAATTGAAAAAAACAAAGATGCCATTGCCAAAAACAACGAAAGCATTGAA
GATCTGTATGATTTTGGTCATGAAGTTGCCGAAAGCATTGGTGAAATTCATGCACATAACGAA
GCACAGAATGAAACCCTGAAAGGTCTGATTACCAACAGCATCGAAAATACCAATAACATTACC
AAAAACAAAGCAGATATTCAGGCGCTGGAAAATAATGTTGTGGAAGAACTGTTTAATCTGAGC
GGTCGTCTGATTGATCAGAAAGCCGATATCGATAATAACATTAACAACATTTATGAACTGGCA
CAGCAGCAGGATCAGCATAGCAGCGATATCAAAACCCTGAAAAAAAACGTTGAAGAAGGTCTG
CTGGAACTGTCTGGTCACCTGATCGATCAGAAAACTGATATTGCCCAGAATCAGGCAAATATT
CAGGATCTGGCCACCTATAATGAACTGCAGGATCAGTATGCACAGAAACAGACCGAAGCAATT
GATGCCCTGAATAAAGCGAGCAGCGAAAACACCCAGAATATCGAAGATCTGGCAGCATACAAC
GAACTGCAGGATGCCTATGCAAAACAGCAGACTGAAGCCATCGACGCACTGAACAAGGCAAGC
TCTGAAAACACGCAGAACATTGAAGATCTGGCTGCCTATAATGAATTACAGGATGCGTATGCC
AAACAGCAGACCGAAGCGATTGATGCGCTGAACAAAGCCTCTTCTGAAAATACACAGAATATC
GCCAAAAATCAGGCCGATATTGCCAACAATATCAATAATATCTATGAACTGGCCCAGCAGCAG
GATCAGCACTCTTCTGATATCAAAACACTGGCAAAAGCAAGCGCAGCAAATACCGATCGTATT
GCGAAAAACAAGCCGATGCAGATGCAAGCTTTGAAACACTGACGAAAAACCAGAACACCCTG
ATTGAAAAAGATAAAGAACATGATAAACTGATCACCGCCAATAAAACCGCAATTGATGCAAAT
AAAGCCAGCGCAGATACCAAATTTGCAGCAACCGCAGATGCAATTACCAAAAATGGCAATGCC
ATCACCAAAAATGCCAAAAGCATTACCGATCTGGGCACCAAAGTTGATGGTTTTGATAGCCGT
GTGACCGCACTGGATACCAAAGTTAATGCATTTGATGGTCGTATTACCGCTCTGGATAGTAAA
GTTGAAAATGGTATGGCAGCACAGGCAGCACACCACTAA MC-009 (Protein)-(M)(UspA2 31-564)(HH) SEQ ID NO: 69
MAKNDITLEDLPYLIKKIDQNELEADIGDITALEKYLALSQYGNILALEELNKALEELDEDVG
WNQNDIANLEDDVETLTKNQNALAEQGEAIKEDLQGLADFVEGQEGKILQNETSIKKNTQRNL
VNGFEIEKNKDAIAKNNESIEDLYDFGHEVAESIGEIHAHNEAQNETLKGLITNSIENTNNIT
KNKADIQALENNVVEELFNLSGRLIDQKADIDNNINNIYELAQQQDQHSSDIKTLKKNVEEGL
LELSGHLIDQKTDIAQNQANIQDLATYNELQDQYAQKQTEAIDALNKASSENTQNIEDLAAYN
ELQDAYAKQQTEAIDALNKASSENTQNIEDLAAYNELQDAYAKQQTEAIDALNKASSENTQNI
AKNQADIANNINNIYELAQQQDQHSSDIKTLAKASAANTDRIAKNKADADASFETLTKNQNTL
IEKDKEHDKLITANKTAIDANKASADTKFAATADAITKNGNAITKNAKSITDLGTKVDGFDSR
VTALDTKVNAFDGRITALDSKVENGMAAQAAHH MC-010 (DNA)-SEQ ID NO: 70
ATGCAGGCCAAAAATGATATTACCCTGGAAGATCTGCCGTATCTGATCAAAAAAATCGATCAG
AACGAACTGGAAGCCGATATTGGTGATATTACCGCACTGGAAAAATATCTGGCACTGAGCCAG
TATGGAAATATTCTGGCCCTGGAAGAACTGAATAAAGCTCTGGAAGAGCTGGATGAAGATGTG
GGTTGGAATCAGAATGATATCGCCAATCTGGAAGATGATGTTGAAACCCTGACCAAAAATCAG
AATGCACTGGCAGAACAGGGTGAAGCAATTAAAGAAGATCTGCAGGGTCTGGCAGATTTTGTT
GAAGGTCAGGAAGGCAAATTCTGCAGAACGAAACCAGCATCAAAAAAAACACCCAGCGTAAT
CTGGTGAATGGCTTTGAAATTGAAAAAAACAAAGATGCCATTGCCAAAAACAACGAAAGCATT
GAAGATCTGTATGATTTTGGTCATGAAGTTGCCGAAAGCATTGGTGAAATTCATGCACATAAC
GAAGCACAGAATGAAACCCTGAAAGGTCTGATTACCAACAGCATCGAAAATACCAATAACATT
ACCAAAAACAAAGCAGATATTCAGGCGCTGGAAAATAATGTTGTGGAAGAACTGTTTAATCTG

PROTEIN CONSTRUCT SEQUENCES:

```
AGCGGTCGTCTGATTGATCAGAAAGCCGATATCGATAATAACATTAACAACATTTATGAACTG
GCACAGCAGCAGGATCAGCATAGCAGCGATATCAAAACCCTGAAAAAAACGTTGAAGAAGGT
CTGCTGGAACTGTCTGGTCACCTGATCGATCAGAAAACTGATATTGCCCAGAATCAGGCAAAT
ATTCAGGATCTGGCCACCTATAATGAACTGCAGGATCAGTATGCACAGAAACAGACCGAAGCA
ATTGATGCCCTGAATAAAGCGAGCAGCGAAAACACCCAGAATATCGAAGATCTGGCAGCATAC
AACGAACTGCAGGATGCCTATGCAAAACAGCAGACTGAAGCCATCGACGCACTGAACAAGGCA
AGCTCTGAAAACACGCAGAACATTGAAGATCTGGCTGCCTATAATGAATTACAGGATGCGTAT
GCCAAACAGCAGACCGAAGCGATTGATGCGCTGAACAAAGCCTCTTCTGAAAATACACAGAAT
ATCGCCAAAAATCAGGCCGATATTGCCAACAATATCAATAATATCTATGAACTGGCCCAGCAG
CAGGATCAGCACTCTTCTGATATCAAAACACTGGCAAAAGCAAGCGCAGCAAATACCGATCGT
ATTGCGAAAAACAAAGCCGATGCAGATGCAAGCTTTGAAACACTGACGAAAAACCAGAACACC
CTGATTGAAAAAGATAAAGAACATGATAAACTGATCACCGCCAATAAAACCGCAATTGATGCA
AATAAAGCCAGCGCAGATACCAAATTTGCAGCAACCGCAGATGCAATTACCAAAAATGGCAAT
GCCATCACCAAAAATGCCAAAAGCATTACCGATCTGGGCACCAAAGTTGATGGTTTTGATAGC
CGTGTGACCGCACTGGATACCAAAGTTAATGCATTTGATGGTCGTATTACCGCTCTGGATAGT
AAAGTTGAAAATGGTATGGCAGCACAGGCAGCATAA
```

MC-010 (Protein)-(M)(UspA2 amino acids 30-564) SEQ ID NO: 71
MQAKNDITLEDLPYLIKKIDQNELEADIGDITALEKYLALSQYGNILALEELNKALEELDEDV
GWNQNDIANLEDDVETLTKNQNALAEQGEAIKEDLQGLADFVEGQEGKILQNETSIKKNTQRN
LVNGFEIEKNKDAIAKNNESIEDLYDFGHEVAESIGEIHAHNEAQNETLKGLITNSIENTNNI
TKNKADIQALENNVVEELFNLSGRLIDQKADIDNNINNIYELAQQQDQHSSDIKTLKKNVEEG
LLELSGHLIDQKTDIAQNQANIQDLATYNELQDQYAQKQTEAIDALNKASSENTQNIEDLAAY
NELQDAYAKQQTEAIDALNKASSENTQNIEDLAAYNELQDAYAKQQTEAIDALNKASSENTQN
IAKNQADIANNINNIYELAQQQDQHSSDIKTLAKASAANTDRIAKNKADADASFETLTKNQNT
LIEKDKEHDKLITANKTAIDANKASADTKFAATADAITKNGNAITKNAKSITDLGTKVDGFDS
RVTALDTKVNAFDGRITALDSKVENGMAAQAA MC-011 (DNA)-SEQ ID NO: 72
```
ATGGCGAAAAATGATATTACCCTGGAAGATCTGCCGTATCTGATCAAAAAAATCGATCAGAAC
GAACTGGAAGCCGATATTGGTGATATTACCGCACTGGAAAAATATCTGGCACTGAGCCAGTAT
GGAAATATTCTGGCCCTGGAAGAACTGAATAAAGCTCTGGAAGAGCTGGATGAAGATGTGGAT
TGGAATCAGAATGATATCGCCAATCTGGAAGATGATGTTGAAACCCTGACCAAAAATCAGAAT
GCACTGGCAGAACAGGGTGAAGCAATTAAAGAAGATCTGCAGGGTCTGGCAGATTTTGTTGAA
GGTCAGGAAGGCAAAATTCTGCAGAACGAAACCAGCATCAAAAAAAACACCCAGCGTAATCTG
GTGAATGGCTTTGAAATTGAAAAAAACAAAGATGCCATTGCCAAAAACAACGAAAGCATTGAA
GATCTGTATGATTTTGGTCATGAAGTTGCCGAAAGCATTGGTGAAATTCATGCACATAACGAA
GCACAGAATGAAACCCTGAAAGGTCTGATTACCAACAGCATCGAAAATACCAATAACATTACC
AAAAACAAAGCAGATATTCAGGCGCTGGAAAATAATGTTGTGGAAGAACTGTTTAATCTGAGC
GGTCGTCTGATTGATCAGAAAGCCGATATCGATAATAACATTAACAACATTTATGAACTGGCA
CAGCAGCAGGATCAGCATAGCAGCGATATCAAAACCCTGAAAAAAAACGTTGAAGAAGGTCTG
CTGGAACTGTCTGGTCACCTGATCGATCAGAAAACTGATATTGCCCAGAATCAGGCAAATATT
CAGGATCTGGCCACCTATAATGAACTGCAGGATCAGTATGCACAGAAACAGACCGAAGCAATT
GATGCCCTGAATAAAGCGAGCAGCGAAAACACCCAGAATATCGAAGATCTGGCAGCATACAAC
GAACTGCAGGATGCCTATGCAAAACAGCAGACTGAAGCCATCGACGCACTGAACAAGGCAAGC
TCTGAAAACACGCAGAACATTGAAGATCTGGCTGCCTATAATGAATTACAGGATGCGTATGCC
AAACAGCAGACCGAAGCGATTGATGCGCTGAACAAAGCCTCTTCTGAAAATACACAGAATATC
GCCAAAAATCAGGCCGATATTGCCAACAATATCAATAATATCTATGAACTGGCCCAGCAGCAG
GATCAGCACTCTTCTGATATCAAAACACTGGCAAAAGCAAGCGCAGCAAATACCGATCGTATT
GCGAAAAACAAAGCCGATGCAGATGCAAGCTTTGAAACACTGACGAAAAACCAGAACACCCTG
ATTGAAAAAGATAAGAACATGATAAACTGATCACCGCCAATAAAACCGCAATTGATGCAAAT
AAAGCCAGCGCAGATACCAAATTTGCAGCAACCGCAGATGCAATTACCAAAAATGGCAATGCC
ATCACCAAAAATGCCAAAAGCATTACCGATCTGGGCACCAAAGTTGATGGTTTTGATAGCCGT
GTGACCGCACTGGATACCAAAGCAAGCCATCATCATCACCACCACTAA
```

MC-011 (Protein)-(M)(UspA2 amino acids 31-540)(ASHHHHHH) SEQ ID NO: 73
MAKNDITLEDLPYLIKKIDQNELEADIGDITALEKYLALSQYGNILALEELNKALEELDEDVG
WNQNDIANLEDDVETLTKNQNALAEQGEAIKEDLQGLADFVEGQEGKILQNETSIKKNTQRNL
VNGFEIEKNKDAIAKNNESIEDLYDFGHEVAESIGEIHAHNEAQNETLKGLITNSIENTNNIT
KNKADIQALENNVVEELFNLSGRLIDQKADIDNNINNIYELAQQQDQHSSDIKTLKKNVEEGL
LELSGHLIDQKTDIAQNQANIQDLATYNELQDQYAQKQTEAIDALNKASSENTQNIEDLAAYN
ELQDAYAKQQTEAIDALNKASSENTQNIEDLAAYNELQDAYAKQQTEAIDALNKASSENTQNI
AKNQADIANNINNIYELAQQQDQHSSDIKTLAKASAANTDRIAKNKADADASFETLTKNQNTL
IEKDKEHDKLITANKTAIDANKASADTKFAATADAITKNGNAITKNAKSITDLGTKVDGFDSR
VTALDTKASHHHHHH

Vector Construction and Transformation

DNA Sequence for UspA2 from strain ATCC 25238-SEQ ID NO: 74.
```
ATGAAAACCATGAAACTTCTCCCTCTAAAAATCGCTGTAACCAGTGCCAT
GATTATTGGCTTGGGTGCGGCATCTACTGCGAATGCGCAGGCTAAAAATG
ATATAACTTTAGAGGATTTACCATATTTAATAAAAAAGATTGACCAAAAT
GAATTGGAAGCAGATATCGGAGATATTACTGCTCTTGAAAAGTATCTAGC
ACTTAGCCAGTATGGCAATATTTTAGCTCTAGAAGAGCTCAACAAGGCTC
TAGAAGAGCTCGACGAGGATGTTGGATGGAATCAGAATGATATTGCAAAC
```

-continued
```
TTGGAAGATGATGTTGAAACGCTCACCAAAAATCAAAATGCTTTGGCTGA

ACAAGGTGAGGCAATTAAAGAAGATCTTCAAGGGCTTGCAGATTTTGTAG

AAGGGCAAGAGGGTAAAATTCTACAAAATGAAACTTCAATTAAAAAAAAT

ACTCAGAGAAACCTTGTCAATGGGTTTGAGATTGAGAAAAATAAAGATGC

TATTGCTAAAAACAATGAGTCTATCGAAGATCTTTATGATTTTGGTCATG

AGGTTGCAGAAAGTATAGGCGAGATACATGCTCATAATGAAGCGCAAAAT

GAAACTCTTAAAGGCTTGATAACAAACAGTATTGAGAATACTAATAATAT

TACCAAAAACAAAGCTGACATCCAAGCACTTGAAAACAATGTCGTAGAAG

AACTATTCAATCTAAGCGGTCGCCTAATTGATCAAAAAGCAGATATTGAT

AATAACATCAACAATATCTATGAGCTGGCACAACAGCAAGATCAGCATAG

CTCTGATATCAAAACACTTAAAAAAAATGTCGAAGAAGGTTTGTTGGAGC

TAAGCGGTCACCTAATTGATCAAAAAACAGATATTGCTCAAAACCAAGCT

AACATCCAAGATCTGGCCACTTACAACGAGCTACAAGACCAGTATGCTCA

AAAGCAAACCGAAGCGATTGACGCTCTAAATAAAGCAAGCTCTGAGAATA

CACAAAACATCGAAGATCTGGCCGCTTACAACGAGCTACAAGATGCCTAT

GCCAAACAGCAAACCGAAGCAATTGACGCTCTAAATAAAGCAAGCTCTGA

GAATACACAAAACATCGAAGATCTGGCCGCTTACAACGAGCTACAAGATG

CCTATGCCAAACAGCAAACCGAAGCCATTGACGCTCTAAATAAAGCAAGC

TCTGAGAATACACAAAACATTGCTAAAAACCAAGCGGATATTGCTAATAA

CATCAACAATATCTATGAGCTGGCACAACAGCAAGATCAGCATAGCTCTG

ATATCAAAACCTTGGCAAAAGCAAGTGCTGCCAATACTGATCGTATTGCT

AAAAACAAAGCCGATGCTGATGCAAGTTTTGAAACGCTCACCAAAAATCA

AAATACTTTGATTGAAAAAGATAAAGAGCATGACAAATTAATTACTGCAA

ACAAAACTGCGATTGATGCCAATAAAGCATCTGCGGATACCAAGTTTGCA

GCGACAGCAGACGCCATTACCAAAAATGGAAATGCTATCACTAAAAACGC

AAAATCTATCACTGATTTGGGCACTAAAGTGGATGGTTTTGACAGTCGTG

TAACTGCATTAGACACCAAAGTCAATGCCTTTGATGGTCGTATCACAGCT

TTAGACAGTAAAGTTGAAAACGGTATGGCTGCCCAAGCTGCCCTAAGTGG

TCTATTCCAGCCTTATAGCGTTGGTAAGTTTAATGCGACCGCTGCACTTG

GTGGCTATGGCTCAAAATCTGCGGTTGCTATCGGTGCTGGCTATCGTGTG

AATCCAAATCTGGCGTTTAAAGCTGGTGCGGCGATTAATACCAGTGGTAA

TAAAAAAGGCTCTTATAACATCGGTGTGAATTACGAGTTCTAA
```

Protein Sequence for UspA2 from strain ATCC 25238.—SEQ ID NO. 1 as described above.

Vector Construction

To generate the construct MC-001, DNA fragment coding for an UspA2 gene fragment (amino acids 30 to 540 from strain ATCC 25238) including the NdeI/XhoI restriction sites to facilitate the cloning (the starting methionine is encoded by NdeI site) and the DNA sequence corresponding to the AS (alanine serine) amino acids linker and 6×his amino acids was codon-optimized (non-native) and synthesized by GENEART (a US registered trademark). Codon-optimized means that the nucleotide sequence was changed from the native sequence without changing the amino acid sequence in order to better fit with the codon usage in Escherichia coli for optimal expression. The UspA2 fragment was cloned according to standard methods into the pET-26b expression vector using the NdeI/XhoI restriction sites.

To generate MC-002, MC-003, and MC-004 constructs, a polymerase chain reaction was performed to amplify the UspA2 gene fragment (amino acids 30-540 from strain ATCC 25238) using the MC-001 construct as a template, the primer UspA2Nde opt (which contains the methionine start codon), and the primer UspA2opt delta His, A2opt 1His delta AS, and A2opt 2His delta AS, respectively. The UspA2 fragment was cloned according to standard methods into the pET-26b expression vector using the NdeI/XhoI restriction sites.

To generate the construct MC-005, a polymerase chain reaction was performed to amplify the UspA2 gene fragment (amino acids 30-519 from strain ATCC 25238) using the MC-001 vector as a template with the primers UspA2Nde opt (which contains the methionine start codon) and R delta hairpin A2opt His. DNA sequence corresponding to NdeI restriction site was incorporated into the 5' primer and XhoI restriction site was incorporated into the 3' primer. In addition, DNA sequence corresponding to the AS amino acids linker and 6×his amino acids was incorporated into the 3' primer. The generated PCR product was then inserted into the pET-26b(+) cloning vector (NOVAGEN (a US registered trademark)).

To generate the construct MC-006, a polymerase chain reaction was performed to amplify the UspA2 gene fragment (amino acids 30-519 from strain ATCC 25238) using the MC-005 construct as a template with the primers UspA2Nde opt (which contains the methionine start codon) and delta His delta hélice. DNA sequence corresponding to NdeI restriction site was incorporated into the 5' primer and XhoI restriction site was incorporated into the 3' primer. The generated PCR product was then inserted into the pET-26b(+) cloning vector (NOVAGEN (a US registered trademark)).

To generate the construct MC-007, DNA fragment coding for an UspA2 gene fragment (amino acids 30 to 564 from strain ATCC 25238) including the NdeI/XhoI restriction sites to facilitate the cloning (starting methionine is encoded by NdeI site) and the DNA sequence corresponding to the AS amino acids linker and 6×his amino acids was codon-optimized and synthesized by GENEART (a US registered trademark) (plasmid: 1026399). The UspA2 fragment was cloned according to standard methods into the pET-26b expression vector using the NdeI/XhoI restriction sites.

To generate the construct MC-008, a polymerase chain reaction was performed to amplify the UspA2 gene fragment (amino acids 30-564 from strain ATCC 25238) using the MC-007 construct as a template with the primers UspA2Nde opt (which contains the methionine start codon) and 2His hélice deltaAS. DNA sequence corresponding to NdeI restriction site was incorporated into the 5' primer and XhoI restriction site was incorporated into the 3' primer. The generated PCR product was then inserted into the pET-26b(+) cloning vector (NOVAGEN (a US registered trademark)).

To generate the construct MC-009, a polymerase chain reaction was performed to amplify the UspA2 gene fragment (amino acids 31-564 from strain ATCC 25238) using the 1026399 plasmid as the template and the primers N-term cyto Abis (which contains the methionine start codon) and 2His hélice deltaAS. DNA sequence corresponding to NdeI restriction site was incorporated into the 5' primer including the glutamine deletion and XhoI restriction site was incorporated into the 3' primer including two histidine residues. The generated PCR product was then inserted into the pET-26b(+) cloning vector (NOVAGEN (a US registered trademark)). DNA sequencing of the final construct was performed to confirm the correct sequence.

To generate the construct MC-010, a polymerase chain reaction was performed to amplify the UspA2 gene fragment (amino acids 30-564 from strain ATCC 25238) using the MC-007 construct as a template with the primers UspA2 Nde opt (which contains the methionine start codon) and cyto hélice dHis dAS. DNA sequence corresponding to NdeI restriction site was incorporated into the 5' primer and XhoI restriction site was incorporated into the 3' primer. The generated PCR product was then inserted into the pET-26b(+) cloning vector (NOVAGEN (a US registered trademark)).

To generate the construct MC-011, a polymerase chain reaction was performed to amplify the UspA2 gene fragment (amino acids 31-540 from strain ATCC 25238) using the MC-001 construct as a template with the primers N-term cyto Abis (which contains the methionine start codon) and N-term reverse. DNA sequence corresponding to NdeI restriction site was incorporated into the 5' primer and XhoI restriction site was incorporated into the 3' primer. The generated PCR product was then inserted into the pET-26b(+) cloning vector (NOVAGEN (a US registered trademark)).

A detailed list of PCR primer sequences used for amplifications is illustrated in Table 3. The polymerase chain reaction was performed using Expand High Fidelity PCR System kit (Roche) according to manufacturer's recommendations. Ligation was performed using Rapid DNA Ligation Kit (Roche) according to manufacturer's recommendations.

Transformation

*Escherichia coli* (*E. coli*) BLR (DE3), modified BLR (DE3) or B834(DE3) cells were transformed with plasmid DNA according to standard methods with $CaCl_2$-treated cells (Hanahan D. «Plasmid transformation by Simanis.» In Glover, D. M. (Ed), DNA cloning. IRL Press London. (1985): p. 109-135). Briefly, BLR (DE3) competent cells were gently thawed on ice. Approximately 4 μl of plasmid (10-100 ng) were mixed using 50-100 μl competent cells. Thereafter, this formulation was incubated on ice for 5 min. To perform the transformation reaction, the formulation was heat pulsed at 42° C. for 30 seconds then incubated on ice for 2 minutes. Approximately 0.5 ml of SOC medium (Super Optimal broth with Catabolite repression) was added to the transformed cells and the cell culture was incubated at 37° C. for one hour before plating on Luria-Bertani (LB) agar with 50 μg/ml kanamycin. Around 150 μl of transformed cell culture was plated and incubated overnight at 37° C.

BLR (DE3): BLR is a recA⁻ derivative of BL21 (F⁻ ompT hsdSB(rB- mB-) gal dcm (DE3). This *E. coli* strain used for expression of recombinant proteins improves plasmid monomer yields and may help stabilize target plasmids containing repetitive sequences or whose products may cause the loss of the DE3 prophage (Studier, F. W. (1991) J. Mol. Biol. 219: 37-44). The detailed genotype of *E. coli* BLR (DE3) has been published by NOVAGEN (a US registered trademark). (F- ompT hsdSB (rB- mB-) gal dcm Δ(srl-recA)306::Tn10 (TetR) (DE3).

B834 (DE3) is the parental strain for BL21. These hosts are methionine auxotrophs and allow high specific activity labeling of target proteins with 35S-methionine and selenomethionine for crystallography. The detailed genotype of *E. coli* B834 (DE3) has been published by NOVAGEN (a US registered trademark): F⁻ ompT $hsdS_B(r_B\text{-}\ m_B\text{-})$ gal dcm met (DE3).

Modified BLR (DE3): In order to prevent (phospho) gluconoylation, Pgl gene was inserted in the biotin locus

TABLE 3

PCR primer sequences used for UspA2 amplifications

| Primer ID | DNA Sequence 5'-3' |
|---|---|
| UspA2 Nde opt | GAATTCTTAATTAACATATGCAGGCCAAAAATGATATTACCCTG (SEQ ID NO: 75) |
| UspA2opt delta His | GGCGCGCCTCGAGTTATTATTTGGTATCCAGTGCGGTCACACG (SEQ ID NO: 76) |
| UspA2opt 1His delta AS | GGCGCGCCTCGAGTTAGTGTTTGGTATCCAGTGCGGTCACACG (SEQ ID NO: 77) |
| UspA2opt 2His delta AS | GGCGCGCCTCGAGTTAGTGGTGTTTGGTATCCAGTGCGGTCACACG (SEQ ID NO: 78) |
| R delta hairpin A2opt His | GGCGCGCCTCGAGTTAGTGGTGGTGATGATGATGGCTTGCGCTTTTGGCATTTTTG GTGATGGCAT (SEQ ID NO: 79) |
| Delta His delta hélice | CCGCTCGAGCTAGCTTTTGGCATTTTTGGTGATGGC (SEQ ID NO: 80) |
| N term cytoAbis | GGAATTCCATATGGCGAAAAATGATATTACCCTGGAAGATCTG (SEQ ID NO: 81) |
| 2His hélice delta AS | GGCGCGCCTCGAGTTAGTGGTGTGCTGCCTGTGCTGCCATACCATT (SEQ ID NO: 82) |
| Cyto hence dHis dAS | GGCGCGCCTCGAGTTATGCTGCCTGTGCTGCCATACCATT (SEQ ID NO: 83) |
| N term reverse | CAGTTCATTATAGGTGGCCAGATCCTG (SEQ ID NO: 84) | located in the BLR (DE3) genome. In addition, to prevent the Ile-Val substitutions, the C219Y mutation in the threonine deaminase gene was corrected.

Genotype: (F- ompT hsdSB (rB- mB-) gal dcm Δ(srl-recA)306::Tn10 (TetR); Δ(bioA-bioD)::Pgl; TD+ (C21919 (DE3).

Example 2: Protein Expression Using Shake Flask

*Escherichia coli* strains transformed with recombinant plasmid were used to inoculate 100 ml of LB broth (Becton, Dickinson and Company)±1% (weight/volume, w/v) glucose (Laboratoire MAT, catalogue number: GR-0101) and 50 µg/ml kanamycin (Sigma). This preculture was generally grown overnight at 37° C. Twelve ml of the preculture is used to inoculate 500 ml LB broth+50 µg/ml kanamycine. Cultures were incubated at 37° C. with agitation of 150 RPM to reach an O.D.$_{600nm}$ of ~0.6.

At an O.D.$_{600nm}$ ~0.6, the BLR (DE3) cultures were induced for the expression of the recombinant protein by addition of 1 mM isopropyl β-D-1-thiogalactopyranoside (IPTG; EMD Chemicals Inc., catalogue number: 5815) and incubated overnight at 23° C. with agitation of 150 RPM. After the induction period, the cultures were centrifuged at 6370 g for 20 minutes and the pellets from 350 ml culture were frozen at −20° C. separately.

Example 3: Protein Purification Using Phosphate Buffer (MC-001 Construct and MC-011 Construct)

Each bacterial pellet obtained after induction in shake flask was resuspended in 30 ml 20 mM potassium phosphate buffer (pH 8.0) containing 10 mM NaCl and Roche COMPLETE (a US registered trademark) Protease Inhibitor Cocktail (1 tablet/50 ml buffer). Cell lysis is performed by 3× French Press extractions (20 000 psi) and clarification is performed by 30 minutes centrifugation at 23700 g. Supernatant is harvested and filtrated on 0.22 µm.

6×His tagged-proteins were purified on immobilized metal affinity chromatography (IMAC) using XK16 column and 20 ml NiNTA resin (Qiagen) previously equilibrated with 20 mM potassium phosphate buffer (pH 8.0) containing 10 mM NaCl or PBS buffer pH 8.0 containing 500 mM arginine. The soluble components were loaded on at up to 4 ml/min (producing a "flow through fraction"). After loading on the column, the column was washed with 60 ml of 20 mM potassium phosphate buffer (pH 8.0) containing 10 mM NaCl at a rate of 4 ml/min producing a "wash fraction #1. A second wash using same buffer+10 mM imidazole was performed, producing a "wash fraction #2. Elution was performed using same buffer containing 200 or/and 500 mM imidazole.

Samples from elution fractions were analyzed by sodium dodecyl sulfate polyacrylamide gel electrophoresis (SDS-PAGE). Samples containing the protein were dialyzed against 5 liters of 20 mM potassium phosphate buffer (pH 8.0) containing 10 mM NaCl. Protein concentration was determined using Lowry method.

Example 4: Protein Purification Using Arginine Containing Buffer (MC-001, MC-005 and MC-007)

Each bacterial pellet obtained after induction in shake flask (Example 3) or fermenter (Example 5) was resuspended in 30 ml PBS buffer+500 mM arginine pH8.0 and Roche COMPLETE (a US registered trademark) Protease Inhibitor Cocktail (1 tablet/50 ml buffer). Alternatively, fermentation cell paste (≈7 g) was resuspended in 90 ml PBS buffer containing 500 mM arginine pH8.0 and Roche COMPLETE (a US registered trademark) Protease Inhibitor Cocktail (1 tablet/50 ml buffer).

Cell lysis was performed by 2 or 3× French Press extractions (20 000 psi) and clarification was performed by 30 minutes centrifugation at 23 700 g 4° C. Supernatant was harvested and filtrated on 0.22 µm. 6×His tagged-proteins were purified on immobilized metal affinity chromatography (IMAC) using XK16 column and 80 ml NiNTA resin (Qiagen) previously equilibrated with PBS buffer+500 mM arginine pH 8.0. The soluble components were loaded on at up to 4 ml/min (producing a "flow through fraction"). After loading on the column, the column was washed with the same buffer, then with 20 mM potassium phosphate buffer (pH 8.0) containing 10 mM NaCl at a rate of 4-6 ml/min producing a "wash fraction #1." A second wash using same buffer+10 mM imidazole was performed, producing a "wash fraction #2." Elution was performed using same buffer+200 mM imidazole or 500 mM imidazole. In further elution vials, 5 mM EDTA final concentration was added.

Samples from elution fractions were analyzed by sodium dodecyl sulfate polyacrylamide gel electrophoresis (SDS-PAGE). Samples containing the proteins were dialyzed against 5 liters of 20 mM potassium phosphate buffer (pH 8.0) containing 10 mM NaCl and 5 mM EDTA. Protein concentration was determined using Lowry method.

This protocol may be used with other 6×His tagged-proteins.

Example 5: Fermentation

The following fermentation procedure may be used:
Working seeds are frozen aliquots of flask-grown *Escherichia coli* BLR(DE3) or BLR(DE3)-derived strains transformed with a pET26b derivative containing a sequence coding for a specific antigen candidate recombinant protein construct.

A working seed (WS) is removed from frozen storage, thawed and used to inoculate an Erlenmeyer flask containing pre-culture media. Manipulation of the seed and flask culture are performed aseptically under a Laminar Air Flow (LAF) Hood or Biological Safety Cabinet (BSC). The pre-culture flask is incubated typically between 30° C.-37° C. under 200 RPM agitation speed for the time needed to reach an Optical Density at 650 nm (OD$_{650nm}$) between 1.0 and 3.0, typically between 4-6 hrs.

A 20 L fermentor is prepared by Clean-In-Place followed by an automated steam sterilisation sequence. Starting medium is transferred aseptically into the fermentor. A bottle filled with NH$_4$OH 25% is aseptically connected to the fermentor for automatic pH control. The initial pH of the starting medium is adjusted to target pH by addition of NH$_4$OH solution. Irradiated antifoam is added using a syringe through a septum in the head-plate. A bottle filled with Feed medium is aseptically connected to the fermentor. Feed addition is controlled by either a pO2-cascade (control dissolved oxygen) to or a pre-programmed feed-curve. Agitation is controlled either by a pO2-cascade or a pre-programmed agitation-curve.

Initial fermentor parameters are typically as follows:
Temperature: 28° C.-32° C.
Pressure: 0.5 barg (7 psi)
Air flow rate: 2 VVM (Vessel Volumes per Minute)
pH: Regulated at 6.8 by addition of NH$_4$OH 25%.
An aliquot of this pre-culture (typically between 5 ml-50 ml) is used to inoculate the starting fermentor media by syringe addition through a septum on the fermentor headplate. The phases of Fermentation Culture are:

Batch Phase: Biomass is accumulated using carbon source in starting media.

Fed-batch Phase: Feed media is introduced either according to pO2-cascade control or pre-programmed feed curve. Biomass accumulation continues on carbon source in feed media.

Induction Phase: Expression of the recombinant protein antigen is induced by addition of IPTG solution to the culture in the fermentor.

At harvest, the culture is collected typically in 1 L centrifugation bottles and centrifuged to separate the solid pellet (cell-paste) fraction from the liquid supernatant fraction. The supernatant is discarded, and the wet cell weight (solid pellet) is recorded and the cell-paste bags stored at −20° C.

The following procedure may also be used:

*Escherichia coli* Standard Pre-Culture

Each standard pre-culture were prepared using a frozen seed culture of *Escherichia coli* strains. These strains are BLR(DE3) strains transformed with a pET26b derivative containing a sequence coding for the specific construct to be evaluated.

The seed culture was thawed to room temperature and 400 µl were used to inoculate a 2 litre Erlenmeyer flask containing 400 ml of preculture medium (adapted from Zabriskie et al. (J. Ind. Microbiol. 2:87-95 (1987)).

The inoculated flask was then incubated at 37° C. (±1° C.) and 200 rpm. The pre-culture was stopped after 6 h of incubation. At this step the optical density at 650 nm ($OD_{650nm}$) is about 2. The pre-culture was used to inoculate medium in a fermenter as soon as the culture was stopped.

20L Scale Fedbatch Fermentation

Method

A 20 litre fermenter (Biolafitte) was used. Nine litres of batch phase medium were aseptically transferred into the fermenter. The pH of the medium was readjusted to 6.8 with base addition. 1 ml of undiluted irradiated antifoam (SAG 471) was also added to the fermenter. The temperature (28° C.), head pressure (0.5 bar), aeration rate (20 litres sparged air per minute) and initial agitation speed (300 rpm) were then set prior to inoculation. The level of dissolved oxygen in these conditions was 100%. The head pressure and aeration rate were maintained at a constant level during the fermentation.

Inoculation was achieved by the addition of an equivalent 10 ml OD650 nm=2 of pre-culture (prepared as described above, in Example 2) following the next formula:

$$\text{Preculture Volume (ml)} = \frac{20}{\text{Preculture Final } OD650 \text{ nm}}$$

During batch phase (0-15 h), the temperature was maintained at 28° C. The level of dissolved oxygen was set at 20%. The level of dissolved oxygen (DO) was regulated by increasing stirring when the DO fell below 20%. Glucose exhaustion resulted in an increase in DO and a concomitant decrease in stirring.

When glucose is exhausted, the feeding rate is started based on a pH signal that increases above 7.0. From this point forward, the feeding rate was controlled by oxygen demand, increasing the flow rate when dissolved oxygen tends to drop below the 20% set point. At this step the agitation speed is maintained at 900 rpm.

During the fed-batch phase (before induction), the pH was maintained at 6.8 by addition of base, the temperature was regulated at 30° C.

Two strategies were applied to produce the protein:

The "High Cell Density Induction" (HCDI) is applied when culture is induced with 1 mM IPTG (isopropyl-beta-D-thiogalactopyranoside) at an optical density of 80±5, typically reached after 40 h of culture. The temperature was maintained at 28° C. and feeding rate still controlled by oxygen demand with a constant agitation speed at 900 rpm.

The "Low Cell Density Induction" (LCDI) process means an induction at an optical density of 40±5 usually reached after 24 h of culture. The temperature was decreased to 30° C. and the constant feeding rate of 0.5 ml/min is applied. Then 1 mM IPTG is added to the culture. At this step, the DO level was maintained at 20% by controlling the stirring rate.

At the end of the induction phase (72 h), cell paste was collected by centrifugation (6,500×g, 4° C. for 1 h), and stored at −20° C.

FIGS. 1 and 2 illustrate a typical fermentation profile with the HCDI and the LCD processes and the parameters monitored during 20 L-scale fed-batch fermentation.

Table 4 sets forth the constructs evaluated in fermenter and UspA2 yield obtained for each one.

TABLE 4

| Construct ID | Name | Helix | His tag | Process used | UspA2 Yield (g/l) |
| --- | --- | --- | --- | --- | --- |
| MC-008 | UspA2 + Helix + 2 His | Full | 2 res | HCDI | 2.21 |
| MC-007 | UspA2 + Helix + 6 His | Full | 6 res | LCDI | 2.60 |
| MC-010 | UspA2 + Helix | Full | No | HCDI | 0.22 |
| MC-005 | UspA2 ΔHelix + 6 His | No | 6 res | LCDI | 1.92 |
| MC-006 | UspA2 ΔHelix | No | No | LCDI | 1.14 |
| MC-004 | UspA2 + ½ Helix + 2 His | ½ | 2 res | LCDI | 0.92 |
| MC-001 | UspA2 + ½ Helix + 6 His | ½ | 6 res | HCDI | 3.68 |
| MC-002 | UspA2 + ½ Helix | ½ | No | HCDI | 0.49 |

His = histidine

FIG. 3 depicts in graphical form the UspA2 yield in Table 4 from the constructs evaluated in fermenter.

In this figure, UspA2 yield is affected by histidine residues present in the construct. ($p<0.05$, one way, three levels, Type II ANOVA). A positive correlation between the number of histidine residues and UspA2 fermentation yield was observed, with a yield increase higher than 400% between 0 and 6 residues in fed-batch fermentations.

It was also observed that one histidine residue added to half-helix pattern (MC-003 construct) produced a UspA2 yield of about 1 g/l of protein.

Example 6: Protein Characterization

Analytical Ultracentrifugation

Analytical ultracentrifugation is used to determine the homogeneity and size distribution in solution of the different species within a protein sample by measuring the rate at which molecules move in response to a centrifugal force. This is based on the calculation of the coefficients of sedimentation of the different species that are obtained by sedimentation velocity experiment, which depend on their molecular shape and mass.

The following protein samples were spun in a Beckman-Coulter ProteomeLab XL-1 analytical ultracentrifuge at 28 000RPM after the AN-60Ti rotor had been equilibrated to 15° C.

a. MC-005 lot BMP53, 675 μg/ml in 20 mM NaPO$_4$, 10 mM NaCl, pH8.0 b. MC-001 lot BMP13, 545 μg/ml in 20 mM NaPO$_4$, 10 mM NaCl, pH8.0 c. MC-001 lot BMP14, 545 μg/ml in 20 mM NaPO$_4$, 10 mM NaCl, pH8.0 d. MC-001 lot BMP54, 445 μg/ml in 20 mM NaPO$_4$, 10 mM NaCl, pH8.0 e. MC-007 lot BMP70, 510 μg/ml in 20 mM NaPO$_4$, 10 mM NaCl, pH8.0

For data collection, from 133 to 325 scans were recorded at 280 nm every 5 minutes.

Data analysis was performed using the program SEDFIT (available through the National Institutes for Health) for determination of the C(S) distribution. The C(S) distribution is a representation of the relative intensity of the different components in a mixture of macromolecules separated by their coefficient of sedimentation, which is a function of molecule size and conformation. Determination of the partial specific volume of the proteins at 15° C. was performed with the SEDNTERP software from their amino acid sequence. SEDNTERP (SEDNTERP is distributed and supported through the Biomolecular Interaction Technologies Center at the University of New Hampshire) was also used to determine the viscosity and the density of the buffer at 15° C.

Determination of the relative abundance of all species has been performed by considering the total area under the curve of the overall distribution as 100% of the sample and by calculating the percentage of this total area represented by the contribution of every species. C(S) distribution plot (concentration vs sedimentation coefficient) has been used for that calculation, considering that it's a better representation of the raw data than the C(M) distribution (concentration vs molecular weight).

Analytical ultracentrifugation of the different purified constructs allowed observation that UspA2 Δhelix, UspA2½ helix and UspA2 full helix with C-terminal his tag are present mainly as trimers in solution when 500 mM L-arginine is added during cell lysis prior to purification (FIGS. 4, 5, 7 and 8).

A heterogeneous size distribution has been observed for UspA2½ helix when no L-arginine was added during cell lysis. Two major populations are observed. It was not possible to confirm the molecular weight of the species detected by AUC (analytical ultracentrifugation) with this protein preparation, since the frictional ratio which is essential for molecular weight estimation needs to be calculated from an homogeneous sample. However, based on sedimentation coefficients, none of the observed species seem to correspond to the trimer observed in other samples.

FIG. 4 illustrates the molecular weight distribution of purified MC-005 determined by sedimentation velocity analytical ultracentrifugation. The majority of protein is found as a trimer, with a small proportion of a higher molecular weight oligomer that may correspond to dimer of trimer.

FIG. 5 illustrates the molecular weight distribution of purified MC-001 determined by sedimentation velocity analytical ultracentrifugation. Majority of protein is found as a trimer.

FIG. 6 illustrates the molecular weight distribution of purified MC-001 determined by sedimentation velocity analytical ultracentrifugation. The sample presents multiple species and is highly polydisperse. The sedimentation coefficient of the major species detected doesn't correspond to the one of the trimers normally detected in the other lots.

FIG. 7 illustrates the molecular weight distribution of purified MC-001 determined by sedimentation velocity analytical ultracentrifugation. The majority of protein is found as a trimer.

FIG. 8 illustrates the molecular weight distribution of purified MC-007 determined by sedimentation velocity analytical ultracentrifugation. The majority of protein is found as a trimer.

Circular Dichroism/Secondary Structure

Circular dichroism (CD) is used to determine the secondary structure composition of a protein by measuring the difference in the absorption of left-handed polarized light versus right-handed polarized light which is due to structural asymmetry. The shape and the magnitude of the CD spectra in the far-UV region (190-250 nm) are different whether a protein exhibits a beta-sheet, alpha-helix or random coil structure. The relative abundance of each secondary structure type in a given protein sample can be calculated by comparison to reference spectra.

Far UV spectra are measured using an optical path of 0.01 cm from 178 to 250 nm, with a 1 nm resolution and bandwidth on a Jasco J-720 spectropolarimeter. Temperature of the cell is maintained at different temperatures by a Peltier thermostated RTE-111 cell block. A nitrogen flow of 10 L/min is maintained during the measurements.

Concentration of the following protein constructs was adjusted to 400 μg/ml in 20 mM NaPO$_4$, 10 mM NaCl, pH8.0 buffer.

a. MC-005 lot BMP53, in 20 mM NaPO$_4$, 10 mM NaCl, pH8.0 b. MC-001 lot BMP13, in 20 mM NaPO$_4$, 10 mM NaCl, pH8.0 c. MC-001 lot BMP14, in 20 mM NaPO$_4$, 10 mM NaCl, pH8.0 d. MC-001 lot BMP54, in 20 mM NaPO$_4$, 10 mM NaCl, pH8.0 e. MC-007 lot BMP70, in 20 mM NaPO$_4$, 10 mM NaCl, pH8.0

Calculations of secondary structures have been done using the following algorithms:

Selcon 3 (Sreerama and Woody, Anal. Biochem. (1993), 209, 32; Sreerama and Woody, Biochemistry, 33, 10022-25 (1994); Sreerama et al. Protein Science, 8, 370-380 (1999); Johnson W. C. Jr., Proteins: Str. Func. Genet. 35, 307-312 (1999))

CDSSTR (Johnson W. C. Proteins: Struc. Func. Genet. 35, 307-312 (1999) modified by Sreerama. N. (Anal. Biochem., 287, 252 (2000)).

Displayed results are an average of the percentage calculated with both algorithms and are subjected to a 5% error margin.

Results of the secondary structure calculations for fermentor expressed proteins are displayed in Table 5, considering a 5% error margin.

TABLE 5

| Secondary structure calculations at 22° C. | | | |
|---|---|---|---|
| Protein | Helix | Beta | random |
| MC-005 BMP53 | 40.8 | 26.4 | 34.1 |
| MC-007 BMP70 | 58.2 | 18.2 | 24.7 |
| MC-001 BMP54 | 53.7 | 14.2 | 34.4 |

Calculations are compatible with the shape and visual analysis of the spectra, where helical content increases with the intensity of minima at 208 and 220 nm. Proteins are composed of a high proportion of helical structures, with presence of beta structures.

Superposition of the spectra on FIG. 9 shows no significant difference in the shape between constructs. Spectra of MC-005 helix shows a lower intensity which could account for a lower alpha structure that is coherent with the absence of C-terminal helix.

FIG. 9 illustrates the far-UV circular dichroism spectra of UspA2 constructs MC-001, MC-005 and MC007 giving an indication of protein secondary structures. Superposition of spectra clearly shows that constructs containing half and full C-terminal helix have no detectable difference in their secondary structures, while the construct without helix generates a spectra with a difference in intensity that could account for a different secondary structure content.

Thermal Unfolding

Measurement of far-UV CD spectra at different temperatures during thermal unfolding suggested that MC-005 is less thermally stable than MC-007. The spectra observed at 33° C. for MC-005 is similar to the typical spectra of an unfolded protein. For the MC-007 construct, even if partial loss of secondary structures is observed at 33° C., the complete unfolding seems to occur between 35° C. and 37° C. This may be an indication of higher thermal stability of the full helix containing construct MC-007.

FIG. 10 illustrates secondary structures monitoring by circular dichroism during thermal unfolding of MC-005 (UspA2Δhelix+6His). Visual analysis of the spectra clearly shows that the protein loses most of its secondary structures at 33° C.

FIG. 11 illustrates secondary structures monitoring by circular dichroism during thermal unfolding of MC-007 (UspA2+helix+6His). Visual analysis of the spectra shows that loss of secondary structure is slower compared to the construct without helix. Structural changes are detectable upon heating to 33° C., but complete unfolding seems to occur between 35° C. and 37° C.

Differential Scanning Calorimetry (DSC) Thermal Unfolding

Thermal transitions of different UspA2 constructs were compared in order to evaluate the effect of C-terminal helix modifications on thermal stability of the proteins.

Analysis was done on VP-DSC from MicroCal (part of GE Healthcare). The buffer 20 mM $NaPO_4$, 10 mM NaCl, 5 mM EDTA, pH8 was used as reference and subtracted from the scans. Proteins were equilibrated at initial temperature for 15 minutes before temperature ramping DSC scans were then conducted from 10° C. to 60° C. at a heating rate 90° C./hr.

Two transitions were detected in MC-001 and MC-007 constructs and only one in MC-005. Values of the transitions (or Tm) of the different constructs can be found on Table 6.

While the lower Tm of all three proteins is around 32° C., the main difference is the value of the second Tm. The construct containing a full helix (MC-007) has a higher Tm at 37.5° C. compared to 34.5° C. for the half helix (MC-001).

It has been demonstrated that for MC-001 and MC-007, the first Tm around 32° C. is reversible, while the higher Tm is irreversible. For MC-005, the only Tm detected is irreversible.

This may be an indication of a higher thermal stability of full helix containing construct MC-007.

TABLE 6

Melting points of UspA2 constructs measured by DSC

| Constructs | [mg/mL] | $Tm_1$ (° C.) | $Tm_2$ (° C.) |
| --- | --- | --- | --- |
| MC-005 lotBMP53 | 0.400 | 31.74 | — |
| MC-001 lotBMP54 | 0.400 | 32.02 | 34.51 |
| MC-007 lotBMP70 | 0.400 | 32.19 | 37.50 |

Mass Spectrometry

UspA2 protein samples were prepared by protein precipitation with $CHCl_3$/MeOH/$H_2O$ system. The protein pellet was centrifuged at the bottom of the eppendorf tube before being gently dried under nitrogen. The dried pellet was then dissolved in 2 μl of pure formic acid before being diluted with 3 μl of ultrapure water and 5 μl of sinapinic acid. Sinapinic acid used as matrix for MALDI-TOF (Matrix-Assisted Laser Desorption/Ionisation followed by Time-Of-Flight spectrometry analyser) analysis is prepared in 50% $CH_3CN$/50% $H_2O$ supplemented by TFA 0.1% final concentration.

1 μl of the sample+matrix mixture was spotted onto a Bruker 384 ground stainless steel MALDI target and let to dry for crystallization at room temperature and atmospheric pressure (dried droplet method).

UspA2 mass spectrometry analysis was performed on a Bruker Ultraflex 2 MALDI-TOF mass spectrometer (Bruker Daltonics, Bremen, Germany) in positive ionization and linear mode. Protein samples, co-crystallized in sinapinic acid matrix, were irradiated by a smartbeam laser. Mass measurement of intact UspA2 protein were done over 10.000-100.000 Da mass range with an acceleration voltage of 25 kVolts. Laser attenuation was fine-tuned in order to get the best protein signal as possible and to avoid any fragmentation as well as background over-ionization phenomena. Calibration of the mass spectrometer was performed in close external method with homologous matrix and using the commercial Bruker Protein Calibration mixture 2, by accurate measures on the following calibrators: $[M+2H]^{2+}$ (mass measured by MS detector following addition of two H+ ions to the protein during ionisation) species of protein A at m/z 22307 Da, $[M+H]^+$ species of trypsinogen at m/z 23982 Da, [M+H]+species of protein A at m/z 44613 Da and [M+H]+species of bovine albumin at m/z 66431 Da°. Each presented spectrum results from the sum of 500 individual shots.

The following samples were analyzed:
MC-001 construct with MQAK amino acids (SEQ ID NO: 85) in N-terminal produced in shake flask, lot opt-01, MC-011 construct with MAK amino acids in N-terminal produced in shake flask, lot BMP37.

In Table 7 and FIG. 12, MC-001 protein with MQAK amino acids (SEQ ID NO: 85) at the N-terminal extremity has been shown to be at least partially demethionylated, as shown by the measured molecular mass of 57427 Da, compared to the expected mass of 57565 Da. The other peak of 57620 Da may represent the complete non-demethionylated protein, N-acetylated protein, or another modified protein population.

FIG. 12 illustrates the MALDI spectrum of MC-001 lot opt-01. The mass observed at 57427 Da may be coherent with the demethionylated protein, while the peak at 57620 Da could correspond to the complete protein.

As shown in Table 7 and FIG. 13, MC-011 protein with MAK amino acids at the N-terminal extremity gave a major population in MALDI-MS that may correspond to the demethionylated protein, with a mass of 57265 Da, compared to 57437 Da for the expected mass based on complete amino acid sequence. The two other peaks at +186 Da and +366 Da are not close to any expected post-translational modifications, so they couldn't be identified by this experiment.

TABLE 7

Molecular mass of two UspA2 constructs as measured by MALDI-MS. Both constructs have a main measured mass lower than the one expected from amino acid sequence. The mass of the major population obtained with both constructs may be coherent with a demethionylated protein.

| Protein | Theoretical mass (Da) | Measured mass (Da) | Comment |
| --- | --- | --- | --- |
| MC-001 lot opt-01 | 57565.8 | ~57427.9 | Coherent with demethionylation (57434.6) |
| | | ~57620.3 | Coherent with protein containing N-terminal methionine |
| MC-011 lot BMP37 | 57437.6 | 57265.2 | Coherent with demethionylation (57306.4) |

N-Terminal Sequencing by Edman's Degradation

In order to evaluate if the optimisation of the N-terminal region (optimisation of the amino acid sequence next to the N-terminal methionine) leads to demethionylation of the protein, N-terminal sequencing has been done on the MC-011 construct carrying MAK amino acids on his N-terminal extremity.

The proteins were separated by SDS PAGE on a Novex 4%-20% polyacrylamide gel from Invitrogen, before transfer onto Problot PVDF (polyvinylidence diluoride) (Bio-Rad) membrane. The membrane was stained with amido-black. The band of interest was then cut and analysis was carried out according to the manufacturer's protocol using an Applied Biosystems Procise sequencer system. Twelve cycles of Edman's degradation were performed.

The N-terminal amino acid sequence obtained is AKN-DITLEDLP (SEQ ID NO:86), which corresponds to the N-terminal extremity of the protein starting at the amino acid number two after the initial methionine. This indicates that the mature protein is mainly demethionylated.

Example 7: UspA2 Construct MC-001: Bactericidal Activity

Bactericidal Assay

Moraxella catarrhalis was cultivated overnight on Petri dish at 37° C.+5% CO2. Bacteria were transferred in 12 ml HBSS-BSA (Hank's Buffered Salt Solution with Bovine Serum Album) 0.1% buffer in order to get an $OD_{620}$ of 0.650. Serum samples were heated for 45 min at 56° C. to inactivate the endogenous complement. Serial two-fold dilutions of sera in SBA buffer (HBSS-BSA 0.1%) were added on a 96-well round bottom microtitre plate (25 µl/well). Subsequently, 50 µl of SBA buffer were added in each well. Then 25 µl of Moraxella catarrhalis strains at 4 $10^4$ cfu/mL were added to the wells containing sera and incubated for 15 min at room temperature. Finally 25 µl of freshly thawed baby rabbit complement diluted ⅛ in HBSS-BSA 0.1% were added to reach a final volume of 125 µl. Plates were incubated for 1 h at 37° C. with orbital shaking (210 rpm). The reaction was stopped by laying the microplate on ice for at least 5 min.

After homogenization, various dilutions of the suspension (a mixture of bacteria, serum, complement and buffer, at a volume of 125 µl as discussed in the previous paragraph) were added onto chocolate agar plates and incubated for 24 hours at 37° C. with 5% $CO_2$ and Moraxella catarrhalis colonies were counted.

Eight wells without serum sample were used as bacterial controls to determine the number of Moraxella catarrhalis colonies per well. The mean number of CFU (colony forming unit) of the control wells was determined and used for the calculation of the killing activity for each serum sample. The bactericidal titers were expressed at the reciprocal dilution of serum inducing 50% of killing.

Anti-UspA2 antisera generated in mice, guinea pigs and rabbits against MC-001 were tested in the bactericidal assay described here above against 20 different Moraxella catarrhalis strains isolated from various tissues (blood, sputum, nose, middle ear fluids) in various countries (US, Finland, Netherlands, Norway, Sweden).

As shown below anti-UspA2 antibodies were able to induce a cross-bactericidal killing of Moraxella catarrhalis, whatever the percentage of homology of the UspA2 expressed by the tested strain. Moreover bactericidal activity was also shown against strains which only express UspA1 or the chimeric protein UspA2H. As expected, no or only weak bactericidal antibody titres were measured against UspA1 and UspA2 double knock-out mutants.

TABLE 8

Cross-bactericidal activity of anti-UspA2 MC-001 antibodies generated in mouse, guinea pig and rabbit. 1 + 2 KO is a double knock out, UspA1 & UspA2. 1KO is a UspA1 knockout only. MEF (AOM) = Middle Ear Fluid (Acute Otitis Media). "/" in the Isolate source column = not aware of the isolate source.

| | Strains | Isolate source | UspA gene present | Identity %* versus the vaccine sequence ATCC25238 | Anti-UspA2 antiserum bactericidal activity | | |
| --- | --- | --- | --- | --- | --- | --- | --- |
| | | | | | Mouse | Guinea pig | Rabbit |
| ATCC | 25238 | / | UspA1/UspA2 | 45.2/100 | +++ | ++ | +++ |
| | 43617 | Bronchitis | UspA1 | 40.1 | + | + | + |
| American | 2926 | / | UspA1 | 36.4 | − | +/− | − |
| | 2933 | / | UspA1/UspA2 | 44.6/62.4 | − | ++ | ++ |
| | 2912 | / | UspA1/UspA2 | 39.3/64.6 | ++ | ++ | +++ |
| | 2908 | / | UspA1/UspA2 | 43.3/52.8 | +++ | +++ | +++ |
| Finnish | 307 | MEF (AOM) | UspA1/UspA2 | 47.6/70.1 | − | ++ | +++ |
| | 353 | MEF (AOM) | UspA1/UspA2 | 45/61.8 | + | ++ | ++ |
| | 358 | MEF (AOM) | UspA1/UspA2 | 47/61.5 | +++ | +++ | +++ |
| | 216 | MEF (AOM) | UspA1/UspA2 | 46.6/66.9 | +++ | +++ | +++ |

TABLE 8-continued

Cross-bactericidal activity of anti-UspA2 MC-001 antibodies generated in mouse, guinea pig and rabbit.
1 + 2 KO is a double knock out, UspA1 & UspA2. 1KO is a UspA1 knockout only. MEF (AOM) =
Middle Ear Fluid (Acute Otitis Media). "/" in the Isolate source column = not aware of the isolate source.

|  | Strains | Isolate source | UspA gene present | Identity %* versus the vaccine sequence ATCC25238 | Anti-UspA2 antiserum bactericidal activity | | |
|---|---|---|---|---|---|---|---|
|  |  |  |  |  | Mouse | Guinea pig | Rabbit |
| Dutch | N9 | nose | UspA1/UspA2H | 41.1/70.1 | ++ | +++ | +++ |
|  | H2 | sputum | UspA1/UspA2 | 47/61.6 | +++ | +++ | +++ |
|  | F10 | sputum | UspA1/UspA2 | 42.9/61.1 | ++ | +++ | +++ |
| Norvegian | 1 | Tracheotomy (Pneumonia) | UspA1/UspA2 | 44.6/60.9 | +++ | +++ | +++ |
|  | 13 | Tracheotomy (Pneumonia) | UspA1/UspA2 | 47.8/55 | ++ | +++ | +++ |
|  | 20 | Tracheotomy (Pneumonia) | UspA1/UspA2 | 33.7/60.6 | +++ | ++ | +++ |
|  | 25 | Tracheotomy (Pneumonia) | UspA1/UspA2 | 47.8/55 | ++ | +++ | +++ |
|  | 27 | Tracheotomy (Pneumonia) | UspA1/UspA2 | 46/76.1 | ++ | +++ | +++ |
|  | 36 | Tracheotomy (Pneumonia) | UspA1/UspA2 | 53.6/61.6 | + | ++ | ++ |
| Swedish | BBH18 WT | sputum | UspA1/UspA2H | 42.9/57.3 | +++ | +++ | +++ |
|  | BBH18 (1 + 2KO) |  | — | — | + | − | − |
|  | BBH18 (1KO) |  | UspA2H | 57.3 | +++ | +++ | +++ |
|  | RH4 WT | blood | UspA1/UspA2H | 37.4/59.9 | not done | ++ | ++ |
|  | RH4 (1 + 2KO) |  | — | — | − | − | + |

*determined using the software GapL/ClustalX versus the ATCC25238 UspA2 fragment AA30-540.
+++ >50000
++ >20000
+ >500
− <200

TABLE 9

UspA Expression in the *M. catarrhalis* strains in Table 8.

|  | Strains | UspA1 expression | UspA2 expression | UspA2H expression |
|---|---|---|---|---|
| ATCC | 25238 | Yes | Yes | No |
|  | 43617 | Yes | stop codon | No |
| American | 2926 | Yes | No | stop codon |
|  | 2933 | Yes | Yes | No |
|  | 2912 | Yes | Yes | No |
|  | 2908 | Yes | Yes | No |
| Finnish | 307 | Yes | Yes | No |
|  | 353 | Yes | Yes | No |
|  | 358 | Yes | Yes | No |
|  | 216 | Yes | Yes | No |
| Dutch | N9 | Yes | No | Yes |
|  | H2 | Yes | Yes | No |
|  | F10 | Yes | Yes | No |
| Norvegian | 1 | Yes | Yes | No |
|  | 13 | Yes | Yes | No |
|  | 20 | Yes | Yes | No |
|  | 25 | Yes | Yes | No |
|  | 27 | Yes | Yes | No |
|  | 36 | Yes | Yes | No |
| Swedish | BBH18 WT | Yes | No | Yes |
|  | BBH18 (1 + 2KO) | No | No | No |
|  | BBH18 (1KO) | No | No | Yes |
|  | RH4 WT | Yes | No | Yes |
|  | RH4 (1 + 2KO) | No | No | No |

Example 8: Protection in a Mouse Model of Lung Colonization (MC-001)

Five weeks-old female Balb/c mice (n=8/5 groups) were immunized by the intramuscular route at days 0, 14 and 28 with 50 µl of vaccine containing 10 µg of UspA2 construct MC-001 formulated within AS02V. Mice were intranasally challenged at day 42 with $5 \cdot 10^5$ CFU of various *Moraxella catarrhalis* strains. Bacteria were counted in lungs collected 0, 3 and 6 hours post-challenge. Differences between groups were analysed using the Dunnet test.

As summarised in Table 10, UspA2 construct MC-001 induced a significant protection against both homologous and heterologous strains, including the strain 43617 which does express UspA1 but not UspA2 and the BBH18 strain which expresses the chimeric protein UspA2H (constituted of the N-terminal sequence from UspA1 and the C-terminal sequence from UspA2).

TABLE 10

Protective efficacy of UspA2. MC-001 construct.

| Strain | UspA expressed | Identity %* versus the vaccinal sequence ATCC25238 | $Log_{10}$ cfu/ml | | p value |
|---|---|---|---|---|---|
|  |  |  | Control group | Vaccine group |  |
| 25238 | UspA1 & UspA2 | 45.2/100 | 5.2 | 3.1 | 0.01 |
| 43617 | UspA1 | 40.1 | 4.9 | 3.6 | 0.01 |
| F10 | UspA1 & UspA2 | 42.9/61.1 | 4.3 | 3.9 | 0.25 |
| F10 | UspA1 & UspA2 | 42.9/61.1 | 4.4 | 3.6 | 0.01 |
| BBH18 | UspA1 & UspA2H | 42.9/57.3 | 4.3 | 3.5 | 0.01 |
| 20 | UspA1 & UspA2 | 33.7/60.6 | 4.4 | 3.9 | 0.02 |

*determined using the GapL/ClustalX software versus the ATCC25238 UspA2 fragment AA 30-540 p values in bold are significant (p < 0.05)

Example 9: UspA2 Construct MC-007: Antibody Bactericidal Activity

Bactericidal Assay

*Moraxella catarrhalis* 25238 was cultivated overnight on Petri dish at 37° C.+5% $CO_2$. Bacteria were transferred in 12 ml HBSS-BSA 0.1% buffer in order to get an $OD_{620}$ of 0.650. Serum samples were heated for 45 min at 56° C. to inactivate the endogenous complement. Serial two-fold dilutions of sera in SBA buffer (HBSS-BSA 0.1%) were added on a 96-well round bottom microtitre plate (25 µl/well). Subsequently, 50 µl of SBA buffer were added in each well. Then 25 µl of *Moraxella catarrhalis* 25238 strain at $4 \cdot 10^4$ cfu/mL were added to the wells containing sera and incubated for 15 min at room temperature. Finally 25 µl of freshly thawed baby rabbit complement diluted ⅛ in HBSS-BSA 0.1% were added to reach a final volume of 125 µl. Plates were incubated for 1 h at 37° C. with orbital shaking (210 rpm). The reaction was stopped by laying the microplate on ice for at least 5 min. After homogenization, various dilutions of the suspension were added onto chocolate agar plates and incubated for 24 hours at 37° C. with 5% $CO_2$ and *Moraxella* colonies were counted. Eight wells without serum sample were used as bacterial controls to determine the number of *Moraxella catarrhalis* colonies per well. The mean number of CFU of the control wells was determined and used for the calculation of the killing activity for each serum sample. The bactericidal titers were expressed at the reciprocal dilution of serum inducing 50% of killing.

Anti-UspA2 antisera generated in mice with UspA2 construct MC-001 or MC-007 were tested in a bactericidal assay using the protocol described above against the 25238 *Moraxella catarrhalis* homologous strain.

As shown in Table 11, the MC-007 UspA2 construct elicited a high bactericidal response, similar to that induced by the MC-001.

TABLE 11

Bactericidal activity of anti-UspA2 MC-001 and MC-007 antibodies. Normal mouse sera = sera from mice immunized with AS02V only, not with UspA2.

| Samples | Bactericidal titers |
| --- | --- |
| Normal mouse sera (AS02V) | – |
| Mouse Anti-Killed whole cells 25238 | ++ |
| Mouse anti-UspA2 against UspA2 MC-001 | +++ |
| Mouse anti-UspA2 against UspA2 MC-007 | +++ |

Example 10: UspA2 Construct MC-007: Protective Efficacy in a Lung Challenge Model Protection in a Mouse Model of Lung Colonization Five weeks-old female Balb/c mice (8 mice per group, 5 groups max per time point) were immunized by the intramuscular route at days 0, 14 and 28 with 50 µl of vaccine containing 10 µg of UspA2 construct MC-001 formulated with AS02V or MC-007 formulated within AS02V. Mice were intranasally challenged at day 42 with 5 $10^5$ CFU of *Moraxella catarrhalis* strain ATCC (a US registered trademark) 25238™. Mice were immunized with 10 µg of killed whole cells from *Moraxella catarrhalis* strain ATCC (a US registered trademark) 25238™ (as positive control) (*M. cat.* WC 25238 in FIG. 14) or with AS02V alone (as negative control). Bacteria were counted in lungs collected 0, 3 and 6 hours post-challenge. Differences between groups were analysed using the Dunnet test.

As shown in FIG. 14, both UspA2 constructs were similarly protective against ATCC (a US registered trademark) strain 25238™.

Example 11: Immunogenicity of UspA2 MC-009 Protein Formulations in Mice

Groups of 25 female Balb/c mice were immunized by the intramuscular (IM) route at days 0, 14 and 28 with 50 µl of the following formulations:
MC-009 (1 µg) AlPO4 (1000 µg/ml)
MC-009 (1 µg) AS04C (AlPO$_4$/MPL 100/100 per ml)
MC-009 (1 µg) AS01E (QS21/MPL 50/50 per ml)

Anti-IgG levels were determined in individual sera collected at days 28 (PII) and 42 (PIII) using the following protocol:

ELISA to Measure Anti-UspA2 Antibodies.

Plates were coated overnight at 4° C. with 100 µl per well of UspA2 construct MC-009 at 4 µg/ml in carbonate buffer pH 9.6. The plates were washed three times with NaCl 0.09% TWEEN (a US registered trademark) 20 (polysorbate 20) 0.05%. After washing, serial two fold dilutions of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA Sigma P8787) and 5 µl of $H_2O_2$ in 10 ml of citrate 0.1M PH (pH) 4.5) was added to each well (100 µl/well) for 15 min in darkness. The reaction was stopped by addition of 50 µl of HCl 1N and the absorbance was read at 490 nm (620 nm for the reference filter).

The titers were calculated by the 4-parameters method using the SOFTMAX (a US registered trademark) Pro software.

As shown in FIG. 15, UspA2 induced high antibody levels with each adjuvant formulation.

Bactericidal Assay

The bactericidal assay was performed against *M. catarrhalis* strain (ATCC (a US registered trademark) 25238™) expressing a homologous full length UspA2 using the following protocol: *Moraxella catarrhalis* strain ATCC (a US registered trademark) 25238™ was cultivated overnight on Petri dish at 37° C.+5% $CO_2$. Bacteria were transferred in 10 ml of BHi (broth heart infusion) in order to get an $OD_{620}$ of 0.650. Serum samples were heated for 45 min at 56° C. to inactivate the endogenous complement. Serial two-fold dilutions of sera in SBA buffer (HBSS-BSA 0.1%) were added on a 96-well round bottom microtitre plate (25 µl/well). Subsequently, 50 µl of SBA buffer were added in each well. Then 25 µl of *Moraxella catarrhalis* strain 25238™ at 4 $10^3$ cfu/mL were added to the wells containing sera and incubated for 15 min at room temperature. Finally 25 µl of freshly thawed baby rabbit complement diluted ⅛ in HBSS-BSA 0.1% were added to reach a final volume of 125 µl. Plates were incubated for 1 h at 37° C. with orbital shaking (210 rpm). The reaction was stopped by laying the microplate on ice for at least 5 min. A 20 µl aliquot of each well of the plate was then transferred into the corresponding well of a 96-well flat bottom microplate and 50 µl of Mueller Hinton Broth-0.9% agar was added to each well. 50 µl of PBS 0.9% agar was added as a second layer. After 3 hours at 37° C. with 5% $CO_2$ plates were incubated overnight at 25° C., *Moraxella* colonies were counted using an automated image analysis system (KS 400, Zeiss, Oberkochen, Germany). Eight wells without serum sample were used as bacterial controls to determine the number of *Moraxella* per well. The mean number of CFU of the control wells was determined and used for the calculation of the killing activity for each serum sample. The bactericidal titers were expressed at the reciprocal dilution of serum inducing 50% of killing.

FIG. 16 illustrates the bactericidal titers induced by UspA2 against a homologous strain. In this experiment, UspA2 induced high levels of bactericidal antibodies for each adjuvant formulation. Sera were tested at PIII; five pools of five sera samples were tested.

Example 12: Immunogenicity of UspA2 in Combination with PD and PE-PilA NTHi Antigens Immunization Protocol Groups of 25 female Balb/c mice were immunized by the intramuscular (IM) route at days 0, 14 and 28 with 50 µl of the following formulations:
UspA2 construct MC-009 (1 µg) AlPO4
UspA2 construct MC-009 (1 µg) AS04C
UspA2 construct MC-009 (1 µg) AS01E
UspA2-PD-PEPilA (UspA2 construct MC-009, PEPilA construct LVL-735) AlPO4 (1 ug of each of UspA2, PD and PEPilA; 1000 mg/ml AlPO4)
UspA2-PD-PEPilA (UspA2 construct MC-009, PEPilA construct LVL-735) AS04C AlPO4 (1 ug of each of UspA2, PD and PEPilA; 100/100 per ml AlPO4/MPL)
UspA2-PD-PEPilA (UspA2 construct MC-009, PEPilA construct LVL-735) AS01E (1 ug of each of UspA2, PD and PEPilA; 50/50 per ml QS21/MPL)

ELISA to Measure Anti-UspA2 Antibodies

Anti-UspA2 IgG levels were determined in individual sera collected at days 28 and 42 using the following protocol.

Plates were coated overnight at 4° C. with 100 µl per well of UspA2 construct MC-009 at 4 µg/ml in carbonate buffer pH 9.6. The plates were washed three times with NaCl 0.09% TWEEN (a US registered trademark) 20 (polysorbate 20) 0.05%. After washing, serial two fold dilutions of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA Sigma P8787) and 5 µl of $H_2O_2$ in 10 ml of citrate 0.1M PH (pH) 4.5) was added to each well (100 µl/well) for 15 min in darkness. The reaction was stopped by addition of 50 µl of HCl 1N and the absorbance was read at 490 nm (620 nm for the reference filter). The titers were calculated by the 4-parameters method using the SOFTMAX (a US registered trademark) Pro software.

ELISA to Measure Anti-PE Antibodies

Plates were coated overnight at 4° C. with 100 µl per well of 2 µg/ml of UspA2 in carbonate buffer pH 9.6. The plates were washed three times with NaCl 0.09% TWEEN (a US registered trademark) 0.05%. After washing, serial two fold dilution of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA and 5 µl of $H_2O_2$ in 10 ml of citrate 0.1M PH 4.5) was added to each well (100 µl/well) for 15 min in darkness. The reaction was stopped by addition of 50 µl of HCl 1N and the absorbance was read at 490 nm (620 nm for the reference filter).

The titers were calculated by the 4-parameters method using the SOFTMAX (a US registered trademark) Pro software.

ELISA to Measure Anti-PilA Antibodies

Plates were coated overnight at 4° C. with 100 µl per well of 4 µg/ml of PilA in carbonate buffer pH 9.6. The plates were washed three times with NaCl 0.09% TWEEN (a US registered trademark) 0.05%. After washing, serial two fold dilution of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA and 5 µl of $H_2O_2$ in 10 ml of citrate 0.1M PH 4.5) was added to each well (100 µl/well) for 15 min in darkness. The reaction was stopped by addition of 50 µl of HCl 1N and the absorbance was read at 490 nm (620 nm for the reference filter).

The titers were calculated by the 4-parameters method using the SOFTMAX (a US registered trademark) Pro software.

ELISA to Measure Anti-PD Antibodies

Plates were coated overnight at 4° C. with 100 µl per well of 8 µg/ml of PD in carbonate buffer pH 9.6. The plates were washed three times with NaCl 0.09% TWEEN (a US registered trademark) 0.05%. After washing, serial two fold dilution of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA and 5 µl of $H_2O_2$ in 10 ml of citrate 0.1M PH 4.5) was added to each well (100 µl/well) for 15 min in darkness. The reaction was stopped by addition of 50 µl of HCl 1N and the absorbance was read at 490 nm (620 nm for the reference filter).

The titers were calculated by the 4-parameters method using the SOFTMAX (a US registered trademark) Pro software.

Bactericidal Assay

Bactericidal titres were measured in pooled sera (5 pools/group) collected at day 42 using the following protocol:

*Moraxella catarrhalis* was cultivated overnight on Petri dish at 37° C.+5% CO2. Bacteria were transferred in 10 ml BHi (broth heart infusion) medium in order to get an $OD_{620}$ of 0.650. Serum samples were heated for 45 min at 56° C. to inactivate the endogenous complement. Serial two fold dilutions of sera in SBA buffer (HBSS-BSA 0.1%) were added on a 96-well round bottom microtitre plate (25 µl/well).

Subsequently, 50 µl of SBA buffer were added in each well. Then 25 µl of *Moraxella catarrhalis* strain 25238 at 4 $10^3$ cfu/mL were added to the wells containing sera and incubated for 15 min at room temperature. Finally 25 µl of freshly thawed baby rabbit complement diluted ⅛ in HBSS-BSA 0.1% were added to reach a final volume of 125 µl. Plates were incubated for 1 h at 37° C. with orbital shaking (210 rpm). The reaction was stopped by laying the microplate on ice for at least 5 min. A 20 µl aliquot of each well of the plate was then transferred into the corresponding well of a 96-well flat bottom microplate and 50 µl of Mueller Hinton Broth-0.9% agar was added to each well. 50 µl of PBS 0.9% agar was added as a second layer. After 3 hours at 37° C. with 5% $CO_2$ plates were incubated overnight at 25° C. *Moraxella* colonies were counted using an automated image analysis system (KS 400, Zeiss, Oberkochen, Germany). Eight wells without serum sample were used as bacterial controls to determine the number of *Moraxella* per well. The mean number of CFU of the control wells was determined and used for the calculation of the killing activity for each serum sample. The bactericidal titers were expressed at the reciprocal dilution of serum inducing 50% of killing.

The bactericidal assay was performed against *Moraxella catarrhalis* strain 25238™, expressing a homologous UspA2.

A negative impact of the presence of PD and PE-PilA antigens on UspA2 IgG levels was observed in AS04C (post III) and AS01E (post II) formulations (FIG. 17). However the impact remained limited (≤2 fold antibody decrease) and was not confirmed in the bactericidal assay (FIG. 18). The IgG responses induced against PD, PE and PilA in mice by PE-PEPi1A-UspA2 vaccine are shown in FIG. 19, FIG. 20 and FIG. 21, respectively.

Therefore, UspA2 was immunogenic when combined with PD and PE-PilA.

Example 13: UspA2 Construct MC-009: Immunogenicity of PD and PE-PilA NTHi Antigens in Combination with UspA2 in Mice Immunization Protocol Groups of 25 female Balb/c mice were immunized by the intramuscular (IM) route at days 0, 14 and 28 with 50 µl of the following formulations:

PD-PEPilA (1 µg of PD and 1 ug of PEPiIA construct LVL-735) AS01E
UspA2-PD-PEPilA (1 µg of UspA2 construct MC-009, PD and PEPiIA construct LVL-735) AS01E The ELISA IgG levels to PD, PE and PilA were determined in individual sera collected at days 28 (PII) and 42 (PIII).

ELISA to Measure Anti-PE Antibodies

Plates were coated overnight at 4° C. with 100 µl per well of 2 µg/ml of UspA2 in carbonate buffer pH 9.6. The plates were washed three times with NaCl 0.09% TWEEN (a US registered trademark) 0.05%. After washing, serial two fold dilution of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA and 5 µl of $H_2O_2$ in 10 ml of citrate 0.1M PH 4.5) was added to each well (100 µl/well) for 15 min in darkness. The reaction was stopped by addition of 50 µl of HCl 1N and the absorbance was read at 490 nm (620 nm for the reference filter).

The titers were calculated by the 4-parameters method using the SOFTMAX (a US registered trademark) Pro software.

ELISA to Measure Anti-PilA Antibodies

Plates were coated overnight at 4° C. with 100 µl per well of 4 µg/ml of PilA in carbonate buffer pH 9.6. The plates were washed three times with NaCl 0.09% TWEEN (a US registered trademark) 0.05%. After washing, serial two fold dilution of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA and 5 µl of $H_2O_2$ in 10 ml of citrate 0.1M PH 4.5) was added to each well (100 µl/well) for 15 min in darkness. The reaction was stopped by addition of 50 µl of HCl 1N and the absorbance was read at 490 nm (620 nm for the reference filter).

The titers were calculated by the 4-parameters method using the SOFTMAX (a US registered trademark) Pro software.

ELISA to Measure Anti-PD Antibodies

Plates were coated overnight at 4° C. with 100 µl per well of 8 µg/ml of PD in carbonate buffer pH 9.6. The plates were washed three times with NaCl 0.09% TWEEN (a US registered trademark) 0.05%. After washing, serial two fold dilution of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA and 5 µl of $H_2O_2$ in 10 ml of citrate 0.1M PH 4.5) was added to each well (100 µl/well) for 15 min in darkness. The reaction was stopped by addition of 50 µl of HCl 1N and the absorbance was read at 490 nm (620 nm for the reference filter).

The titers were calculated by the 4-parameters method using the SOFTMAX (a US registered trademark) Pro software.

No major impact of the addition of UspA2 on PD and PEPiIA immunogenicity in AS01E was observed as shown in FIGS. 22, 23 and 24.

Example 14: Safety of a Tetravalent Vaccine Formulation Containing UspA2 in a Mouse *Moraxella catarrhalis* Lung Inflammation Model To mitigate the risk of inducing undesirable inflammatory responses in the lungs of COPD patients upon immunization with a candidate vaccine aiming at preventing the exacerbations due to Non-typeable *Haemophilus influenzae* (NTHi) and *Moraxella catarrhalis* (*M. cat.*), various animal models were developed and used to assess the safety of this vaccine. The formulation tested contained three NTHi antigens (PD, PE and PilA, with the two last ones combined as a PEPiIA fusion protein), one *M. cat.* antigen (UspA2) and the Adjuvant System $01_E$ (AS01$_E$).

Two models were particularly dedicated to evaluate the safety of the UspA2 component of the vaccine.

Model 1:

Objective

This model aimed at assessing the possible induction of undesirable immune responses in inflamed lungs upon vaccination.

Study Design

C57Bl/6 mice were sensitized by three intranasal administrations of 25 µg of heat-inactivated *M. cat.* strain ATCC (a US registered trademark) 25238™ whole cells (expressing an UspA2 which is 100% homologous to the vaccine UspA2) at days 0, 7 and 14. This treatment induced in the lungs a perivascular and peribronchiolar inflammation (with formation of lymphoid aggregates), alveolitis, pneumonitis, fibrosis and a strong *M. cat.* whole cell-specific IL-17$^+$ CD4$^+$ T cell response, which altogether mimicked the inflammatory process observed in the lungs of COPD patients (except emphysema).

The mice were then vaccinated at day 42 by the intramuscular route with $\frac{1}{10}^{th}$ of human dose of the following formulations:

PD 10 µg/PEPilA (LVL735 construct, described in WO2012/139225) 10 µg/UspA2 (MC009 construct) 10 µg/AS01$_E$ PD 10 µg/PEPilA (LVL735 construct) 10 µg/UspA2 (MC009 construct) 3.3 µg/AS01$_E$ AS01$_E$ (negative control)

PBS (negative control)

To assess the impact of these formulations on the sensitization-induced lung inflammation:

Mice were daily monitored from day 43 to day 49 to look at mortality and any clinical signs indicating the induction of adverse events (prostration, piloerection, hunched position).

A histological analysis of the lungs was performed at days 2, 7 and 14 post-vaccination (with 5 mice per group and time-point) to look at a possible aggravation of the inflammation.

The induction of potentially undesirable T cell responses was evaluated on pools of lungs collected at days 7 and 14 post-vaccination (with 4 pools/group/time-point and the lungs of 3 mice per pool). The lung T cells were re-stimulated overnight either with UspA2 peptides, heat-inactivated *M. cat.* whole cells (WC) or medium (as a negative control) and then analyzed by flow cytometry for the expression of CD5, CD4, CD8, IL-17, IL-13, TNFα and IFNγ.

Results

No mortality or adverse event was reported.

Lung histology (FIGS. 25 to 29):

The alterations observed in the lungs were similar in severity in all groups and characterized by slight to moderate perivascular/bronchiolar mononuclear cell infiltrates.

No alveolitis and/or pneumonitis related to vaccination were observed.

T cell response:

Strong CD4+ T cell responses (mainly IL-17 and TNFα producing cells) were measured in the lungs upon re-stimulation with WC, but regardless of the formulation administered (vaccines or adjuvant alone or PBS) (FIGS. 30 to 33). Low or no lung CD8+ T cell responses were observed (data not shown).

No detectable T cell response was re-stimulated by UspA2 peptides, whatever the group, indicating that no UspA2-specific response was primed or boosted post-vaccination (data not shown).

Model 2:

Objective

This model aimed at assessing the possible induction of undesirable immune responses in inflamed lungs upon vaccination and *M. cat.* challenge.

Study Design

C57Bl/6 mice were successively:

Sensitized by three intranasal administrations of 25 µg of heat-inactivated *M. cat.* strain 25238 WC (expressing an UspA2 which is 100% homologous to the vaccine UspA2) at days 0, 7 and 14 (as in Model 1).

Vaccinated at day 42 by the intramuscular route with ⅒$^{th}$ of human dose of the following formulations (as in Model 1):

PD (10 µg/PEPilA (LVL735 construct) 10 µg/UspA2 (MC009 construct) 10 µg/AS01$_E$ PD 10 µg/PEPilA (LVL735 construct) 10 µg/UspA2 (MC009 construct) 3.3 µg/AS01$_E$ AS01$_E$ (negative control)

PBS (negative control)

Challenged by one intranasal administration of 25 µg of heat-inactivated *M. cat.* strain F10 WC (expressing an UspA2 which shares 53% homology with the vaccine UspA2) or by one intranasal administration of PBS as a control, both at day 56. The challenge strain was different from the sensitization strain to mimic the situation observed in COPD patients who experience new exacerbations due to newly acquired *M. cat.* strains.

To assess the impact of vaccination and challenge on the sensitization-induced lung inflammation:

Mice were daily monitored from day 43 to day 63 to look at mortality and any clinical signs indicating the induction of adverse events (prostration, piloerection, hunched position).

The induction of potentially undesirable T cell responses was evaluated on pools of lungs collected at days 7 and 14 post-challenge (with 4 pools/group/time-point and the lungs of 3 mice per pool). The lung T cells were re-stimulated overnight either with UspA2 peptides, heat-inactivated *M. cat.* F10 WC or medium (as a negative control) and then analyzed by flow cytometry for the expression of CD5, CD4, CD8, IL-17, IL-13, TNFα and IFNγ.

Results

No mortality or adverse event was reported.

T cell response:

Strong post-challenge CD4+ T cell responses (mainly IL-17 and TNFα producing cells) were measured in the lungs upon re-stimulation with F10 WC, regardless of the formulation administered (vaccines or adjuvant alone or PBS) (FIGS. 34 to 37). Not surprisingly, these responses were higher in mice challenged with inactivated bacteria than in mice challenged with PBS. Whatever the challenge, low or no lung CD8+ T cell responses were observed (data not shown).

No detectable T cell response was re-stimulated by UspA2 peptides, whatever the group, indicating that no UspA2-specific response was primed or boosted post-challenge (data not shown).

CONCLUSION

The PD/PEPilA/UspA2/AS01$_E$ formulations tested and more specifically the UspA2 component of these vaccines were shown safe in a mouse *M. cat.* lung inflammation model.

The invention claimed is:

1. A protein of formula I:

A-(R₁)ₘ—(B)ₙ  (formula I)

wherein:
A is an immunogenic fragment of UspA2 selected from the group consisting of amino acids 30-540 of SEQ ID NO: 1 (SEQ ID NO: 39), amino acids 31-540 of SEQ ID NO: 1 (SEQ ID NO: 40), amino acids 30-519 of SEQ ID NO: 1 (SEQ ID NO: 41), amino acids 30-564 of SEQ ID NO: 1 (SEQ ID NO: 42) and amino acids 31-564 of SEQ ID NO: 1 (SEQ ID NO: 43);
R₁ is AS (alanine serine);
m is 0, 1 or 2;
B is histidine; and
n is 0, 1, 2, 3, 4, 5, or 6,
wherein when m is 0, n is not 0.

2. The protein according to claim 1 further comprising a methionine at the amino terminal.

3. An immunogenic composition comprising the protein according to claim 2, wherein A is SEQ ID NO: 43, and a pharmaceutically acceptable excipient.

4. The immunogenic composition according to claim 3, further comprising an antigen from *Haemophilus influenzae*.

5. The immunogenic composition according to claim 4, wherein the antigen from *Haemophilus influenzae* is Protein D.

6. The immunogenic composition according to claim 5, further comprising Protein E from *Haemophilus influenzae*.

7. The immunogenic composition according to claim 6, further comprising Pilin A from *Haemophilus influenzae*.

8. The immunogenic composition according to claim 7, wherein the Protein E and Pilin A from *Haemophilus influenzae* is present as a PE-PilA fusion protein.

9. The immunogenic composition according to claim 3 further comprising an adjuvant.

10. The immunogenic composition according to claim 8, wherein the PE-PIIA fusion protein is LVL735.

11. The immunogenic composition according to claim 9, wherein the adjuvant is AS01E.

12. A protein of formula I:

A-(R₁)ₘ—(B)ₙ  (formula I)

wherein:
A is an immunogenic fragment of UspA2 having amino acids 31-564 of SEQ ID NO: 1 (SEQ ID NO: 43);
R₁ is an amino acid;
m is 0, 1 or 2,
B is histidine; and
n is 0, 1, 2, 3, 4, 5, or 6,
wherein when m is 0, n is not 0.

13. The protein according to claim 12, further comprising a methionine at the amino terminal.

14. An immunogenic composition comprising the protein according to claim 13 and a pharmaceutically acceptable excipient.

15. The immunogenic composition according to claim 14, further comprising an antigen from *Haemophilus influenzae*.

16. The immunogenic composition according to claim 15, wherein the antigen from *Haemophilus influenzae* is Protein D.

17. The immunogenic composition according to claim 16, further comprising Protein E from *Haemophilus influenzae*.

18. The immunogenic composition according to claim 17, further comprising Pilin A from *Haemophilus influenzae*.

19. The Immunogenic composition according to claim 18, wherein the Protein E and Pilin A from *Haemophilus influenzae* is a PE-PilA fusion protein.

20. The immunogenic composition according to claim 15, further comprising an adjuvant.

21. The immunogenic composition according to claim 19, wherein the PE-PIIA fusion protein is LVL735.

22. The immunogenic composition according to claim 20, wherein the adjuvant is AS01E.

* * * * *

SEQUENCE LISTING

<160> NUMBER OF SEQ ID NOS: 88

<210> SEQ ID NO 1
<211> LENGTH: 630
<212> TYPE: PRT
<213> ORGANISM: Moraxalla catarrhalis

<400> SEQUENCE: 1

```
Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ala Lys
            20                  25                  30

Asn Asp Ile Thr Leu Glu Asp Leu Pro Tyr Leu Ile Lys Lys Ile Asp
        35                  40                  45

Gln Asn Glu Leu Glu Ala Asp Ile Gly Asp Ile Thr Ala Leu Glu Lys
    50                  55                  60

Tyr Leu Ala Leu Ser Gln Tyr Gly Asn Ile Leu Ala Leu Glu Glu Leu
65                  70                  75                  80

Asn Lys Ala Leu Glu Glu Leu Asp Glu Asp Val Gly Trp Asn Gln Asn
                85                  90                  95

Asp Ile Ala Asn Leu Glu Asp Val Glu Thr Leu Thr Lys Asn Gln
            100                 105                 110

Asn Ala Leu Ala Glu Gln Gly Glu Ala Ile Lys Glu Asp Leu Gln Gly
        115                 120                 125

Leu Ala Asp Phe Val Glu Gly Gln Glu Gly Lys Ile Leu Gln Asn Glu
130                 135                 140

Thr Ser Ile Lys Lys Asn Thr Gln Arg Asn Leu Val Asn Gly Phe Glu
145                 150                 155                 160

Ile Glu Lys Asn Lys Asp Ala Ile Ala Lys Asn Asn Glu Ser Ile Glu
                165                 170                 175

Asp Leu Tyr Asp Phe Gly His Glu Val Ala Glu Ser Ile Gly Glu Ile
            180                 185                 190

His Ala His Asn Glu Ala Gln Asn Glu Thr Leu Lys Gly Leu Ile Thr
        195                 200                 205

Asn Ser Ile Glu Asn Thr Asn Asn Ile Thr Lys Asn Lys Ala Asp Ile
210                 215                 220

Gln Ala Leu Glu Asn Asn Val Val Glu Glu Leu Phe Asn Leu Ser Gly
225                 230                 235                 240

Arg Leu Ile Asp Gln Lys Ala Asp Ile Asp Asn Asn Ile Asn Asn Ile
                245                 250                 255

Tyr Glu Leu Ala Gln Gln Gln Asp Gln His Ser Ser Asp Ile Lys Thr
            260                 265                 270

Leu Lys Lys Asn Val Glu Glu Gly Leu Leu Glu Leu Ser Gly His Leu
        275                 280                 285

Ile Asp Gln Lys Thr Asp Ile Ala Gln Asn Gln Ala Asn Ile Gln Asp
290                 295                 300

Leu Ala Thr Tyr Asn Glu Leu Gln Asp Gln Tyr Ala Gln Lys Gln Thr
305                 310                 315                 320

Glu Ala Ile Asp Ala Leu Asn Lys Ala Ser Ser Glu Asn Thr Gln Asn
                325                 330                 335

Ile Glu Asp Leu Ala Ala Tyr Asn Glu Leu Gln Asp Ala Tyr Ala Lys
            340                 345                 350

Gln Gln Thr Glu Ala Ile Asp Ala Leu Asn Lys Ala Ser Ser Glu Asn
        355                 360                 365

Thr Gln Asn Ile Glu Asp Leu Ala Ala Tyr Asn Glu Leu Gln Asp Ala
370                 375                 380

Tyr Ala Lys Gln Gln Thr Glu Ala Ile Asp Ala Leu Asn Lys Ala Ser
385                 390                 395                 400

Ser Glu Asn Thr Gln Asn Ile Ala Lys Asn Gln Ala Asp Ile Ala Asn
                405                 410                 415
```

-continued

```
Asn Ile Asn Asn Ile Tyr Glu Leu Ala Gln Gln Asp Gln His Ser
                420                 425                 430
Ser Asp Ile Lys Thr Leu Ala Lys Ala Ser Ala Ala Asn Thr Asp Arg
            435                 440                 445
Ile Ala Lys Asn Lys Ala Asp Ala Ser Phe Glu Thr Leu Thr
    450                 455                 460
Lys Asn Gln Asn Thr Leu Ile Glu Lys Asp Lys His Asp Lys Leu
465                 470                 475                 480
Ile Thr Ala Asn Lys Thr Ala Ile Asp Ala Asn Lys Ala Ser Ala Asp
                485                 490                 495
Thr Lys Phe Ala Ala Thr Ala Asp Ala Ile Thr Lys Asn Gly Asn Ala
            500                 505                 510
Ile Thr Lys Asn Ala Lys Ser Ile Thr Asp Leu Gly Thr Lys Val Asp
    515                 520                 525
Gly Phe Asp Ser Arg Val Thr Ala Leu Asp Thr Lys Val Asn Ala Phe
            530                 535                 540
Asp Gly Arg Ile Thr Ala Leu Asp Ser Lys Val Glu Asn Gly Met Ala
545                 550                 555                 560
Ala Gln Ala Ala Leu Ser Gly Leu Phe Gln Pro Tyr Ser Val Gly Lys
                565                 570                 575
Phe Asn Ala Thr Ala Ala Leu Gly Gly Tyr Gly Ser Lys Ser Ala Val
            580                 585                 590
Ala Ile Gly Ala Gly Tyr Arg Val Asn Pro Asn Leu Ala Phe Lys Ala
    595                 600                 605
Gly Ala Ala Ile Asn Thr Ser Gly Asn Lys Lys Gly Ser Tyr Asn Ile
            610                 615                 620
Gly Val Asn Tyr Glu Phe
625                 630

<210> SEQ ID NO 2
<211> LENGTH: 613
<212> TYPE: PRT
<213> ORGANISM: Moraxella catarrhalis

<400> SEQUENCE: 2

Met Lys Thr Met Lys Leu Leu Pro Leu Lys Ile Ala Val Thr Ser Ala
1               5                   10                  15
Met Ile Ile Gly Leu Gly Ala Ala Ser Thr Ala Asn Ala Gln Ser Arg
            20                  25                  30
Asp Arg Ser Leu Glu Asp Ile Gln Asp Ser Ile Ser Lys Leu Val Gln
        35                  40                  45
Asp Asp Ile Asn Thr Leu Lys Gln Asp Gln Gln Lys Met Asn Lys Tyr
    50                  55                  60
Leu Leu Leu Asn Gln Leu Ala Asn Thr Leu Ile Thr Asp Glu Leu Asn
65                  70                  75                  80
Asn Asn Val Ile Lys Asn Thr Asn Ser Ile Glu Ala Leu Gly Asp Glu
                85                  90                  95
Ile Gly Trp Leu Glu Asn Asp Ile Ala Asp Leu Glu Glu Gly Val Glu
            100                 105                 110
Glu Leu Thr Lys Asn Gln Asn Thr Leu Ile Glu Lys Asp Glu Glu His
        115                 120                 125
Asp Arg Leu Ile Ala Gln Asn Gln Ala Asp Ile Gln Thr Leu Glu Asn
    130                 135                 140
Asn Val Val Glu Glu Leu Phe Asn Leu Ser Gly Arg Leu Ile Asp Gln
145                 150                 155                 160
```

```
Glu Ala Asp Ile Ala Lys Asn Asn Ala Ser Ile Glu Glu Leu Tyr Asp
            165                 170                 175
Phe Asp Asn Glu Val Ala Glu Arg Ile Gly Glu Ile His Ala Tyr Thr
        180                 185                 190
Glu Glu Val Asn Lys Thr Leu Glu Asn Leu Ile Thr Asn Ser Val Lys
        195                 200                 205
Asn Thr Asp Asn Ile Asp Lys Asn Lys Ala Asp Ile Asp Asn Asn Ile
    210                 215                 220
Asn His Ile Tyr Glu Leu Ala Gln Gln Gln Asp Gln His Ser Ser Asp
225                 230                 235                 240
Ile Lys Thr Leu Lys Asn Asn Val Glu Glu Gly Leu Leu Glu Leu Ser
            245                 250                 255
Gly His Leu Ile Asp Gln Lys Ala Asp Leu Thr Lys Asp Ile Lys Ala
            260                 265                 270
Leu Glu Ser Asn Val Glu Glu Gly Leu Leu Asp Leu Ser Gly Arg Leu
        275                 280                 285
Leu Asp Gln Lys Ala Asp Leu Thr Lys Asp Ile Lys Ala Leu Glu Ser
        290                 295                 300
Asn Val Glu Glu Gly Leu Leu Asp Leu Ser Gly Arg Leu Leu Asp Gln
305                 310                 315                 320
Lys Ala Asp Ile Ala Gln Asn Gln Thr Asp Ile Gln Asp Leu Ala Ala
            325                 330                 335
Tyr Asn Glu Leu Gln Asp Gln Tyr Ala Gln Lys Gln Thr Glu Ala Ile
            340                 345                 350
Asp Ala Leu Asn Lys Ala Ser Ser Glu Asn Thr Gln Asn Ile Glu Asp
        355                 360                 365
Leu Ala Ala Tyr Asn Glu Leu Gln Asp Ala Tyr Ala Lys Gln Gln Thr
        370                 375                 380
Glu Ala Ile Asp Ala Leu Asn Lys Ala Ser Ser Glu Asn Thr Gln Asn
385                 390                 395                 400
Ile Ala Lys Asn Gln Ala Asp Ile Ala Asn Asn Ile Asn Asn Ile Tyr
            405                 410                 415
Glu Leu Ala Gln Gln Gln Asp Gln His Ser Ser Asp Ile Lys Thr Leu
            420                 425                 430
Ala Lys Ala Ser Ala Ala Asn Thr Asn Arg Ile Ala Thr Ala Glu Leu
        435                 440                 445
Gly Ile Ala Glu Asn Lys Lys Asp Ala Gln Ile Ala Lys Ala Gln Ala
        450                 455                 460
Asn Ala Asn Lys Thr Ala Ile Asp Glu Asn Lys Ala Ser Ala Asp Thr
465                 470                 475                 480
Lys Phe Ala Ala Thr Ala Asp Ala Ile Thr Lys Asn Gly Asn Ala Ile
            485                 490                 495
Thr Lys Asn Ala Lys Ser Ile Thr Asp Leu Gly Thr Lys Val Asp Gly
            500                 505                 510
Phe Asp Gly Arg Val Thr Ala Leu Asp Thr Lys Val Asn Ala Phe Asp
        515                 520                 525
Gly Arg Ile Thr Ala Leu Asp Ser Lys Val Glu Asn Gly Met Ala Ala
        530                 535                 540
Gln Ala Ala Leu Ser Gly Leu Phe Gln Pro Tyr Ser Val Gly Lys Phe
545                 550                 555                 560
Asn Ala Thr Ala Ala Leu Gly Gly Tyr Gly Ser Lys Ser Ala Val Ala
            565                 570                 575
```

```
Ile Gly Ala Gly Tyr Arg Val Asn Pro Asn Leu Ala Phe Lys Ala Gly
            580                 585                 590

Ala Ala Ile Asn Thr Ser Gly Asn Lys Gly Ser Tyr Asn Ile Gly
        595                 600                 605

Val Asn Tyr Glu Phe
        610

<210> SEQ ID NO 3
<211> LENGTH: 644
<212> TYPE: PRT
<213> ORGANISM: Moraxella catarrhalis

<400> SEQUENCE: 3

Met Lys Thr Met Lys Leu Leu Pro Leu Lys Ile Ala Val Thr Ser Ala
1               5                   10                  15

Leu Ile Ile Gly Leu Gly Ala Ala Ser Thr Ala Asn Ala Gln Gln Gln
            20                  25                  30

Leu Gln Thr Glu Thr Phe Leu Pro Asn Phe Leu Ser Asn Asp Asn Tyr
        35                  40                  45

Asp Leu Thr Asp Pro Phe Tyr His Asn Met Ile Leu Gly Asp Thr Ala
    50                  55                  60

Leu Leu Asp Lys Gln Asp Gly Ser Gln Pro Gln Leu Lys Phe Tyr Ser
65                  70                  75                  80

Asn Asp Lys Asp Ser Val Pro Asp Ser Leu Leu Phe Ser Lys Leu Leu
                85                  90                  95

His Glu Gln Gln Leu Asn Gly Phe Lys Lys Gly Asp Thr Ile Ile Pro
            100                 105                 110

Leu Asp Lys Asp Gly Lys Pro Val Tyr Gln Val Asp Tyr Lys Leu Asp
        115                 120                 125

Gly Lys Gly Lys Lys Gln Lys Arg Arg Gln Val Tyr Ser Val Thr Thr
    130                 135                 140

Lys Thr Ala Thr Asp Asp Val Asn Ser Ala Tyr Ser Arg Gly Ile
145                 150                 155                 160

Leu Gly Lys Val Asp Asp Leu Asp Asp Glu Met Asn Phe Leu Asn His
                165                 170                 175

Asp Ile Thr Ser Leu Tyr Asp Val Thr Ala Asn Gln Gln Asp Ala Ile
            180                 185                 190

Lys Asp Leu Lys Lys Gly Val Lys Gly Leu Asn Lys Glu Leu Lys Glu
        195                 200                 205

Leu Asp Lys Glu Val Gly Val Leu Ser Arg Asp Ile Gly Ser Leu Asn
    210                 215                 220

Asp Asp Val Ala Gln Asn Asn Glu Ser Ile Glu Asp Leu Tyr Asp Phe
225                 230                 235                 240

Ser Gln Glu Val Ala Asp Ser Ile Gly Glu Ile His Ala His Asn Lys
                245                 250                 255

Ala Gln Asn Glu Thr Leu Gln Asp Leu Ile Thr Asn Ser Val Glu Asn
            260                 265                 270

Thr Asn Asn Ile Thr Lys Asn Lys Ala Asp Ile Gln Ala Leu Glu Asn
        275                 280                 285

Asn Val Val Glu Glu Leu Phe Asn Leu Ser Gly Arg Leu Ile Asp Gln
    290                 295                 300

Lys Ala Asp Leu Thr Lys Asp Ile Lys Thr Leu Glu Ser Asn Val Glu
305                 310                 315                 320

Glu Gly Leu Leu Glu Leu Ser Gly His Leu Ile Asp Gln Lys Ala Asp
                325                 330                 335
```

Ile Ala Lys Asn Gln Ala Asp Ile Ala Gln Asn Gln Ala Asn Ile Gln
                340                 345                 350

Asp Leu Ala Ala Tyr Asn Glu Leu Gln Asp Ala Tyr Ala Lys Gln Gln
                355                 360                 365

Thr Glu Ala Ile Asp Ala Leu Asn Lys Ala Ser Ser Glu Asn Thr Gln
370                 375                 380

Asn Ile Glu Asp Leu Ala Ala Tyr Asn Glu Leu Gln Asp Ala Tyr Ala
385                 390                 395                 400

Lys Gln Gln Thr Glu Ala Ile Asp Ala Leu Asn Lys Ala Ser Ser Glu
                405                 410                 415

Asn Thr Gln Asn Ile Ala Lys Asn Gln Ala Asp Ile Ala Asn Asn Ile
                420                 425                 430

Asn Asn Ile Tyr Glu Leu Ala Gln Gln Gln Asp Gln His Ser Ser Asp
                435                 440                 445

Ile Lys Thr Leu Ala Lys Ala Ser Ala Ala Asn Thr Asp Arg Ile Ala
                450                 455                 460

Lys Asn Lys Ala Asp Ala Asp Ala Ser Phe Glu Thr Leu Thr Lys Asn
465                 470                 475                 480

Gln Asn Thr Leu Ile Glu Lys Asp Lys Glu His Asp Lys Leu Ile Thr
                485                 490                 495

Ala Asn Lys Thr Ala Ile Asp Glu Asn Lys Ala Ser Ala Asp Thr Lys
                500                 505                 510

Phe Ala Ala Thr Ala Asp Ala Ile Thr Lys Asn Gly Asn Ala Ile Thr
                515                 520                 525

Lys Asn Ala Lys Ser Ile Thr Asp Leu Gly Thr Lys Val Asp Gly Phe
                530                 535                 540

Asp Ser Arg Val Thr Ala Leu Asp Thr Lys Val Asn Ala Phe Asp Gly
545                 550                 555                 560

Arg Ile Thr Ala Leu Asp Ser Lys Val Glu Asn Gly Met Ala Ala Gln
                565                 570                 575

Ala Ala Leu Ser Gly Leu Phe Gln Pro Tyr Ser Val Gly Lys Phe Asn
                580                 585                 590

Ala Thr Ala Ala Leu Gly Gly Tyr Gly Ser Lys Ser Ala Val Ala Ile
                595                 600                 605

Gly Ala Gly Tyr Arg Val Asn Pro Asn Leu Ala Phe Lys Ala Gly Ala
                610                 615                 620

Ala Ile Asn Thr Ser Gly Asn Lys Lys Gly Ser Tyr Asn Ile Gly Val
625                 630                 635                 640

Asn Tyr Glu Phe

<210> SEQ ID NO 4
<211> LENGTH: 591
<212> TYPE: PRT
<213> ORGANISM: Moraxella catarrhalis

<400> SEQUENCE: 4

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Leu Val
                20                  25                  30

Glu Arg Phe Phe Pro Asn Ile Phe Leu Asp Lys Pro Leu Ala Lys Gln
                35                  40                  45

His Tyr His Asn Val Val Val Gly Asp Thr Ser Ile Val Ser Asp Leu
                50                  55                  60

-continued

Gln Ser Asn Ser Asp Gln Leu Lys Phe Tyr Ser Asp Asp Glu Gly Leu
65                  70                  75                  80

Val Pro Asp Ser Leu Leu Phe Asn Lys Met Leu His Glu Gln Leu Leu
            85                  90                  95

Asn Gly Phe Lys Glu Gly Asp Thr Ile Ile Pro Leu Asp Glu Asn Gly
                100                 105                 110

Lys Pro Val Tyr Lys Val Asp Tyr Lys Leu Asp Gly Lys Glu Pro Arg
            115                 120                 125

Lys Val Tyr Ser Val Thr Thr Lys Ile Ala Thr Ala Glu Asp Val Ala
130                 135                 140

Thr Ser Ser Tyr Ala Asn Gly Ile Gln Lys Asp Ile Asp Asp Leu Tyr
145                 150                 155                 160

Asp Phe Asp His Gln Val Thr Glu Arg Leu Thr Gln His Gly Lys Thr
                165                 170                 175

Ile Tyr Arg Asn Gly Glu Arg Ile Leu Ala Asn Glu Glu Ser Val Gln
            180                 185                 190

Tyr Leu Asn Lys Glu Val Gln Asn Asn Ile Glu His Ile Tyr Glu Leu
            195                 200                 205

Ala Gln Gln Gln Asp Gln His Ser Ser Asp Ile Lys Thr Leu Glu Ser
210                 215                 220

Asn Val Glu Lys Gly Leu Leu Glu Leu Ser Gly His Leu Ile Asp Gln
225                 230                 235                 240

Lys Ala Asp Leu Thr Lys Asp Ile Lys Thr Leu Glu Ser Asn Val Glu
                245                 250                 255

Glu Gly Leu Leu Asp Leu Ser Gly Arg Leu Ile Asp Gln Lys Ala Asp
            260                 265                 270

Leu Thr Lys Asp Ile Lys Thr Leu Glu Ser Asn Val Glu Glu Gly Leu
            275                 280                 285

Leu Asp Leu Ser Gly Arg Leu Ile Asp Gln Lys Ala Asp Ile Ala Gln
290                 295                 300

Asn Gln Ala Asn Ile Gln Asp Leu Ala Ala Tyr Asn Glu Leu Gln Asp
305                 310                 315                 320

Gln Tyr Ala Gln Lys Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
            355                 360                 365

Asn Lys Ala Ser Ser Glu Asn Thr Gln Asn Ile Ala Lys Asn Gln Ala
370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asn Arg Ile Ala Thr Ala Glu Leu Gly Ile Ala Glu Asn Lys
            420                 425                 430

Lys Asp Ala Gln Ile Ala Lys Ala Gln Ala Asn Ala Asn Lys Thr Ala
            435                 440                 445

Ile Asp Glu Asn Lys Ala Ser Ala Asp Thr Lys Phe Ala Ala Thr Ala
450                 455                 460

Asp Ala Ile Thr Lys Asn Gly Asn Ala Ile Thr Lys Asn Ala Lys Ser
465                 470                 475                 480

-continued

```
Ile Thr Asp Leu Gly Thr Lys Val Asp Gly Phe Asp Ser Arg Val Thr
                485                 490                 495
Ala Leu Asp Thr Lys Val Asn Ala Phe Asp Gly Arg Ile Thr Ala Leu
            500                 505                 510
Asp Ser Lys Val Glu Asn Gly Met Ala Ala Gln Ala Ala Leu Ser Gly
        515                 520                 525
Leu Phe Gln Pro Tyr Ser Val Gly Lys Phe Asn Ala Thr Ala Ala Leu
    530                 535                 540
Gly Gly Tyr Gly Ser Lys Ser Ala Val Ala Ile Gly Ala Gly Tyr Arg
545                 550                 555                 560
Val Asn Pro Asn Leu Ala Phe Lys Ala Gly Ala Ile Asn Thr Ser
                565                 570                 575
Gly Asn Lys Lys Gly Ser Tyr Asn Ile Gly Val Asn Tyr Glu Phe
            580                 585                 590

<210> SEQ ID NO 5
<211> LENGTH: 687
<212> TYPE: PRT
<213> ORGANISM: Moraxella catarrhalis

<400> SEQUENCE: 5

Met Lys Thr Met Lys Leu Leu Pro Leu Lys Ile Ala Val Thr Ser Ala
1               5                   10                  15
Met Ile Ile Gly Leu Gly Ala Ala Ser Thr Ala Asn Ala Gln Gln Gln
            20                  25                  30
Gln Gln Gln Gln Gln Gln Gln Ser Arg Thr Glu Ile Phe Phe Pro
        35                  40                  45
Asn Ile Phe Phe Asn Glu Asn His Asp Glu Leu Asp Asp Ala Tyr His
    50                  55                  60
Asn Ile Ile Leu Gly Asp Thr Ala Leu Leu Asp Lys Gln Asp Gly Ser
65                  70                  75                  80
Gln Pro Gln Leu Lys Phe Tyr Ser Asn Asp Lys Asp Ser Val Pro Asp
                85                  90                  95
Ser Leu Leu Phe Ser Lys Leu Leu His Glu Gln Gln Leu Asn Gly Phe
            100                 105                 110
Lys Lys Gly Asp Thr Ile Ile Pro Leu Asp Lys Asp Gly Lys Pro Val
        115                 120                 125
Tyr Gln Val Asp Tyr Lys Leu Asp Gly Lys Gly Lys Lys Gln Lys Arg
    130                 135                 140
Arg Gln Val Tyr Ser Val Thr Thr Lys Thr Ala Thr Asp Asp Val
145                 150                 155                 160
Asn Ser Ala Tyr Ser Arg Gly Ile Leu Gly Lys Val Asp Asp Leu Asp
                165                 170                 175
Asp Glu Met Asn Phe Leu Asn His Asp Ile Thr Ser Leu Tyr Asp Val
            180                 185                 190
Thr Ala Asn Gln Gln Asp Ala Ile Lys Gly Leu Lys Lys Gly Val Lys
        195                 200                 205
Gly Leu Asn Lys Glu Leu Lys Glu Leu Asp Lys Glu Val Gly Val Leu
    210                 215                 220
Ser Arg Asp Ile Gly Ser Leu Asn Asp Val Ala Gln Asn Asn Glu
225                 230                 235                 240
Ser Ile Glu Asp Leu Tyr Asp Phe Ser Gln Glu Val Ala Asp Ser Ile
                245                 250                 255
Gly Glu Ile His Ala His Asn Lys Ala Gln Asn Glu Thr Leu Gln Asp
            260                 265                 270
```

```
Leu Ile Thr Asn Ser Val Glu Asn Thr Asn Ile Thr Lys Asn Lys
            275                 280                 285

Ala Asp Ile Gln Ala Leu Glu Asn Asn Val Val Glu Glu Leu Phe Asn
290                 295                 300

Leu Ser Gly Arg Leu Ile Asp Gln Lys Ala Asp Leu Thr Lys Asp Ile
305                 310                 315                 320

Lys Thr Leu Glu Ser Asn Val Glu Glu Gly Leu Leu Glu Leu Ser Gly
                325                 330                 335

His Leu Ile Asp Gln Lys Ala Asp Ile Ala Lys Asn Gln Ala Asp Ile
            340                 345                 350

Ala Gln Asn Gln Ala Asn Ile Gln Asp Leu Ala Ala Tyr Asn Glu Leu
            355                 360                 365

Gln Asp Ala Tyr Ala Lys Gln Gln Thr Glu Ala Ile Asp Ala Leu Asn
370                 375                 380

Lys Ala Ser Ser Glu Asn Thr Gln Asn Ile Glu Asp Leu Ala Ala Tyr
385                 390                 395                 400

Asn Glu Leu Gln Asp Ala Tyr Ala Lys Gln Gln Thr Glu Ala Ile Asp
                405                 410                 415

Ala Leu Asn Lys Ala Ser Ser Glu Asn Thr Gln Asn Ile Glu Asp Leu
            420                 425                 430

Ala Ala Tyr Asn Glu Leu Gln Asp Ala Tyr Ala Lys Gln Gln Thr Glu
            435                 440                 445

Ala Ile Asp Ala Leu Asn Lys Ala Ser Ser Glu Asn Thr Gln Asn Ile
            450                 455                 460

Ala Lys Asn Gln Ala Asp Ile Ala Asn Asn Ile Asn Asn Ile Tyr Glu
465                 470                 475                 480

Leu Ala Gln Gln Gln Asp Gln His Ser Ser Asp Ile Lys Thr Leu Ala
                485                 490                 495

Lys Ala Ser Ala Ala Asn Thr Asp Arg Ile Ala Lys Asn Lys Ala Asp
            500                 505                 510

Ala Asp Ala Ser Phe Glu Thr Leu Thr Lys Asn Gln Asn Thr Leu Ile
            515                 520                 525

Glu Lys Asp Lys Glu His Asp Lys Leu Ile Thr Ala Asn Lys Thr Ala
            530                 535                 540

Ile Asp Glu Asn Lys Ala Ser Ala Asp Thr Lys Phe Ala Ala Thr Ala
545                 550                 555                 560

Asp Ala Ile Thr Lys Asn Gly Asn Ala Ile Thr Lys Asn Ala Lys Ser
                565                 570                 575

Ile Thr Asp Leu Gly Thr Lys Val Asp Ala Phe Asp Gly Arg Val Thr
            580                 585                 590

Ala Leu Asp Thr Lys Val Asn Ala Phe Asp Gly Arg Ile Thr Ala Leu
            595                 600                 605

Asp Ser Lys Val Glu Asn Gly Met Ala Ala Gln Ala Ala Leu Ser Gly
            610                 615                 620

Leu Phe Gln Pro Tyr Ser Val Gly Lys Phe Asn Ala Thr Ala Ala Leu
625                 630                 635                 640

Gly Gly Tyr Gly Ser Lys Ser Ala Val Ala Ile Gly Ala Gly Tyr Arg
                645                 650                 655

Val Asn Pro Asn Leu Ala Phe Lys Ala Gly Ala Ala Ile Asn Thr Ser
            660                 665                 670

Gly Asn Lys Lys Gly Ser Tyr Asn Ile Gly Val Asn Tyr Glu Phe
            675                 680                 685
```

```
<210> SEQ ID NO 6
<211> LENGTH: 683
<212> TYPE: PRT
<213> ORGANISM: Moraxella catarrhalis

<400> SEQUENCE: 6

Met Lys Thr Met Lys Leu Leu Pro Leu Lys Ile Ala Val Thr Ser Ala
1               5                   10                  15

Met Ile Val Gly Leu Gly Met Ala Ser Thr Ala Asn Ala Gln Gln Gln
            20                  25                  30

Lys Ser Pro Lys Thr Glu Thr Phe Leu Pro Asn Ile Phe Phe Asn Glu
        35                  40                  45

Tyr Ala Asp Asp Leu Asp Thr Leu Tyr His Asn Met Ile Leu Gly Asp
50                  55                  60

Thr Ala Ile Thr His Asp Asp Gln Tyr Lys Phe Tyr Ala Asp Asp Ala
65                  70                  75                  80

Thr Glu Val Pro Asp Ser Leu Phe Phe Asn Lys Ile Leu His Asp Gln
                85                  90                  95

Leu Leu Tyr Gly Phe Lys Glu Gly Asp Lys Ile Ile Pro Leu Asp Glu
            100                 105                 110

Asn Gly Lys Pro Val Tyr Lys Leu Asp Lys Arg Leu Glu Asn Gly Val
        115                 120                 125

Gln Lys Thr Val Tyr Ser Val Thr Thr Lys Thr Ala Thr Ala Asp Asp
130                 135                 140

Val Asn Ser Ala Tyr Ser Arg Gly Ile Gln Gly Asp Ile Asp Asp Leu
145                 150                 155                 160

Tyr Glu Ala Asn Lys Glu Asn Val Asn Arg Leu Ile Glu His Gly Asp
                165                 170                 175

Lys Ile Phe Ala Asn Glu Glu Ser Val Gln Tyr Leu Asn Arg Glu Val
            180                 185                 190

Gln Asn Asn Ile Glu Asn Ile His Glu Leu Ala Gln Gln Gln Asp Gln
        195                 200                 205

His Ser Ser Asp Ile Lys Thr Leu Lys Lys Asn Val Glu Lys Asp Leu
210                 215                 220

Leu Asp Leu Ser Gly Arg Leu Ile Ala Gln Lys Glu Asp Ile Ala Gln
225                 230                 235                 240

Asn Gln Thr Asp Ile Gln Asp Leu Ala Thr Tyr Asn Glu Leu Gln Asp
                245                 250                 255

Gln Tyr Ala Gln Lys Gln Thr Glu Ala Ile Asp Ala Leu Asn Lys Ala
            260                 265                 270

Ser Ser Glu Asn Thr Gln Asn Ile Ala Lys Asn Ser Asn His Ile Lys
        275                 280                 285

Thr Leu Glu Asn Asn Ile Glu Glu Gly Leu Leu Glu Leu Ser Gly His
290                 295                 300

Leu Ile Asp Gln Lys Ala Asp Leu Thr Lys Asp Ile Lys Ala Leu Glu
305                 310                 315                 320

Ser Asn Val Glu Glu Gly Leu Leu Asp Leu Ser Gly Arg Leu Ile Asp
                325                 330                 335

Gln Lys Ala Asp Ile Ala Gln Asn Gln Ala Asn Ile Gln Asp Leu Ala
            340                 345                 350

Ala Tyr Asn Glu Leu Gln Asp Ala Tyr Ala Lys Gln Gln Thr Glu Ala
        355                 360                 365

Ile Asp Ala Leu Asn Lys Ala Ser Ser Glu Asn Thr Gln Asn Ile Glu
370                 375                 380
```

-continued

Asp Leu Ala Ala Tyr Asn Glu Leu Gln Asp Ala Tyr Lys Gln Gln
385                 390                 395                 400

Thr Glu Ala Ile Asp Ala Leu Asn Lys Ala Ser Ser Glu Asn Thr Gln
            405                 410                 415

Asn Ile Glu Asp Leu Ala Ala Tyr Asn Glu Leu Gln Asp Ala Tyr Ala
        420                 425                 430

Lys Gln Gln Thr Glu Ala Ile Asp Ala Leu Asn Lys Ala Ser Ser Glu
    435                 440                 445

Asn Thr Gln Asn Ile Ala Lys Asn Gln Ala Asp Ile Ala Asn Asn Ile
450                 455                 460

Asn Asn Ile Tyr Glu Leu Ala Gln Gln Asp Gln His Ser Ser Asp
465                 470                 475                 480

Ile Lys Thr Leu Ala Lys Ala Ser Ala Ala Asn Thr Asp Arg Ile Ala
                485                 490                 495

Lys Asn Lys Ala Asp Ala Asp Ala Ser Phe Glu Thr Leu Thr Lys Asn
            500                 505                 510

Gln Asn Thr Leu Ile Glu Lys Asp Lys Glu His Asp Lys Leu Ile Thr
        515                 520                 525

Ala Asn Lys Thr Ala Ile Asp Ala Asn Lys Ala Ser Ala Asp Thr Lys
    530                 535                 540

Phe Ala Ala Thr Ala Asp Ala Ile Thr Lys Asn Gly Asn Ala Ile Thr
545                 550                 555                 560

Lys Asn Ala Lys Ser Ile Thr Asp Leu Gly Thr Lys Val Asp Gly Phe
                565                 570                 575

Asp Gly Arg Val Thr Ala Leu Asp Thr Lys Val Asn Ala Leu Asp Thr
            580                 585                 590

Lys Val Asn Ala Phe Asp Gly Arg Ile Thr Ala Leu Asp Ser Lys Val
        595                 600                 605

Glu Asn Gly Met Ala Ala Gln Ala Ala Leu Ser Gly Leu Phe Gln Pro
610                 615                 620

Tyr Ser Val Gly Lys Phe Asn Ala Thr Ala Ala Leu Gly Gly Tyr Gly
625                 630                 635                 640

Ser Lys Ser Ala Val Ala Ile Gly Ala Gly Tyr Arg Val Asn Pro Asn
                645                 650                 655

Leu Ala Phe Lys Ala Gly Ala Ala Ile Asn Thr Ser Gly Asn Lys Lys
            660                 665                 670

Gly Ser Tyr Asn Ile Gly Val Asn Tyr Glu Phe
        675                 680

<210> SEQ ID NO 7
<211> LENGTH: 684
<212> TYPE: PRT
<213> ORGANISM: Moraxella catarrhalis

<400> SEQUENCE: 7

Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
            20                  25                  30

Lys Ser Pro Lys Thr Glu Ile Phe Leu Pro Asn Leu Phe Asp Asn Asp
        35                  40                  45

Asn Thr Glu Leu Thr Asp Pro Leu Tyr His Asn Met Ile Leu Gly Asn
50                  55                  60

Thr Ala Leu Leu Thr Gln Glu Asn Gln Tyr Lys Phe Tyr Ala Asp Asp
65                  70                  75                  80

```
Gly Asn Gly Val Pro Asp Ser Leu Leu Phe Asn Lys Ile Leu His Asp
                 85                  90                  95

Gln Leu Leu His Gly Phe Lys Glu Gly Thr Ile Ile Pro Leu Asp
            100                 105                 110

Glu Asn Gly Lys Pro Val Tyr Lys Leu Asp Ser Ile Val Glu Gln Gly
            115                 120                 125

Lys Thr Lys Thr Val Tyr Ser Val Thr Thr Lys Thr Ala Thr Ala Asp
130                 135                 140

Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
            180                 185                 190

Val Gln Asn Asn Ile Glu Asn Ile His Glu Leu Ala Gln Gln Gln Asp
            195                 200                 205

Gln His Ser Ser Asp Ile Lys Thr Leu Lys Lys Asn Val Glu Lys Asp
210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
            275                 280                 285

Lys Thr Leu Glu Asn Asn Ile Glu Glu Gly Leu Leu Glu Leu Ser Gly
            290                 295                 300

His Leu Ile Asp Gln Lys Ala Asp Leu Thr Lys Asp Ile Lys Ala Leu
305                 310                 315                 320

Glu Ser Asn Val Glu Glu Gly Leu Leu Asp Leu Ser Gly Arg Leu Ile
                325                 330                 335

Asp Gln Lys Ala Asp Ile Ala Gln Asn Gln Ala Asn Ile Gln Asp Leu
            340                 345                 350

Ala Ala Tyr Asn Glu Leu Gln Asp Ala Tyr Ala Lys Gln Gln Thr Glu
            355                 360                 365

Ala Ile Asp Ala Leu Asn Lys Ala Ser Ser Glu Asn Thr Gln Asn Ile
            370                 375                 380

Glu Asp Leu Ala Ala Tyr Asn Glu Leu Gln Asp Ala Tyr Ala Lys Gln
385                 390                 395                 400

Gln Thr Glu Ala Ile Asp Ala Leu Asn Lys Ala Ser Ser Glu Asn Thr
                405                 410                 415

Gln Asn Ile Glu Asp Leu Ala Ala Tyr Asn Glu Leu Gln Asp Ala Tyr
            420                 425                 430

Ala Lys Gln Gln Thr Glu Ala Ile Asp Ala Leu Asn Lys Ala Ser Ser
            435                 440                 445

Glu Asn Thr Gln Asn Ile Ala Lys Asn Gln Ala Asp Ile Ala Asn Asn
            450                 455                 460

Ile Asn Asn Ile Tyr Glu Leu Ala Gln Gln Gln Asp Gln His Ser Ser
465                 470                 475                 480

Asp Ile Lys Thr Leu Ala Lys Ala Ser Ala Ala Asn Thr Asp Arg Ile
                485                 490                 495
```

```
Ala Lys Asn Lys Ala Asp Ala Asp Ala Ser Phe Glu Thr Leu Thr Lys
                500                 505                 510

Asn Gln Asn Thr Leu Ile Glu Lys Asp Lys Glu His Asp Lys Leu Ile
            515                 520                 525

Thr Ala Asn Lys Thr Ala Ile Asp Ala Asn Lys Ala Ser Ala Asp Thr
        530                 535                 540

Lys Phe Ala Ala Thr Ala Asp Ala Ile Thr Lys Asn Gly Asn Ala Ile
545                 550                 555                 560

Thr Lys Asn Ala Lys Ser Ile Thr Asp Leu Gly Thr Lys Val Asp Gly
                565                 570                 575

Phe Asp Gly Arg Val Thr Ala Leu Asp Thr Lys Val Asn Ala Leu Asp
            580                 585                 590

Thr Lys Val Asn Ala Phe Asp Gly Arg Ile Thr Ala Leu Asp Ser Lys
        595                 600                 605

Val Glu Asn Gly Met Ala Ala Gln Ala Ala Leu Ser Gly Leu Phe Gln
610                 615                 620

Pro Tyr Ser Val Gly Lys Phe Asn Ala Thr Ala Ala Leu Gly Gly Tyr
625                 630                 635                 640

Gly Ser Lys Ser Ala Val Ala Ile Gly Ala Gly Tyr Arg Val Asn Pro
                645                 650                 655

Asn Leu Ala Phe Lys Ala Gly Ala Ala Ile Asn Thr Ser Gly Asn Lys
            660                 665                 670

Lys Gly Ser Tyr Asn Ile Gly Val Asn Tyr Glu Phe
                675                 680

<210> SEQ ID NO 8
<211> LENGTH: 684
<212> TYPE: PRT
<213> ORGANISM: Moraxella catarrhalis

<400> SEQUENCE: 8

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Gln Gln
            20                  25                  30

Gln Lys Thr Lys Thr Glu Val Phe Leu Pro Asn Leu Phe Asp Asn Asp
        35                  40                  45

Tyr Tyr Asp Leu Thr Asp Pro Leu Tyr His Ser Met Ile Leu Gly Asp
    50                  55                  60

Thr Ala Thr Leu Phe Asp Gln Gln Asp Asn Ser Lys Ser Gln Leu Lys
65                  70                  75                  80

Phe Tyr Ser Asn Asp Lys Asp Ser Val Pro Asp Ser Leu Leu Phe Ser
                85                  90                  95

Lys Leu Leu His Glu Gln Gln Leu Asn Gly Phe Lys Ala Gly Asp Thr
            100                 105                 110

Ile Ile Pro Leu Asp Lys Asp Gly Lys Pro Val Tyr Thr Gln Asp Thr
        115                 120                 125

Arg Thr Lys Asp Gly Lys Val Glu Thr Val Tyr Ser Val Thr Thr Lys
    130                 135                 140

Ile Ala Thr Gln Asp Asp Val Glu Gln Ser Ala Tyr Ser Arg Gly Ile
145                 150                 155                 160

Gln Gly Asp Ile Asp Asp Leu Tyr Asp Ile Asn Arg Glu Val Asn Glu
                165                 170                 175

Tyr Leu Lys Ala Thr His Asp Tyr Asn Glu Arg Gln Thr Glu Ala Ile
            180                 185                 190
```

```
Asp Ala Leu Asn Lys Ala Ser Ser Ala Asn Thr Asp Arg Ile Asp Thr
        195                 200                 205
Ala Glu Glu Arg Ile Asp Lys Asn Glu Tyr Asp Ile Lys Ala Leu Glu
    210                 215                 220
Ser Asn Val Gly Lys Asp Leu Leu Asp Leu Ser Gly Arg Leu Ile Ala
225                 230                 235                 240
Gln Lys Glu Asp Ile Asp Asn Ile Asn His Ile Tyr Glu Leu Ala
                245                 250                 255
Gln Gln Gln Asp Gln His Ser Ser Asp Ile Lys Thr Leu Lys Asn Asn
            260                 265                 270
Val Glu Glu Gly Leu Leu Glu Leu Ser Gly His Leu Ile Asp Gln Lys
        275                 280                 285
Ala Asp Leu Thr Lys Asp Ile Lys Thr Leu Glu Asn Asn Ile Glu Glu
    290                 295                 300
Gly Leu Leu Glu Leu Ser Gly His Leu Ile Asp Gln Lys Ala Asp Leu
305                 310                 315                 320
Thr Lys Asp Ile Lys Thr Leu Glu Asn Asn Ile Glu Glu Gly Leu Leu
                325                 330                 335
Glu Leu Ser Gly His Leu Ile Asp Gln Lys Ala Asp Ile Ala Gln Asn
            340                 345                 350
Gln Ala Asn Ile Gln Asp Leu Ala Ala Tyr Asn Glu Leu Gln Asp Gln
        355                 360                 365
Tyr Ala Gln Lys Gln Thr Glu Ala Ile Asp Ala Leu Asn Lys Ala Ser
    370                 375                 380
Ser Glu Asn Thr Gln Asn Ile Glu Asp Leu Ala Ala Tyr Asn Glu Leu
385                 390                 395                 400
Gln Asp Ala Tyr Ala Lys Gln Gln Thr Glu Ala Ile Asp Ala Leu Asn
                405                 410                 415
Lys Ala Ser Ser Glu Asn Thr Gln Asn Ile Glu Asp Leu Ala Ala Tyr
            420                 425                 430
Asn Glu Leu Gln Asp Ala Tyr Ala Lys Gln Gln Thr Glu Ala Ile Asp
        435                 440                 445
Ala Leu Asn Lys Ala Ser Ser Glu Asn Thr Gln Asn Ile Ala Lys Asn
    450                 455                 460
Gln Ala Asp Ile Ala Asn Asn Ile Asn Asn Ile Tyr Glu Leu Ala Gln
465                 470                 475                 480
Gln Gln Asp Gln His Ser Ser Asp Ile Lys Thr Leu Ala Lys Val Ser
                485                 490                 495
Ala Ala Asn Thr Asp Arg Ile Ala Lys Asn Lys Ala Asp Ala Asp Ala
            500                 505                 510
Ser Phe Glu Thr Leu Thr Lys Asn Gln Asn Thr Leu Ile Glu Lys Asp
        515                 520                 525
Lys Glu His Asp Lys Leu Ile Thr Ala Asn Lys Thr Ala Ile Asp Ala
    530                 535                 540
Asn Lys Ala Ser Ala Asp Thr Lys Phe Ala Ala Thr Ala Asp Ala Ile
545                 550                 555                 560
Thr Lys Asn Gly Asn Ala Ile Thr Lys Asn Ala Lys Ser Ile Thr Asp
                565                 570                 575
Leu Gly Thr Lys Val Asp Gly Phe Asp Gly Arg Val Thr Ala Leu Asp
            580                 585                 590
Thr Lys Val Asn Ala Phe Asp Gly Arg Ile Thr Ala Leu Asp Ser Lys
        595                 600                 605
```

```
Val Glu Asn Gly Met Ala Ala Gln Ala Ala Leu Ser Gly Leu Phe Gln
    610                 615                 620

Pro Tyr Ser Val Gly Lys Phe Asn Ala Thr Ala Ala Leu Gly Gly Tyr
625                 630                 635                 640

Gly Ser Lys Ser Ala Val Ala Ile Gly Ala Gly Tyr Arg Val Asn Pro
                645                 650                 655

Asn Leu Ala Phe Lys Ala Gly Ala Ala Ile Asn Thr Ser Gly Asn Lys
            660                 665                 670

Lys Gly Ser Tyr Asn Ile Gly Val Asn Tyr Glu Phe
        675                 680
```

<210> SEQ ID NO 9
<211> LENGTH: 684
<212> TYPE: PRT
<213> ORGANISM: Moraxella catarrhalis

<400> SEQUENCE: 9

```
Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
            20                  25                  30

Lys Ser Pro Lys Thr Glu Ile Phe Leu Pro Asn Leu Phe Asp Asn Asp
        35                  40                  45

Asn Thr Glu Leu Thr Asp Pro Leu Tyr His Asn Met Ile Leu Gly Asn
50                  55                  60

Thr Ala Leu Leu Thr Gln Glu Asn Gln Tyr Lys Phe Tyr Ala Asp Asp
65                  70                  75                  80

Gly Asn Gly Val Pro Asp Ser Leu Leu Phe Asn Lys Ile Leu His Asp
                85                  90                  95

Gln Leu Leu His Gly Phe Lys Lys Gly Asp Thr Ile Ile Pro Leu Asp
            100                 105                 110

Glu Asn Gly Lys Pro Val Tyr Lys Leu Asp Ser Ile Val Glu Gln Gly
        115                 120                 125

Lys Thr Lys Thr Val Tyr Ser Val Thr Thr Lys Thr Ala Thr Ala Asp
130                 135                 140

Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
            180                 185                 190

Val Gln Asn Asn Ile Glu Asn Ile Tyr Glu Leu Val Gln Gln Gln Asp
        195                 200                 205

Gln His Ser Ser Asp Ile Lys Thr Leu Lys Lys Asn Val Glu Lys Asp
210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
        275                 280                 285

Lys Thr Leu Glu Asn Asn Ile Glu Glu Gly Leu Leu Glu Leu Ser Gly
290                 295                 300
```

His Leu Ile Asp Gln Lys Ala Asp Leu Thr Lys Asp Ile Lys Ala Leu
305                 310                 315                 320

Glu Ser Asn Val Glu Glu Gly Leu Leu Asp Leu Ser Gly Arg Leu Ile
            325                 330                 335

Asp Gln Lys Ala Asp Ile Ala Gln Asn Gln Ala Asn Ile Gln Asp Leu
            340                 345                 350

Ala Ala Tyr Asn Glu Leu Gln Asp Ala Tyr Ala Lys Gln Gln Thr Glu
            355                 360                 365

Ala Ile Asp Ala Leu Asn Lys Ala Ser Ser Glu Asn Thr Gln Asn Ile
370                 375                 380

Glu Asp Leu Ala Ala Tyr Asn Glu Leu Gln Asp Ala Tyr Ala Lys Gln
385                 390                 395                 400

Gln Thr Glu Ala Ile Asp Ala Leu Asn Lys Ala Ser Ser Glu Asn Thr
            405                 410                 415

Gln Asn Ile Glu Asp Leu Ala Ala Tyr Asn Glu Leu Gln Asp Ala Tyr
            420                 425                 430

Ala Lys Gln Gln Thr Glu Ala Ile Asp Ala Leu Asn Lys Ala Ser Ser
            435                 440                 445

Glu Asn Thr Gln Asn Ile Ala Lys Asn Gln Ala Asp Ile Ala Asn Asn
450                 455                 460

Ile Asn Asn Ile Tyr Glu Leu Ala Gln Gln Gln Asp Gln His Ser Ser
465                 470                 475                 480

Asp Ile Lys Thr Leu Ala Lys Ser Ala Ala Asn Thr Asp Arg Ile
            485                 490                 495

Ala Lys Asn Lys Ala Asp Ala Asp Ala Ser Phe Glu Thr Leu Thr Lys
            500                 505                 510

Asn Gln Asn Thr Leu Ile Glu Lys Asp Lys Glu His Asp Lys Leu Ile
            515                 520                 525

Thr Ala Asn Lys Thr Ala Ile Asp Ala Asn Lys Ala Ser Ala Asp Thr
530                 535                 540

Lys Phe Ala Ala Thr Ala Asp Ala Ile Thr Lys Asn Gly Asn Ala Ile
545                 550                 555                 560

Thr Lys Asn Ala Lys Ser Ile Thr Asp Leu Gly Thr Lys Val Asp Gly
            565                 570                 575

Phe Asp Gly Arg Val Thr Ala Leu Asp Thr Lys Val Asn Ala Leu Asp
            580                 585                 590

Thr Lys Val Asn Ala Phe Asp Gly Arg Ile Thr Ala Leu Asp Ser Lys
            595                 600                 605

Val Glu Asn Gly Met Ala Ala Gln Ala Ala Leu Ser Gly Leu Phe Gln
            610                 615                 620

Pro Tyr Ser Val Gly Lys Phe Asn Ala Thr Ala Leu Gly Gly Tyr
625                 630                 635                 640

Gly Ser Lys Ser Ala Val Ala Ile Gly Ala Gly Tyr Arg Val Asn Pro
            645                 650                 655

Asn Leu Ala Phe Lys Ala Gly Ala Ala Ile Asn Thr Ser Gly Asn Lys
            660                 665                 670

Lys Gly Ser Tyr Asn Ile Gly Val Asn Tyr Glu Phe
            675                 680

<210> SEQ ID NO 10
<211> LENGTH: 574
<212> TYPE: PRT
<213> ORGANISM: Moraxella catarrhalis

```
<400> SEQUENCE: 10

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Leu Ala
            20                  25                  30

Glu Gln Phe Phe Pro Asn Ile Phe Ser Asn His Ala Pro Val Lys Gln
        35                  40                  45

His Tyr His Asn Val Val Gly Asp Thr Ser Ile Val Glu Asn Leu
    50                  55                  60

Gln Asp Ser Asp Asp Thr Gln Leu Lys Phe Tyr Ser Asn Asp Glu Tyr
65                  70                  75                  80

Ser Val Pro Asp Ser Leu Leu Phe Asn Lys Met Leu His Glu Gln Gln
                85                  90                  95

Leu Asn Gly Phe Lys Lys Gly Asp Thr Ile Ile Pro Leu Asp Glu Asn
            100                 105                 110

Gly Lys Pro Val Tyr Lys Val Asp Tyr Lys Leu Asp Gly Gln Glu Pro
            115                 120                 125

Arg Arg Val Tyr Ser Val Thr Thr Lys Ile Ala Thr Gln Asp Asp Val
    130                 135                 140

Asp Asn Ser Pro Tyr Ser Arg Gly Ile Gln Gly Asp Ile Asp Asp Leu
145                 150                 155                 160

Tyr Glu Ala Asn Lys Glu Asn Val Asn Arg Leu Ile Glu His Gly Asp
                165                 170                 175

Lys Ile Phe Ala Asn Glu Glu Ser Val Gln Tyr Leu Asn Lys Glu Val
            180                 185                 190

Gln Asn Asn Ile Glu Asn Ile Tyr Glu Leu Ala Gln Gln Gln Asp Gln
        195                 200                 205

His Ser Ser Asp Ile Lys Thr Leu Lys Lys Asn Val Glu Glu Gly Leu
    210                 215                 220

Leu Glu Leu Ser Gly His Leu Ile Asp Gln Lys Ala Asp Leu Thr Lys
225                 230                 235                 240

Asp Ile Lys Thr Leu Glu Ser Asn Val Glu Glu Gly Leu Leu Glu Leu
                245                 250                 255

Ser Gly His Leu Ile Asp Gln Lys Ala Asp Ile Ala Lys Asn Gln Ala
            260                 265                 270

Asp Ile Ala Gln Asn Gln Ala Asn Ile Gln Asp Leu Ala Ala Tyr Asn
        275                 280                 285

Glu Leu Gln Asp Ala Tyr Ala Lys Gln Gln Thr Glu Ala Ile Asp Ala
    290                 295                 300

Leu Asn Lys Ala Ser Ser Glu Asn Thr Gln Asn Ile Glu Asp Leu Ala
305                 310                 315                 320

Ala Tyr Asn Glu Leu Gln Asp Ala Tyr Ala Lys Gln Gln Thr Glu Ala
                325                 330                 335

Ile Asp Ala Leu Asn Lys Ala Ser Ser Glu Asn Thr Gln Asn Ile Ala
            340                 345                 350

Lys Asn Gln Ala Asp Ile Ala Asn Asn Ile Asn Asn Ile Tyr Glu Leu
        355                 360                 365

Ala Gln Gln Gln Asp Gln His Ser Ser Asp Ile Lys Thr Leu Ala Lys
    370                 375                 380

Ala Ser Ala Ala Asn Thr Asp Arg Ile Ala Lys Asn Lys Ala Asp Ala
385                 390                 395                 400

Asp Ala Ser Phe Glu Thr Leu Thr Lys Asn Gln Asn Thr Leu Ile Glu
                405                 410                 415
```

```
Lys Asp Lys Glu His Asp Lys Leu Ile Thr Ala Asn Lys Thr Ala Ile
                420                 425                 430

Asp Ala Asn Lys Ala Ser Ala Asp Thr Lys Phe Ala Thr Ala Asp
                435                 440                 445

Ala Ile Thr Lys Asn Gly Asn Ala Ile Thr Lys Asn Ala Lys Ser Ile
    450                 455                 460

Thr Asp Leu Gly Thr Lys Val Asp Ala Phe Asp Gly Arg Val Thr Ala
465                 470                 475                 480

Leu Asp Thr Lys Val Asn Ala Phe Asp Gly Arg Ile Thr Ala Leu Asp
                485                 490                 495

Ser Lys Val Glu Asn Gly Met Ala Ala Gln Ala Ala Leu Ser Gly Leu
                500                 505                 510

Phe Gln Pro Tyr Ser Val Gly Lys Phe Asn Ala Thr Ala Ala Leu Gly
                515                 520                 525

Gly Tyr Gly Ser Lys Ser Ala Val Ala Ile Gly Ala Gly Tyr Arg Val
                530                 535                 540

Asn Pro Asn Leu Ala Phe Lys Ala Gly Ala Ala Ile Asn Thr Ser Gly
545                 550                 555                 560

Asn Lys Lys Gly Ser Tyr Asn Ile Gly Val Asn Tyr Glu Phe
                565                 570

<210> SEQ ID NO 11
<211> LENGTH: 678
<212> TYPE: PRT
<213> ORGANISM: Moraxella catarrhalis

<400> SEQUENCE: 11

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Gln Gln
                20                  25                  30

Pro Gln Thr Glu Thr Phe Phe Pro Asn Ile Phe Phe Asn Glu Asn His
                35                  40                  45

Asp Ala Leu Asp Asp Val Tyr His Asn Met Ile Leu Gly Asp Thr Ala
    50                  55                  60

Ile Thr Gln Asp Asn Gln Tyr Lys Phe Tyr Ala Asp Ala Ile Ser Glu
65                  70                  75                  80

Val Pro Asp Ser Leu Leu Phe Asn Lys Ile Leu His Asp Gln Gln Leu
                85                  90                  95

Asn Gly Phe Lys Glu Gly Asp Thr Ile Ile Pro Leu Asp Glu Asn Gly
                100                 105                 110

Lys Pro Val Tyr Lys Leu Asp Glu Lys Val Glu Asn Gly Val Lys Lys
                115                 120                 125

Ser Val Tyr Ser Val Thr Thr Lys Thr Ala Thr Arg Ala Asp Val Glu
                130                 135                 140

Gln Ser Ala Tyr Ser Arg Gly Ile Gln Gly Asp Ile Asp Asp Leu Tyr
145                 150                 155                 160

Glu Ala Asn Lys Glu Asn Val Asn Arg Leu Ile Glu His Gly Asp Lys
                165                 170                 175

Ile Phe Ala Asn Glu Glu Ser Val Gln Tyr Leu Asn Lys Glu Val Gln
                180                 185                 190

Asn Asn Ile Glu Asn Ile His Glu Leu Ala Gln Gln Asp Gln His
                195                 200                 205

Ser Ser Asp Ile Lys Thr Leu Lys Lys Asn Val Glu Glu Gly Leu Leu
                210                 215                 220
```

```
Glu Leu Ser Gly His Leu Ile Asp Gln Lys Ala Asp Leu Thr Lys Asp
225                 230                 235                 240

Ile Lys Thr Leu Glu Ser Asn Val Glu Glu Gly Leu Leu Asp Leu Ser
            245                 250                 255

Gly Arg Leu Leu Asp Gln Lys Ala Asp Ile Ala Gln Asn Gln Ala Asn
                260                 265                 270

Ile Gln Asp Leu Ala Ala Tyr Asn Glu Leu Gln Asp Ala Tyr Ala Lys
            275                 280                 285

Gln Gln Thr Glu Ala Ile Asp Ala Leu Asn Lys Ala Ser Ser Glu Asn
        290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                325                 330                 335

Ser Glu Asn Thr Gln Asn Ile Glu Asp Leu Ala Ala Tyr Asn Glu Leu
            340                 345                 350

Gln Asp Ala Tyr Ala Lys Gln Gln Thr Glu Ala Ile Asp Ala Leu Asn
        355                 360                 365

Lys Ala Ser Ser Glu Asn Thr Gln Asn Ile Glu Asp Leu Ala Ala Tyr
370                 375                 380

Asn Glu Leu Gln Asp Ala Tyr Ala Lys Gln Gln Thr Glu Ala Ile Asp
385                 390                 395                 400

Ala Leu Asn Lys Ala Ser Ser Glu Asn Thr Gln Asn Ile Glu Asp Leu
                405                 410                 415

Ala Ala Tyr Asn Glu Leu Gln Asp Ala Tyr Ala Lys Gln Gln Thr Glu
            420                 425                 430

Ala Ile Asp Ala Leu Asn Lys Ala Ser Ser Glu Asn Thr Gln Asn Ile
        435                 440                 445

Ala Lys Asn Gln Ala Asp Ile Ala Asn Asn Ile Asn Asn Ile Tyr Glu
450                 455                 460

Leu Ala Gln Gln Gln Asp Gln His Ser Ser Asp Ile Lys Thr Leu Ala
465                 470                 475                 480

Lys Ala Ser Ala Ala Asn Thr Asp Arg Ile Ala Lys Asn Lys Ala Asp
                485                 490                 495

Ala Asp Ala Ser Phe Glu Thr Leu Thr Lys Asn Gln Asn Thr Leu Ile
            500                 505                 510

Glu Lys Asp Lys Glu His Asp Lys Leu Ile Thr Ala Asn Lys Thr Ala
        515                 520                 525

Ile Asp Ala Asn Lys Ala Ser Ala Asp Thr Lys Phe Ala Ala Thr Ala
530                 535                 540

Asp Ala Ile Thr Lys Asn Gly Asn Ala Ile Thr Lys Asn Ala Lys Ser
545                 550                 555                 560

Ile Thr Asp Leu Gly Thr Lys Val Asp Ala Phe Asp Gly Arg Val Thr
                565                 570                 575

Ala Leu Asp Thr Lys Val Asn Ala Leu Asp Thr Lys Val Asn Ala Phe
            580                 585                 590

Asp Gly Arg Ile Thr Ala Leu Asp Ser Lys Val Glu Asn Gly Met Ala
        595                 600                 605

Ala Gln Ala Ala Leu Ser Gly Leu Phe Gln Pro Tyr Ser Val Gly Lys
        610                 615                 620

Phe Asn Ala Thr Ala Ala Leu Gly Gly Tyr Gly Ser Lys Ser Ala Val
625                 630                 635                 640
```

```
Ala Ile Gly Ala Gly Tyr Arg Val Asn Pro Asn Leu Ala Phe Lys Ala
                    645                 650                 655

Gly Ala Ala Ile Asn Thr Ser Gly Asn Lys Lys Gly Ser Tyr Asn Ile
            660                 665                 670

Gly Val Asn Tyr Glu Phe
        675

<210> SEQ ID NO 12
<211> LENGTH: 678
<212> TYPE: PRT
<213> ORGANISM: Moraxella catarrhalis

<400> SEQUENCE: 12

Met Lys Thr Met Lys Leu Leu Pro Leu Lys Ile Ala Val Thr Ser Ala
1               5                   10                  15

Met Ile Val Gly Leu Gly Ala Ala Ser Thr Ala Asn Ala Gln Gln Gln
            20                  25                  30

Gln Gln Pro Arg Thr Glu Thr Phe Phe Pro Asn Ile Phe Phe Asn Glu
        35                  40                  45

Asn His Asp Ala Leu Asp Val Tyr His Asn Met Ile Leu Gly Asp
    50                  55                  60

Thr Ala Ile Thr Gln Asp Asn Gln Tyr Lys Phe Tyr Ala Asp Ala Ile
65                  70                  75                  80

Ser Glu Val Pro Asp Ser Leu Leu Phe Asn Lys Ile Leu His Asp Gln
                85                  90                  95

Gln Leu Asn Gly Phe Lys Glu Gly Asp Thr Ile Ile Pro Leu Asp Glu
            100                 105                 110

Asn Gly Lys Pro Val Tyr Lys Leu Asp Glu Lys Val Glu Asn Gly Val
        115                 120                 125

Lys Lys Ser Val Tyr Ser Val Thr Thr Lys Thr Ala Thr Arg Ala Asp
    130                 135                 140

Val Glu Gln Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
            180                 185                 190

Val Gln Asn Asn Ile Glu Asn Ile His Glu Leu Ala Gln Gln Gln Asp
        195                 200                 205

Gln His Ser Ser Asp Ile Lys Thr Leu Lys Lys Asn Val Glu Lys Asp
    210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
        275                 280                 285

Lys Thr Leu Glu Asn Asn Ile Glu Glu Gly Leu Leu Glu Leu Ser Gly
    290                 295                 300

His Leu Ile Asp Gln Lys Ala Asp Leu Thr Lys Asp Ile Lys Thr Leu
305                 310                 315                 320

Glu Asn Asn Ile Glu Glu Gly Leu Leu Glu Leu Ser Gly His Leu Ile
                325                 330                 335
```

Asp Gln Lys Ala Asp Leu Thr Lys Asp Ile Lys Ala Leu Glu Ser Asn
                340                 345                 350

Val Glu Glu Gly Leu Leu Asp Leu Ser Gly Arg Leu Leu Asp Gln Lys
            355                 360                 365

Ala Asp Ile Ala Gln Asn Gln Ala Asn Ile Gln Asp Leu Ala Ala Tyr
        370                 375                 380

Asn Glu Leu Gln Asp Gln Tyr Ala Gln Lys Gln Thr Glu Ala Ile Asp
385                 390                 395                 400

Ala Leu Asn Lys Ala Ser Ser Glu Asn Thr Gln Asn Ile Glu Asp Leu
                405                 410                 415

Ala Ala Tyr Asn Glu Leu Gln Asp Ala Tyr Ala Lys Gln Thr Glu
            420                 425                 430

Ala Ile Asp Ala Leu Asn Lys Ala Ser Ser Glu Asn Thr Gln Asn Ile
        435                 440                 445

Ala Lys Asn Gln Ala Asp Ile Ala Asn Ile Asn Asn Ile Tyr Glu
            450                 455                 460

Leu Ala Gln Gln Gln Asp Gln His Ser Ser Asp Ile Lys Thr Leu Ala
465                 470                 475                 480

Lys Ala Ser Ala Ala Asn Thr Asp Arg Ile Ala Lys Asn Lys Ala Asp
                485                 490                 495

Ala Asp Ala Ser Phe Glu Thr Leu Thr Lys Asn Gln Asn Thr Leu Ile
            500                 505                 510

Glu Lys Asp Lys Glu His Asp Lys Leu Ile Thr Ala Asn Lys Thr Ala
        515                 520                 525

Ile Asp Thr Asn Lys Ala Ser Ala Asp Thr Lys Phe Ala Ala Thr Ala
530                 535                 540

Asp Ala Ile Thr Lys Asn Gly Asn Ala Ile Thr Lys Asn Ala Lys Ser
545                 550                 555                 560

Ile Thr Asp Leu Gly Thr Lys Val Asp Gly Phe Asp Gly Arg Val Thr
                565                 570                 575

Ala Leu Asp Thr Lys Val Asn Ala Leu Asp Thr Lys Val Asn Ala Phe
            580                 585                 590

Asp Gly Arg Ile Thr Ala Leu Asp Ser Lys Val Glu Asn Gly Met Ala
        595                 600                 605

Ala Gln Ala Ala Leu Ser Gly Leu Phe Gln Pro Tyr Ser Val Gly Lys
            610                 615                 620

Phe Asn Ala Thr Ala Ala Leu Gly Gly Tyr Gly Ser Lys Ser Ala Val
625                 630                 635                 640

Ala Ile Gly Ala Gly Tyr Arg Val Asn Pro Asn Leu Ala Phe Lys Ala
                645                 650                 655

Gly Ala Ala Ile Asn Thr Ser Gly Asn Lys Lys Gly Ser Tyr Asn Ile
            660                 665                 670

Gly Val Asn Tyr Glu Phe
        675

<210> SEQ ID NO 13
<211> LENGTH: 587
<212> TYPE: PRT
<213> ORGANISM: Moraxella catarrhalis

<400> SEQUENCE: 13

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Leu Val

```
                20                  25                  30
Glu Arg Phe Phe Pro Asn Ile Phe Leu Asp Lys Pro Leu Ala Lys Gln
            35                  40                  45
His Tyr His Asn Val Val Gly Asp Thr Ser Ile Val Ser Asp Leu
 50                  55                  60
Gln Ser Asn Ser Asp Gln Leu Lys Phe Tyr Ser Asp Asp Glu Gly Leu
 65                  70                  75                  80
Val Pro Asp Ser Leu Leu Phe Asn Lys Met Leu His Glu Gln Leu Leu
                85                  90                  95
Asn Gly Phe Lys Glu Gly Asp Thr Ile Ile Pro Leu Asp Glu Asn Gly
                100                 105                 110
Lys Pro Val Tyr Lys Val Asp Tyr Lys Leu Asp Gly Lys Glu Pro Arg
                115                 120                 125
Lys Val Tyr Ser Val Thr Thr Lys Ile Ala Thr Ala Glu Asp Val Ala
                130                 135                 140
Thr Ser Ser Tyr Ala Asn Gly Ile Gln Lys Asp Ile Asp Asp Leu Tyr
145                 150                 155                 160
Asp Phe Asp His Gln Val Thr Glu Arg Leu Thr Gln His Gly Lys Thr
                165                 170                 175
Ile Tyr Arg Asn Gly Glu Arg Ile Leu Ala Asn Glu Glu Ser Val Gln
                180                 185                 190
Tyr Leu Asn Lys Glu Val Gln Asn Asn Ile Glu His Ile Tyr Glu Leu
                195                 200                 205
Ala Gln Gln Gln Asp Gln His Ser Ser Asp Ile Lys Thr Leu Glu Ser
                210                 215                 220
Asn Val Glu Lys Gly Leu Leu Glu Leu Ser Gly His Leu Ile Asp Gln
225                 230                 235                 240
Lys Ala Asp Leu Thr Lys Asp Ile Lys Thr Leu Glu Asn Asn Val Glu
                245                 250                 255
Glu Gly Leu Leu Asp Leu Ser Gly Arg Leu Ile Asp Gln Lys Ala Asp
                260                 265                 270
Ile Ala Gln Asn Gln Ala Asn Ile Gln Asp Leu Ala Ala Tyr Asn Glu
                275                 280                 285
Leu Gln Asp Gln Tyr Ala Gln Lys Gln Thr Glu Ala Ile Asp Ala Leu
                290                 295                 300
Asn Lys Ala Ser Ser Glu Asn Thr Gln Asn Ile Glu Asp Leu Ala Ala
305                 310                 315                 320
Tyr Asn Glu Leu Gln Asp Ala Tyr Ala Lys Gln Gln Thr Glu Ala Ile
                325                 330                 335
Asp Ala Leu Asn Lys Ala Ser Ser Glu Asn Thr Gln Asn Ile Ala Lys
                340                 345                 350
Asn Gln Ala Asp Ile Ala Asn Ile Asn Asn Ile Tyr Glu Leu Ala
                355                 360                 365
Gln Gln Gln Asp Gln His Ser Ser Asp Ile Lys Thr Leu Ala Lys Ala
                370                 375                 380
Ser Ala Ala Asn Thr Asp Arg Ile Ala Lys Asn Lys Ala Asp Ala Asp
385                 390                 395                 400
Ala Ser Phe Glu Thr Leu Thr Lys Asn Gln Asn Thr Leu Ile Glu Lys
                405                 410                 415
Asp Lys Glu His Asp Lys Leu Ile Thr Ala Asn Lys Thr Ala Ile Asp
                420                 425                 430
Thr Asn Lys Ala Ser Ala Asp Thr Lys Phe Ala Ala Thr Ala Asp Ala
                435                 440                 445
```

```
Ile Thr Lys Asn Gly Asn Ala Ile Thr Lys Asn Ala Lys Ser Ile Thr
    450                 455                 460

Asp Leu Gly Thr Lys Val Asp Gly Phe Asp Ser Arg Val Thr Ala Leu
465                 470                 475                 480

Asp Thr Lys Val Asn Ala Leu Asp Thr Lys Val Asn Ala Leu Asp Thr
                485                 490                 495

Lys Val Asn Ala Phe Asp Gly Arg Ile Thr Ala Leu Asp Ser Lys Val
                500                 505                 510

Glu Asn Gly Met Ala Ala Gln Ala Ala Leu Ser Gly Leu Phe Gln Pro
            515                 520                 525

Tyr Ser Val Gly Lys Phe Asn Ala Thr Ala Ala Leu Gly Gly Tyr Gly
    530                 535                 540

Ser Lys Ser Ala Val Ala Ile Gly Ala Gly Tyr Arg Val Asn Pro Asn
545                 550                 555                 560

Leu Ala Phe Lys Ala Gly Ala Ala Ile Asn Thr Ser Gly Asn Lys Lys
                565                 570                 575

Gly Ser Tyr Asn Ile Gly Val Asn Tyr Glu Phe
            580                 585

<210> SEQ ID NO 14
<211> LENGTH: 678
<212> TYPE: PRT
<213> ORGANISM: Moraxella catarrhalis

<400> SEQUENCE: 14

Met Lys Thr Met Lys Leu Leu Pro Leu Lys Ile Ala Val Thr Ser Ala
1               5                   10                  15

Met Ile Val Gly Leu Gly Ala Ala Ser Thr Ala Asn Ala Gln Gln Gln
            20                  25                  30

Gln Gln Pro Arg Thr Glu Thr Phe Phe Pro Asn Ile Phe Phe Asn Glu
        35                  40                  45

Asn His Asp Ala Leu Asp Asp Val Tyr His Asn Met Ile Leu Gly Asp
    50                  55                  60

Thr Ala Ile Thr Gln Asp Asn Gln Tyr Lys Phe Tyr Ala Asp Ala Ile
65                  70                  75                  80

Ser Glu Val Pro Asp Ser Leu Leu Phe Asn Lys Ile Leu His Asp Gln
                85                  90                  95

Gln Leu Asn Gly Phe Lys Glu Gly Asp Thr Ile Ile Pro Leu Asp Glu
            100                 105                 110

Asn Gly Lys Pro Val Tyr Lys Leu Asp Glu Lys Val Glu Asn Gly Val
        115                 120                 125

Lys Lys Ser Val Tyr Ser Val Thr Thr Lys Thr Ala Thr Arg Ala Asp
    130                 135                 140

Val Glu Gln Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Ser Val Gln Tyr Leu Asn Arg Glu
            180                 185                 190

Val Gln Asn Asn Ile Glu Asn His Glu Leu Ala Gln Gln Gln Asp
        195                 200                 205

Gln His Ser Ser Asp Ile Lys Thr Leu Lys Lys Asn Val Glu Lys Asp
    210                 215                 220

Leu Leu Asp Leu Ser Gly Arg Leu Ile Ala Gln Lys Glu Asp Ile Ala
```

-continued

```
            225                 230                 235                 240
        Gln Asn Gln Thr Asp Ile Gln Asp Leu Ala Thr Tyr Asn Glu Leu Gln
                            245                 250                 255
        Asp Gln Tyr Ala Gln Lys Gln Thr Glu Ala Ile Asp Ala Leu Asn Lys
                            260                 265                 270
        Ala Ser Ser Glu Asn Thr Gln Asn Ile Ala Lys Asn Ser Asn His Ile
                            275                 280                 285
        Lys Thr Leu Glu Asn Asn Ile Glu Glu Gly Leu Leu Glu Leu Ser Gly
                    290                 295                 300
        His Leu Ile Asp Gln Lys Ala Asp Leu Thr Lys Asp Ile Lys Thr Leu
        305                 310                 315                 320
        Glu Asn Asn Ile Glu Glu Gly Leu Leu Glu Leu Ser Gly His Leu Ile
                                325                 330                 335
        Asp Gln Lys Ala Asp Leu Thr Lys Asp Ile Lys Ala Leu Glu Ser Asn
                            340                 345                 350
        Val Glu Glu Gly Leu Leu Asp Leu Ser Gly Arg Leu Leu Asp Gln Lys
                        355                 360                 365
        Ala Asp Ile Ala Gln Asn Gln Ala Asn Ile Gln Asp Leu Ala Ala Tyr
                    370                 375                 380
        Asn Glu Leu Gln Asp Gln Tyr Ala Gln Lys Gln Thr Glu Ala Ile Asp
        385                 390                 395                 400
        Ala Leu Asn Lys Ala Ser Ser Glu Asn Thr Gln Asn Ile Glu Asp Leu
                            405                 410                 415
        Ala Ala Tyr Asn Glu Leu Gln Asp Ala Tyr Ala Lys Gln Gln Thr Glu
                        420                 425                 430
        Ala Ile Asp Ala Leu Asn Lys Ala Ser Ser Glu Asn Thr Gln Asn Ile
                    435                 440                 445
        Ala Lys Asn Gln Ala Asp Ile Ala Asn Asn Ile Asn Asn Ile Tyr Glu
                    450                 455                 460
        Leu Ala Gln Gln Gln Asp Gln His Ser Ser Asp Ile Lys Thr Leu Ala
        465                 470                 475                 480
        Lys Ala Ser Ala Ala Asn Thr Asp Arg Ile Ala Lys Asn Lys Ala Asp
                            485                 490                 495
        Ala Asp Ala Ser Phe Glu Thr Leu Thr Lys Asn Gln Asn Thr Leu Ile
                        500                 505                 510
        Glu Lys Asp Lys Glu His Asp Lys Leu Ile Thr Ala Asn Lys Thr Ala
                    515                 520                 525
        Ile Asp Thr Asn Lys Ala Ser Ala Asp Thr Lys Phe Ala Ala Thr Ala
                530                 535                 540
        Asp Ala Ile Thr Lys Asn Gly Asn Ala Ile Thr Lys Asn Ala Lys Ser
        545                 550                 555                 560
        Ile Thr Asp Leu Gly Thr Lys Val Asp Gly Phe Asp Gly Arg Val Thr
                            565                 570                 575
        Ala Leu Asp Thr Lys Val Asn Ala Leu Asp Thr Lys Val Asn Ala Phe
                        580                 585                 590
        Asp Gly Arg Ile Thr Ala Leu Asp Ser Lys Val Glu Asn Gly Met Ala
                    595                 600                 605
        Ala Gln Ala Ala Leu Ser Gly Leu Phe Gln Pro Tyr Ser Val Gly Lys
                    610                 615                 620
        Phe Asn Ala Thr Ala Ala Leu Gly Gly Tyr Gly Ser Lys Ser Ala Val
        625                 630                 635                 640
        Ala Ile Gly Ala Gly Tyr Arg Val Asn Pro Asn Leu Ala Phe Lys Ala
                            645                 650                 655
```

```
Gly Ala Ala Ile Asn Thr Ser Gly Asn Lys Gly Ser Tyr Asn Ile
            660                 665                 670

Gly Val Asn Tyr Glu Phe
        675

<210> SEQ ID NO 15
<211> LENGTH: 616
<212> TYPE: PRT
<213> ORGANISM: Moraxella catarrhalis

<400> SEQUENCE: 15

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Val Arg
            20                  25                  30

Asp Lys Ser Leu Glu Asp Ile Glu Ala Leu Leu Gly Lys Ile Asp Ile
        35                  40                  45

Ser Lys Leu Glu Lys Glu Lys Lys Gln Gln Thr Glu Leu Gln Lys Tyr
    50                  55                  60

Leu Leu Leu Ser Gln Tyr Ala Asn Val Leu Thr Met Glu Glu Leu Asn
65                  70                  75                  80

Lys Asn Val Glu Lys Asn Thr Asn Ser Ile Glu Ala Leu Gly Tyr Glu
                85                  90                  95

Ile Gly Trp Leu Glu Asn Asp Ile Ala Asp Leu Glu Glu Gly Val Glu
            100                 105                 110

Glu Leu Thr Lys Asn Gln Asn Thr Leu Ile Glu Lys Asp Glu His
        115                 120                 125

Asp Arg Leu Ile Ala Gln Asn Gln Ala Asp Ile Lys Thr Leu Glu Asn
    130                 135                 140

Asn Val Val Glu Glu Leu Phe Asn Leu Ser Asp Arg Leu Ile Asp Gln
145                 150                 155                 160

Glu Ala Asp Ile Ala Lys Asn Asn Ala Ser Ile Glu Glu Leu Tyr Asp
                165                 170                 175

Phe Asp Asn Glu Val Ala Glu Arg Ile Gly Glu Ile His Ala Tyr Thr
            180                 185                 190

Glu Glu Val Asn Lys Thr Leu Glu Lys Leu Ile Thr Asn Ser Val Lys
        195                 200                 205

Asn Thr Asp Asn Ile Asp Lys Asn Lys Ala Asp Ile Gln Ala Leu Glu
    210                 215                 220

Asn Asn Val Glu Glu Gly Leu Leu Glu Leu Ser Gly His Leu Ile Asp
225                 230                 235                 240

Gln Lys Ala Asp Leu Thr Lys Asp Ile Lys Ala Leu Glu Ser Asn Val
                245                 250                 255

Glu Glu Gly Leu Leu Asp Leu Ser Gly Arg Leu Leu Asp Gln Lys Ala
            260                 265                 270

Asp Ile Ala Lys Asn Gln Ala Asp Ile Ala Gln Asn Thr Asp Ile
        275                 280                 285

Gln Asp Leu Ala Ala Tyr Asn Glu Leu Gln Asp Gln Tyr Ala Gln Lys
    290                 295                 300

Gln Thr Glu Ala Ile Asp Ala Leu Asn Lys Ala Ser Ser Glu Asn Thr
305                 310                 315                 320

Gln Asn Ile Glu Asp Leu Ala Ala Tyr Asn Glu Leu Gln Asp Ala Tyr
                325                 330                 335

Ala Lys Gln Gln Thr Glu Ala Ile Asp Ala Leu Asn Lys Ala Ser Ser
```

```
                340                 345                 350
Glu Asn Thr Gln Asn Ile Glu Asp Leu Ala Ala Tyr Asn Glu Leu Gln
            355                 360                 365

Asp Ala Tyr Ala Lys Gln Gln Thr Glu Ala Ile Asp Ala Leu Asn Lys
370                 375                 380

Ala Ser Ser Glu Asn Thr Gln Asn Ile Ala Lys Asn Gln Ala Asp Ile
385                 390                 395                 400

Ala Asn Asn Ile Asn Asn Ile Tyr Glu Leu Ala Gln Gln Gln Asp Gln
                405                 410                 415

His Ser Ser Asp Ile Lys Thr Leu Ala Lys Val Ser Ala Ala Asn Thr
            420                 425                 430

Asp Arg Ile Ala Lys Asn Lys Ala Asp Ala Asp Ala Ser Phe Glu Thr
        435                 440                 445

Leu Thr Lys Asn Gln Asn Thr Leu Ile Glu Lys Asp Lys Glu His Asp
    450                 455                 460

Lys Leu Ile Thr Ala Asn Lys Thr Ala Ile Asp Ala Asn Lys Ala Ser
465                 470                 475                 480

Ala Asp Thr Lys Phe Ala Ala Thr Ala Asp Ala Ile Thr Lys Asn Gly
                485                 490                 495

Asn Ala Ile Thr Lys Asn Ala Lys Ser Ile Thr Asp Leu Gly Thr Lys
            500                 505                 510

Val Asp Gly Phe Asp Ser Arg Val Thr Ala Leu Asp Thr Lys Val Asn
        515                 520                 525

Ala Phe Asp Gly Arg Ile Thr Ala Leu Asp Ser Lys Val Glu Asn Gly
    530                 535                 540

Met Ala Ala Gln Ala Ala Leu Ser Gly Leu Phe Gln Pro Tyr Ser Val
545                 550                 555                 560

Gly Lys Phe Asn Ala Thr Ala Ala Leu Gly Tyr Gly Ser Lys Ser
                565                 570                 575

Ala Val Ala Ile Gly Ala Gly Tyr Arg Val Asn Pro Asn Leu Ala Phe
            580                 585                 590

Lys Ala Gly Ala Ala Ile Asn Thr Ser Gly Asn Lys Lys Gly Ser Tyr
        595                 600                 605

Asn Ile Gly Val Asn Tyr Glu Phe
    610                 615

<210> SEQ ID NO 16
<211> LENGTH: 676
<212> TYPE: PRT
<213> ORGANISM: Moraxella catarrhalis

<400> SEQUENCE: 16

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Thr
            20                  25                  30

Glu Thr Phe Leu Pro Asn Leu Phe Asp Asn Asp Tyr Thr Glu Thr Thr
        35                  40                  45

Asp Pro Leu Tyr His Gly Met Ile Leu Gly Asn Thr Ala Ile Thr Gln
    50                  55                  60

Asp Thr Gln Tyr Lys Phe Tyr Ala Glu Asn Gly Asn Glu Val Pro Asp
65                  70                  75                  80

Ser Leu Phe Phe Asn Lys Ile Leu His Asp Gln Gln Leu Asn Gly Phe
                85                  90                  95
```

-continued

```
Lys Glu Gly Asp Thr Ile Ile Pro Leu Asp Glu Asn Gly Lys Pro Val
                100                 105                 110
Tyr Lys Leu Asp Glu Ile Thr Glu Asn Gly Val Lys Arg Lys Val Tyr
            115                 120                 125
Ser Val Thr Thr Lys Thr Ala Thr Arg Glu Asp Val Glu Gln Ser Ala
        130                 135                 140
Tyr Ser Arg Gly Ile Gln Gly Asp Ile Asp Asp Leu Tyr Glu Ala Asn
145                 150                 155                 160
Lys Glu Asn Val Asn Arg Leu Ile Glu His Gly Asp Lys Ile Phe Ala
                165                 170                 175
Asn Glu Glu Ser Val Gln Tyr Leu Asn Lys Glu Val Gln Asn Asn Ile
            180                 185                 190
Glu Asn Ile His Glu Leu Ala Gln Gln Asp Gln His Ser Ser Asp
        195                 200                 205
Ile Lys Thr Leu Lys Lys Asn Val Glu Glu Gly Leu Leu Glu Leu Ser
    210                 215                 220
Gly His Leu Ile Asp Gln Lys Ala Asp Leu Thr Lys Asp Ile Lys Ala
225                 230                 235                 240
Leu Glu Ser Asn Val Glu Glu Gly Leu Leu Asp Leu Ser Gly His Leu
                245                 250                 255
Ile Asp Gln Lys Ala Asp Leu Thr Lys Asp Ile Lys Ala Leu Glu Ser
            260                 265                 270
Asn Val Glu Glu Gly Leu Leu Asp Leu Ser Gly Arg Leu Leu Asp Gln
        275                 280                 285
Lys Ala Asp Ile Ala Lys Asn Gln Ala Asp Ile Ala Gln Asn Gln Thr
    290                 295                 300
Asp Ile Gln Asp Leu Ala Ala Tyr Asn Glu Leu Gln Asp Gln Tyr Ala
305                 310                 315                 320
Gln Lys Gln Thr Glu Ala Ile Asp Ala Leu Asn Lys Ala Ser Ser Glu
                325                 330                 335
Asn Thr Gln Asn Ile Glu Asp Leu Ala Ala Tyr Asn Glu Leu Gln Asp
            340                 345                 350
Gln Tyr Ala Gln Lys Gln Thr Glu Ala Ile Asp Ala Leu Asn Lys Ala
        355                 360                 365
Ser Ser Glu Asn Thr Gln Asn Ile Glu Asp Leu Ala Ala Tyr Asn Glu
    370                 375                 380
Leu Gln Asp Gln Tyr Ala Gln Lys Gln Thr Glu Ala Ile Asp Ala Leu
385                 390                 395                 400
Asn Lys Ala Ser Ser Glu Asn Thr Gln Asn Ile Glu Asp Leu Ala Ala
                405                 410                 415
Tyr Asn Glu Leu Gln Asp Gln Tyr Ala Gln Lys Gln Thr Glu Ala Ile
            420                 425                 430
Asp Ala Leu Asn Lys Ala Ser Ser Glu Asn Thr Gln Asn Ile Ala Lys
        435                 440                 445
Asn Gln Ala Asp Ile Ala Asn Asn Ile Asn Asn Ile Tyr Glu Leu Ala
    450                 455                 460
Gln Gln Gln Asp Gln His Ser Ser Asp Ile Lys Thr Leu Ala Lys Ala
465                 470                 475                 480
Ser Ala Ala Asn Thr Asp Arg Ile Ala Lys Asn Lys Ala Asp Ala Asp
                485                 490                 495
Ala Ser Phe Glu Thr Leu Thr Lys Asn Gln Asn Thr Leu Ile Glu Lys
            500                 505                 510
Asp Lys Glu His Asp Lys Leu Ile Thr Ala Asn Lys Thr Ala Ile Asp
```

```
            515                 520                 525
Ala Asn Lys Ala Ser Ala Asp Thr Lys Phe Ala Ala Thr Ala Asp Ala
    530                 535                 540

Ile Thr Lys Asn Gly Asn Ala Ile Thr Lys Asn Ala Lys Ser Ile Thr
545                 550                 555                 560

Asp Leu Gly Thr Lys Val Asp Gly Phe Asp Gly Arg Val Thr Ala Leu
                565                 570                 575

Asp Thr Lys Val Asn Ala Leu Asp Thr Lys Val Asn Ala Phe Asp Gly
            580                 585                 590

Arg Ile Thr Ala Leu Asp Ser Lys Val Glu Asn Gly Met Ala Ala Gln
        595                 600                 605

Ala Ala Leu Ser Gly Leu Phe Gln Pro Tyr Ser Val Gly Lys Phe Asn
    610                 615                 620

Ala Thr Ala Ala Leu Gly Gly Tyr Gly Ser Lys Ser Ala Val Ala Ile
625                 630                 635                 640

Gly Ala Gly Tyr Arg Val Asn Pro Asn Leu Ala Phe Lys Ala Gly Ala
                645                 650                 655

Ala Ile Asn Thr Ser Gly Asn Lys Lys Gly Ser Tyr Asn Ile Gly Val
            660                 665                 670

Asn Tyr Glu Phe
        675

<210> SEQ ID NO 17
<211> LENGTH: 629
<212> TYPE: PRT
<213> ORGANISM: Moraxella catarrhalis

<400> SEQUENCE: 17

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Asn Gly
            20                  25                  30

Thr Ser Thr Lys Leu Lys Asn Leu Lys Glu Tyr Ala Gln Tyr Leu Asp
        35                  40                  45

Asn Tyr Ala Gln Tyr Leu Asp Asp Ile Asp Asp Leu Asp Lys Glu
    50                  55                  60

Val Gly Glu Leu Ser Gln Asn Ile Ala Lys Asn Gln Ala Asn Ile Lys
65                  70                  75                  80

Asp Leu Asn Lys Lys Leu Ser Arg Asp Ile Asp Ser Leu Arg Glu Asp
                85                  90                  95

Val Tyr Asp Asn Gln Tyr Glu Ile Val Asn Asn Gln Ala Asp Ile Glu
            100                 105                 110

Lys Asn Gln Asp Asp Ile Lys Glu Leu Glu Asn Asn Val Gly Lys Glu
        115                 120                 125

Leu Leu Asn Leu Ser Gly Arg Leu Leu Asp Gln Lys Ala Asp Ile Asp
    130                 135                 140

Asn Asn Ile Asn Asn Ile Tyr Glu Leu Ala Gln Gln Asp Gln His
145                 150                 155                 160

Ser Ser Asp Ile Lys Thr Leu Lys Lys Asn Val Glu Glu Gly Leu Leu
                165                 170                 175

Glu Leu Ser Gly His Leu Ile Asp Gln Lys Ser Asp Ile Ala Gln Asn
            180                 185                 190

Gln Thr Asp Ile Gln Asp Leu Ala Thr Tyr Asn Glu Leu Gln Asp Gln
        195                 200                 205
```

-continued

```
Tyr Ala Gln Lys Gln Thr Glu Ala Ile Asp Ala Leu Asn Lys Ala Ser
    210                 215                 220
Ser Glu Asn Thr Gln Asn Ile Glu Asp Leu Ala Ala Tyr Asn Glu Leu
225                 230                 235                 240
Gln Asp Ala Tyr Ala Lys Gln Gln Thr Glu Ala Ile Asp Ala Leu Asn
                245                 250                 255
Lys Ala Ser Ser Glu Asn Thr Gln Asn Ile Gln Asp Leu Ala Ala Tyr
            260                 265                 270
Asn Glu Leu Gln Asp Ala Tyr Ala Lys Gln Gln Thr Glu Ala Ile Asp
        275                 280                 285
Ala Leu Asn Lys Ala Ser Ser Glu Asn Thr Gln Asn Ile Glu Asp Leu
    290                 295                 300
Ala Ala Tyr Asn Glu Leu Gln Asp Ala Tyr Ala Lys Gln Gln Thr Glu
305                 310                 315                 320
Ala Ile Asp Ala Leu Asn Lys Ala Ser Ser Glu Asn Thr Gln Asn Ile
                325                 330                 335
Glu Asp Leu Ala Ala Tyr Asn Glu Leu Gln Asp Ala Tyr Ala Lys Gln
            340                 345                 350
Gln Thr Glu Ala Ile Asp Ala Leu Asn Lys Ala Ser Ser Glu Asn Thr
        355                 360                 365
Gln Asn Ile Glu Asp Leu Ala Ala Tyr Asn Glu Leu Gln Asp Ala Tyr
    370                 375                 380
Ala Lys Gln Gln Thr Glu Ala Ile Asp Ala Leu Asn Lys Ala Ser Ser
385                 390                 395                 400
Glu Asn Thr Gln Asn Ile Ala Lys Asn Gln Ala Asp Ile Ala Asn Asn
                405                 410                 415
Ile Asn Asn Ile Tyr Glu Leu Ala Gln Gln Gln Asp Gln His Ser Ser
            420                 425                 430
Asp Ile Lys Thr Leu Ala Lys Ala Ser Ala Ala Asn Thr Asp Arg Ile
        435                 440                 445
Ala Lys Asn Lys Ala Asp Ala Asp Ala Ser Phe Glu Thr Leu Thr Lys
    450                 455                 460
Asn Gln Asn Thr Leu Ile Glu Lys Asp Lys Glu His Asp Lys Leu Ile
465                 470                 475                 480
Thr Ala Asn Lys Thr Ala Ile Asp Ala Asn Lys Ala Ser Ala Asp Thr
                485                 490                 495
Lys Phe Ala Ala Thr Ala Asp Ala Ile Thr Lys Asn Gly Asn Ala Ile
            500                 505                 510
Thr Lys Asn Ala Lys Ser Ile Thr Asp Leu Gly Thr Lys Val Asp Ala
        515                 520                 525
Phe Asp Gly Arg Val Thr Ala Leu Asp Thr Lys Val Asn Ala Phe Asp
    530                 535                 540
Gly Arg Ile Thr Ala Leu Asp Ser Lys Val Glu Asn Gly Met Ala Ala
545                 550                 555                 560
Gln Ala Ala Leu Ser Gly Leu Phe Gln Pro Tyr Ser Val Gly Lys Phe
                565                 570                 575
Asn Ala Thr Ala Ala Leu Gly Gly Tyr Gly Ser Lys Ser Ala Val Ala
            580                 585                 590
Ile Gly Ala Gly Tyr Arg Val Asn Pro Asn Leu Ala Phe Lys Ala Gly
        595                 600                 605
Ala Ala Ile Asn Thr Ser Gly Asn Lys Lys Gly Ser Tyr Asn Ile Gly
    610                 615                 620
Val Asn Tyr Glu Phe
```

<210> SEQ ID NO 18
<211> LENGTH: 683
<212> TYPE: PRT
<213> ORGANISM: Moraxella catarrhalis

<400> SEQUENCE: 18

```
Met Lys Thr Met Lys Leu Leu Pro Leu Lys Ile Ala Val Thr Ser Ala
1               5                   10                  15

Met Ile Val Gly Leu Gly Met Ala Ser Thr Ala Asn Ala Gln Gln Gln
            20                  25                  30

Arg Ser Pro Lys Thr Glu Thr Phe Leu Pro Asn Ile Phe Phe Asn Glu
        35                  40                  45

Tyr Ala Asp Asp Leu Asp Thr Leu Tyr His Asn Met Ile Leu Gly Asp
    50                  55                  60

Thr Ala Ile Thr His Asp Asp Gln Tyr Lys Phe Tyr Ala Asp Asp Ala
65                  70                  75                  80

Thr Glu Val Pro Asp Ser Leu Phe Phe Asn Lys Ile Leu His Asp Gln
                85                  90                  95

Leu Leu Tyr Gly Phe Lys Glu Gly Asp Lys Ile Pro Leu Asp Glu
            100                 105                 110

Asn Gly Lys Pro Val Tyr Lys Leu Asp Lys Arg Leu Asp Asn Gly Val
            115                 120                 125

Gln Lys Thr Val Tyr Ser Val Thr Thr Lys Thr Ala Thr Ala Asp Asp
130                 135                 140

Val Asn Ser Ala Tyr Ser Arg Gly Ile Gln Gly Asp Ile Asp Asp Leu
145                 150                 155                 160

Tyr Glu Ala Asn Lys Glu Asn Val Asn Arg Leu Ile Glu His Gly Asp
                165                 170                 175

Lys Ile Phe Ala Asn Glu Glu Ser Val Gln Tyr Leu Asn Lys Glu Val
            180                 185                 190

Gln Asn Asn Ile Glu Asn Ile His Glu Leu Ala Gln Gln Gln Asp Gln
        195                 200                 205

His Ser Ser Asp Ile Lys Thr Leu Lys Lys Asn Val Glu Glu Gly Leu
    210                 215                 220

Leu Glu Leu Ser Gly His Leu Ile Asp Gln Lys Thr Asp Ile Ala Gln
225                 230                 235                 240

Asn Gln Thr Asp Ile Gln Asp Leu Ala Thr Tyr Asn Glu Leu Gln Asp
                245                 250                 255

Gln Tyr Ala Gln Lys Gln Thr Glu Ala Ile Asp Ala Leu Asn Lys Ala
            260                 265                 270

Ser Ser Glu Asn Thr Gln Asn Ile Ala Lys Asn Ser Asn Arg Ile Lys
        275                 280                 285

Ala Leu Glu Asn Asn Ile Glu Glu Gly Leu Leu Glu Leu Ser Gly His
    290                 295                 300

Leu Ile Asp Gln Lys Ala Asp Leu Thr Lys Asp Ile Lys Ala Leu Glu
305                 310                 315                 320

Ser Asn Val Glu Glu Gly Leu Leu Asp Leu Ser Gly Arg Leu Ile Asp
                325                 330                 335

Gln Lys Ala Asp Ile Ala Gln Asn Gln Ala Asn Ile Gln Asp Leu Ala
            340                 345                 350

Ala Tyr Asn Glu Leu Gln Asp Ala Tyr Ala Lys Gln Gln Thr Glu Ala
        355                 360                 365
```

```
Ile Asp Ala Leu Asn Lys Ala Ser Ser Glu Asn Thr Gln Asn Ile Glu
    370                 375                 380

Asp Leu Ala Ala Tyr Asn Glu Leu Gln Asp Ala Tyr Ala Lys Gln Gln
385                 390                 395                 400

Thr Glu Ala Ile Asp Ala Leu Asn Lys Ala Ser Ser Glu Asn Thr Gln
                405                 410                 415

Asn Ile Glu Asp Leu Ala Ala Tyr Asn Glu Leu Gln Asp Ala Tyr Ala
            420                 425                 430

Lys Gln Gln Thr Glu Ala Ile Asp Ala Leu Asn Lys Ala Ser Ser Glu
        435                 440                 445

Asn Thr Gln Asn Ile Ala Lys Asn Gln Ala Asp Ile Ala Asn Asn Ile
450                 455                 460

Asn Asn Ile Tyr Glu Leu Ala Gln Gln Asp Gln His Ser Ser Asp
465                 470                 475                 480

Ile Lys Thr Leu Ala Lys Ala Ser Ala Ala Asn Thr Asp Arg Ile Ala
                485                 490                 495

Lys Asn Lys Ala Asp Ala Asp Ala Ser Phe Glu Thr Leu Thr Lys Asn
            500                 505                 510

Gln Asn Thr Leu Ile Glu Lys Asp Lys Glu His Asp Lys Leu Ile Thr
        515                 520                 525

Ala Asn Lys Thr Ala Ile Asp Ala Asn Lys Ala Ser Ala Asp Thr Lys
530                 535                 540

Phe Ala Ala Thr Ala Asp Ala Ile Thr Lys Asn Gly Asn Ala Ile Thr
545                 550                 555                 560

Lys Asn Ala Lys Ser Ile Thr Asp Leu Gly Thr Lys Val Asp Gly Phe
                565                 570                 575

Asp Gly Arg Val Thr Ala Leu Asp Thr Lys Val Asn Ala Leu Asp Thr
            580                 585                 590

Lys Val Asn Ala Phe Asp Gly Arg Ile Thr Ala Leu Asp Ser Lys Val
        595                 600                 605

Glu Asn Gly Met Ala Ala Gln Ala Ala Leu Ser Gly Leu Phe Gln Pro
610                 615                 620

Tyr Ser Val Gly Lys Phe Asn Ala Thr Ala Ala Leu Gly Gly Tyr Gly
625                 630                 635                 640

Ser Lys Ser Ala Val Ala Ile Gly Ala Gly Tyr Arg Val Asn Pro Asn
                645                 650                 655

Leu Ala Phe Lys Ala Gly Ala Ala Ile Asn Thr Ser Gly Asn Lys Lys
            660                 665                 670

Gly Ser Tyr Asn Ile Gly Val Asn Tyr Glu Phe
        675                 680

<210> SEQ ID NO 19
<211> LENGTH: 700
<212> TYPE: PRT
<213> ORGANISM: Moraxella catarrhalis

<400> SEQUENCE: 19

Met Lys Thr Met Lys Leu Leu Pro Leu Lys Ile Ala Val Thr Ser Ala
1               5                   10                  15

Met Ile Val Gly Leu Gly Ala Ala Ser Thr Ala Asn Ala Gln Ala Gln
                20                  25                  30

Ser Asn Arg Ser Leu Asp Gln Val Gln Ala Leu Leu Arg Gly Ile Asp
            35                  40                  45

Glu Thr Lys Ile Lys Lys Glu Ile Gln Gln Ser Gln Gln Pro Glu Leu
        50                  55                  60
```

-continued

```
Asn Lys Tyr Leu Thr Phe Asn Gln Leu Ala Asn Ala Leu Asn Ile Glu
 65                  70                  75                  80

Glu Leu Asn Asn Asn Val Gln Lys Asn Thr Gln Arg Leu Asp Ser Ala
                 85                  90                  95

Ala Thr Leu Tyr Gly Asp Leu Ser Lys Thr Val Pro Lys Ser Ile Lys
            100                 105                 110

Glu Asn Lys Glu Ser Ile Lys Glu Asn Lys Glu Ser Ile Lys Glu Asn
        115                 120                 125

Lys Glu Ser Ile Lys Glu Asn Lys Glu Ser Ile Lys Glu Asn Lys Glu
130                 135                 140

Ser Ile Lys Glu Asn Lys Glu Ser Ile Thr Thr Leu Thr Arg Lys Ser
145                 150                 155                 160

Phe Gln Asn Gln Val Asp Ile Val Arg Asn Asn Ala Ser Ile Glu Asp
                165                 170                 175

Leu Tyr Ala Tyr Gly Gln Glu Val Ala Lys Ser Ile Gly Glu Ile His
            180                 185                 190

Ala Tyr Thr Glu Glu Val Asn Lys Thr Leu Glu Asn Leu Ile Thr Asn
        195                 200                 205

Ser Val Glu Asn Thr Asn Asn Ile Thr Lys Asn Lys Ala Asp Ile Gln
210                 215                 220

Ala Leu Glu Asn Asn Val Val Glu Glu Leu Phe Asn Leu Ser Gly Arg
225                 230                 235                 240

Leu Ile Asp Gln Lys Ala Asp Ile Asp Asn Asn Ile Asn Asn Ile Tyr
                245                 250                 255

Glu Leu Ala Gln Gln Asp Gln His Ser Ser Asp Ile Lys Thr Leu
            260                 265                 270

Lys Lys Asn Val Glu Glu Gly Leu Leu Glu Leu Ser Gly His Leu Ile
        275                 280                 285

Asp Gln Lys Ala Asp Leu Thr Lys Asp Ile Lys Thr Leu Glu Ser Asn
290                 295                 300

Val Glu Glu Gly Leu Leu Asp Leu Ser Gly Arg Leu Leu Asp Gln Lys
305                 310                 315                 320

Ala Asp Ile Ala Gln Asn Gln Ala Asn Ile Gln Asp Leu Ala Ala Tyr
                325                 330                 335

Asn Glu Leu Gln Asp Ala Tyr Ala Lys Gln Gln Thr Glu Ala Ile Asp
            340                 345                 350

Ala Leu Asn Lys Ala Ser Ser Glu Asn Thr Gln Asn Ile Glu Asp Leu
        355                 360                 365

Ala Ala Tyr Asn Glu Leu Gln Asp Ala Tyr Ala Lys Gln Gln Thr Glu
370                 375                 380

Ala Ile Asp Ala Leu Asn Lys Ala Ser Ser Glu Asn Thr Gln Asn Ile
385                 390                 395                 400

Glu Asp Leu Ala Ala Tyr Asn Glu Leu Gln Asp Ala Tyr Ala Lys Gln
                405                 410                 415

Gln Thr Glu Ala Ile Asp Ala Leu Asn Lys Ala Ser Ser Glu Asn Thr
            420                 425                 430

Gln Asn Ile Glu Asp Leu Ala Ala Tyr Asn Glu Leu Gln Asp Ala Tyr
        435                 440                 445

Ala Lys Gln Gln Thr Glu Ala Ile Asp Ala Leu Asn Lys Ala Ser Ser
450                 455                 460

Glu Asn Thr Gln Asn Ile Ala Lys Asn Gln Ala Asp Ile Ala Asn Asn
465                 470                 475                 480
```

```
Ile Asn Asn Ile Tyr Glu Leu Ala Gln Gln Asp Gln His Ser Ser
                485                 490                 495

Asp Ile Lys Thr Leu Ala Lys Ala Ser Ala Ala Asn Thr Asp Arg Ile
            500                 505                 510

Ala Lys Asn Lys Ala Asp Ala Asp Ala Ser Phe Glu Thr Leu Thr Lys
            515                 520                 525

Asn Gln Asn Thr Leu Ile Glu Lys Asp Lys Glu His Asp Lys Leu Ile
            530                 535                 540

Thr Ala Asn Lys Thr Val Ile Asp Ala Asn Lys Ala Ser Ala Asp Thr
545                 550                 555                 560

Lys Phe Ala Ala Thr Ala Asp Ala Ile Thr Lys Asn Gly Asn Ala Ile
            565                 570                 575

Thr Lys Asn Ala Lys Ser Ile Thr Asp Leu Gly Thr Lys Val Asp Gly
            580                 585                 590

Phe Asp Gly Arg Val Thr Ala Leu Asp Thr Lys Val Asn Ala Leu Asp
            595                 600                 605

Thr Lys Val Asn Ala Phe Asp Gly Arg Ile Thr Ala Leu Asp Ser Lys
            610                 615                 620

Val Glu Asn Gly Met Ala Ala Gln Ala Ala Leu Ser Gly Leu Phe Gln
625                 630                 635                 640

Pro Tyr Ser Val Gly Lys Phe Asn Ala Thr Ala Ala Leu Gly Gly Tyr
            645                 650                 655

Gly Ser Lys Ser Ala Val Ala Ile Gly Ala Gly Tyr Arg Val Asn Pro
            660                 665                 670

Asn Leu Ala Phe Lys Ala Gly Ala Ala Ile Asn Thr Ser Gly Asn Lys
            675                 680                 685

Lys Gly Ser Tyr Asn Ile Gly Val Asn Tyr Glu Phe
            690                 695                 700

<210> SEQ ID NO 20
<211> LENGTH: 676
<212> TYPE: PRT
<213> ORGANISM: Moraxella catarrhalis

<400> SEQUENCE: 20

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Thr
            20                  25                  30

Glu Thr Phe Leu Pro Asn Leu Phe Asp Asn Asp Tyr Ile Glu Thr Thr
            35                  40                  45

Asp Pro Leu Tyr His Gly Met Ile Leu Gly Asn Thr Ala Ile Thr Gln
        50                  55                  60

Asp Thr Gln Tyr Lys Phe Tyr Ala Glu Asn Gly Asn Glu Val Pro Asp
65                  70                  75                  80

Ser Leu Phe Phe Asn Lys Ile Leu His Asp Gln Leu Asn Gly Phe
            85                  90                  95

Lys Glu Gly Asp Thr Ile Ile Pro Leu Asp Glu Asn Gly Lys Pro Val
            100                 105                 110

Tyr Lys Leu Asp Glu Ile Thr Glu Asn Gly Val Lys Arg Lys Val Tyr
            115                 120                 125

Ser Val Thr Thr Lys Thr Ala Thr Arg Glu Asp Val Glu Gln Ser Ala
            130                 135                 140

Tyr Ser Arg Gly Ile Gln Gly Asp Ile Asp Asp Leu Tyr Glu Ala Asn
145                 150                 155                 160
```

```
Lys Glu Asn Val Asn Arg Leu Ile Glu His Gly Asp Lys Ile Phe Ala
                165                 170                 175

Asn Glu Glu Ser Val Gln Tyr Leu Asn Lys Glu Val Gln Asn Asn Ile
            180                 185                 190

Glu Asn Ile His Glu Leu Ala Gln Gln Asp Gln His Ser Ser Asp
        195                 200                 205

Ile Lys Thr Leu Lys Lys Asn Val Glu Glu Gly Leu Leu Glu Leu Ser
    210                 215                 220

Gly His Leu Ile Asp Gln Lys Ala Asp Leu Thr Lys Asp Ile Lys Thr
225                 230                 235                 240

Leu Glu Asn Asn Val Glu Glu Gly Leu Leu Glu Leu Ser Gly His Leu
                245                 250                 255

Ile Asp Gln Lys Ala Asp Leu Thr Lys Asp Ile Lys Ala Leu Glu Ser
            260                 265                 270

Asn Val Glu Glu Gly Leu Leu Asp Leu Ser Gly Arg Leu Leu Asp Gln
        275                 280                 285

Lys Ala Asp Ile Ala Lys Asn Gln Ala Asp Ile Ala Gln Asn Gln Thr
290                 295                 300

Asp Ile Gln Asp Leu Ala Ala Tyr Asn Glu Leu Gln Asp Gln Tyr Ala
305                 310                 315                 320

Gln Lys Gln Thr Glu Ala Ile Asp Ala Leu Asn Lys Ala Ser Ser Glu
                325                 330                 335

Asn Thr Gln Asn Ile Glu Asp Leu Ala Ala Tyr Asn Glu Leu Gln Asp
            340                 345                 350

Gln Tyr Ala Gln Lys Gln Thr Glu Ala Ile Asp Ala Leu Asn Lys Ala
        355                 360                 365

Ser Ser Glu Asn Thr Gln Asn Ile Glu Asp Leu Ala Ala Tyr Asn Glu
    370                 375                 380

Leu Gln Asp Gln Tyr Ala Gln Lys Gln Thr Glu Ala Ile Asp Ala Leu
385                 390                 395                 400

Asn Lys Ala Ser Ser Glu Asn Thr Gln Asn Ile Glu Asp Leu Ala Ala
                405                 410                 415

Tyr Asn Glu Leu Gln Asp Gln Tyr Ala Gln Lys Gln Thr Glu Ala Ile
            420                 425                 430

Asp Ala Leu Asn Lys Ala Ser Ser Glu Asn Thr Gln Asn Ile Ala Lys
        435                 440                 445

Asn Gln Ala Asp Ile Ala Asn Asn Ile Asn Asn Ile Tyr Glu Leu Ala
    450                 455                 460

Gln Gln Gln Asp Gln His Ser Ser Asp Ile Lys Thr Leu Ala Lys Ala
465                 470                 475                 480

Ser Ala Ala Asn Thr Asp Arg Ile Ala Lys Asn Lys Ala Asp Ala Asp
                485                 490                 495

Ala Ser Phe Glu Thr Leu Thr Lys Asn Gln Asn Thr Leu Ile Glu Lys
            500                 505                 510

Asp Lys Glu His Asp Lys Leu Ile Thr Ala Asn Lys Thr Ala Ile Asp
        515                 520                 525

Ala Asn Lys Ala Ser Ala Asp Thr Lys Phe Ala Ala Thr Ala Asp Ala
    530                 535                 540

Ile Thr Lys Asn Gly Asn Ala Ile Thr Lys Asn Ala Lys Ser Ile Thr
545                 550                 555                 560

Asp Leu Gly Thr Lys Val Asp Gly Phe Asp Gly Arg Val Thr Ala Leu
                565                 570                 575
```

```
Asp Thr Lys Val Asn Ala Leu Asp Thr Lys Val Asn Ala Phe Asp Gly
            580                 585                 590

Arg Ile Thr Ala Leu Asp Ser Lys Val Glu Asn Gly Met Ala Ala Gln
        595                 600                 605

Ala Ala Leu Ser Gly Leu Phe Gln Pro Tyr Ser Val Gly Lys Phe Asn
610                 615                 620

Ala Thr Ala Ala Leu Gly Gly Tyr Gly Ser Lys Ser Ala Val Ala Ile
625                 630                 635                 640

Gly Ala Gly Tyr Arg Val Asn Pro Asn Leu Ala Phe Lys Ala Gly Ala
                645                 650                 655

Ala Ile Asn Thr Ser Gly Asn Lys Lys Gly Ser Tyr Asn Ile Gly Val
            660                 665                 670

Asn Tyr Glu Phe
            675

<210> SEQ ID NO 21
<211> LENGTH: 678
<212> TYPE: PRT
<213> ORGANISM: Moraxella catarrhalis

<400> SEQUENCE: 21

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Leu Ala
            20                  25                  30

Glu Gln Phe Phe Pro Asn Ile Phe Ser Asn His Ala Pro Val Lys Gln
        35                  40                  45

His Tyr His Asn Val Val Gly Asp Thr Ser Ile Val Glu Asn Leu
    50                  55                  60

Gln Asp Ser Asp Asp Thr Gln Leu Lys Phe Tyr Ser Asn Asp Glu Tyr
65                  70                  75                  80

Ser Val Pro Asp Ser Leu Leu Phe Asn Lys Met Leu His Glu Gln Gln
                85                  90                  95

Leu Asn Gly Phe Lys Lys Gly Asp Thr Ile Ile Pro Leu Asp Glu Asn
            100                 105                 110

Gly Lys Pro Val Tyr Lys Val Asp Tyr Lys Leu Asp Gly Gln Glu Pro
        115                 120                 125

Arg Arg Val Tyr Ser Val Thr Thr Lys Ile Ala Thr Gln Asp Asp Val
    130                 135                 140

Asp Asn Ser Pro Tyr Ser Arg Gly Ile Gln Gly Asp Ile Asp Leu
145                 150                 155                 160

Tyr Glu Ala Asn Lys Glu Asn Val Asn Arg Leu Ile Glu His Gly Asp
                165                 170                 175

Lys Ile Phe Ala Asn Glu Glu Ser Gln Tyr Leu Asn Lys Glu Val
            180                 185                 190

Gln Asn Asn Ile Glu Asn Ile Tyr Glu Leu Ala Gln Gln Asp Gln
        195                 200                 205

His Ser Ser Asp Ile Lys Thr Leu Lys Lys Asn Val Glu Glu Gly Leu
    210                 215                 220

Leu Glu Leu Ser Gly Arg Leu Ile Asp Gln Lys Ala Asp Ile Ala Gln
225                 230                 235                 240

Asn Gln Ala Asn Ile Gln Asp Leu Ala Ala Tyr Asn Glu Leu Gln Asp
                245                 250                 255

Gln Tyr Ala Gln Lys Gln Thr Glu Ala Ile Asp Ala Leu Asn Lys Ala
            260                 265                 270
```

-continued

```
Ser Ser Glu Asn Thr Gln Asn Ile Glu Asp Leu Ala Ala Tyr Asn Glu
        275                 280                 285

Leu Gln Asp Ala Tyr Ala Lys Gln Gln Thr Glu Ala Ile Asp Ala Leu
        290                 295                 300

Asn Lys Ala Ser Ser Glu Asn Thr Gln Asn Ile Glu Asp Leu Ala Ala
305                 310                 315                 320

Tyr Asn Glu Leu Gln Asp Ala Tyr Ala Lys Gln Gln Thr Glu Ala Ile
                325                 330                 335

Asp Ala Leu Asn Lys Ala Ser Ser Glu Asn Thr Gln Asn Ile Glu Asp
                340                 345                 350

Leu Ala Ala Tyr Asn Glu Leu Gln Asp Ala Tyr Ala Lys Gln Gln Thr
                355                 360                 365

Glu Ala Ile Asp Ala Leu Asn Lys Ala Ser Ser Glu Asn Thr Gln Asn
        370                 375                 380

Ile Glu Asp Leu Ala Ala Tyr Asn Glu Leu Gln Asp Ala Tyr Ala Lys
385                 390                 395                 400

Gln Gln Thr Glu Ala Ile Asp Ala Leu Asn Lys Ala Ser Ser Glu Asn
                405                 410                 415

Thr Gln Asn Ile Glu Asp Leu Ala Ala Tyr Asn Glu Leu Gln Asp Ala
                420                 425                 430

Tyr Ala Lys Gln Gln Thr Glu Ala Ile Asp Ala Leu Asn Lys Ala Ser
        435                 440                 445

Ser Glu Asn Thr Gln Asn Ile Ala Lys Asn Gln Ala Asp Ile Ala Asn
        450                 455                 460

Asn Ile Asn Asn Ile Tyr Glu Leu Ala Gln Gln Gln Asp Gln His Ser
465                 470                 475                 480

Ser Asp Ile Lys Thr Leu Ala Lys Val Ser Ala Ala Asn Thr Asp Arg
                485                 490                 495

Ile Ala Lys Asn Lys Ala Asp Ala Asp Ala Ser Phe Glu Thr Leu Thr
                500                 505                 510

Lys Asn Gln Asn Thr Leu Ile Glu Lys Asp Lys Glu His Asp Lys Leu
        515                 520                 525

Ile Thr Ala Asn Lys Thr Ala Ile Asp Ala Asn Lys Ala Ser Ala Asp
        530                 535                 540

Thr Lys Phe Ala Ala Thr Ala Asp Ala Ile Thr Lys Asn Gly Asn Ala
545                 550                 555                 560

Ile Thr Lys Asn Ala Lys Ser Ile Thr Asp Leu Gly Thr Lys Val Asp
                565                 570                 575

Gly Phe Asp Gly Arg Val Thr Ala Leu Asp Thr Lys Val Asn Ala Phe
                580                 585                 590

Asp Gly Arg Ile Thr Ala Leu Asp Ser Lys Val Glu Asn Gly Met Ala
        595                 600                 605

Ala Gln Ala Ala Leu Ser Gly Leu Phe Gln Pro Tyr Ser Val Gly Lys
        610                 615                 620

Phe Asn Ala Thr Ala Ala Leu Gly Gly Tyr Gly Ser Lys Ser Ala Val
625                 630                 635                 640

Ala Ile Gly Ala Gly Tyr Arg Val Asn Pro Asn Leu Ala Phe Lys Ala
                645                 650                 655

Gly Ala Ala Ile Asn Thr Ser Gly Asn Lys Lys Gly Ser Tyr Asn Ile
                660                 665                 670

Gly Val Asn Tyr Glu Phe
                675
```

<210> SEQ ID NO 22
<211> LENGTH: 613
<212> TYPE: PRT
<213> ORGANISM: Moraxella catarrhalis

<400> SEQUENCE: 22

```
Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ser Arg
            20                  25                  30

Asp Arg Ser Leu Glu Asp Ile Gln Asp Ser Ile Ser Lys Leu Val Gln
        35                  40                  45

Asp Asp Ile Asn Thr Leu Lys Gln Asp Gln Gln Lys Met Asn Lys Tyr
    50                  55                  60

Leu Leu Leu Asn Gln Leu Ala Asn Thr Leu Ile Thr Asp Glu Leu Asn
65                  70                  75                  80

Asn Asn Val Ile Lys Asn Thr Asn Ser Ile Glu Ala Leu Gly Asp Glu
                85                  90                  95

Ile Gly Trp Leu Glu Asn Asp Ile Ala Asp Leu Glu Glu Gly Val Glu
            100                 105                 110

Glu Leu Thr Lys Asn Gln Asn Thr Leu Ile Glu Lys Asp Glu Glu His
        115                 120                 125

Asp Arg Leu Ile Ala Gln Asn Gln Ala Asp Ile Gln Thr Leu Glu Asn
    130                 135                 140

Asn Val Val Glu Glu Leu Phe Asn Leu Ser Gly Arg Leu Ile Asp Gln
145                 150                 155                 160

Glu Ala Asp Ile Ala Lys Asn Ala Ser Ile Glu Glu Leu Tyr Asp
                165                 170                 175

Phe Asp Asn Glu Val Ala Glu Arg Ile Gly Glu Ile His Ala Tyr Thr
            180                 185                 190

Glu Glu Val Asn Lys Thr Leu Glu Asn Leu Ile Thr Asn Ser Val Lys
        195                 200                 205

Asn Thr Asp Asn Ile Asp Lys Asn Lys Ala Asp Ile Asp Asn Asn Ile
    210                 215                 220

Asn His Ile Tyr Glu Leu Ala Gln Gln Gln Asp Gln His Ser Ser Asp
225                 230                 235                 240

Ile Lys Thr Leu Lys Asn Asn Val Glu Glu Gly Leu Leu Glu Leu Ser
                245                 250                 255

Gly His Leu Ile Asp Gln Lys Ala Asp Leu Thr Lys Asp Ile Lys Ala
            260                 265                 270

Leu Glu Ser Asn Val Glu Glu Gly Leu Leu Asp Leu Ser Gly Arg Leu
        275                 280                 285

Leu Asp Gln Lys Ala Asp Leu Thr Lys Asp Ile Lys Ala Leu Glu Ser
    290                 295                 300

Asn Val Glu Glu Gly Leu Leu Asp Leu Ser Gly Arg Leu Leu Asp Gln
305                 310                 315                 320

Lys Ala Asp Ile Ala Gln Asn Gln Thr Asp Ile Gln Asp Leu Ala Ala
                325                 330                 335

Tyr Asn Glu Leu Gln Asp Gln Tyr Ala Gln Lys Gln Thr Glu Ala Ile
            340                 345                 350

Asp Ala Leu Asn Lys Ala Ser Ser Glu Asn Thr Gln Asn Ile Glu Asp
        355                 360                 365

Leu Ala Ala Tyr Asn Glu Leu Gln Asp Ala Tyr Ala Lys Gln Gln Thr
    370                 375                 380
```

-continued

Glu Ala Ile Asp Ala Leu Asn Lys Ala Ser Ser Glu Asn Thr Gln Asn
385                 390                 395                 400

Ile Ala Lys Asn Gln Ala Asp Ile Ala Asn Ile Asn Asn Ile Tyr
            405                 410                 415

Glu Leu Ala Gln Gln Gln Asp Gln His Ser Ser Asp Ile Lys Thr Leu
            420                 425                 430

Ala Lys Ala Ser Ala Ala Asn Thr Asn Arg Ile Ala Thr Ala Glu Leu
            435                 440                 445

Gly Ile Ala Glu Asn Lys Lys Asp Ala Gln Ile Ala Lys Ala Gln Ala
            450                 455                 460

Asn Ala Asn Lys Thr Ala Ile Asp Glu Asn Lys Ala Ser Ala Asp Thr
465                 470                 475                 480

Lys Phe Ala Ala Thr Ala Asp Ala Ile Thr Lys Asn Gly Asn Ala Ile
            485                 490                 495

Thr Lys Asn Ala Lys Ser Ile Thr Asp Leu Gly Thr Lys Val Asp Gly
            500                 505                 510

Phe Asp Gly Arg Val Thr Ala Leu Asp Thr Lys Val Asn Ala Phe Asp
            515                 520                 525

Gly Arg Ile Thr Ala Leu Asp Ser Lys Val Glu Asn Gly Met Ala Ala
            530                 535                 540

Gln Ala Ala Leu Ser Gly Leu Phe Gln Pro Tyr Ser Val Gly Lys Phe
545                 550                 555                 560

Asn Ala Thr Ala Ala Leu Gly Gly Tyr Gly Ser Lys Ser Ala Val Ala
            565                 570                 575

Ile Gly Ala Gly Tyr Arg Val Asn Pro Asn Leu Ala Phe Lys Ala Gly
            580                 585                 590

Ala Ala Ile Asn Thr Ser Gly Asn Lys Lys Gly Ser Tyr Asn Ile Gly
            595                 600                 605

Val Asn Tyr Glu Phe
    610

<210> SEQ ID NO 23
<211> LENGTH: 589
<212> TYPE: PRT
<213> ORGANISM: Moraxella catarrhalis

<400> SEQUENCE: 23

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Thr
            20                  25                  30

Asn Lys Asp Ile Thr Leu Glu Asp Val Leu Lys Ser Ile Glu Glu Ile
            35                  40                  45

Asp Pro Tyr Glu Leu Arg Asp Tyr Ile Glu Tyr Pro Thr Ala Ile Glu
        50                  55                  60

Arg Phe Leu Leu Leu Ser Gln Tyr Gly Asn Thr Leu Thr Leu Glu Glu
65                  70                  75                  80

Phe Asp Asn Asp Ile Glu Leu Leu Asp Gln Asp Val Glu Asp Leu Glu
                85                  90                  95

Glu Ser Val Thr Glu Leu Ala Lys Asn Gln Asn Ser Leu Ile Glu Gln
            100                 105                 110

Gly Glu Ala Ile Lys Glu Asp Leu Gln Gly Leu Ala Asp Phe Val Glu
            115                 120                 125

Arg Gln Glu Asp Lys Ile Leu Gln Asn Glu Thr Ser Ile Lys Lys Asn

-continued

```
            130                 135                 140
Thr Gln Arg Asn Leu Val Asn Gly Phe Glu Ile Glu Lys Asn Lys Asp
145                 150                 155                 160

Ala Ile Ala Lys Asn Asn Glu Ser Ile Glu Asp Leu Tyr Asp Phe Gly
                165                 170                 175

His Glu Val Ala Lys Ser Ile Gly Glu Ile His Ala His Asn Glu Ala
                180                 185                 190

Gln Asn Glu Thr Leu Lys Asp Leu Ile Thr Asn Ser Val Lys Asn Thr
                195                 200                 205

Asp Asn Ile Thr Lys Asn Lys Ala Asp Ile Gln Ala Leu Glu Ser Asn
            210                 215                 220

Val Glu Lys Gly Leu Leu Glu Leu Ser Gly His Leu Ile Asp Gln Lys
225                 230                 235                 240

Ala Asp Ile Asp Asn Asn Ile Asn Asn Ile His Glu Leu Ala Gln Gln
                245                 250                 255

Gln Asp Gln His Ser Ser Asp Ile Lys Thr Leu Lys Lys Asn Val Glu
                260                 265                 270

Glu Gly Leu Leu Glu Leu Ser Gly His Leu Ile Asp Gln Lys Ser Asp
                275                 280                 285

Ile Ala Gln Asn Gln Ala Asn Ile Gln Asp Leu Ala Thr Tyr Asn Glu
290                 295                 300

Leu Gln Asp Gln Tyr Ala Gln Lys Gln Thr Glu Ala Ile Asp Ala Leu
305                 310                 315                 320

Asn Lys Ala Ser Ser Glu Asn Thr Gln Asn Ile Glu Asp Leu Ala Ala
                325                 330                 335

Tyr Asn Glu Leu Gln Asp Ala Tyr Ala Lys Gln Gln Thr Glu Ala Ile
                340                 345                 350

Asp Ala Leu Asn Lys Ala Ser Ser Glu Asn Thr Gln Asn Ile Ala Lys
                355                 360                 365

Asn Gln Ala Asp Ile Ala Asn Asn Ile Asn Asn Ile Tyr Glu Leu Ala
            370                 375                 380

Gln Gln Gln Asp Gln His Ser Ser Asp Ile Lys Thr Leu Ala Lys Ala
385                 390                 395                 400

Ser Ala Ala Asn Thr Asp Arg Ile Ala Lys Asn Lys Ala Asp Ala Asp
                405                 410                 415

Ala Ser Phe Glu Thr Leu Thr Lys Asn Gln Asn Thr Leu Ile Glu Lys
                420                 425                 430

Asp Lys Glu His Asp Lys Leu Ile Thr Ala Asn Lys Thr Ala Ile Asp
                435                 440                 445

Ala Asn Lys Ala Ser Ala Asp Thr Lys Phe Ala Ala Thr Ala Asp Ala
            450                 455                 460

Ile Thr Lys Asn Gly Asn Ala Ile Thr Lys Asn Ala Lys Ser Ile Thr
465                 470                 475                 480

Asp Leu Gly Thr Lys Val Asp Gly Phe Asp Ser Arg Val Thr Ala Leu
                485                 490                 495

Asp Thr Lys Val Asn Ala Phe Asp Gly Arg Ile Thr Ala Leu Asp Ser
                500                 505                 510

Lys Val Glu Asn Gly Met Ala Ala Gln Ala Ala Leu Ser Gly Leu Phe
                515                 520                 525

Gln Pro Tyr Ser Val Gly Lys Phe Asn Ala Thr Ala Ala Leu Gly Gly
            530                 535                 540

Tyr Gly Ser Lys Ser Ala Val Ala Ile Gly Ala Gly Tyr Arg Val Asn
545                 550                 555                 560
```

-continued

Pro Asn Leu Ala Phe Lys Ala Gly Ala Ala Ile Asn Thr Ser Gly Asn
                565                 570                 575

Lys Lys Gly Ser Tyr Asn Ile Gly Val Asn Tyr Glu Phe
            580                 585

<210> SEQ ID NO 24
<211> LENGTH: 684
<212> TYPE: PRT
<213> ORGANISM: Moraxella catarrhalis

<400> SEQUENCE: 24

Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
            20                  25                  30

Lys Ser Pro Lys Thr Glu Ile Phe Leu Pro Asn Leu Phe Asp Asn Asp
        35                  40                  45

Asn Thr Glu Leu Thr Asp Pro Leu Tyr His Asn Met Ile Leu Gly Asn
    50                  55                  60

Thr Ala Leu Leu Thr Gln Glu Asn Gln Tyr Lys Phe Tyr Ala Asp Asp
65                  70                  75                  80

Gly Asn Gly Val Pro Asp Ser Leu Leu Phe Asn Lys Ile Leu His Asp
                85                  90                  95

Gln Leu Leu His Gly Phe Lys Glu Gly Asp Thr Ile Ile Pro Leu Asp
            100                 105                 110

Glu Asn Gly Lys Pro Val Tyr Lys Leu Asp Ser Ile Val Glu Gln Gly
        115                 120                 125

Lys Thr Lys Thr Val Tyr Ser Val Thr Thr Lys Thr Ala Thr Ala Asp
    130                 135                 140

Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
            180                 185                 190

Val Gln Asn Asn Ile Glu Asn Ile His Glu Leu Ala Gln Gln Gln Asp
        195                 200                 205

Gln His Ser Ser Asp Ile Lys Thr Leu Lys Lys Asn Val Glu Lys Asp
    210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
        275                 280                 285

Lys Thr Leu Glu Asn Asn Ile Glu Glu Gly Leu Leu Glu Leu Ser Gly
    290                 295                 300

His Leu Ile Asp Gln Lys Ala Asp Leu Thr Asp Ile Lys Ala Leu
305                 310                 315                 320

Glu Ser Asn Val Glu Glu Gly Leu Leu Asp Leu Ser Gly Arg Leu Ile
                325                 330                 335

Asp Gln Lys Ala Asp Ile Ala Gln Asn Gln Ala Asn Ile Gln Asp Leu

```
                    340                 345                 350
Ala Ala Tyr Asn Glu Leu Gln Asp Ala Tyr Ala Lys Gln Gln Thr Glu
                355                 360                 365

Ala Ile Asp Ala Leu Asn Lys Ala Ser Ser Glu Asn Thr Gln Asn Ile
            370                 375                 380

Glu Asp Leu Ala Ala Tyr Asn Glu Leu Gln Asp Ala Tyr Ala Lys Gln
385                 390                 395                 400

Gln Thr Glu Ala Ile Asp Ala Leu Asn Lys Ala Ser Ser Glu Asn Thr
                405                 410                 415

Gln Asn Ile Glu Asp Leu Ala Ala Tyr Asn Glu Leu Gln Asp Ala Tyr
            420                 425                 430

Ala Lys Gln Gln Thr Glu Ala Ile Asp Ala Leu Asn Lys Ala Ser Ser
        435                 440                 445

Glu Asn Thr Gln Asn Ile Ala Lys Asn Gln Ala Asp Ile Ala Asn Asn
    450                 455                 460

Ile Asn Asn Ile Tyr Glu Leu Ala Gln Gln Gln Asp Gln His Ser Ser
465                 470                 475                 480

Asp Ile Lys Thr Leu Ala Lys Ala Ser Ala Ala Asn Thr Asp Arg Ile
                485                 490                 495

Ala Lys Asn Lys Ala Asp Ala Asp Ala Ser Phe Glu Thr Leu Thr Lys
            500                 505                 510

Asn Gln Asn Thr Leu Ile Glu Lys Asp Lys Glu His Asp Lys Leu Ile
        515                 520                 525

Thr Ala Asn Lys Thr Ala Ile Asp Ala Asn Lys Ala Ser Ala Asp Thr
    530                 535                 540

Lys Phe Ala Ala Thr Ala Asp Ala Ile Thr Lys Asn Gly Asn Ala Ile
545                 550                 555                 560

Thr Lys Asn Ala Lys Ser Ile Thr Asp Leu Gly Thr Lys Val Asp Gly
                565                 570                 575

Phe Asp Gly Arg Val Thr Ala Leu Asp Thr Lys Val Asn Ala Leu Asp
            580                 585                 590

Thr Lys Val Asn Ala Phe Asp Gly Arg Ile Thr Ala Leu Asp Ser Lys
        595                 600                 605

Val Glu Asn Gly Met Ala Ala Gln Ala Ala Leu Ser Gly Leu Phe Gln
    610                 615                 620

Pro Tyr Ser Val Gly Lys Phe Asn Ala Thr Ala Ala Leu Gly Gly Tyr
625                 630                 635                 640

Gly Ser Lys Ser Ala Val Ala Ile Gly Ala Gly Tyr Arg Val Asn Pro
            645                 650                 655

Asn Leu Ala Phe Lys Ala Gly Ala Ala Ile Asn Thr Ser Gly Asn Lys
        660                 665                 670

Lys Gly Ser Tyr Asn Ile Gly Val Asn Tyr Glu Phe
    675                 680

<210> SEQ ID NO 25
<211> LENGTH: 650
<212> TYPE: PRT
<213> ORGANISM: Moraxella catarrhalis

<400> SEQUENCE: 25

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Gln Gln
            20                  25                  30
```

-continued

```
Gln Lys Thr Lys Thr Glu Val Phe Leu Pro Asn Leu Phe Tyr Asn Asp
         35                  40                  45

Tyr Ile Glu Glu Thr Asp Leu Leu Tyr His Asn Met Ile Leu Gly Asp
 50                  55                  60

Thr Ala Leu Val Asp Arg Gln Asn Tyr Ser Asn Ser Gln Leu Lys
 65                  70                  75                  80

Phe Tyr Ser Asn Asp Glu Glu Ser Val Pro Asp Ser Leu Leu Phe Ser
                 85                  90                  95

Lys Met Leu Asn Asn Gln Gln Leu Asn Gly Phe Lys Ala Gly Asp Ile
                100                 105                 110

Ile Ile Pro Val Asp Ala Asn Gly Gln Val Ile Tyr Gln Lys Asp Thr
                115                 120                 125

Arg Val Glu Gly Gly Lys Thr Arg Thr Val Leu Ser Val Thr Thr Lys
130                 135                 140

Ile Ala Thr Gln Gln Asp Val Asp Ser Ala Tyr Ser Arg Gly Ile Gln
145                 150                 155                 160

Gly Lys Val Asn Asp Leu Asp Asp Glu Met Asn Phe Leu Asn His Asp
                165                 170                 175

Ile Thr Ser Leu Tyr Asp Val Thr Ala Asn Gln Gln Asp Asp Ile Lys
                180                 185                 190

Gly Leu Lys Lys Gly Val Lys Asp Leu Lys Lys Gly Val Lys Gly Leu
                195                 200                 205

Asn Lys Glu Leu Lys Glu Leu Asp Lys Glu Val Gly Val Leu Ser Arg
                210                 215                 220

Asp Ile Gly Ser Leu Asn Asp Asp Val Ala Gln Asn Asn Glu Ser Ile
225                 230                 235                 240

Glu Asp Leu Tyr Asp Phe Ser Gln Glu Val Ala Asp Ser Ile Gly Glu
                245                 250                 255

Ile His Ala His Asn Lys Ala Gln Asn Glu Thr Leu Gln Asp Leu Ile
                260                 265                 270

Thr Asn Ser Val Glu Asn Thr Asn Asn Ile Thr Lys Asn Lys Ala Asp
                275                 280                 285

Ile Gln Ala Leu Glu Asn Asn Val Val Glu Glu Leu Phe Asn Leu Ser
                290                 295                 300

Gly Arg Leu Ile Asp Gln Lys Ala Asp Leu Thr Lys Asp Ile Lys Thr
305                 310                 315                 320

Leu Glu Ser Asn Val Glu Glu Gly Leu Leu Glu Leu Ser Gly His Leu
                325                 330                 335

Ile Asp Gln Lys Ala Asp Ile Ala Lys Asn Gln Ala Asp Ile Ala Gln
                340                 345                 350

Asn Gln Ala Asn Ile Gln Asp Leu Ala Ala Tyr Asn Glu Leu Gln Asp
                355                 360                 365

Ala Tyr Ala Lys Gln Gln Thr Glu Ala Ile Asp Ala Leu Asn Lys Ala
                370                 375                 380

Ser Ser Glu Asn Thr Gln Asn Ile Glu Asp Leu Ala Ala Tyr Asn Glu
385                 390                 395                 400

Leu Gln Asp Ala Tyr Ala Lys Gln Gln Thr Glu Ala Ile Asp Ala Leu
                405                 410                 415

Asn Lys Ala Ser Ser Glu Asn Thr Gln Asn Ile Ala Lys Asn Gln Ala
                420                 425                 430

Asp Ile Ala Asn Asn Ile Asn Asn Ile Tyr Glu Leu Ala Gln Gln Gln
                435                 440                 445

Asp Gln His Ser Ser Asp Ile Lys Thr Leu Ala Lys Ala Ser Ala Ala
```

```
                450                 455                 460
Asn Thr Asp Arg Ile Ala Lys Asn Lys Ala Asp Ala Asp Ala Ser Phe
465                 470                 475                 480

Glu Thr Leu Thr Lys Asn Gln Asn Thr Leu Ile Glu Lys Asp Lys Glu
                485                 490                 495

His Asp Lys Leu Ile Thr Ala Asn Lys Thr Ala Ile Asp Glu Asn Lys
                500                 505                 510

Ala Ser Ala Asp Thr Lys Phe Ala Ala Thr Ala Asp Ala Ile Thr Lys
                515                 520                 525

Asn Gly Asn Ala Ile Thr Lys Asn Ala Lys Ser Ile Thr Asp Leu Gly
                530                 535                 540

Thr Lys Val Asp Gly Phe Asp Gly Arg Val Thr Ala Leu Asp Thr Lys
545                 550                 555                 560

Val Asn Ala Phe Asp Gly Arg Ile Thr Ala Leu Asp Ser Lys Val Glu
                565                 570                 575

Asn Gly Met Ala Ala Gln Ala Ala Leu Ser Gly Leu Phe Gln Pro Tyr
                580                 585                 590

Ser Val Gly Lys Phe Asn Ala Thr Ala Ala Leu Gly Gly Tyr Gly Ser
                595                 600                 605

Lys Ser Ala Val Ala Ile Gly Ala Gly Tyr Arg Val Asn Pro Asn Leu
                610                 615                 620

Ala Phe Lys Ala Gly Ala Ala Ile Asn Thr Ser Gly Asn Lys Lys Gly
625                 630                 635                 640

Ser Tyr Asn Ile Gly Val Asn Tyr Glu Phe
                645                 650

<210> SEQ ID NO 26
<211> LENGTH: 616
<212> TYPE: PRT
<213> ORGANISM: Moraxella catarrhalis

<400> SEQUENCE: 26

Met Lys Thr Met Lys Leu Leu Pro Leu Lys Ile Ala Val Thr Ser Ala
1               5                   10                  15

Leu Ile Val Gly Leu Gly Ala Val Ser Thr Thr Asn Ala Gln Ala Gln
                20                  25                  30

Ser Arg Ser Leu Asp Gln Ile Gln Thr Lys Leu Ala Asp Leu Ala Gly
                35                  40                  45

Lys Ile Ala Ala Gly Lys Asn Gly Gly Gln Asn Gln Asn Asn
50                  55                  60

Gln Asn Asp Ile Asn Lys Tyr Leu Phe Leu Ser Gln Tyr Ala Asn Ile
65                  70                  75                  80

Leu Thr Met Glu Glu Leu Asn Asn Asn Val Val Lys Asn Ser Ser Ser
                85                  90                  95

Ile Glu Thr Leu Glu Thr Asp Phe Gly Trp Leu Glu Asn Asp Val Ala
                100                 105                 110

Asp Leu Glu Asp Gly Val Glu Glu Leu Thr Lys Asn Gln Asn Thr Leu
                115                 120                 125

Ile Glu Lys Asp Glu Glu His Asp Arg Leu Ile Ala Gln Asn Gln Ala
                130                 135                 140

Asp Ile Gln Thr Leu Glu Asn Asn Val Val Glu Glu Leu Phe Asn Leu
145                 150                 155                 160

Ser Asp Arg Leu Ile Asp Gln Lys Ala Asp Ile Ala Lys Asn Gln Ala
                165                 170                 175
```

-continued

```
Asp Ile Ala Gln Asn Asn Glu Ser Ile Glu Leu Tyr Asp Phe Asp
            180                 185                 190
Asn Glu Val Ala Glu Lys Ile Gly Glu Ile His Ala Tyr Thr Glu Glu
        195                 200                 205
Val Asn Lys Thr Leu Gln Asp Leu Ile Thr Asn Ser Val Lys Asn Thr
    210                 215                 220
Asp Asn Ile Asp Lys Asn Lys Ala Asp Ile Asp Asn Asn Ile Asn His
225                 230                 235                 240
Ile Tyr Glu Leu Ala Gln Gln Gln Asp Gln His Ser Ser Asp Ile Lys
                245                 250                 255
Thr Leu Lys Asn Asn Val Glu Glu Gly Leu Leu Glu Leu Ser Gly His
            260                 265                 270
Leu Ile Asp Gln Lys Ala Asp Leu Thr Lys Asp Ile Lys Thr Leu Glu
        275                 280                 285
Asn Asn Val Glu Glu Gly Leu Leu Asp Leu Ser Gly Arg Leu Ile Asp
    290                 295                 300
Gln Lys Ala Asp Ile Ala Lys Asn Gln Ala Asp Ile Ala Gln Asn Gln
305                 310                 315                 320
Thr Asp Ile Gln Asp Leu Ala Ala Tyr Asn Glu Leu Gln Asp Gln Tyr
                325                 330                 335
Ala Gln Lys Gln Thr Glu Ala Ile Asp Ala Leu Asn Lys Ala Ser Ser
            340                 345                 350
Glu Asn Thr Gln Asn Ile Glu Asp Leu Ala Ala Tyr Asn Glu Leu Gln
        355                 360                 365
Asp Ala Tyr Ala Lys Gln Gln Thr Glu Ala Ile Asp Ala Leu Asn Lys
    370                 375                 380
Ala Ser Ser Glu Asn Thr Gln Asn Ile Ala Lys Asn Gln Ala Asp Ile
385                 390                 395                 400
Ala Asn Asn Ile Asn Asn Ile Tyr Glu Leu Ala Gln Gln Gln Asp Gln
                405                 410                 415
His Ser Ser Asp Ile Lys Thr Leu Ala Lys Ala Ser Ala Ala Asn Thr
            420                 425                 430
Asp Arg Ile Ala Lys Asn Lys Ala Asp Ala Asp Ala Ser Phe Glu Thr
        435                 440                 445
Leu Thr Lys Asn Gln Asn Thr Leu Ile Glu Lys Asp Lys Glu His Asp
    450                 455                 460
Lys Leu Ile Thr Ala Asn Lys Thr Ala Ile Asp Glu Asn Lys Ala Ser
465                 470                 475                 480
Ala Asp Thr Lys Phe Ala Ala Thr Ala Asp Ala Ile Thr Lys Asn Gly
                485                 490                 495
Asn Ala Ile Thr Lys Asn Ala Lys Ser Ile Thr Asp Leu Gly Thr Lys
            500                 505                 510
Val Asp Gly Phe Asp Gly Arg Val Thr Ala Leu Asp Thr Lys Val Asn
        515                 520                 525
Ala Phe Asp Gly Arg Ile Thr Ala Leu Asp Ser Lys Val Glu Asn Gly
    530                 535                 540
Met Ala Ala Gln Ala Ala Leu Ser Gly Leu Phe Gln Pro Tyr Ser Val
545                 550                 555                 560
Gly Lys Phe Asn Ala Thr Ala Ala Leu Gly Gly Tyr Gly Ser Lys Ser
                565                 570                 575
Ala Val Ala Ile Gly Ala Gly Tyr Arg Val Asn Pro Asn Leu Ala Phe
            580                 585                 590
Lys Ala Gly Ala Ala Ile Asn Thr Ser Gly Asn Lys Lys Gly Ser Tyr
```

-continued

```
            595                 600                 605
Asn Ile Gly Val Asn Tyr Glu Phe
    610                 615

<210> SEQ ID NO 27
<211> LENGTH: 668
<212> TYPE: PRT
<213> ORGANISM: Moraxella catarrhalis

<400> SEQUENCE: 27

Met Lys Thr Met Lys Leu Leu Pro Leu Lys Ile Ala Val Thr Ser Ala
1               5                   10                  15

Leu Ile Val Gly Leu Gly Thr Ala Ser Thr Ala Asn Ala Gln Val Ala
            20                  25                  30

Ser Pro Ala Asn Gln Lys Ile Gln Gln Lys Ile Lys Lys Val Arg Lys
        35                  40                  45

Glu Leu Arg Gln Asp Ile Lys Ser Leu Arg Asn Asp Ile Asp Ser Asn
    50                  55                  60

Thr Ala Asp Ile Gly Ser Leu Asn Asp Asp Val Ala Asp Asn Gln Asp
65                  70                  75                  80

Asp Ile Leu Asp Asn Gln Ala Asp Ile Ala Lys Asn Gln Asp Asp Ile
                85                  90                  95

Glu Lys Asn Gln Ala Asp Ile Lys Glu Leu Asp Lys Glu Val Gly Val
            100                 105                 110

Leu Ser Arg Glu Ile Gly Ser Leu Asn Asp Asp Ile Ala Asp Asn Tyr
        115                 120                 125

Thr Asp Ile Ile Asp Asn Tyr Thr Asp Ile Ile Asp Asn Gln Ala Asn
    130                 135                 140

Ile Ala Lys Asn Gln Asp Asp Ile Glu Lys Asn Gln Ala Asp Ile Lys
145                 150                 155                 160

Glu Leu Asp Lys Glu Val Gly Val Leu Ser Arg Glu Ile Gly Ser Leu
                165                 170                 175

Asn Asp Asp Val Ala Asp Asn Gln Asp Asp Ile Ala Lys Asn Gln Ala
            180                 185                 190

Asp Ile Gln Thr Leu Glu Asn Asn Val Glu Glu Gly Leu Leu Glu Leu
        195                 200                 205

Ser Gly His Leu Leu Asp Gln Lys Ala Asp Ile Asp Asn Asn Ile Asn
    210                 215                 220

Asn Ile Tyr Glu Leu Ala Gln Gln Asp Gln His Ser Ser Asp Ile
225                 230                 235                 240

Lys Thr Leu Lys Lys Asn Val Glu Glu Gly Leu Leu Glu Leu Ser Gly
                245                 250                 255

His Leu Ile Asp Gln Lys Thr Asp Ile Ala Gln Asn Gln Ala Asn Ile
            260                 265                 270

Gln Asp Leu Ala Thr Tyr Asn Glu Leu Gln Asp Gln Tyr Ala Gln Glu
        275                 280                 285

Gln Thr Glu Ala Ile Asp Ala Leu Asn Lys Ala Ser Ser Glu Asn Thr
    290                 295                 300

Gln Asn Ile Ala Lys Asn Ser Asn Arg Ile Lys Ala Leu Glu Ser Asn
305                 310                 315                 320

Val Glu Glu Gly Leu Leu Glu Leu Ser Gly His Leu Ile Asp Gln Lys
                325                 330                 335

Ala Asp Leu Thr Lys Asp Ile Lys Ala Leu Glu Ser Asn Val Glu Glu
            340                 345                 350
```

Gly Leu Leu Glu Leu Ser Gly His Leu Ile Asp Gln Lys Ala Asp Ile
            355                 360                 365

Ala Gln Asn Gln Ala Asn Ile Gln Asp Leu Ala Ala Tyr Asn Glu Leu
    370                 375                 380

Gln Asp Gln Tyr Ala Gln Lys Gln Thr Glu Ala Ile Asp Ala Leu Asn
385                 390                 395                 400

Lys Ala Ser Ser Glu Asn Thr Gln Asn Ile Glu Asp Leu Ala Ala Tyr
                405                 410                 415

Asn Glu Leu Gln Asp Ala Tyr Ala Lys Gln Gln Thr Glu Ala Ile Asp
            420                 425                 430

Ala Leu Asn Lys Ala Ser Ser Glu Asn Thr Gln Asn Ile Ala Lys Asn
        435                 440                 445

Gln Ala Asp Ile Ala Asn Asn Ile Asn Asn Ile Tyr Glu Leu Ala Gln
    450                 455                 460

Gln Gln Asp Gln His Ser Ser Asp Ile Lys Thr Leu Ala Lys Ala Ser
465                 470                 475                 480

Ala Ala Asn Thr Asp Arg Ile Ala Lys Asn Lys Ala Asp Ala Asp Ala
                485                 490                 495

Ser Phe Glu Thr Leu Thr Lys Asn Gln Asn Thr Leu Ile Glu Lys Asp
            500                 505                 510

Lys Glu His Asp Lys Leu Ile Thr Ala Asn Lys Thr Ala Ile Asp Ala
        515                 520                 525

Asn Lys Val Ser Ala Asp Thr Lys Phe Ala Ala Thr Ala Asp Ala Ile
    530                 535                 540

Thr Lys Asn Gly Asn Ala Ile Thr Lys Asn Ala Lys Ser Ile Thr Asp
545                 550                 555                 560

Leu Gly Thr Lys Val Asp Ala Phe Asp Ser Arg Val Thr Ala Leu Asp
                565                 570                 575

Thr Lys Val Asn Ala Phe Asp Gly Arg Ile Thr Ala Leu Asp Ser Lys
            580                 585                 590

Val Glu Asn Gly Met Ala Ala Gln Ala Ala Leu Ser Gly Leu Phe Gln
        595                 600                 605

Pro Tyr Ser Val Gly Lys Phe Asn Ala Thr Ala Ala Leu Gly Gly Tyr
    610                 615                 620

Gly Ser Lys Ser Ala Val Ala Ile Gly Ala Gly Tyr Arg Val Asn Pro
625                 630                 635                 640

Asn Leu Ala Phe Lys Ala Gly Ala Ala Ile Asn Thr Ser Gly Asn Lys
                645                 650                 655

Lys Gly Ser Tyr Asn Ile Gly Val Asn Tyr Glu Phe
            660                 665

<210> SEQ ID NO 28
<211> LENGTH: 674
<212> TYPE: PRT
<213> ORGANISM: Moraxella catarrhalis

<400> SEQUENCE: 28

Met Lys Thr Met Lys Leu Leu Pro Leu Lys Ile Ala Val Thr Ser Ala
1               5                   10                  15

Met Ile Val Gly Leu Gly Ala Thr Ser Thr Val Asn Ala Gln Val Val
            20                  25                  30

Glu Gln Phe Phe Pro Asn Ile Phe Phe Asn Glu Asn His Asp Glu Leu
        35                  40                  45

Asp Asp Ala Tyr His Asn Met Ile Leu Gly Asp Thr Ala Ile Val Ser
    50                  55                  60

```
Asn Ser Gln Asp Asn Ser Thr Gln Leu Lys Phe Tyr Ser Asn Asp Glu
 65                  70                  75                  80

Asp Ser Val Pro Asp Ser Leu Leu Phe Ser Lys Leu Leu His Glu Gln
             85                  90                  95

Gln Leu Asn Gly Phe Lys Ala Gly Asp Thr Ile Ile Pro Leu Asp Lys
            100                 105                 110

Asp Gly Lys Pro Val Tyr Thr Lys Asp Thr Arg Thr Lys Asp Gly Lys
            115                 120                 125

Val Glu Thr Val Tyr Ser Val Thr Lys Ile Ala Thr Gln Asp Asp
            130                 135                 140

Val Glu Gln Ser Ala Tyr Ser Arg Gly Ile Gln Gly Asp Ile Asp Asp
145                 150                 155                 160

Leu Tyr Asp Ile Asn Arg Glu Val Asn Glu Tyr Leu Lys Ala Thr His
                165                 170                 175

Asp Tyr Asn Glu Arg Gln Thr Glu Ala Ile Asp Ala Leu Asn Lys Ala
            180                 185                 190

Ser Ser Ala Asn Thr Asp Arg Ile Asp Thr Ala Glu Glu Arg Ile Asp
            195                 200                 205

Lys Asn Glu Tyr Asp Ile Lys Ala Leu Glu Ser Asn Val Glu Glu Gly
210                 215                 220

Leu Leu Glu Leu Ser Gly His Leu Ile Asp Gln Lys Ala Asp Leu Thr
225                 230                 235                 240

Lys Asp Ile Lys Ala Leu Glu Ser Asn Val Glu Gly Leu Leu Glu
            245                 250                 255

Leu Ser Gly His Leu Ile Asp Gln Lys Ala Asp Leu Thr Lys Asp Ile
                260                 265                 270

Lys Ala Leu Glu Ser Asn Val Glu Gly Leu Leu Asp Leu Ser Gly
            275                 280                 285

Arg Leu Ile Asp Gln Lys Ala Asp Ile Ala Gln Asn Gln Ala Asn Ile
    290                 295                 300

Gln Asp Leu Ala Ala Tyr Asn Glu Leu Gln Asp Ala Tyr Ala Lys Gln
305                 310                 315                 320

Gln Thr Glu Ala Ile Asp Ala Leu Asn Lys Ala Ser Ser Glu Asn Thr
            325                 330                 335

Gln Asn Ile Glu Asp Leu Ala Ala Tyr Asn Glu Leu Gln Asp Ala Tyr
            340                 345                 350

Ala Lys Gln Gln Thr Glu Ala Ile Asp Ala Leu Asn Lys Ala Ser Ser
        355                 360                 365

Glu Asn Thr Gln Asn Ile Glu Asp Leu Ala Ala Tyr Asn Glu Leu Gln
        370                 375                 380

Asp Ala Tyr Ala Lys Gln Gln Thr Glu Ala Ile Asp Ala Leu Asn Lys
385                 390                 395                 400

Ala Ser Ser Glu Asn Thr Gln Asn Ile Glu Asp Leu Ala Ala Tyr Asn
            405                 410                 415

Glu Leu Gln Asp Ala Tyr Ala Lys Gln Gln Thr Glu Ala Ile Asp Ala
            420                 425                 430

Leu Asn Lys Ala Ser Ser Glu Asn Thr Gln Asn Ile Ala Lys Asn Gln
            435                 440                 445

Ala Asp Ile Ala Asn Asn Ile Asn Asn Ile Tyr Glu Leu Ala Gln Gln
            450                 455                 460

Gln Asp Gln His Ser Ser Asp Ile Lys Thr Leu Ala Lys Ala Ser Ala
465                 470                 475                 480
```

-continued

```
Ala Asn Thr Asp Arg Ile Ala Lys Asn Lys Ala Asp Ala Asp Ala Ser
                485                 490                 495

Phe Glu Thr Leu Thr Lys Asn Gln Asn Thr Leu Ile Glu Lys Asp Lys
            500                 505                 510

Glu His Asp Lys Leu Ile Thr Ala Asn Lys Thr Ala Ile Asp Ala Asn
        515                 520                 525

Lys Ala Ser Ala Asp Thr Lys Phe Ala Ala Thr Ala Asp Ala Ile Thr
    530                 535                 540

Lys Asn Gly Asn Ala Ile Thr Lys Asn Ala Lys Ser Ile Thr Asp Leu
545                 550                 555                 560

Gly Thr Lys Val Asp Gly Phe Asp Gly Arg Val Thr Ala Leu Asp Thr
                565                 570                 575

Lys Val Asn Ala Leu Asp Thr Lys Val Asn Ala Phe Asp Gly Arg Ile
            580                 585                 590

Thr Ala Leu Asp Ser Lys Val Glu Asn Gly Met Ala Ala Gln Ala Ala
        595                 600                 605

Leu Ser Gly Leu Phe Gln Pro Tyr Ser Val Gly Lys Phe Asn Ala Thr
    610                 615                 620

Ala Ala Leu Gly Gly Tyr Gly Ser Lys Ser Ala Val Ala Ile Gly Ala
625                 630                 635                 640

Gly Tyr Arg Val Asn Pro Asn Leu Ala Phe Lys Ala Gly Ala Ala Ile
                645                 650                 655

Asn Thr Ser Gly Asn Lys Lys Gly Ser Tyr Asn Ile Gly Val Asn Tyr
            660                 665                 670

Glu Phe

<210> SEQ ID NO 29
<211> LENGTH: 613
<212> TYPE: PRT
<213> ORGANISM: Moraxella catarrhalis

<400> SEQUENCE: 29

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ser Arg
            20                  25                  30

Asp Arg Ser Leu Glu Asp Ile Gln Asp Ser Ile Ser Lys Leu Val Gln
        35                  40                  45

Asp Asp Ile Asp Thr Leu Lys Gln Asp Gln Lys Met Asn Lys Tyr
    50                  55                  60

Leu Leu Leu Asn Gln Leu Ala Asn Thr Leu Ile Thr Asp Glu Leu Asn
65                  70                  75                  80

Asn Asn Val Ile Lys Asn Thr Asn Ser Ile Glu Ala Leu Gly Asp Glu
                85                  90                  95

Ile Gly Trp Leu Glu Asn Asp Ile Ala Asp Leu Glu Glu Gly Val Glu
            100                 105                 110

Glu Leu Thr Lys Asn Gln Asn Thr Leu Ile Glu Lys Asp Glu His
        115                 120                 125

Asp Arg Leu Ile Ala Gln Asn Gln Ala Asp Ile Gln Thr Leu Glu Asn
    130                 135                 140

Asn Val Val Glu Glu Leu Phe Asn Leu Ser Gly Arg Leu Ile Asp Gln
145                 150                 155                 160

Glu Ala Asp Ile Ala Lys Asn Asn Ala Ser Ile Glu Glu Leu Tyr Asp
                165                 170                 175
```

```
Phe Asp Asn Glu Val Ala Glu Arg Ile Gly Glu Ile His Ala Tyr Thr
                180                 185                 190
Glu Glu Val Asn Lys Thr Leu Glu Asn Leu Ile Thr Asn Ser Val Lys
            195                 200                 205
Asn Thr Asp Asn Ile Asp Lys Asn Lys Ala Asp Ile Asp Asn Asn Ile
210                 215                 220
Asn His Ile Tyr Glu Leu Ala Gln Gln Asp Gln His Ser Ser Asp
225                 230                 235                 240
Ile Lys Thr Leu Lys Asn Asn Val Glu Glu Gly Leu Leu Glu Leu Ser
                245                 250                 255
Gly His Leu Ile Asp Gln Lys Ala Asp Leu Thr Lys Asp Ile Lys Ala
                260                 265                 270
Leu Glu Ser Asn Val Glu Glu Gly Leu Leu Asp Leu Ser Gly Arg Leu
            275                 280                 285
Leu Asp Gln Lys Ala Asp Leu Thr Lys Asp Ile Lys Ala Leu Glu Ser
290                 295                 300
Asn Val Glu Glu Gly Leu Leu Asp Leu Ser Gly Arg Leu Leu Asp Gln
305                 310                 315                 320
Lys Ala Asp Ile Ala Gln Asn Gln Thr Asp Ile Gln Asp Leu Ala Ala
                325                 330                 335
Tyr Asn Glu Leu Gln Asp Gln Tyr Ala Gln Lys Gln Thr Glu Ala Ile
                340                 345                 350
Asp Ala Leu Asn Lys Ala Ser Ser Glu Asn Thr Gln Asn Ile Glu Asp
            355                 360                 365
Leu Ala Ala Tyr Asn Glu Leu Gln Asp Ala Tyr Ala Lys Gln Gln Thr
370                 375                 380
Glu Ala Ile Asp Ala Leu Asn Lys Ala Ser Ser Glu Asn Thr Gln Asn
385                 390                 395                 400
Ile Ala Lys Asn Gln Ala Asp Ile Ala Asn Asn Ile Asn Asn Ile Tyr
                405                 410                 415
Glu Leu Ala Gln Gln Gln Asp Gln His Ser Ser Asp Ile Lys Thr Leu
                420                 425                 430
Ala Lys Ala Ser Ala Ala Asn Thr Asn Arg Ile Ala Thr Ala Glu Leu
            435                 440                 445
Gly Ile Ala Glu Asn Lys Lys Asp Ala Gln Ile Ala Lys Ala Gln Ala
450                 455                 460
Asn Ala Asn Lys Thr Ala Ile Asp Glu Asn Lys Ala Ser Ala Asp Thr
465                 470                 475                 480
Lys Phe Ala Ala Thr Ala Asp Ala Ile Thr Lys Asn Gly Asn Ala Ile
                485                 490                 495
Thr Lys Asn Ala Lys Ser Ile Thr Asp Leu Gly Thr Lys Val Asp Gly
            500                 505                 510
Phe Asp Gly Arg Val Thr Ala Leu Asp Thr Lys Val Asn Ala Phe Asp
515                 520                 525
Gly Arg Ile Thr Ala Leu Asp Ser Lys Val Glu Asn Gly Met Ala Ala
530                 535                 540
Gln Ala Ala Leu Ser Gly Leu Phe Gln Pro Tyr Ser Val Gly Lys Phe
545                 550                 555                 560
Asn Ala Thr Ala Ala Leu Gly Gly Tyr Gly Ser Lys Ser Ala Val Ala
                565                 570                 575
Ile Gly Ala Gly Tyr Arg Val Asn Pro Asn Leu Ala Phe Lys Ala Gly
                580                 585                 590
Ala Ala Ile Asn Thr Ser Gly Asn Lys Lys Gly Ser Tyr Asn Ile Gly
```

Val Asn Tyr Glu Phe
610

<210> SEQ ID NO 30
<211> LENGTH: 576
<212> TYPE: PRT
<213> ORGANISM: Moraxella catarrhalis

<400> SEQUENCE: 30

Met Lys Thr Met Lys Leu Leu Pro Leu Lys Ile Ala Val Thr Ser Ala
1               5                   10                  15

Met Ile Val Gly Leu Gly Ala Thr Ser Thr Val Asn Ala Gln Val Val
            20                  25                  30

Glu Gln Phe Phe Pro Asn Ile Phe Phe Asn Glu Asn His Asp Glu Leu
        35                  40                  45

Asp Asp Ala Tyr His Asn Met Ile Leu Gly Asp Thr Ala Ile Val Ser
    50                  55                  60

Asn Ser Gln Asp Asn Ser Thr Gln Leu Lys Phe Tyr Ser Asn Asp Glu
65                  70                  75                  80

Asp Ser Val Pro Asp Ser Leu Leu Phe Ser Lys Leu Leu His Glu Gln
                85                  90                  95

Gln Leu Asn Gly Phe Lys Ala Gly Asp Thr Ile Ile Pro Leu Asp Lys
            100                 105                 110

Asp Gly Lys Pro Val Tyr Thr Lys Asp Thr Arg Thr Lys Asp Gly Lys
        115                 120                 125

Val Glu Thr Val Tyr Ser Val Thr Thr Lys Ile Ala Thr Gln Asp Asp
    130                 135                 140

Val Glu Gln Ser Ala Tyr Ser Arg Gly Ile Gln Gly Asp Ile Asp Asp
145                 150                 155                 160

Leu Tyr Asp Ile Asn Arg Glu Val Asn Glu Tyr Leu Lys Ala Thr His
                165                 170                 175

Asp Tyr Asn Glu Arg Gln Thr Glu Ala Ile Asp Ala Leu Asn Lys Ala
            180                 185                 190

Ser Ser Ala Asn Thr Asp Arg Ile Asp Thr Ala Glu Glu Arg Ile Asp
        195                 200                 205

Lys Asn Glu Tyr Asp Ile Lys Ala Leu Glu Ser Asn Val Glu Glu Gly
    210                 215                 220

Leu Leu Glu Leu Ser Gly His Leu Ile Asp Gln Lys Ala Asp Leu Thr
225                 230                 235                 240

Lys Asp Ile Lys Ala Leu Glu Ser Asn Val Glu Glu Gly Leu Leu Glu
                245                 250                 255

Leu Ser Gly His Leu Ile Asp Gln Lys Ala Asp Leu Thr Lys Asp Ile
            260                 265                 270

Lys Ala Leu Glu Ser Asn Val Glu Glu Gly Leu Leu Asp Leu Ser Gly
        275                 280                 285

Arg Leu Leu Asp Gln Lys Ala Asp Ile Ala Lys Asn Gln Ala Asp Ile
    290                 295                 300

Ala Gln Asn Gln Thr Asp Ile Gln Asp Leu Ala Ala Tyr Asn Glu Leu
305                 310                 315                 320

Gln Asp Ala Tyr Ala Lys Gln Gln Thr Glu Ala Ile Asp Ala Leu Asn
                325                 330                 335

Lys Ala Ser Ser Glu Asn Thr Gln Asn Ile Ala Lys Asn Gln Ala Asp
            340                 345                 350

```
Ile Ala Asn Asn Ile Asn Asn Ile Tyr Glu Leu Ala Gln Gln Asp
            355                 360                 365

Gln His Ser Ser Asp Ile Lys Thr Leu Ala Lys Ala Ser Ala Ala Asn
        370                 375                 380

Thr Asp Arg Ile Ala Lys Asn Lys Ala Asp Ala Asp Ala Ser Phe Glu
385                 390                 395                 400

Thr Leu Thr Lys Asn Gln Asn Thr Leu Ile Glu Lys Asp Lys Glu His
            405                 410                 415

Asp Lys Leu Ile Thr Ala Asn Lys Thr Ala Ile Asp Ala Asn Lys Ala
            420                 425                 430

Ser Ala Asp Thr Lys Phe Ala Ala Thr Ala Asp Ala Ile Thr Lys Asn
        435                 440                 445

Gly Asn Ala Ile Thr Lys Asn Ala Lys Ser Ile Thr Asp Leu Gly Thr
        450                 455                 460

Lys Val Asp Gly Phe Asp Gly Arg Val Thr Ala Leu Asp Thr Lys Val
465                 470                 475                 480

Asn Ala Leu Asp Thr Lys Val Asn Ala Phe Asp Gly Arg Ile Thr Ala
            485                 490                 495

Leu Asp Ser Lys Val Glu Asn Gly Met Ala Gln Ala Ala Leu Ser
            500                 505                 510

Gly Leu Phe Gln Pro Tyr Ser Val Gly Lys Phe Asn Ala Thr Ala Ala
        515                 520                 525

Leu Gly Gly Tyr Gly Ser Lys Ser Ala Val Ala Ile Gly Ala Gly Tyr
        530                 535                 540

Arg Val Asn Pro Asn Leu Ala Phe Lys Ala Gly Ala Ala Ile Asn Thr
545                 550                 555                 560

Ser Gly Asn Lys Lys Gly Ser Tyr Asn Ile Gly Val Asn Tyr Glu Phe
            565                 570                 575

<210> SEQ ID NO 31
<211> LENGTH: 684
<212> TYPE: PRT
<213> ORGANISM: Moraxella catarrhalis

<400> SEQUENCE: 31

Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
            20                  25                  30

Lys Ser Pro Lys Thr Glu Ile Phe Leu Pro Asn Leu Phe Asp Asn Asp
        35                  40                  45

Asn Thr Glu Leu Thr Asp Pro Leu Tyr His Asn Met Ile Leu Gly Asn
50                  55                  60

Thr Ala Leu Leu Thr Gln Glu Asn Gln Tyr Lys Phe Tyr Ala Asp Asp
65                  70                  75                  80

Gly Asn Gly Val Pro Asp Ser Leu Leu Phe Asn Lys Ile Leu His Asp
            85                  90                  95

Gln Leu Leu His Gly Phe Lys Glu Gly Asp Thr Ile Ile Pro Leu Asp
        100                 105                 110

Glu Asn Gly Lys Pro Val Tyr Lys Leu Asp Ser Ile Val Glu Gln Gly
        115                 120                 125

Lys Thr Lys Thr Val Tyr Ser Val Thr Thr Lys Thr Ala Thr Ala Asp
        130                 135                 140

Asp Val Asn Ser Ala Tyr Ser Arg Gly Ile Gln Gly Asp Ile Asp Asp
145                 150                 155                 160
```

-continued

Leu Tyr Glu Ala Asn Lys Glu Asn Val Asn Arg Leu Ile Glu His Gly
            165                 170                 175

Asp Lys Ile Phe Ala Asn Glu Glu Ser Val Gln Tyr Leu Asn Arg Glu
            180                 185                 190

Val Gln Asn Asn Ile Glu Asn Ile His Glu Leu Ala Gln Gln Gln Asp
            195                 200                 205

Gln His Ser Ser Asp Ile Lys Thr Leu Lys Lys Asn Val Glu Lys Asp
            210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
            245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
            275                 280                 285

Lys Thr Leu Glu Asn Asn Ile Glu Glu Gly Leu Leu Glu Leu Ser Gly
            290                 295                 300

His Leu Ile Asp Gln Lys Ala Asp Leu Thr Lys Asp Ile Lys Ala Leu
305                 310                 315                 320

Glu Ser Asn Val Glu Glu Gly Leu Leu Asp Leu Ser Gly Arg Leu Ile
            325                 330                 335

Asp Gln Lys Ala Asp Ile Ala Gln Asn Gln Ala Asn Ile Gln Asp Leu
            340                 345                 350

Ala Ala Tyr Asn Glu Leu Gln Asp Ala Tyr Ala Lys Gln Gln Thr Glu
            355                 360                 365

Ala Ile Asp Ala Leu Asn Lys Ala Ser Ser Glu Asn Thr Gln Asn Ile
370                 375                 380

Glu Asp Leu Ala Ala Tyr Asn Glu Leu Gln Asp Ala Tyr Ala Lys Gln
385                 390                 395                 400

Gln Thr Glu Ala Ile Asp Ala Leu Asn Lys Ala Ser Ser Glu Asn Thr
            405                 410                 415

Gln Asn Ile Glu Asp Leu Ala Ala Tyr Asn Glu Leu Gln Asp Ala Tyr
            420                 425                 430

Ala Lys Gln Gln Thr Glu Ala Ile Asp Ala Leu Asn Lys Ala Ser Ser
            435                 440                 445

Glu Asn Thr Gln Asn Ile Ala Lys Gln Ala Asp Ile Ala Asn Asn
            450                 455                 460

Ile Asn Asn Ile Tyr Glu Leu Ala Gln Gln Gln Asp Gln His Ser Ser
465                 470                 475                 480

Asp Ile Lys Thr Leu Ala Lys Ala Ser Ala Asn Thr Asp Arg Ile
            485                 490                 495

Ala Lys Asn Lys Ala Asp Ala Asp Ala Ser Phe Glu Thr Leu Thr Lys
            500                 505                 510

Asn Gln Asn Thr Leu Ile Glu Lys Asp Lys Glu His Asp Lys Leu Ile
            515                 520                 525

Thr Ala Asn Lys Thr Ala Ile Asp Ala Asn Lys Ala Ser Ala Asp Thr
            530                 535                 540

Lys Phe Ala Ala Thr Ala Asp Ala Ile Thr Lys Asn Gly Asn Ala Ile
545                 550                 555                 560

Thr Lys Asn Ala Lys Ser Ile Thr Asp Leu Gly Thr Lys Val Asp Gly
            565                 570                 575

```
Phe Asp Gly Arg Val Thr Ala Leu Asp Thr Lys Val Asn Ala Leu Asp
                580                 585                 590

Thr Lys Val Asn Ala Phe Asp Gly Arg Ile Thr Ala Leu Asp Ser Lys
            595                 600                 605

Val Glu Asn Gly Met Ala Ala Gln Ala Ala Leu Ser Gly Leu Phe Gln
        610                 615                 620

Pro Tyr Ser Val Gly Lys Phe Asn Ala Thr Ala Leu Gly Gly Tyr
625                 630                 635                 640

Gly Ser Lys Ser Ala Val Ala Ile Gly Ala Gly Tyr Arg Val Asn Pro
                645                 650                 655

Asn Leu Ala Phe Lys Ala Gly Ala Ala Ile Asn Thr Ser Gly Asn Lys
            660                 665                 670

Lys Gly Ser Tyr Asn Ile Gly Val Asn Tyr Glu Phe
            675                 680

<210> SEQ ID NO 32
<211> LENGTH: 686
<212> TYPE: PRT
<213> ORGANISM: Moraxella catarrhalis

<400> SEQUENCE: 32

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ala Thr
            20                  25                  30

Glu Thr Phe Leu Pro Asn Leu Phe Asp Asn Asp Tyr Thr Glu Thr Thr
        35                  40                  45

Asp Pro Leu Tyr His Gly Met Ile Leu Gly Asn Thr Ala Ile Thr Gln
50                  55                  60

Asp Thr Gln Tyr Lys Phe Tyr Ala Glu Asn Gly Asn Glu Val Pro Asp
65                  70                  75                  80

Ser Leu Phe Phe Asn Lys Ile Leu His Asp Gln Gln Leu Asn Gly Phe
                85                  90                  95

Lys Glu Gly Asp Thr Ile Ile Pro Leu Asp Glu Asn Gly Lys Pro Val
            100                 105                 110

Tyr Lys Leu Asp Glu Ile Thr Glu Asn Gly Val Lys Arg Lys Val Tyr
        115                 120                 125

Ser Val Thr Thr Lys Thr Ala Thr Arg Glu Asp Val Glu Gln Ser Ala
130                 135                 140

Tyr Ser Arg Gly Ile Gln Gly Asp Ile Asp Asp Leu Tyr Glu Ala Asn
145                 150                 155                 160

Lys Glu Asn Val Asn Arg Leu Ile Glu His Gly Asp Lys Ile Phe Ala
                165                 170                 175

Asn Glu Glu Ser Val Gln Tyr Leu Asn Lys Glu Val Gln Asn Asn Ile
            180                 185                 190

Glu Asn Ile His Glu Leu Ala Gln Gln Gln Asp Gln His Ser Ser Asp
        195                 200                 205

Ile Lys Thr Leu Lys Lys Asn Val Glu Glu Gly Leu Leu Glu Leu Ser
210                 215                 220

Gly Arg Leu Ile Ala Gln Lys Glu Asp Ile Ala Gln Asn Gln Thr Asp
225                 230                 235                 240

Ile Gln Asp Leu Ala Thr Tyr Asn Glu Leu Gln Asp Gln Tyr Ala Gln
                245                 250                 255

Lys Gln Thr Glu Ala Ile Asp Ala Leu Asn Lys Ala Ser Ser Glu Asn
            260                 265                 270
```

```
Thr Gln Asn Ile Ala Lys Asn Ser Asn His Ile Lys Thr Leu Glu Asn
            275                 280                 285
Asn Ile Glu Glu Gly Leu Leu Glu Leu Ser Gly His Leu Ile Asp Gln
            290                 295                 300
Lys Ala Asp Leu Thr Lys Asp Ile Lys Ala Leu Glu Ser Asn Val Glu
305                 310                 315                 320
Glu Gly Leu Leu Asp Leu Ser Gly Arg Leu Leu Asp Gln Lys Ala Asp
                    325                 330                 335
Ile Ala Lys Asn Gln Ala Asp Ile Ala Gln Asn Gln Thr Asp Ile Gln
                340                 345                 350
Asp Leu Ala Ala Tyr Asn Glu Leu Gln Asp Gln Tyr Ala Gln Lys Gln
                355                 360                 365
Thr Glu Ala Ile Asp Ala Leu Asn Lys Ala Ser Ser Glu Asn Thr Gln
            370                 375                 380
Asn Ile Glu Asp Leu Ala Ala Tyr Asn Glu Leu Gln Asp Ala Tyr Ala
385                 390                 395                 400
Lys Gln Gln Thr Glu Ala Ile Asp Ala Leu Asn Lys Ala Ser Ser Glu
                    405                 410                 415
Asn Thr Gln Asn Ile Glu Asp Leu Ala Ala Tyr Asn Glu Leu Gln Asp
                420                 425                 430
Ala Tyr Ala Lys Gln Gln Thr Glu Ala Ile Asp Ala Leu Asn Lys Ala
                435                 440                 445
Ser Ser Glu Asn Thr Gln Asn Ile Ala Lys Asn Gln Ala Asp Ile Ala
            450                 455                 460
Asn Asn Ile Asn Asn Ile Tyr Glu Leu Ala Gln Gln Gln Asp Gln His
465                 470                 475                 480
Ser Ser Asp Ile Lys Thr Leu Ala Lys Ala Ser Ala Ala Asn Thr Asp
                    485                 490                 495
Arg Ile Ala Lys Asn Lys Ala Asp Ala Asp Ala Ser Phe Glu Thr Leu
                500                 505                 510
Thr Lys Asn Gln Asn Thr Leu Ile Glu Lys Asp Lys Glu His Asp Lys
            515                 520                 525
Leu Ile Thr Ala Asn Lys Thr Ala Ile Asp Ala Asn Lys Ala Ser Ala
            530                 535                 540
Asp Thr Lys Phe Ala Ala Thr Ala Asp Ala Ile Thr Lys Asn Gly Asn
545                 550                 555                 560
Ala Ile Thr Lys Asn Ala Lys Ser Ile Thr Asp Leu Gly Thr Lys Val
                565                 570                 575
Asp Gly Phe Asp Gly Arg Val Thr Ala Leu Asp Thr Lys Val Asn Ala
                580                 585                 590
Leu Asp Thr Lys Val Asn Ala Phe Asp Gly Arg Ile Thr Ala Leu Asp
                595                 600                 605
Ser Lys Val Glu Asn Gly Met Ala Ala Gln Ala Ala Leu Ser Gly Leu
            610                 615                 620
Phe Gln Pro Tyr Ser Val Gly Lys Phe Asn Ala Thr Ala Ala Leu Gly
625                 630                 635                 640
Gly Tyr Gly Ser Lys Ser Ala Val Ala Ile Gly Ala Gly Tyr Arg Val
                    645                 650                 655
Asn Pro Asn Leu Ala Phe Lys Ala Gly Ala Ala Ile Asn Thr Ser Gly
                660                 665                 670
Asn Lys Lys Gly Ser Tyr Asn Ile Gly Val Asn Tyr Glu Phe
                675                 680                 685
```

```
<210> SEQ ID NO 33
<211> LENGTH: 630
<212> TYPE: PRT
<213> ORGANISM: Moraxella catarrhalis

<400> SEQUENCE: 33

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ala Lys
            20                  25                  30

Asn Asp Ile Thr Leu Glu Asp Leu Pro Tyr Leu Ile Lys Lys Ile Asp
        35                  40                  45

Gln Asn Glu Leu Glu Ala Asp Ile Gly Asp Ile Thr Ala Leu Glu Lys
    50                  55                  60

Tyr Leu Ala Leu Ser Gln Tyr Gly Asn Ile Leu Ala Leu Glu Glu Leu
65                  70                  75                  80

Asn Lys Ala Leu Glu Glu Leu Asp Glu Asp Val Gly Trp Asn Gln Asn
                85                  90                  95

Asp Ile Ala Asn Leu Glu Asp Asp Val Glu Thr Leu Thr Lys Asn Gln
            100                 105                 110

Asn Ala Leu Ala Glu Gln Gly Glu Ala Ile Lys Glu Asp Leu Gln Gly
        115                 120                 125

Leu Ala Asp Phe Val Glu Gly Gln Glu Gly Lys Ile Leu Gln Asn Glu
    130                 135                 140

Thr Ser Ile Lys Lys Asn Thr Gln Arg Asn Leu Val Asn Gly Phe Glu
145                 150                 155                 160

Ile Glu Lys Asn Lys Asp Ala Ile Ala Lys Asn Asn Glu Ser Ile Glu
                165                 170                 175

Asp Leu Tyr Asp Phe Gly His Glu Val Ala Glu Ser Ile Gly Glu Ile
            180                 185                 190

His Ala His Asn Glu Ala Gln Asn Glu Thr Leu Lys Gly Leu Ile Thr
        195                 200                 205

Asn Ser Ile Glu Asn Thr Asn Asn Ile Thr Lys Asn Lys Ala Asp Ile
    210                 215                 220

Gln Ala Leu Glu Asn Asn Val Val Glu Glu Leu Phe Asn Leu Ser Gly
225                 230                 235                 240

Arg Leu Ile Asp Gln Lys Ala Asp Ile Asp Asn Asn Ile Asn Asn Ile
                245                 250                 255

Tyr Glu Leu Ala Gln Gln Gln Asp Gln His Ser Ser Asp Ile Lys Thr
            260                 265                 270

Leu Lys Lys Asn Val Glu Glu Gly Leu Leu Glu Leu Ser Gly His Leu
        275                 280                 285

Ile Asp Gln Lys Thr Asp Ile Ala Gln Asn Gln Asn Ile Gln Asp
    290                 295                 300

Leu Ala Thr Tyr Asn Glu Leu Gln Asp Gln Tyr Ala Gln Lys Gln Thr
305                 310                 315                 320

Glu Ala Ile Asp Ala Leu Asn Lys Ala Ser Ser Glu Asn Thr Gln Asn
                325                 330                 335

Ile Glu Asp Leu Ala Ala Tyr Asn Glu Leu Gln Asp Ala Tyr Ala Lys
            340                 345                 350

Gln Gln Thr Glu Ala Ile Asp Ala Leu Asn Lys Ala Ser Ser Glu Asn
        355                 360                 365

Thr Gln Asn Ile Glu Asp Leu Ala Ala Tyr Asn Glu Leu Gln Asp Ala
    370                 375                 380
```

```
Tyr Ala Lys Gln Gln Thr Glu Ala Ile Asp Ala Leu Asn Lys Ala Ser
385                 390                 395                 400

Ser Glu Asn Thr Gln Asn Ile Ala Lys Asn Gln Ala Asp Ile Ala Asn
                405                 410                 415

Asn Ile Asn Asn Ile Tyr Glu Leu Ala Gln Gln Asp Gln His Ser
            420                 425                 430

Ser Asp Ile Lys Thr Leu Ala Lys Ala Ser Ala Asn Thr Asp Arg
        435                 440                 445

Ile Ala Lys Asn Lys Ala Asp Ala Asp Ala Ser Phe Glu Thr Leu Thr
450                 455                 460

Lys Asn Gln Asn Thr Leu Ile Glu Lys Asp Lys Glu His Asp Lys Leu
465                 470                 475                 480

Ile Thr Ala Asn Lys Thr Ala Ile Asp Ala Asn Lys Ala Ser Ala Asp
                485                 490                 495

Thr Lys Phe Ala Ala Thr Ala Asp Ala Ile Thr Lys Asn Gly Asn Ala
            500                 505                 510

Ile Thr Lys Asn Ala Lys Ser Ile Thr Asp Leu Gly Thr Lys Val Asp
        515                 520                 525

Gly Phe Asp Ser Arg Val Thr Ala Leu Asp Thr Lys Val Asn Ala Phe
530                 535                 540

Asp Gly Arg Ile Thr Ala Leu Asp Ser Lys Val Glu Asn Gly Met Ala
545                 550                 555                 560

Ala Gln Ala Ala Leu Ser Gly Leu Phe Gln Pro Tyr Ser Val Gly Lys
                565                 570                 575

Phe Asn Ala Thr Ala Ala Leu Gly Gly Tyr Gly Ser Lys Ser Ala Val
            580                 585                 590

Ala Ile Gly Ala Gly Tyr Arg Val Asn Pro Asn Leu Ala Phe Lys Ala
        595                 600                 605

Gly Ala Ala Ile Asn Thr Ser Gly Asn Lys Lys Gly Ser Tyr Asn Ile
610                 615                 620

Gly Val Asn Tyr Glu Phe
625                 630

<210> SEQ ID NO 34
<211> LENGTH: 616
<212> TYPE: PRT
<213> ORGANISM: Moraxella catarrhalis

<400> SEQUENCE: 34

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Gln
            20                  25                  30

Asp Arg Ser Leu Glu Gln Ile Gln Asp Lys Leu Ala Asn Leu Val Glu
        35                  40                  45

Lys Ile Glu Gln Ala Lys Ser Gln Asn Gly Gln Ser Gln Lys Asp Ile
    50                  55                  60

Asn Gln Tyr Leu Leu Leu Ser Gln Tyr Ala Asn Val Leu Thr Met Glu
65                  70                  75                  80

Glu Leu Asn Asn Asn Val Val Lys Asn Ser Ser Ile Glu Thr Leu
                85                  90                  95

Asp Asn Asp Ile Ala Trp Leu Asn Asp Leu Ile Asp Leu Asp Lys
            100                 105                 110

Glu Val Gly Val Leu Ser Arg Asp Ile Gly Ser Leu His Asp Asp Val
```

-continued

```
            115                 120                 125
Ala Gln Asn Gln Ala Asp Ile Lys Thr Leu Lys Asn Val Val Glu
130                 135                 140

Glu Leu Phe Asn Leu Ser Asp Arg Leu Ile Asp Gln Glu Ala Asp Ile
145                 150                 155                 160

Ala Gln Asn Asn Glu Ser Ile Glu Asp Leu Tyr Asp Phe Gly Arg Glu
                165                 170                 175

Val Ala Glu Ser Ile Gly Glu Ile His Ala His Asn Glu Ala Gln Asn
            180                 185                 190

Glu Thr Leu Lys Asp Leu Ile Thr Asn Ser Val Lys Asn Thr Asp Asn
        195                 200                 205

Ile Thr Lys Asn Lys Ala Asp Ile Gln Ala Leu Glu Asn Asp Val Gly
    210                 215                 220

Lys Glu Leu Leu Asn Leu Ser Gly Arg Leu Ile Asp Gln Lys Ala Asp
225                 230                 235                 240

Ile Asp Asn Asn Ile Asn His Ile Tyr Glu Leu Ala Gln Gln Gln Asp
                245                 250                 255

Gln His Ser Ser Asp Ile Lys Thr Leu Lys Asn Asn Val Glu Glu Gly
            260                 265                 270

Leu Leu Glu Leu Ser Gly His Leu Ile Asp Gln Lys Ala Asp Leu Thr
        275                 280                 285

Lys Asp Ile Lys Ala Leu Glu Ser Asn Val Glu Glu Gly Leu Leu Asp
    290                 295                 300

Leu Ser Gly Arg Leu Leu Asp Gln Lys Ala Asp Ile Ala Gln Asn Gln
305                 310                 315                 320

Ala Asn Ile Gln Asp Leu Ala Ala Tyr Asn Glu Leu Gln Asp Ala Tyr
                325                 330                 335

Ala Lys Gln Gln Thr Glu Ala Ile Asp Ala Leu Asn Lys Ala Ser Ser
            340                 345                 350

Glu Asn Thr Gln Asn Ile Glu Asp Leu Ala Ala Tyr Asn Glu Leu Gln
        355                 360                 365

Asp Ala Tyr Ala Lys Gln Gln Thr Glu Ala Ile Asp Ala Leu Asn Lys
    370                 375                 380

Ala Ser Ser Glu Asn Thr Gln Asn Ile Ala Lys Asn Gln Ala Asp Ile
385                 390                 395                 400

Ala Asn Asn Ile Asn Asn Ile Tyr Glu Leu Ala Gln Gln Gln Asp Gln
                405                 410                 415

His Ser Ser Asp Ile Lys Thr Leu Ala Lys Ala Ser Ala Ala Asn Thr
            420                 425                 430

Asp Arg Ile Ala Lys Asn Lys Ala Asp Ala Asp Ala Ser Phe Glu Thr
        435                 440                 445

Leu Thr Lys Asn Gln Asn Thr Leu Ile Glu Lys Asp Lys Glu His Asp
    450                 455                 460

Lys Leu Ile Thr Ala Asn Lys Thr Ala Ile Asp Ala Asn Lys Ala Ser
465                 470                 475                 480

Ala Asp Thr Lys Phe Ala Ala Thr Ala Asp Ala Ile Thr Lys Asn Gly
                485                 490                 495

Asn Ala Ile Thr Lys Asn Ala Lys Ser Ile Thr Asp Leu Gly Thr Lys
            500                 505                 510

Val Asp Gly Phe Asp Ser Arg Val Thr Ala Leu Asp Thr Lys Val Asn
        515                 520                 525

Ala Phe Asp Gly Arg Ile Thr Ala Leu Asp Ser Lys Val Glu Asn Gly
    530                 535                 540
```

```
Met Ala Gln Ala Ala Leu Ser Gly Leu Phe Gln Pro Tyr Ser Val
545                 550                 555                 560

Gly Lys Phe Asn Ala Thr Ala Leu Gly Tyr Gly Ser Lys Ser
                565                 570                 575

Ala Val Ala Ile Gly Ala Gly Tyr Arg Val Asn Pro Asn Leu Ala Phe
            580                 585                 590

Lys Ala Gly Ala Ala Ile Asn Thr Ser Gly Asn Lys Lys Gly Ser Tyr
            595                 600                 605

Asn Ile Gly Val Asn Tyr Glu Phe
            610                 615

<210> SEQ ID NO 35
<211> LENGTH: 614
<212> TYPE: PRT
<213> ORGANISM: Moraxella catarrhalis

<400> SEQUENCE: 35

Met Lys Thr Met Lys Leu Leu Pro Leu Lys Ile Ala Val Thr Ser Ala
1               5                   10                  15

Met Ile Ile Gly Leu Gly Ala Thr Ser Thr Val Asn Ala Gln Val Val
            20                  25                  30

Glu Gln Phe Phe Pro Asn Ile Phe Asn Glu Asn His Asp Glu Leu
        35                  40                  45

Asp Asp Ala Tyr His Asn Met Ile Leu Gly Asp Thr Ala Ile Val Ser
    50                  55                  60

Asn Ser Gln Asp Asn Ser Thr Gln Leu Lys Phe Tyr Ser Asn Asp Glu
65                  70                  75                  80

Asp Ser Val Pro Asp Ser Leu Leu Phe Ser Lys Leu Leu His Glu Gln
                85                  90                  95

Gln Leu Asn Gly Phe Lys Ala Gly Asp Thr Ile Ile Pro Leu Asp Lys
            100                 105                 110

Asp Gly Lys Pro Val Tyr Thr Lys Asp Thr Arg Thr Lys Asp Gly Lys
            115                 120                 125

Val Glu Thr Val Tyr Ser Val Thr Thr Lys Ile Ala Thr Gln Asp Asp
    130                 135                 140

Val Glu Gln Ser Ala Tyr Ser Arg Gly Ile Gln Gly Asp Ile Asp Asp
145                 150                 155                 160

Leu Tyr Asp Ile Asn Arg Glu Val Asn Glu Tyr Leu Lys Ala Thr His
                165                 170                 175

Asp Tyr Asn Glu Arg Gln Thr Glu Ala Ile Asp Ala Leu Asn Lys Ala
            180                 185                 190

Ser Ser Ala Asn Thr Asp Arg Ile Asp Thr Ala Glu Glu Arg Ile Asp
            195                 200                 205

Lys Asn Glu Tyr Asp Ile Lys Ala Leu Glu Ser Asn Val Gly Lys Asp
    210                 215                 220

Leu Leu Asp Leu Ser Gly Arg Leu Ile Ala Gln Lys Glu Asp Ile Asp
225                 230                 235                 240

Asn Asn Ile Asn His Ile Tyr Glu Leu Ala Gln Gln Asp Gln His
                245                 250                 255

Ser Ser Asp Ile Lys Thr Leu Lys Asn Asn Val Glu Glu Gly Leu Leu
            260                 265                 270

Glu Leu Ser Gly His Leu Ile Asp Gln Lys Ala Asp Leu Thr Lys Asp
        275                 280                 285

Ile Lys Thr Leu Glu Ser Asn Val Glu Glu Gly Leu Leu Asp Leu Ser
```

```
            290                 295                 300
Gly Arg Leu Ile Asp Gln Lys Ala Asp Ile Ala Gln Asn Gln Ala Asn
305                 310                 315                 320

Ile Gln Asp Leu Ala Ala Tyr Asn Glu Leu Gln Asp Gln Tyr Ala Gln
                325                 330                 335

Lys Gln Thr Glu Ala Ile Asp Ala Leu Asn Lys Ala Ser Ser Glu Asn
            340                 345                 350

Thr Gln Asn Ile Glu Asp Leu Ala Ala Tyr Asn Glu Leu Gln Asp Ala
        355                 360                 365

Tyr Ala Lys Gln Gln Thr Glu Ala Ile Asp Ala Leu Asn Lys Ala Ser
370                 375                 380

Ser Glu Asn Thr Gln Asn Ile Ala Lys Asn Gln Ala Asp Ile Ala Asn
385                 390                 395                 400

Asn Ile Asn Asn Ile Tyr Glu Leu Ala Gln Gln Asp Gln His Ser
                405                 410                 415

Ser Asp Ile Lys Thr Leu Ala Lys Val Ser Ala Ala Asn Thr Asp Arg
            420                 425                 430

Ile Ala Lys Asn Lys Ala Asp Ala Asp Ala Ser Phe Glu Thr Leu Thr
        435                 440                 445

Lys Asn Gln Asn Thr Leu Ile Glu Lys Asp Lys Glu His Asp Lys Leu
    450                 455                 460

Ile Thr Ala Asn Lys Thr Ala Ile Asp Ala Asn Lys Ala Ser Ala Asp
465                 470                 475                 480

Thr Lys Phe Ala Ala Thr Ala Asp Ala Ile Thr Lys Asn Gly Asn Ala
                485                 490                 495

Ile Thr Lys Asn Ala Lys Ser Ile Thr Asp Leu Gly Thr Lys Val Asp
            500                 505                 510

Gly Phe Asp Gly Arg Val Thr Ala Leu Asp Thr Lys Val Asn Ala Phe
        515                 520                 525

Asp Gly Arg Ile Thr Ala Leu Asp Ser Lys Val Glu Asn Gly Met Ala
    530                 535                 540

Ala Gln Ala Ala Leu Ser Gly Leu Phe Gln Pro Tyr Ser Val Gly Lys
545                 550                 555                 560

Phe Asn Ala Thr Ala Ala Leu Gly Gly Tyr Gly Ser Lys Ser Ala Val
                565                 570                 575

Ala Ile Gly Ala Gly Tyr Arg Val Asn Pro Asn Leu Ala Phe Lys Ala
            580                 585                 590

Gly Ala Ala Ile Asn Thr Ser Gly Asn Lys Lys Gly Ser Tyr Asn Ile
        595                 600                 605

Gly Val Asn Tyr Glu Phe
        610

<210> SEQ ID NO 36
<211> LENGTH: 679
<212> TYPE: PRT
<213> ORGANISM: Moraxella catarrhalis

<400> SEQUENCE: 36

Met Lys Thr Met Lys Leu Pro Pro Leu Lys Ile Ala Val Thr Ser Ala
1               5                   10                  15

Met Ile Ile Gly Leu Gly Ala Ala Ser Thr Ala Asn Ala Gln Thr Thr
            20                  25                  30

Glu Thr Phe Leu Pro Asn Leu Phe Asp Asn Asp Tyr Glu Thr Thr
        35                  40                  45
```

```
Asp Pro Leu Tyr His Gly Met Ile Leu Gly Asp Thr Ala Ile Thr Gln
    50              55                  60

Asp Thr Gln Tyr Lys Phe Tyr Ala Glu Asn Gly Asn Glu Val Pro Asp
65              70                  75                  80

Ser Leu Phe Phe Asn Lys Ile Leu His Asp Gln Leu Leu Asn Gly Phe
                85                  90                  95

Lys Ala Gly Asp Thr Ile Ile Pro Leu Asp Glu Asn Gly Lys Pro Val
                100                 105                 110

Tyr Lys Leu Asp Glu Arg Thr Glu Asn Gly Val Lys Arg Lys Val Tyr
            115                 120                 125

Ser Val Thr Thr Lys Thr Ala Thr Gln Ala Asp Val Glu Gln Ser Ala
    130                 135                 140

Tyr Ser Arg Gly Ile Gln Gly Asp Ile Asp Asp Leu Tyr Glu Ala Asn
145                 150                 155                 160

Lys Glu Asn Val Asn Arg Leu Ile Glu His Gly Asp Lys Ile Phe Ala
                165                 170                 175

Asn Glu Glu Ser Val Gln Tyr Leu Asn Arg Glu Val Gln Asn Asn Ile
            180                 185                 190

Glu Asn Ile His Glu Leu Ala Gln Gln Asp Gln His Ser Ser Asp
            195                 200                 205

Ile Lys Thr Leu Lys Lys Asn Val Glu Lys Asp Leu Leu Asp Leu Ser
    210                 215                 220

Gly Arg Leu Ile Ala Gln Lys Glu Asp Ile Ala Gln Asn Gln Thr Asp
225                 230                 235                 240

Ile Gln Asp Leu Ala Thr Tyr Asn Glu Leu Gln Asp Gln Tyr Ala Gln
                245                 250                 255

Lys Gln Thr Glu Ala Ile Asp Ala Leu Asn Lys Ala Ser Ser Glu Asn
            260                 265                 270

Thr Gln Asn Ile Ala Lys Asn Ser Asn His Ile Lys Thr Leu Glu Asn
            275                 280                 285

Asn Ile Glu Glu Cys Leu Leu Glu Leu Ser Gly His Leu Ile Asp Gln
    290                 295                 300

Lys Ala Asp Leu Thr Lys Asp Ile Lys Ala Leu Glu Ser Asn Val Glu
305                 310                 315                 320

Glu Gly Leu Leu Asp Leu Ser Gly Arg Leu Ile Asp Gln Lys Ala Asp
                325                 330                 335

Ile Ala Gln Asn Gln Ala Asn Ile Gln Asp Leu Ala Ala Tyr Asn Glu
            340                 345                 350

Leu Gln Asp Ala Tyr Ala Lys Gln Gln Thr Glu Ala Ile Asp Ala Leu
    355                 360                 365

Asn Lys Ala Ser Ser Glu Asn Thr Gln Asn Ile Glu Asp Leu Ala Ala
    370                 375                 380

Tyr Asn Glu Leu Gln Asp Ala Tyr Ala Lys Gln Gln Thr Glu Ala Ile
385                 390                 395                 400

Asp Ala Leu Asn Lys Ala Ser Ser Glu Asn Thr Gln Asn Ile Glu Asp
                405                 410                 415

Leu Ala Ala Tyr Asn Glu Leu Gln Asp Ala Tyr Ala Lys Gln Gln Thr
            420                 425                 430

Glu Ala Ile Asp Ala Leu Asn Lys Ala Ser Ser Glu Asn Thr Gln Asn
            435                 440                 445

Ile Ala Lys Asn Gln Ala Asp Ile Ala Asn Asn Ile Asn Asn Ile Tyr
    450                 455                 460

Glu Leu Ala Gln Gln Gln Asp Gln His Ser Ser Asp Ile Lys Thr Leu
```

```
                   465                 470                 475                 480

Ala Lys Ala Ser Ala Ala Asn Thr Asp Arg Ile Ala Lys Asn Lys Ala
                485                 490                 495

Asp Ala Asp Ala Ser Phe Glu Thr Leu Thr Lys Asn Gln Asn Thr Leu
            500                 505                 510

Ile Glu Lys Asp Lys Glu His Asp Lys Leu Ile Thr Ala Asn Lys Thr
        515                 520                 525

Ala Ile Asp Ala Asn Lys Ala Ser Ala Asp Thr Lys Phe Ala Ala Thr
    530                 535                 540

Ala Asp Ala Ile Thr Lys Asn Gly Asn Ala Ile Thr Lys Asn Ala Lys
545                 550                 555                 560

Ser Ile Thr Asp Leu Gly Thr Lys Val Asp Gly Phe Asp Gly Arg Val
                565                 570                 575

Thr Ala Leu Asp Thr Lys Val Asn Ala Leu Asp Thr Lys Val Asn Ala
            580                 585                 590

Phe Asp Gly Arg Ile Thr Ala Leu Asp Ser Lys Val Glu Asn Gly Met
        595                 600                 605

Ala Ala Gln Ala Ala Leu Ser Gly Leu Phe Gln Pro Tyr Ser Val Gly
    610                 615                 620

Lys Phe Asn Ala Thr Ala Ala Leu Gly Gly Tyr Gly Ser Lys Ser Ala
625                 630                 635                 640

Val Ala Ile Gly Ala Gly Tyr Arg Val Asn Pro Asn Leu Ala Phe Lys
                645                 650                 655

Ala Gly Ala Ala Ile Asn Thr Ser Gly Asn Lys Lys Gly Ser Tyr Asn
            660                 665                 670

Ile Gly Val Asn Tyr Glu Phe
        675

<210> SEQ ID NO 37
<211> LENGTH: 724
<212> TYPE: PRT
<213> ORGANISM: Moraxella catarrhalis

<400> SEQUENCE: 37

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Glu Thr
                20                  25                  30

Leu Glu Glu Val Leu Glu Ser Ile Lys Gln Ile Asn Glu Gln Asp Leu
            35                  40                  45

Gln Asp Asp Ile Gly Tyr Asn Ser Ala Leu Asp Arg Tyr Leu Val Leu
        50                  55                  60

Ser Gln Tyr Gly Asn Leu Leu Ile Ala Lys Glu Leu Asn Glu Asn Val
65                  70                  75                  80

Glu Lys Asn Ser Asn Ser Ile Ala Lys Asn Ser Asn Ser Ile Ala Asp
                85                  90                  95

Leu Glu Ala Asp Val Gly Tyr Leu Ala Glu Asn Gln Asn Thr Leu Ile
            100                 105                 110

Glu Gln Asn Glu Thr Ile Asn Gln Glu Leu Glu Gly Ile Thr His Glu
        115                 120                 125

Leu Glu Ser Phe Ile Ala Tyr Ala His Ala Gln Asp Gln Lys Asn Leu
    130                 135                 140

Val Asn Glu Phe Glu Ile Glu Lys Asn Lys Asp Ala Ile Ala Lys Asn
145                 150                 155                 160
```

```
Asn Glu Ser Ile Glu Asp Leu Tyr Asp Phe Gly His Glu Val Ala Glu
                165                 170                 175
Ser Ile Gly Glu Ile His Ala Tyr Thr Glu Glu Val Asn Lys Thr Leu
            180                 185                 190
Glu Asn Leu Ile Thr Asn Ser Val Lys Asn Thr Asp Asn Ile Thr Lys
            195                 200                 205
Asn Lys Ala Asp Ile Gln Ala Leu Glu Ser Asn Val Glu Lys Glu Leu
            210                 215                 220
Leu Asn Leu Ser Gly Arg Leu Ile Asp Gln Lys Ala Asp Ile Asp Asn
225                 230                 235                 240
Asn Ile Asn His Ile Tyr Glu Leu Ala Gln Gln Gln Asp Gln His Ser
                245                 250                 255
Ser Asp Ile Lys Thr Leu Lys Lys Asn Val Glu Glu Gly Leu Leu Glu
            260                 265                 270
Leu Ser Gly His Leu Ile Asp Gln Lys Ser Asp Ile Ala Gln Asn Gln
            275                 280                 285
Thr Asp Ile Gln Asp Leu Ala Thr Tyr Asn Glu Leu Gln Asp Gln Tyr
            290                 295                 300
Ala Gln Lys Gln Thr Glu Ala Ile Asp Ala Leu Asn Lys Ala Ser Ser
305                 310                 315                 320
Glu Asn Thr Gln Asn Ile Glu Asp Leu Ala Ala Tyr Asn Glu Leu Gln
                325                 330                 335
Asp Ala Tyr Ala Lys Gln Gln Thr Glu Ala Ile Asp Ala Leu Asn Lys
            340                 345                 350
Ala Ser Ser Glu Asn Thr Gln Asn Ile Glu Asp Leu Ala Ala Tyr Asn
            355                 360                 365
Glu Leu Gln Asp Ala Tyr Ala Lys Gln Gln Thr Glu Ala Ile Asp Ala
            370                 375                 380
Leu Asn Lys Ala Ser Ser Glu Asn Thr Gln Asn Ile Glu Asp Leu Ala
385                 390                 395                 400
Ala Tyr Asn Glu Leu Gln Asp Ala Tyr Ala Lys Gln Gln Thr Glu Ala
                405                 410                 415
Ile Asp Ala Leu Asn Lys Ala Ser Ser Glu Asn Thr Gln Asn Ile Glu
            420                 425                 430
Asp Leu Ala Ala Tyr Asn Glu Leu Gln Asp Ala Tyr Ala Lys Gln Gln
            435                 440                 445
Thr Glu Ala Ile Asp Ala Leu Asn Lys Ala Ser Ser Glu Asn Thr Gln
            450                 455                 460
Asn Ile Glu Asp Leu Ala Ala Tyr Asn Glu Leu Gln Asp Ala Tyr Ala
465                 470                 475                 480
Lys Gln Gln Thr Glu Ala Ile Asp Ala Leu Asn Lys Ala Ser Ser Glu
                485                 490                 495
Asn Thr Gln Asn Ile Ala Lys Asn Gln Ala Asp Ile Ala Asn Asn Ile
            500                 505                 510
Asn Asn Ile Tyr Glu Leu Ala Gln Gln Gln Asp Gln His Ser Ser Asp
            515                 520                 525
Ile Lys Thr Leu Ala Lys Ala Ser Ala Ala Asn Thr Asp Arg Ile Ala
            530                 535                 540
Lys Asn Lys Ala Asp Ala Asp Ala Ser Phe Glu Thr Leu Thr Lys Asn
545                 550                 555                 560
Gln Asn Thr Leu Ile Glu Lys Asp Lys Glu His Asp Lys Leu Ile Thr
                565                 570                 575
Ala Asn Lys Thr Ala Ile Asp Ala Asn Lys Ala Ser Ala Asp Thr Lys
```

```
                580                 585                 590
Phe Ala Ala Thr Ala Asp Ala Ile Thr Lys Asn Gly Asn Ala Ile Thr
                595                 600                 605

Lys Asn Ala Lys Ser Ile Thr Asp Leu Gly Thr Lys Val Asp Gly Phe
            610                 615                 620

Asp Ser Arg Val Thr Ala Leu Asp Thr Lys Val Asn Ala Phe Asp Gly
625                 630                 635                 640

Arg Ile Thr Ala Leu Asp Ser Lys Val Glu Asn Gly Met Ala Ala Gln
                645                 650                 655

Ala Ala Leu Ser Gly Leu Phe Gln Pro Tyr Ser Val Gly Lys Phe Asn
                660                 665                 670

Ala Thr Ala Ala Leu Gly Gly Tyr Gly Ser Lys Ser Ala Val Ala Ile
                675                 680                 685

Gly Ala Gly Tyr Arg Val Asn Pro Asn Leu Ala Phe Lys Ala Gly Ala
                690                 695                 700

Ala Ile Asn Thr Ser Gly Asn Lys Lys Gly Ser Tyr Asn Ile Gly Val
705                 710                 715                 720

Asn Tyr Glu Phe

<210> SEQ ID NO 38
<211> LENGTH: 611
<212> TYPE: PRT
<213> ORGANISM: Moraxella catarrhalis

<400> SEQUENCE: 38

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Gln
                20                  25                  30

Ala Arg Asp Arg Ser Leu Glu Asp Ile Gln Ala Leu Ile Gly Asn Ile
            35                  40                  45

Asp Val Asp Lys Ile Arg Ser Gln Lys Gln Lys Asn Pro Glu Ile Phe
    50                  55                  60

Gln Tyr Leu Leu Leu Asn Gln Leu Ser Asn Thr Leu Ile Thr Asp Glu
65                  70                  75                  80

Leu Asn Asn Asn Val Ile Lys Asn Thr Asn Ser Ile Glu Thr Leu Asp
                85                  90                  95

Asn Asp Ile Ala Trp Leu Asn Asp Asp Leu Ile Asp Leu Asp Lys Glu
                100                 105                 110

Val Gly Val Leu Ser Arg Asp Ile Gly Ser Leu His Asp Asp Val Ala
            115                 120                 125

Gln Asn Gln Ala Asp Ile Lys Thr Leu Glu Asn Asn Val Val Glu Glu
    130                 135                 140

Leu Phe Asn Leu Ser Asp Arg Leu Ile Asp Gln Glu Ala Glu Ile Ala
145                 150                 155                 160

Gln Asn Asn Glu Ser Ile Glu Asp Leu Tyr Asp Phe Gly Arg Glu Val
                165                 170                 175

Ala Glu Ser Ile Gly Glu Ile His Ala His Asn Glu Ala Gln Asn Glu
                180                 185                 190

Thr Leu Lys Asp Leu Ile Thr Asn Ser Val Lys Asn Thr Asp Asn Ile
            195                 200                 205

Asp Lys Asn Lys Ala Asp Ile Gln Ala Leu Glu Asn Asn Val Glu Glu
    210                 215                 220

Gly Leu Leu Glu Leu Ser Gly His Leu Ile Asp Gln Lys Ala Asp Leu
```

```
              225                 230                 235                 240
        Thr Lys Asp Ile Lys Ala Leu Glu Ser Asn Val Glu Glu Gly Leu Leu
                        245                 250                 255
        Asp Leu Ser Gly Arg Leu Leu Asp Gln Lys Ala Asp Ile Ala Lys Asn
                        260                 265                 270
        Gln Ala Asp Ile Ala Gln Asn Gln Thr Asp Ile Gln Asp Leu Ala Ala
                        275                 280                 285
        Tyr Asn Glu Leu Gln Asp Gln Tyr Ala Gln Lys Gln Thr Glu Ala Ile
                        290                 295                 300
        Asp Ala Leu Asn Lys Ala Ser Ser Glu Asn Thr Gln Asn Ile Glu Asp
        305                 310                 315                 320
        Leu Ala Ala Tyr Asn Glu Leu Gln Asp Ala Tyr Ala Lys Gln Gln Thr
                        325                 330                 335
        Glu Ala Ile Asp Ala Leu Asn Lys Ala Ser Ser Glu Asn Thr Gln Asn
                        340                 345                 350
        Ile Glu Asp Leu Ala Ala Tyr Asn Glu Leu Gln Asp Ala Tyr Ala Lys
                        355                 360                 365
        Gln Gln Thr Glu Ala Ile Asp Ala Leu Asn Lys Ala Ser Ser Glu Asn
                        370                 375                 380
        Thr Gln Asn Ile Ala Lys Asn Gln Ala Asp Ile Ala Asn Asn Ile Asn
        385                 390                 395                 400
        Asn Ile Tyr Glu Leu Ala Gln Gln Gln Asp Gln His Ser Ser Asp Ile
                        405                 410                 415
        Lys Thr Leu Ala Lys Val Ser Ala Ala Asn Thr Asp Arg Ile Ala Lys
                        420                 425                 430
        Asn Lys Ala Asp Ala Asp Ala Ser Phe Glu Thr Leu Thr Lys Asn Gln
                        435                 440                 445
        Asn Thr Leu Ile Glu Lys Asp Lys Glu His Asp Lys Leu Ile Thr Ala
                        450                 455                 460
        Asn Lys Thr Ala Ile Asp Ala Asn Lys Ala Ser Ala Asp Thr Lys Phe
        465                 470                 475                 480
        Ala Ala Thr Ala Asp Ala Ile Thr Lys Asn Gly Asn Ala Ile Thr Lys
                        485                 490                 495
        Asn Ala Lys Ser Ile Thr Asp Leu Gly Thr Lys Val Asp Gly Phe Asp
                        500                 505                 510
        Ser Arg Val Thr Ala Leu Asp Thr Lys Val Asn Ala Phe Asp Gly Arg
                        515                 520                 525
        Ile Thr Ala Leu Asp Ser Lys Val Glu Asn Gly Met Ala Ala Gln Ala
                        530                 535                 540
        Ala Leu Ser Gly Leu Phe Gln Pro Tyr Ser Val Gly Lys Phe Asn Ala
        545                 550                 555                 560
        Thr Ala Ala Leu Gly Gly Tyr Gly Ser Lys Ser Ala Val Ala Ile Gly
                        565                 570                 575
        Ala Gly Tyr Arg Val Asn Pro Asn Leu Ala Phe Lys Ala Gly Ala Ala
                        580                 585                 590
        Ile Asn Thr Ser Gly Asn Lys Lys Gly Ser Tyr Asn Ile Gly Val Asn
                        595                 600                 605
        Tyr Glu Phe
            610

<210> SEQ ID NO 39
<211> LENGTH: 511
<212> TYPE: PRT
<213> ORGANISM: Moraxella catarrhalis
```

<400> SEQUENCE: 39

```
Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
            20                  25                  30

Leu Glu Lys Tyr Leu Ala Leu Ser Gln Tyr Gly Asn Ile Leu Ala Leu
        35                  40                  45

Glu Glu Leu Asn Lys Ala Leu Glu Glu Leu Asp Glu Asp Val Gly Trp
50                  55                  60

Asn Gln Asn Asp Ile Ala Asn Leu Glu Asp Asp Val Glu Thr Leu Thr
65                  70                  75                  80

Lys Asn Gln Asn Ala Leu Ala Glu Gln Gly Glu Ala Ile Lys Glu Asp
                85                  90                  95

Leu Gln Gly Leu Ala Asp Phe Val Glu Gly Gln Glu Gly Lys Ile Leu
            100                 105                 110

Gln Asn Glu Thr Ser Ile Lys Lys Asn Thr Gln Arg Asn Leu Val Asn
            115                 120                 125

Gly Phe Glu Ile Glu Lys Asn Lys Asp Ala Ile Ala Lys Asn Asn Glu
130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Asn Ile Thr Lys Asn Lys
            180                 185                 190

Ala Asp Ile Gln Ala Leu Glu Asn Asn Val Val Glu Glu Leu Phe Asn
            195                 200                 205

Leu Ser Gly Arg Leu Ile Asp Gln Lys Ala Asp Ile Asp Asn Asn Ile
210                 215                 220

Asn Asn Ile Tyr Glu Leu Ala Gln Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Gly His Leu Ile Asp Gln Lys Thr Asp Ile Ala Gln Asn Gln Ala Asn
            260                 265                 270

Ile Gln Asp Leu Ala Thr Tyr Asn Glu Leu Gln Asp Gln Tyr Ala Gln
            275                 280                 285

Lys Gln Thr Glu Ala Ile Asp Ala Leu Asn Lys Ala Ser Ser Glu Asn
290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                325                 330                 335

Ser Glu Asn Thr Gln Asn Ile Glu Asp Leu Ala Ala Tyr Asn Glu Leu
            340                 345                 350

Gln Asp Ala Tyr Ala Lys Gln Gln Thr Glu Ala Ile Asp Ala Leu Asn
            355                 360                 365

Lys Ala Ser Ser Glu Asn Thr Gln Asn Ile Ala Lys Gln Ala Asp
370                 375                 380

Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
```

```
                        405                 410                 415
Thr Asp Arg Ile Ala Lys Asn Lys Ala Asp Ala Asp Ala Ser Phe Glu
                420                 425                 430

Thr Leu Thr Lys Asn Gln Asn Thr Leu Ile Glu Lys Asp Lys Glu His
            435                 440                 445

Asp Lys Leu Ile Thr Ala Asn Lys Thr Ala Ile Asp Ala Asn Lys Ala
        450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser Ile Thr Asp Leu Gly Thr
                485                 490                 495

Lys Val Asp Gly Phe Asp Ser Arg Val Thr Ala Leu Asp Thr Lys
                500                 505                 510

<210> SEQ ID NO 40
<211> LENGTH: 510
<212> TYPE: PRT
<213> ORGANISM: Moraxella catarrhalis

<400> SEQUENCE: 40

Ala Lys Asn Asp Ile Thr Leu Glu Asp Leu Pro Tyr Leu Ile Lys Lys
1               5                   10                  15

Ile Asp Gln Asn Glu Leu Glu Ala Asp Ile Gly Asp Ile Thr Ala Leu
                20                  25                  30

Glu Lys Tyr Leu Ala Leu Ser Gln Tyr Gly Asn Ile Leu Ala Leu Glu
            35                  40                  45

Glu Leu Asn Lys Ala Leu Glu Glu Leu Asp Glu Asp Val Gly Trp Asn
    50                  55                  60

Gln Asn Asp Ile Ala Asn Leu Glu Asp Asp Val Glu Thr Leu Thr Lys
65                  70                  75                  80

Asn Gln Asn Ala Leu Ala Glu Gln Gly Glu Ala Ile Lys Glu Asp Leu
                85                  90                  95

Gln Gly Leu Ala Asp Phe Val Glu Gly Gln Glu Gly Lys Ile Leu Gln
            100                 105                 110

Asn Glu Thr Ser Ile Lys Lys Asn Thr Gln Arg Asn Leu Val Asn Gly
        115                 120                 125

Phe Glu Ile Glu Lys Asn Lys Asp Ala Ile Ala Lys Asn Asn Glu Ser
130                 135                 140

Ile Glu Asp Leu Tyr Asp Phe Gly His Glu Val Ala Glu Ser Ile Gly
145                 150                 155                 160

Glu Ile His Ala His Asn Glu Ala Gln Asn Glu Thr Leu Lys Gly Leu
                165                 170                 175

Ile Thr Asn Ser Ile Glu Asn Thr Asn Asn Ile Thr Lys Asn Lys Ala
            180                 185                 190

Asp Ile Gln Ala Leu Glu Asn Asn Val Val Glu Glu Leu Phe Asn Leu
        195                 200                 205

Ser Gly Arg Leu Ile Asp Gln Lys Ala Asp Ile Asp Asn Asn Ile Asn
    210                 215                 220

Asn Ile Tyr Glu Leu Ala Gln Gln Gln Asp Gln His Ser Ser Asp Ile
225                 230                 235                 240

Lys Thr Leu Lys Lys Asn Val Glu Glu Gly Leu Leu Glu Leu Ser Gly
                245                 250                 255

His Leu Ile Asp Gln Lys Thr Asp Ile Ala Gln Asn Gln Ala Asn Ile
            260                 265                 270
```

-continued

Gln Asp Leu Ala Thr Tyr Asn Glu Leu Gln Asp Gln Tyr Ala Gln Lys
            275                 280                 285

Gln Thr Glu Ala Ile Asp Ala Leu Asn Lys Ala Ser Ser Glu Asn Thr
        290                 295                 300

Gln Asn Ile Glu Asp Leu Ala Ala Tyr Asn Glu Leu Gln Asp Ala Tyr
305                 310                 315                 320

Ala Lys Gln Gln Thr Glu Ala Ile Asp Ala Leu Asn Lys Ala Ser Ser
                325                 330                 335

Glu Asn Thr Gln Asn Ile Glu Asp Leu Ala Ala Tyr Asn Glu Leu Gln
            340                 345                 350

Asp Ala Tyr Ala Lys Gln Gln Thr Glu Ala Ile Asp Ala Leu Asn Lys
        355                 360                 365

Ala Ser Ser Glu Asn Thr Gln Asn Ile Ala Lys Asn Gln Ala Asp Ile
370                 375                 380

Ala Asn Asn Ile Asn Asn Ile Tyr Glu Leu Ala Gln Gln Gln Asp Gln
385                 390                 395                 400

His Ser Ser Asp Ile Lys Thr Leu Ala Lys Ala Ser Ala Ala Asn Thr
                405                 410                 415

Asp Arg Ile Ala Lys Asn Lys Ala Asp Ala Asp Ala Ser Phe Glu Thr
            420                 425                 430

Leu Thr Lys Asn Gln Asn Thr Leu Ile Glu Lys Asp Lys Glu His Asp
        435                 440                 445

Lys Leu Ile Thr Ala Asn Lys Thr Ala Ile Asp Ala Asn Lys Ala Ser
450                 455                 460

Ala Asp Thr Lys Phe Ala Ala Thr Ala Asp Ala Ile Thr Lys Asn Gly
465                 470                 475                 480

Asn Ala Ile Thr Lys Asn Ala Lys Ser Ile Thr Asp Leu Gly Thr Lys
                485                 490                 495

Val Asp Gly Phe Asp Ser Arg Val Thr Ala Leu Asp Thr Lys
            500                 505                 510

<210> SEQ ID NO 41
<211> LENGTH: 490
<212> TYPE: PRT
<213> ORGANISM: Moraxella catarrhalis

<400> SEQUENCE: 41

Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
            20                  25                  30

Leu Glu Lys Tyr Leu Ala Leu Ser Gln Tyr Gly Asn Ile Leu Ala Leu
        35                  40                  45

Glu Glu Leu Asn Lys Ala Leu Glu Glu Leu Asp Glu Asp Val Gly Trp
    50                  55                  60

Asn Gln Asn Asp Ile Ala Asn Leu Glu Asp Asp Val Glu Thr Leu Thr
65                  70                  75                  80

Lys Asn Gln Asn Ala Leu Ala Glu Gln Gly Glu Ala Ile Lys Glu Asp
                85                  90                  95

Leu Gln Gly Leu Ala Asp Phe Val Glu Gly Glu Gly Lys Ile Leu
            100                 105                 110

Gln Asn Glu Thr Ser Ile Lys Lys Asn Thr Gln Arg Asn Leu Val Asn
        115                 120                 125

Gly Phe Glu Ile Glu Lys Asn Lys Asp Ala Ile Ala Lys Asn Asn Glu
    130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
            165                 170                 175

Leu Ile Thr Asn Ser Ile Glu Asn Thr Asn Asn Ile Thr Lys Asn Lys
        180                 185                 190

Ala Asp Ile Gln Ala Leu Glu Asn Asn Val Val Glu Glu Leu Phe Asn
    195                 200                 205

Leu Ser Gly Arg Leu Ile Asp Gln Lys Ala Asp Ile Asp Asn Asn Ile
210                 215                 220

Asn Asn Ile Tyr Glu Leu Ala Gln Gln Gln Asp Gln His Ser Ser Asp
225                 230                 235                 240

Ile Lys Thr Leu Lys Lys Asn Val Glu Glu Gly Leu Leu Glu Leu Ser
            245                 250                 255

Gly His Leu Ile Asp Gln Lys Thr Asp Ile Ala Gln Asn Gln Ala Asn
        260                 265                 270

Ile Gln Asp Leu Ala Thr Tyr Asn Glu Leu Gln Asp Gln Tyr Ala Gln
    275                 280                 285

Lys Gln Thr Glu Ala Ile Asp Ala Leu Asn Lys Ala Ser Ser Glu Asn
290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
            325                 330                 335

Ser Glu Asn Thr Gln Asn Ile Glu Asp Leu Ala Ala Tyr Asn Glu Leu
        340                 345                 350

Gln Asp Ala Tyr Ala Lys Gln Gln Thr Glu Ala Ile Asp Ala Leu Asn
    355                 360                 365

Lys Ala Ser Ser Glu Asn Thr Gln Asn Ile Ala Lys Asn Gln Ala Asp
370                 375                 380

Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
            405                 410                 415

Thr Asp Arg Ile Ala Lys Asn Lys Ala Asp Ala Asp Ala Ser Phe Glu
        420                 425                 430

Thr Leu Thr Lys Asn Gln Asn Thr Leu Ile Glu Lys Asp Lys Glu His
    435                 440                 445

Asp Lys Leu Ile Thr Ala Asn Lys Thr Ala Ile Asp Ala Asn Lys Ala
450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser
            485                 490

<210> SEQ ID NO 42
<211> LENGTH: 535
<212> TYPE: PRT
<213> ORGANISM: Moraxella catarrhalis

<400> SEQUENCE: 42

Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala

```
                20              25              30
Leu Glu Lys Tyr Leu Ala Leu Ser Gln Tyr Gly Asn Ile Leu Ala Leu
            35              40              45
Glu Glu Leu Asn Lys Ala Leu Glu Glu Leu Asp Glu Asp Val Gly Trp
        50              55              60
Asn Gln Asn Asp Ile Ala Asn Leu Glu Asp Val Glu Thr Leu Thr
65              70              75              80
Lys Asn Gln Asn Ala Leu Ala Glu Gln Gly Glu Ala Ile Lys Glu Asp
                85              90              95
Leu Gln Gly Leu Ala Asp Phe Val Glu Gly Gln Glu Gly Lys Ile Leu
            100             105             110
Gln Asn Glu Thr Ser Ile Lys Lys Asn Thr Gln Arg Asn Leu Val Asn
        115             120             125
Gly Phe Glu Ile Glu Lys Asn Lys Asp Ala Ile Ala Lys Asn Asn Glu
        130             135             140
Ser Ile Glu Asp Leu Tyr Asp Phe Gly His Glu Val Ala Glu Ser Ile
145             150             155             160
Gly Glu Ile His Ala His Asn Glu Ala Gln Asn Glu Thr Leu Lys Gly
            165             170             175
Leu Ile Thr Asn Ser Ile Glu Asn Thr Asn Asn Ile Thr Lys Asn Lys
            180             185             190
Ala Asp Ile Gln Ala Leu Glu Asn Asn Val Val Glu Glu Leu Phe Asn
        195             200             205
Leu Ser Gly Arg Leu Ile Asp Gln Lys Ala Asp Ile Asp Asn Asn Ile
        210             215             220
Asn Asn Ile Tyr Glu Leu Ala Gln Gln Gln Asp Gln His Ser Ser Asp
225             230             235             240
Ile Lys Thr Leu Lys Lys Asn Val Glu Glu Gly Leu Leu Glu Leu Ser
            245             250             255
Gly His Leu Ile Asp Gln Lys Thr Asp Ile Ala Gln Asn Gln Ala Asn
            260             265             270
Ile Gln Asp Leu Ala Thr Tyr Asn Glu Leu Gln Asp Gln Tyr Ala Gln
        275             280             285
Lys Gln Thr Glu Ala Ile Asp Ala Leu Asn Lys Ala Ser Ser Glu Asn
        290             295             300
Thr Gln Asn Ile Glu Asp Leu Ala Ala Tyr Asn Glu Leu Gln Asp Ala
305             310             315             320
Tyr Ala Lys Gln Gln Thr Glu Ala Ile Asp Ala Leu Asn Lys Ala Ser
            325             330             335
Ser Glu Asn Thr Gln Asn Ile Glu Asp Leu Ala Ala Tyr Asn Glu Leu
            340             345             350
Gln Asp Ala Tyr Ala Lys Gln Gln Thr Glu Ala Ile Asp Ala Leu Asn
        355             360             365
Lys Ala Ser Ser Glu Asn Thr Gln Asn Ile Ala Lys Asn Gln Ala Asp
        370             375             380
Ile Ala Asn Asn Ile Asn Asn Ile Tyr Glu Leu Ala Gln Gln Gln Asp
385             390             395             400
Gln His Ser Ser Asp Ile Lys Thr Leu Ala Lys Ala Ser Ala Ala Asn
            405             410             415
Thr Asp Arg Ile Ala Lys Asn Lys Ala Asp Ala Asp Ala Ser Phe Glu
            420             425             430
Thr Leu Thr Lys Asn Gln Asn Thr Leu Ile Glu Lys Asp Lys Glu His
        435             440             445
```

```
Asp Lys Leu Ile Thr Ala Asn Lys Thr Ala Ile Asp Ala Asn Lys Ala
    450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser Ile Thr Asp Leu Gly Thr
                485                 490                 495

Lys Val Asp Gly Phe Asp Ser Arg Val Thr Ala Leu Asp Thr Lys Val
            500                 505                 510

Asn Ala Phe Asp Gly Arg Ile Thr Ala Leu Asp Ser Lys Val Glu Asn
        515                 520                 525

Gly Met Ala Ala Gln Ala Ala
        530             535

<210> SEQ ID NO 43
<211> LENGTH: 534
<212> TYPE: PRT
<213> ORGANISM: Moraxella catarrhalis

<400> SEQUENCE: 43

Ala Lys Asn Asp Ile Thr Leu Glu Asp Leu Pro Tyr Leu Ile Lys Lys
1               5                   10                  15

Ile Asp Gln Asn Glu Leu Glu Ala Asp Ile Gly Asp Ile Thr Ala Leu
                20                  25                  30

Glu Lys Tyr Leu Ala Leu Ser Gln Tyr Gly Asn Ile Leu Ala Leu Glu
            35                  40                  45

Glu Leu Asn Lys Ala Leu Glu Glu Leu Asp Glu Asp Val Gly Trp Asn
        50                  55                  60

Gln Asn Asp Ile Ala Asn Leu Glu Asp Asp Val Glu Thr Leu Thr Lys
65                  70                  75                  80

Asn Gln Asn Ala Leu Ala Glu Gln Gly Glu Ala Ile Lys Glu Asp Leu
                85                  90                  95

Gln Gly Leu Ala Asp Phe Val Glu Gly Gln Gly Lys Ile Leu Gln
            100                 105                 110

Asn Glu Thr Ser Ile Lys Lys Asn Thr Gln Arg Asn Leu Val Asn Gly
            115                 120                 125

Phe Glu Ile Glu Lys Asn Lys Asp Ala Ile Ala Lys Asn Asn Glu Ser
    130                 135                 140

Ile Glu Asp Leu Tyr Asp Phe Gly His Glu Val Ala Glu Ser Ile Gly
145                 150                 155                 160

Glu Ile His Ala His Asn Glu Ala Gln Asn Glu Thr Leu Lys Gly Leu
                165                 170                 175

Ile Thr Asn Ser Ile Glu Asn Thr Asn Asn Ile Thr Lys Asn Lys Ala
            180                 185                 190

Asp Ile Gln Ala Leu Glu Asn Asn Val Val Glu Glu Leu Phe Asn Leu
        195                 200                 205

Ser Gly Arg Leu Ile Asp Gln Lys Ala Asp Ile Asp Asn Asn Ile Asn
    210                 215                 220

Asn Ile Tyr Glu Leu Ala Gln Gln Asp Gln His Ser Ser Asp Ile
225                 230                 235                 240

Lys Thr Leu Lys Lys Asn Val Glu Glu Gly Leu Leu Glu Leu Ser Gly
                245                 250                 255

His Leu Ile Asp Gln Lys Thr Asp Ile Ala Gln Asn Gln Ala Asn Ile
            260                 265                 270

Gln Asp Leu Ala Thr Tyr Asn Glu Leu Gln Asp Gln Tyr Ala Gln Lys
```

```
            275                 280                 285
    Gln Thr Glu Ala Ile Asp Ala Leu Asn Lys Ala Ser Ser Glu Asn Thr
        290                 295                 300

Gln Asn Ile Glu Asp Leu Ala Ala Tyr Asn Glu Leu Gln Asp Ala Tyr
    305                 310                 315                 320

Ala Lys Gln Gln Thr Glu Ala Ile Asp Ala Leu Asn Lys Ala Ser Ser
                    325                 330                 335

Glu Asn Thr Gln Asn Ile Glu Asp Leu Ala Ala Tyr Asn Glu Leu Gln
                340                 345                 350

Asp Ala Tyr Ala Lys Gln Gln Thr Glu Ala Ile Asp Ala Leu Asn Lys
            355                 360                 365

Ala Ser Ser Glu Asn Thr Gln Asn Ile Ala Lys Asn Gln Ala Asp Ile
        370                 375                 380

Ala Asn Asn Ile Asn Asn Ile Tyr Glu Leu Ala Gln Gln Asp Gln
    385                 390                 395                 400

His Ser Ser Asp Ile Lys Thr Leu Ala Lys Ala Ser Ala Ala Asn Thr
                    405                 410                 415

Asp Arg Ile Ala Lys Asn Lys Ala Asp Ala Asp Ala Ser Phe Glu Thr
                420                 425                 430

Leu Thr Lys Asn Gln Asn Thr Leu Ile Glu Lys Asp Lys Glu His Asp
            435                 440                 445

Lys Leu Ile Thr Ala Asn Lys Thr Ala Ile Asp Ala Asn Lys Ala Ser
        450                 455                 460

Ala Asp Thr Lys Phe Ala Ala Thr Ala Asp Ala Ile Thr Lys Asn Gly
    465                 470                 475                 480

Asn Ala Ile Thr Lys Asn Ala Lys Ser Ile Thr Asp Leu Gly Thr Lys
                    485                 490                 495

Val Asp Gly Phe Asp Ser Arg Val Thr Ala Leu Asp Thr Lys Val Asn
                500                 505                 510

Ala Phe Asp Gly Arg Ile Thr Ala Leu Asp Ser Lys Val Glu Asn Gly
            515                 520                 525

Met Ala Ala Gln Ala Ala
        530

<210> SEQ ID NO 44
<211> LENGTH: 148
<212> TYPE: PRT
<213> ORGANISM: Moraxella catarrhalis

<400> SEQUENCE: 44

Gln Ala Lys Asn Asp Ile Thr Leu Glu Asp Leu Pro Tyr Leu Ile Lys
    1               5                   10                  15

Lys Ile Asp Gln Asn Glu Leu Glu Ala Asp Ile Gly Asp Ile Thr Ala
                    20                  25                  30

Leu Glu Lys Tyr Leu Ala Leu Ser Gln Tyr Gly Asn Ile Leu Ala Leu
                35                  40                  45

Glu Glu Leu Asn Lys Ala Leu Glu Glu Leu Asp Glu Asp Val Gly Trp
            50                  55                  60

Asn Gln Asn Asp Ile Ala Asn Leu Glu Asp Asp Val Glu Thr Leu Thr
    65                  70                  75                  80

Lys Asn Gln Asn Ala Leu Ala Glu Gln Gly Glu Ala Ile Lys Glu Asp
                    85                  90                  95

Leu Gln Gly Leu Ala Asp Phe Val Glu Gly Gln Glu Gly Lys Ile Leu
                100                 105                 110
```

Gln Asn Glu Thr Ser Ile Lys Lys Asn Thr Gln Arg Asn Leu Val Asn
            115                 120                 125

Gly Phe Glu Ile Glu Lys Asn Lys Asp Ala Ile Ala Lys Asn Asn Glu
        130                 135                 140

Ser Ile Glu Asp
145

<210> SEQ ID NO 45
<211> LENGTH: 154
<212> TYPE: PRT
<213> ORGANISM: Moraxella catarrhalis

<400> SEQUENCE: 45

Lys Asp Ala Ile Ala Lys Asn Asn Glu Ser Ile Glu Asp Leu Tyr Asp
1               5                   10                  15

Phe Gly His Glu Val Ala Glu Ser Ile Gly Glu Ile His Ala His Asn
            20                  25                  30

Glu Ala Gln Asn Glu Thr Leu Lys Gly Leu Ile Thr Asn Ser Ile Glu
        35                  40                  45

Asn Thr Asn Asn Ile Thr Lys Asn Lys Ala Asp Ile Gln Ala Leu Glu
    50                  55                  60

Asn Asn Val Val Glu Glu Leu Phe Asn Leu Ser Gly Arg Leu Ile Asp
65                  70                  75                  80

Gln Lys Ala Asp Ile Asp Asn Asn Ile Asn Asn Ile Tyr Glu Leu Ala
                85                  90                  95

Gln Gln Gln Asp Gln His Ser Ser Asp Ile Lys Thr Leu Lys Lys Asn
            100                 105                 110

Val Glu Glu Gly Leu Leu Glu Leu Ser Gly His Leu Ile Asp Gln Lys
        115                 120                 125

Thr Asp Ile Ala Gln Asn Gln Ala Asn Ile Gln Asp Leu Ala Thr Tyr
    130                 135                 140

Asn Glu Leu Gln Asp Gln Tyr Ala Gln Lys
145                 150

<210> SEQ ID NO 46
<211> LENGTH: 510
<212> TYPE: PRT
<213> ORGANISM: Moraxella catarrhalis

<400> SEQUENCE: 46

Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
            20                  25                  30

Leu Glu Lys Tyr Leu Ala Leu Ser Gln Tyr Gly Asn Ile Leu Ala Leu
        35                  40                  45

Glu Glu Leu Asn Lys Ala Leu Glu Glu Leu Asp Glu Asp Val Gly Trp
    50                  55                  60

Asn Gln Asn Asp Ile Ala Asn Leu Glu Asp Asp Val Glu Thr Leu Thr
65                  70                  75                  80

Lys Asn Gln Asn Ala Leu Ala Glu Gln Gly Glu Ala Ile Lys Glu Asp
                85                  90                  95

Leu Gln Gly Leu Ala Asp Phe Val Glu Gly Gln Glu Gly Lys Ile Leu
            100                 105                 110

Gln Asn Glu Thr Ser Ile Lys Lys Asn Thr Gln Arg Asn Leu Val Asn
        115                 120                 125

```
Gly Phe Glu Ile Glu Lys Asn Lys Asp Ala Ile Ala Lys Asn Asn Glu
        130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Asn Ile Thr Lys Asn Lys
                180                 185                 190

Ala Asp Ile Gln Ala Leu Glu Asn Val Val Glu Glu Leu Phe Asn
            195                 200                 205

Leu Ser Gly Arg Leu Ile Asp Gln Lys Ala Asp Ile Asp Asn Asn Ile
210                 215                 220

Asn Asn Ile Tyr Glu Leu Ala Gln Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Gly His Leu Ile Asp Gln Lys Thr Asp Ile Ala Gln Asn Gln Ala Asn
                260                 265                 270

Ile Gln Asp Leu Ala Thr Tyr Asn Glu Leu Gln Asp Gln Tyr Ala Gln
            275                 280                 285

Lys Gln Thr Glu Ala Ile Asp Ala Leu Asn Lys Ala Ser Ser Glu Asn
290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                325                 330                 335

Ser Glu Asn Thr Gln Asn Ile Glu Asp Leu Ala Ala Tyr Asn Glu Leu
                340                 345                 350

Gln Asp Ala Tyr Ala Lys Gln Gln Thr Glu Ala Ile Asp Ala Leu Asn
            355                 360                 365

Lys Ala Ser Ser Glu Asn Thr Gln Asn Ile Ala Lys Asn Gln Ala Asp
370                 375                 380

Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
                405                 410                 415

Thr Asp Arg Ile Ala Lys Asn Lys Ala Asp Ala Ser Phe Glu
            420                 425                 430

Thr Leu Thr Lys Asn Gln Asn Thr Leu Ile Glu Lys Asp Lys Glu His
                435                 440                 445

Asp Lys Leu Ile Thr Ala Asn Lys Thr Ala Ile Asp Ala Asn Lys Ala
            450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser Ile Thr Asp Leu Gly Thr
                485                 490                 495

Lys Val Asp Gly Phe Asp Ser Arg Val Thr Ala Leu Asp Thr
                500                 505                 510

<210> SEQ ID NO 47
<211> LENGTH: 511
<212> TYPE: PRT
<213> ORGANISM: Moraxella catarrhalis

<400> SEQUENCE: 47
```

```
Gln Ala Lys Asn Asp Ile Thr Leu Glu Asp Leu Pro Tyr Leu Ile Lys
  1               5                  10                  15

Lys Ile Asp Gln Asn Glu Leu Glu Ala Asp Ile Gly Asp Ile Thr Ala
                 20                  25                  30

Leu Glu Lys Tyr Leu Ala Leu Ser Gln Tyr Gly Asn Ile Leu Ala Leu
             35                  40                  45

Glu Glu Leu Asn Lys Ala Leu Glu Glu Leu Asp Glu Asp Val Gly Trp
         50                  55                  60

Asn Gln Asn Asp Ile Ala Asn Leu Glu Asp Asp Val Glu Thr Leu Thr
 65                  70                  75                  80

Lys Asn Gln Asn Ala Leu Ala Glu Gln Gly Glu Ala Ile Lys Glu Asp
                 85                  90                  95

Leu Gln Gly Leu Ala Asp Phe Val Glu Gly Gln Glu Gly Lys Ile Leu
            100                 105                 110

Gln Asn Glu Thr Ser Ile Lys Lys Asn Thr Gln Arg Asn Leu Val Asn
            115                 120                 125

Gly Phe Glu Ile Glu Lys Asn Lys Asp Ala Ile Ala Lys Asn Asn Glu
        130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Asn Ile Thr Lys Asn Lys
            180                 185                 190

Ala Asp Ile Gln Ala Leu Glu Asn Val Val Glu Glu Leu Phe Asn
            195                 200                 205

Leu Ser Gly Arg Leu Ile Asp Gln Lys Ala Asp Ile Asp Asn Asn Ile
210                 215                 220

Asn Asn Ile Tyr Glu Leu Ala Gln Gln Gln Asp Gln His Ser Ser Asp
225                 230                 235                 240

Ile Lys Thr Leu Lys Lys Asn Val Glu Glu Gly Leu Leu Glu Leu Ser
            245                 250                 255

Gly His Leu Ile Asp Gln Lys Thr Asp Ile Ala Gln Asn Gln Ala Asn
            260                 265                 270

Ile Gln Asp Leu Ala Thr Tyr Asn Glu Leu Gln Asp Gln Tyr Ala Gln
            275                 280                 285

Lys Gln Thr Glu Ala Ile Asp Ala Leu Asn Lys Ala Ser Ser Glu Asn
            290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                325                 330                 335

Ser Glu Asn Thr Gln Asn Ile Glu Asp Leu Ala Ala Tyr Asn Glu Leu
            340                 345                 350

Gln Asp Ala Tyr Ala Lys Gln Gln Thr Glu Ala Ile Asp Ala Leu Asn
            355                 360                 365

Lys Ala Ser Ser Glu Asn Thr Gln Asn Ile Ala Lys Asn Gln Ala Asp
            370                 375                 380

Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
                405                 410                 415
```

Thr Asp Arg Ile Ala Lys Asn Lys Ala Asp Ala Asp Ala Ser Phe Glu
                420                 425                 430

Thr Leu Thr Lys Asn Gln Asn Thr Leu Ile Glu Lys Asp Lys Glu His
            435                 440                 445

Asp Lys Leu Ile Thr Ala Asn Lys Thr Ala Ile Asp Ala Asn Lys Ala
450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser Ile Thr Asp Leu Gly Thr
                485                 490                 495

Lys Val Asp Gly Phe Asp Ser Arg Val Thr Ala Leu Asp Thr Lys
                500                 505                 510

<210> SEQ ID NO 48
<211> LENGTH: 490
<212> TYPE: PRT
<213> ORGANISM: Moraxella catarrhalis

<400> SEQUENCE: 48

Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
                20                  25                  30

Leu Glu Lys Tyr Leu Ala Leu Ser Gln Tyr Gly Asn Ile Leu Ala Leu
            35                  40                  45

Glu Glu Leu Asn Lys Ala Leu Glu Glu Leu Asp Glu Asp Val Gly Trp
    50                  55                  60

Asn Gln Asn Asp Ile Ala Asn Leu Glu Asp Asp Val Glu Thr Leu Thr
65                  70                  75                  80

Lys Asn Gln Asn Ala Leu Ala Glu Gln Gly Glu Ala Ile Lys Glu Asp
                85                  90                  95

Leu Gln Gly Leu Ala Asp Phe Val Glu Gly Gln Glu Gly Lys Ile Leu
            100                 105                 110

Gln Asn Glu Thr Ser Ile Lys Lys Asn Thr Gln Arg Asn Leu Val Asn
        115                 120                 125

Gly Phe Glu Ile Glu Lys Asn Lys Asp Ala Ile Ala Lys Asn Asn Glu
130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Asn Ile Thr Lys Asn Lys
            180                 185                 190

Ala Asp Ile Gln Ala Leu Glu Asn Val Val Glu Glu Leu Phe Asn
        195                 200                 205

Leu Ser Gly Arg Leu Ile Asp Gln Lys Ala Asp Ile Asp Asn Asn Ile
210                 215                 220

Asn Asn Ile Tyr Glu Leu Ala Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Gly His Leu Ile Asp Gln Lys Thr Asp Ile Ala Gln Asn Gln Ala Asn
            260                 265                 270

Ile Gln Asp Leu Ala Thr Tyr Asn Glu Leu Gln Asp Gln Tyr Ala Gln
        275                 280                 285

```
Lys Gln Thr Glu Ala Ile Asp Ala Leu Asn Lys Ala Ser Ser Glu Asn
    290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                325                 330                 335

Ser Glu Asn Thr Gln Asn Ile Glu Asp Leu Ala Ala Tyr Asn Glu Leu
                340                 345                 350

Gln Asp Ala Tyr Ala Lys Gln Gln Thr Glu Ala Ile Asp Ala Leu Asn
            355                 360                 365

Lys Ala Ser Ser Glu Asn Thr Gln Asn Ile Ala Lys Asn Gln Ala Asp
    370                 375                 380

Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
                405                 410                 415

Thr Asp Arg Ile Ala Lys Asn Lys Ala Asp Ala Asp Ala Ser Phe Glu
            420                 425                 430

Thr Leu Thr Lys Asn Gln Asn Thr Leu Ile Glu Lys Asp Lys Glu His
    435                 440                 445

Asp Lys Leu Ile Thr Ala Asn Lys Thr Ala Ile Asp Ala Asn Lys Ala
    450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser
                485                 490

<210> SEQ ID NO 49
<211> LENGTH: 535
<212> TYPE: PRT
<213> ORGANISM: Moraxella catarrhalis

<400> SEQUENCE: 49

Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
                20                  25                  30

Leu Glu Lys Tyr Leu Ala Leu Ser Gln Tyr Gly Asn Ile Leu Ala Leu
            35                  40                  45

Glu Glu Leu Asn Lys Ala Leu Glu Glu Leu Asp Glu Asp Val Gly Trp
    50                  55                  60

Asn Gln Asn Asp Ile Ala Asn Leu Glu Asp Asp Val Glu Thr Leu Thr
65                  70                  75                  80

Lys Asn Gln Asn Ala Leu Ala Glu Gln Gly Glu Ala Ile Lys Glu Asp
                85                  90                  95

Leu Gln Gly Leu Ala Asp Phe Val Glu Gly Glu Gly Lys Ile Leu
            100                 105                 110

Gln Asn Glu Thr Ser Ile Lys Lys Asn Thr Gln Arg Asn Leu Val Asn
    115                 120                 125

Gly Phe Glu Ile Glu Lys Asn Lys Asp Ala Ile Ala Lys Asn Asn Glu
            130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
```

```
                165                 170                 175
Leu Ile Thr Asn Ser Ile Glu Asn Thr Asn Asn Ile Thr Lys Asn Lys
            180                 185                 190

Ala Asp Ile Gln Ala Leu Glu Asn Asn Val Val Glu Glu Leu Phe Asn
        195                 200                 205

Leu Ser Gly Arg Leu Ile Asp Gln Lys Ala Asp Ile Asp Asn Asn Ile
    210                 215                 220

Asn Asn Ile Tyr Glu Leu Ala Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Gly His Leu Ile Asp Gln Lys Thr Asp Ile Ala Gln Asn Gln Ala Asn
            260                 265                 270

Ile Gln Asp Leu Ala Thr Tyr Asn Glu Leu Gln Asp Gln Tyr Ala Gln
        275                 280                 285

Lys Gln Thr Glu Ala Ile Asp Ala Leu Asn Lys Ala Ser Ser Glu Asn
    290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                325                 330                 335

Ser Glu Asn Thr Gln Asn Ile Glu Asp Leu Ala Ala Tyr Asn Glu Leu
            340                 345                 350

Gln Asp Ala Tyr Ala Lys Gln Gln Thr Glu Ala Ile Asp Ala Leu Asn
        355                 360                 365

Lys Ala Ser Ser Glu Asn Thr Gln Asn Ile Ala Lys Asn Gln Ala Asp
    370                 375                 380

Ile Ala Asn Asn Ile Asn Asn Ile Tyr Glu Leu Ala Gln Gln Asp
385                 390                 395                 400

Gln His Ser Ser Asp Ile Lys Thr Leu Ala Lys Ala Ser Ala Ala Asn
                405                 410                 415

Thr Asp Arg Ile Ala Lys Asn Lys Ala Asp Ala Asp Ala Ser Phe Glu
            420                 425                 430

Thr Leu Thr Lys Asn Gln Asn Thr Leu Ile Glu Lys Asp Lys Glu His
        435                 440                 445

Asp Lys Leu Ile Thr Ala Asn Lys Thr Ala Ile Asp Ala Asn Lys Ala
    450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser Ile Thr Asp Leu Gly Thr
                485                 490                 495

Lys Val Asp Gly Phe Asp Ser Arg Val Thr Ala Leu Asp Thr Lys Val
            500                 505                 510

Asn Ala Phe Asp Gly Arg Ile Thr Ala Leu Asp Ser Lys Val Glu Asn
        515                 520                 525

Gly Met Ala Ala Gln Ala Ala
    530                 535

<210> SEQ ID NO 50
<211> LENGTH: 534
<212> TYPE: PRT
<213> ORGANISM: Moraxella catarrhalis

<400> SEQUENCE: 50
```

-continued

```
Ala Lys Asn Asp Ile Thr Leu Glu Asp Leu Pro Tyr Leu Ile Lys Lys
 1               5                  10                  15

Ile Asp Gln Asn Glu Leu Glu Ala Asp Ile Gly Asp Ile Thr Ala Leu
             20                  25                  30

Glu Lys Tyr Leu Ala Leu Ser Gln Tyr Gly Asn Ile Leu Ala Leu Glu
         35                  40                  45

Glu Leu Asn Lys Ala Leu Glu Glu Leu Asp Glu Asp Val Gly Trp Asn
 50                  55                  60

Gln Asn Asp Ile Ala Asn Leu Glu Asp Val Glu Thr Leu Thr Lys
 65                  70                  75                  80

Asn Gln Asn Ala Leu Ala Glu Gln Gly Glu Ala Ile Lys Glu Asp Leu
                 85                  90                  95

Gln Gly Leu Ala Asp Phe Val Glu Gly Gln Glu Gly Lys Ile Leu Gln
                100                 105                 110

Asn Glu Thr Ser Ile Lys Lys Asn Thr Gln Arg Asn Leu Val Asn Gly
                115                 120                 125

Phe Glu Ile Glu Lys Asn Lys Asp Ala Ile Ala Lys Asn Asn Glu Ser
130                 135                 140

Ile Glu Asp Leu Tyr Asp Phe Gly His Glu Val Ala Glu Ser Ile Gly
145                 150                 155                 160

Glu Ile His Ala His Asn Glu Ala Gln Asn Glu Thr Leu Lys Gly Leu
                165                 170                 175

Ile Thr Asn Ser Ile Glu Asn Thr Asn Asn Ile Thr Lys Asn Lys Ala
                180                 185                 190

Asp Ile Gln Ala Leu Glu Asn Asn Val Val Glu Glu Leu Phe Asn Leu
                195                 200                 205

Ser Gly Arg Leu Ile Asp Gln Lys Ala Asp Ile Asp Asn Asn Ile Asn
210                 215                 220

Asn Ile Tyr Glu Leu Ala Gln Gln Gln Asp Gln His Ser Ser Asp Ile
225                 230                 235                 240

Lys Thr Leu Lys Lys Asn Val Glu Glu Gly Leu Leu Glu Leu Ser Gly
                245                 250                 255

His Leu Ile Asp Gln Lys Thr Asp Ile Ala Gln Asn Gln Ala Asn Ile
                260                 265                 270

Gln Asp Leu Ala Thr Tyr Asn Glu Leu Gln Asp Gln Tyr Ala Gln Lys
                275                 280                 285

Gln Thr Glu Ala Ile Asp Ala Leu Asn Lys Ala Ser Ser Glu Asn Thr
                290                 295                 300

Gln Asn Ile Glu Asp Leu Ala Ala Tyr Asn Glu Leu Gln Asp Ala Tyr
305                 310                 315                 320

Ala Lys Gln Gln Thr Glu Ala Ile Asp Ala Leu Asn Lys Ala Ser Ser
                325                 330                 335

Glu Asn Thr Gln Asn Ile Glu Asp Leu Ala Ala Tyr Asn Glu Leu Gln
                340                 345                 350

Asp Ala Tyr Ala Lys Gln Gln Thr Glu Ala Ile Asp Ala Leu Asn Lys
                355                 360                 365

Ala Ser Ser Glu Asn Thr Gln Asn Ile Ala Lys Asn Gln Ala Asp Ile
                370                 375                 380

Ala Asn Asn Ile Asn Ile Tyr Glu Leu Ala Gln Gln Gln Asp Gln
385                 390                 395                 400

His Ser Ser Asp Ile Lys Thr Leu Ala Lys Ala Ser Ala Ala Asn Thr
                405                 410                 415

Asp Arg Ile Ala Lys Asn Lys Ala Asp Ala Asp Ala Ser Phe Glu Thr
```

```
                    420                 425                 430
Leu Thr Lys Asn Gln Asn Thr Leu Ile Glu Lys Asp Lys Glu His Asp
                435                 440                 445

Lys Leu Ile Thr Ala Asn Lys Thr Ala Ile Asp Ala Asn Lys Ala Ser
        450                 455                 460

Ala Asp Thr Lys Phe Ala Thr Ala Asp Ala Ile Thr Lys Asn Gly
465                 470                 475                 480

Asn Ala Ile Thr Lys Asn Ala Lys Ser Ile Thr Asp Leu Gly Thr Lys
                485                 490                 495

Val Asp Gly Phe Asp Ser Arg Val Thr Ala Leu Asp Thr Lys Val Asn
        500                 505                 510

Ala Phe Asp Gly Arg Ile Thr Ala Leu Asp Ser Lys Val Glu Asn Gly
        515                 520                 525

Met Ala Ala Gln Ala Ala
        530

<210> SEQ ID NO 51
<211> LENGTH: 510
<212> TYPE: PRT
<213> ORGANISM: Moraxella catarrhalis

<400> SEQUENCE: 51

Ala Lys Asn Asp Ile Thr Leu Glu Asp Leu Pro Tyr Leu Ile Lys Lys
1               5                   10                  15

Ile Asp Gln Asn Glu Leu Glu Ala Asp Ile Gly Asp Ile Thr Ala Leu
            20                  25                  30

Glu Lys Tyr Leu Ala Leu Ser Gln Tyr Gly Asn Ile Leu Ala Leu Glu
        35                  40                  45

Glu Leu Asn Lys Ala Leu Glu Glu Leu Asp Glu Asp Val Gly Trp Asn
    50                  55                  60

Gln Asn Asp Ile Ala Asn Leu Glu Asp Asp Val Glu Thr Leu Thr Lys
65                  70                  75                  80

Asn Gln Asn Ala Leu Ala Glu Gln Gly Glu Ala Ile Lys Glu Asp Leu
                85                  90                  95

Gln Gly Leu Ala Asp Phe Val Glu Gly Gln Gly Lys Ile Leu Gln
            100                 105                 110

Asn Glu Thr Ser Ile Lys Lys Asn Thr Gln Arg Asn Leu Val Asn Gly
        115                 120                 125

Phe Glu Ile Glu Lys Asn Lys Asp Ala Ile Ala Lys Asn Asn Glu Ser
130                 135                 140

Ile Glu Asp Leu Tyr Asp Phe Gly His Glu Val Ala Glu Ser Ile Gly
145                 150                 155                 160

Glu Ile His Ala His Asn Glu Ala Gln Asn Glu Thr Leu Lys Gly Leu
                165                 170                 175

Ile Thr Asn Ser Ile Glu Asn Thr Asn Asn Ile Thr Lys Asn Lys Ala
            180                 185                 190

Asp Ile Gln Ala Leu Glu Asn Asn Val Val Glu Glu Leu Phe Asn Leu
        195                 200                 205

Ser Gly Arg Leu Ile Asp Gln Lys Ala Asp Ile Asp Asn Asn Ile Asn
    210                 215                 220

Asn Ile Tyr Glu Leu Ala Gln Gln Gln Asp Gln His Ser Ser Asp Ile
225                 230                 235                 240

Lys Thr Leu Lys Lys Asn Val Glu Glu Gly Leu Leu Glu Leu Ser Gly
                245                 250                 255
```

His Leu Ile Asp Gln Lys Thr Asp Ile Ala Gln Asn Gln Ala Asn Ile
            260                 265                 270

Gln Asp Leu Ala Thr Tyr Asn Glu Leu Gln Asp Gln Tyr Ala Gln Lys
        275                 280                 285

Gln Thr Glu Ala Ile Asp Ala Leu Asn Lys Ala Ser Ser Glu Asn Thr
    290                 295                 300

Gln Asn Ile Glu Asp Leu Ala Ala Tyr Asn Glu Leu Gln Asp Ala Tyr
305                 310                 315                 320

Ala Lys Gln Gln Thr Glu Ala Ile Asp Ala Leu Asn Lys Ala Ser Ser
                325                 330                 335

Glu Asn Thr Gln Asn Ile Glu Asp Leu Ala Ala Tyr Asn Glu Leu Gln
            340                 345                 350

Asp Ala Tyr Ala Lys Gln Gln Thr Glu Ala Ile Asp Ala Leu Asn Lys
        355                 360                 365

Ala Ser Ser Glu Asn Thr Gln Asn Ile Ala Lys Asn Gln Ala Asp Ile
    370                 375                 380

Ala Asn Asn Ile Asn Asn Ile Tyr Glu Leu Ala Gln Gln Gln Asp Gln
385                 390                 395                 400

His Ser Ser Asp Ile Lys Thr Leu Ala Lys Ala Ser Ala Ala Asn Thr
                405                 410                 415

Asp Arg Ile Ala Lys Asn Lys Ala Asp Ala Asp Ala Ser Phe Glu Thr
            420                 425                 430

Leu Thr Lys Asn Gln Asn Thr Leu Ile Glu Lys Asp Lys Glu His Asp
        435                 440                 445

Lys Leu Ile Thr Ala Asn Lys Thr Ala Ile Asp Ala Asn Lys Ala Ser
    450                 455                 460

Ala Asp Thr Lys Phe Ala Ala Thr Ala Asp Ala Ile Thr Lys Asn Gly
465                 470                 475                 480

Asn Ala Ile Thr Lys Asn Ala Lys Ser Ile Thr Asp Leu Gly Thr Lys
                485                 490                 495

Val Asp Gly Phe Asp Ser Arg Val Thr Ala Leu Asp Thr Lys
            500                 505                 510

<210> SEQ ID NO 52
<211> LENGTH: 1563
<212> TYPE: DNA
<213> ORGANISM: Artificial Sequence
<220> FEATURE:
<223> OTHER INFORMATION: DNA sequence for MC-001 construct

<400> SEQUENCE: 52
atgcaggcca aaatgatat taccctggaa gatctgccgt atctgatcaa aaaaatcgat      60
cagaacgaac tggaagccga tattggtgat attaccgcac tggaaaaata tctggcactg     120
agccagtatg aaatattct ggccctggaa gaactgaata agctctgga agagctggat      180 gaagatgtgg ttggaatca gaatgatatc gccaatctgg aagatgatgt tgaaaccctg     240
accaaaaatc agaatgcact ggcagaacag ggtgaagcaa ttaaagaaga tctgcagggt    300
ctggcagatt tgttgaagg tcaggaaggc aaaattctgc agaacgaaac cagcatcaaa     360
aaaaacaccc agcgtaatct ggtgaatggc tttgaaattg aaaaaaacaa agatgccatt    420
gccaaaaaca cgaaagcat tgaagatctg tatgattttg tcatgaagt tgccgaaagc      480 attggtgaaa ttcatgcaca taacgaagca cagaatgaaa ccctgaaagg tctgattacc    540
aacagcatcg aaaataccaa taacattacc aaaaacaaag cagatattca ggcgctggaa    600
aataatgttg tggaagaact gtttaatctg agcggtcgtc tgattgatca gaaagccgat    660

```
atcgataata acattaacaa catttatgaa ctggcacagc agcaggatca gcatagcagc   720
gatatcaaaa ccctgaaaaa aaacgttgaa gaaggtctgc tggaactgtc tggtcacctg   780
atcgatcaga aaactgatat tgcccagaat caggcaaata ttcaggatct ggccacctat   840
aatgaactgc aggatcagta tgcacagaaa cagaccgaag caattgatgc cctgaataaa   900
gcgagcagcg aaaacaccca gaatatcgaa gatctggcag catacaacga actgcaggat   960
gcctatgcaa aacagcagac tgaagccatc gacgcactga acaaggcaag ctctgaaaac  1020
acgcagaaca ttgaagatct ggctgcctat aatgaattac aggatgcgta tgccaaacag  1080
cagaccgaag cgattgatgc gctgaacaaa gcctcttctg aaaatacaca gaatatcgcc  1140
aaaaatcagg ccgatattgc caacaatatc aataatatct atgaactggc ccagcagcag  1200
gatcagcact cttctgatat caaaacactg gcaaaagcaa gcgcagcaaa taccgatcgt  1260
attgcgaaaa acaaagccga tgcagatgca agctttgaaa cactgacgaa aaaccagaac  1320
accctgattg aaaagataa  agaacatgat aaactgatca ccgccaataa aaccgcaatt  1380
gatgcaaata aagccagcgc agataccaaa tttgcagcaa ccgcagatgc aattaccaaa  1440
aatggcaatg ccatcaccaa aaatgccaaa agcattaccg atctgggcac caaagttgat  1500
ggttttgata ccgtgtgac  cgcactggat accaaagcaa gccatcatca tcaccaccac  1560
taa                                                                1563

<210> SEQ ID NO 53
<211> LENGTH: 520
<212> TYPE: PRT
<213> ORGANISM: Artificial Sequence
<220> FEATURE:
<223> OTHER INFORMATION: Protein sequence for MC-001 construct

<400> SEQUENCE: 53

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190
```

Lys Ala Asp Ile Gln Ala Leu Glu Asn Asn Val Val Glu Leu Phe
            195                 200                 205

Asn Leu Ser Gly Arg Leu Ile Asp Gln Lys Ala Asp Ile Asp Asn Asn
        210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
                485                 490                 495

Thr Lys Val Asp Gly Phe Asp Ser Arg Val Thr Ala Leu Asp Thr Lys
            500                 505                 510

Ala Ser His His His His His His
        515                 520

<210> SEQ ID NO 54
<211> LENGTH: 1539
<212> TYPE: DNA
<213> ORGANISM: Artificial Sequence
<220> FEATURE:
<223> OTHER INFORMATION: DNA sequence for MC-002 construct

<400> SEQUENCE: 54
atgcaggcca aaaatgatat taccctggaa gatctgccgt atctgatcaa aaaaatcgat      60
cagaacgaac tggaagccga tattggtgat attaccgcac tggaaaaata tctggcactg     120
agccagtatg aaatattct ggccctggaa gaactgaata aagctctgga agagctggat     180

```
gaagatgtgg gttggaatca gaatgatatc gccaatctgg aagatgatgt tgaaaccctg      240
accaaaaatc agaatgcact ggcagaacag ggtgaagcaa ttaaagaaga tctgcagggt      300
ctggcagatt ttgttgaagg tcaggaaggc aaaattctgc agaacgaaac cagcatcaaa      360
aaaaacaccc agcgtaatct ggtgaatggc tttgaaattg aaaaaaacaa agatgccatt      420
gccaaaaaca acgaaagcat tgaagatctg tatgattttg gtcatgaagt tgccgaaagc      480
attggtgaaa ttcatgcaca taacgaagca cagaatgaaa ccctgaaagg tctgattacc      540
aacagcatcg aaaataccaa taacattacc aaaaacaaag cagatattca ggcgctggaa      600
aataatgttg tggaagaact gtttaatctg agcggtcgtc tgattgatca gaaagccgat      660
atcgataata acattaacaa catttatgaa ctggcacagc agcaggatca gcatagcagc      720
gatatcaaaa ccctgaaaaa aaacgttgaa gaaggtctgc tggaactgtc tggtcacctg      780
atcgatcaga aaactgatat tgcccagaat caggcaaata ttcaggatct ggccacctat      840
aatgaactgc aggatcagta tgcacagaaa cagaccgaag caattgatgc cctgaataaa      900
gcgagcagcg aaaacaccca gaatatcgaa gatctggcag catacaacga actgcaggat      960
gcctatgcaa aacagcagac tgaagccatc gacgcactga caaggcaag ctctgaaaac    1020 acgcagaaca ttgaagatct ggctgcctat aatgaattac aggatgcgta tgccaaacag     1080
cagaccgaag cgattgatgc gctgaacaaa gcctcttctg aaaatacaca gaatatcgcc     1140
aaaaatcagg ccgatattgc caacaatatc aataatatct atgaactggc cagcagcag      1200 gatcagcact cttctgatat caaaacactg gcaaagcaa gcgcagcaaa taccgatcgt      1260
attgcgaaaa caaagccga tgcagatgca agctttgaaa cactgacgaa aaaccagaac      1320
accctgattg aaaaagataa agaacatgat aaactgatca ccgccaataa aaccgcaatt     1380
gatgcaaata agccagcgc agataccaaa tttgcagcaa ccgcagatgc aattaccaaa     1440
aatggcaatg ccatcaccaa aaatgccaaa agcattaccg atctgggcac caaagttgat    1500
ggttttgata gccgtgtgac cgcactggat accaaataa                            1539
```

<210> SEQ ID NO 55
<211> LENGTH: 512
<212> TYPE: PRT
<213> ORGANISM: Artificial Sequence
<220> FEATURE:
<223> OTHER INFORMATION: Protein sequence for MC-002 construct

<400> SEQUENCE: 55

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125
```

Asn Gly Phe Glu Ile Glu Lys Asn Lys Asp Ala Ile Ala Lys Asn Asn
130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
            165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
210                 215                 220

Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
            245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
            325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
            405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
            485                 490                 495

Thr Lys Val Asp Gly Phe Asp Ser Arg Val Thr Ala Leu Asp Thr Lys
            500                 505                 510

<210> SEQ ID NO 56
<211> LENGTH: 1614
<212> TYPE: DNA
<213> ORGANISM: Artificial Sequence
<220> FEATURE:

<223> OTHER INFORMATION: DNA sequence for construct

<400> SEQUENCE: 56

```
atgcaggcca aaatgatat taccctggaa gatctgccgt atctgatcaa aaaaatcgat      60
cagaacgaac tggaagccga tattggtgat attaccgcac tggaaaaata tctggcactg     120
agccagtatg gaaatattct ggccctggaa gaactgaata aagctctgga agagctggat     180
gaagatgtgg gttggaatca gaatgatatc gccaatctgg aagatgatgt tgaaaccctg     240
accaaaaatc agaatgcact ggcagaacag ggtgaagcaa ttaaagaaga tctgcagggt     300
ctggcagatt tgttgaaggt tcaggaaggc aaaattctgc agaacgaaac cagcatcaaa     360
aaaaacaccc agcgtaatct ggtgaatggc tttgaaattg aaaaaaacaa agatgccatt     420
gccaaaaaca cgaaagcat tgaagatctg tatgattttg gtcatgaagt tgccgaaagc     480
attggtgaaa ttcatgcaca taacgaagca cagaatgaaa ccctgaaagg tctgattacc     540
aacagcatcg aaaataccaa taacattacc aaaaacaaag cagatattca ggcgctggaa     600
aataatgttg tggaagaact gtttaatctg agcggtcgtc tgattgatca gaaagccgat     660
atcgataata acattaacaa catttatgaa ctggcacagc agcaggatca gcatagcagc     720
gatatcaaaa ccctgaaaaa aaacgttgaa gaaggtctgc tggaactgtc tggtcacctg     780
atcgatcaga aaactgatat tgcccagaat caggcaaata ttcaggatct ggccacctat     840
aatgaactgc aggatcagta tgcacagaaa cagaccgaag caattgatgc cctgaataaa     900
gcgagcagcg aaaacaccca gaatatcgaa gatctggcag catacaacga actgcaggat     960
gcctatgcaa acagcagac tgaagccatc gacgcactga caaggcaag ctctgaaaac       1020
acgcagaaca ttgaagatct ggctgcctat aatgaattac aggatgcgta tgccaaacag    1080
cagaccgaag cgattgatgc gctgaacaaa gcctcttctg aaaatacaca gaatatcgcc    1140
aaaaatcagg ccgatattgc caacaatatc aataatatct atgaactggc ccagcagcag    1200
gatcagcact cttctgatat caaaacactg gcaaaagcaa gcgcagcaaa taccgatcgt    1260
attgcgaaaa acaaagccga tgcagatgca agctttgaaa cactgacgaa aaaccagaac    1320
accctgattg aaaaagataa agaacatgat aaactgatca ccgccaataa aaccgcaatt    1380
gatgcaaata agccagcgc agataccaaa tttgcagcaa ccgcagatgc aattaccaaa    1440
aatggcaatg ccatcaccaa aaatgccaaa agcattaccg atctgggcac caaagttgat    1500
ggttttgata gccgtgtgac cgcactggat accaaagtta atgcatttga tggtcgtatt    1560
accgctctgg atagtaaagt tgaaaatgga atggcagcac aagcagcaca ctaa          1614
```

<210> SEQ ID NO 57
<211> LENGTH: 537
<212> TYPE: PRT
<213> ORGANISM: Artificial Sequence
<220> FEATURE:
<223> OTHER INFORMATION: Protein sequence for construct

<400> SEQUENCE: 57

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60
```

```
Trp Asn Gln Asn Asp Ile Ala Asn Leu Glu Asp Asp Val Glu Thr Leu
 65                  70                  75                  80

Thr Lys Asn Gln Asn Ala Leu Ala Glu Gln Gly Glu Ala Ile Lys Glu
                 85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Ala Asp Ala Ile Thr Lys
465                 470                 475                 480
```

Asn Gly Asn Ala Ile Thr Lys Asn Ala Lys Ser Ile Thr Asp Leu Gly
            485                 490                 495

Thr Lys Val Asp Gly Phe Asp Ser Arg Val Thr Ala Leu Asp Thr Lys
        500                 505                 510

Val Asn Ala Phe Asp Gly Arg Ile Thr Ala Leu Asp Ser Lys Val Glu
        515                 520                 525

Asn Gly Met Ala Ala Gln Ala Ala His
        530                 535

<210> SEQ ID NO 58
<211> LENGTH: 1545
<212> TYPE: DNA
<213> ORGANISM: Artificial Sequence
<220> FEATURE:
<223> OTHER INFORMATION: DNA sequence for MC-004 construct

<400> SEQUENCE: 58

| | |
|---|---|
| atgcaggcca aaaatgatat taccctggaa gatctgccgt atctgatcaa aaaaatcgat | 60 |
| cagaacgaac tggaagccga tattggtgat attaccgcac tggaaaaata tctggcactg | 120 |
| agccagtatg aaatattct ggccctggaa gaactgaata agctctgga gagctggat | 180 |
| gaagatgtgg gttggaatca gaatgatatc gccaatctgg aagatgatgt tgaaccctg | 240 |
| accaaaaatc agaatgcact ggcagaacag ggtgaagcaa ttaaagaaga tctgcagggt | 300 |
| ctggcagatt ttgttgaagg tcaggaaggc aaaattctgc agaacgaaac cagcatcaaa | 360 |
| aaaacacccc agcgtaatct ggtgaatggc tttgaaattg aaaaaaacaa agatgccatt | 420 |
| gccaaaaaca cgaaagcat tgaagatctg tatgattttg tcatgaagt tgccgaaagc | 480 |
| attggtgaaa ttcatgcaca taacgaagca cagaatgaaa ccctgaaagg tctgattacc | 540 |
| aacagcatcg aaaataccaa taacattacc aaaaacaaag cagatattca ggcgctggaa | 600 |
| ataatgttg tggaagaact gtttaatctg agcggtcgtc tgattgatca gaaagccgat | 660 |
| atcgataata cattaacaa catttatgaa ctggcacagc agcaggatca gcatagcagc | 720 |
| gatatcaaaa ccctgaaaaa aaacgttgaa gaaggtctgc tggaactgtc tggtcacctg | 780 |
| atcgatcaga aaactgatat tgcccagaat caggcaaata ttcaggatct ggccaccat | 840 |
| aatgaactgc aggatcagta tgcacagaaa cagaccgaag caattgatgc cctgaataaa | 900 |
| gcgagcagcg aaaacaccca gaatatcgaa gatctggcag catacaacga actgcaggat | 960 |
| gcctatgcaa acagcagac tgaagccatc gacgcactga caaggcaag ctctgaaaac | 1020 |
| acgcagaaca ttgaagatct ggctgcctat aatgaattac aggatgcgta tgccaaacag | 1080 |
| cagaccgaag cgattgatgc gctgaacaaa gcctcttctg aaaatacaca gaatatcgcc | 1140 |
| aaaaatcagg ccgatattgc caacaatatc aataatatct atgaactggc cagcagcag | 1200 |
| gatcagcact cttctgatat caaaacactg gcaaaagcaa gcgcagcaaa taccgatcgt | 1260 |
| attgcgaaaa acaaagccga tgcagatgca agctttgaaa cactgacgaa aaaccagaac | 1320 |
| accctgattg aaaaagataa agaacatgat aaactgatca ccgccaataa aaccgcaatt | 1380 |
| gatgcaaata agccagcgc agataccaaa tttgcagcaa ccgcagatgc aattaccaaa | 1440 |
| aatggcaatg ccatcaccaa aaatgccaaa agcattaccg atctgggcac caaagttgat | 1500 |
| ggttttgata gccgtgtgac cgcactggat accaaacatc attaa | 1545 |

<210> SEQ ID NO 59
<211> LENGTH: 514
<212> TYPE: PRT
<213> ORGANISM: Artificial Sequence
<220> FEATURE:
<223> OTHER INFORMATION: Protein sequence for MC-004 construct

<400> SEQUENCE: 59

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
                20                  25                  30

Ala Leu Glu Lys Tyr Leu Ala Leu Ser Gln Tyr Gly Asn Ile Leu Ala
            35                  40                  45

Leu Glu Glu Leu Asn Lys Ala Leu Glu Glu Leu Asp Glu Asp Val Gly
        50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
385                 390                 395                 400
```

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Asp Ala Ile Thr Lys
465                 470                 475                 480

Asn Gly Asn Ala Ile Thr Lys Asn Ala Lys Ser Ile Thr Asp Leu Gly
                485                 490                 495

Thr Lys Val Asp Gly Phe Asp Ser Arg Val Thr Ala Leu Asp Thr Lys
            500                 505                 510

His His

<210> SEQ ID NO 60
<211> LENGTH: 1500
<212> TYPE: DNA
<213> ORGANISM: Artificial Sequence
<220> FEATURE:
<223> OTHER INFORMATION: DNA sequence for MC-005 construct

<400> SEQUENCE: 60

| | |
|---|---|
| atgcaggcca aaatgatat taccctggaa gatctgccgt atctgatcaa aaaaatcgat | 60 |
| cagaacgaac tggaagccga tattggtgat attaccgcac tggaaaaata tctggcactg | 120 |
| agccagtatg aaatattct ggccctggaa gaactgaata agctctgga gagctggat | 180 |
| gaagatgtgg gttggaatca gaatgatatc gccaatctgg aagatgatgt tgaaaccctg | 240 |
| accaaaaatc agaatgcact ggcagaacag ggtgaagcaa ttaagaaga tctgcagggt | 300 |
| ctggcagatt tgttgaagg tcaggaaggc aaaattctgc agaacgaaac cagcatcaaa | 360 |
| aaaaacaccc agcgtaatct ggtgaatggc tttgaaattg aaaaaaacaa agatgccatt | 420 |
| gccaaaaaca cgaaagcat tgaagatctg tatgattttg gtcatgaagt tgccgaaagc | 480 |
| attggtgaaa ttcatgcaca taacgaagca cagaatgaaa ccctgaaagg tctgattacc | 540 |
| aacagcatcg aaataccaa taacattacc aaaaacaaag cagatattca ggcgctggaa | 600 |
| ataatgttg tggaagaact gtttaatctg agcggtcgtc tgattgatca gaaagccgat | 660 |
| atcgataata acattaacaa catttatgaa ctggcacagc agcaggatca gcatagcagc | 720 |
| gatatcaaaa ccctgaaaaa aaacgttgaa gaaggtctgc tggaactgtc tggtcacctg | 780 |
| atcgatcaga aaactgatat tgcccagaat caggcaaata ttcaggatct ggccaccctat | 840 |
| aatgaactgc aggatcagta tgcacagaaa cagaccgaag caattgatgc cctgaataaa | 900 |
| gcgagcagcg aaaacaccca gaatatcgaa gatctggcag catacaacga actgcaggat | 960 |
| gcctatgcaa acagcagac tgaagccatc gacgcactga caaggcaag ctctgaaaac | 1020 |
| acgcagaaca ttgaagatct ggctgcctat aatgaattac aggatgcgta tgccaaacag | 1080 |
| cagaccgaag cgattgatgc gctgaacaaa gcctcttctg aaaatacaca gaatatcgcc | 1140 |
| aaaaatcagg ccgatattgc caacaatatc aataatatct atgaactggc ccagcagcag | 1200 |
| gatcagcact cttctgatat caaaacactg gcaaaagcaa gcgcagcaaa taccgatcgt | 1260 |
| attgcgaaaa acaagccga tgcagatgca agctttgaaa cactgacgaa aaaccagaac | 1320 |
| accctgattg aaaaagataa agaacatgat aaactgatca ccgccaataa aaccgcaatt | 1380 |

```
gatgcaaata aagccagcgc agataccaaa tttgcagcaa ccgcagatgc aattaccaaa     1440
aatggcaatg ccatcaccaa aaatgccaaa agcgcaagcc atcatcatca ccaccactaa    1500
```

<210> SEQ ID NO 61
<211> LENGTH: 499
<212> TYPE: PRT
<213> ORGANISM: Artificial Sequence
<220> FEATURE:
<223> OTHER INFORMATION: Protein sequence for MC-005 construct

<400> SEQUENCE: 61

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
```

```
              340                 345                 350
Leu Gln Asp Ala Tyr Ala Lys Gln Gln Thr Glu Ala Ile Asp Ala Leu
            355                 360                 365

Asn Lys Ala Ser Ser Glu Asn Thr Gln Asn Ile Ala Lys Asn Gln Ala
        370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ala Ser His His His
                485                 490                 495

His His His

<210> SEQ ID NO 62
<211> LENGTH: 1476
<212> TYPE: DNA
<213> ORGANISM: Artificial Sequence
<220> FEATURE:
<223> OTHER INFORMATION: DNA sequence for MC-006 construct

<400> SEQUENCE: 62
atgcaggcca aaatgatat  accctggaa  gatctgccgt atctgatcaa aaaaatcgat      60
cagaacgaac tggaagccga tattggtgat attaccgcac tggaaaaata tctggcactg     120
agccagtatg gaaatattct ggccctggaa gaactgaata agctctctgga agagctggat    180 gaagatgtgg ttggaatcta gaatgatatc gccaatctgg aagatgatgt tgaaaccctg    240
accaaaaatc agaatgcact ggcagaacag ggtgaagcaa ttaaagaaga tctgcagggt    300
ctggcagatt tgttgaagg  tcaggaaggc aaaattctgc agaacgaaac cagcatcaaa    360
aaaaacaccc agcgtaatct ggtgaatggc tttgaaattg aaaaaacaa  agatgccatt    420 gccaaaaaca cgaaagcat  tgaagatctg tatgattttg tcatgaagt  tgccgaaagc    480 attggtgaaa ttcatgcaca taacgaagca cagaatgaaa ccctgaaagg tctgattacc    540
aacagcatcg aaaataccaa taacattacc aaaaacaaag cagatattca ggcgctggaa    600
aataatgttg tggaagaact gtttaatctg agcggtcgtc tgattgatca gaaagccgat    660
atcgataata acattaacaa catttatgaa ctggcacagc agcaggatca gcatagcagc    720
gatatcaaaa ccctgaaaaa aaacgttgaa gaaggtctgc tggaactgtc tggtcacctg    780
atcgatcaga aaactgatat tgcccagaat caggcaaata ttcaggatct ggccacctat    840
aatgaactgc aggatcagta tgcacagaaa cagaccgaag caattgatgc cctgaataaa    900
gcgagcagcg aaaacaccca gaatatcgaa gatctggcag catacaacga actgcaggat    960
gcctatgcaa acagcagac  tgaagccatc gacgcactga caaggcaag  ctctgaaaac   1020 acgcagaaca ttgaagatct ggctgcctat aatgaattac aggatgcgta tgccaaacag   1080
cagaccgaag cgattgatgc gctgaacaaa gcctcttctg aaaatacaca gaatatcgcc   1140
```

-continued

```
aaaaatcagg ccgatattgc caacaatatc aataatatct atgaactggc ccagcagcag   1200
gatcagcact cttctgatat caaaacactg gcaaaagcaa gcgcagcaaa taccgatcgt   1260
attgcgaaaa acaaagccga tgcagatgca agctttgaaa cactgacgaa aaaccagaac   1320
accctgattg aaaagataa  agaacatgat aaactgatca ccgccaataa aaccgcaatt   1380
gatgcaaata aagccagcgc agataccaaa tttgcagcaa ccgcagatgc aattaccaaa   1440
aatggcaatg ccatcaccaa aaatgccaaa agctaa                             1476
```

```
<210> SEQ ID NO 63
<211> LENGTH: 491
<212> TYPE: PRT
<213> ORGANISM: Artificial Sequence
<220> FEATURE:
<223> OTHER INFORMATION: Protein sequence for MC-006 construct

<400> SEQUENCE: 63

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300
```

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser
                485                 490

<210> SEQ ID NO 64
<211> LENGTH: 1635
<212> TYPE: DNA
<213> ORGANISM: Artificial Sequence
<220> FEATURE:
<223> OTHER INFORMATION: DNA sequence for MC-007 construct

<400> SEQUENCE: 64
atgcaggcca aaatgatat tacccctggaa gatctgccgt atctgatcaa aaaaatcgat      60
cagaacgaac tggaagccga tattggtgat attaccgcac tggaaaaata tctggcactg     120
agccagtatg aaatattct ggccctggaa gaactgaata agctctctgga agagctggat     180 gaagatgtgg ttggaatca gaatgatatc gccaatctgg aagatgatgt tgaaaccctg     240
accaaaaatc agaatgcact ggcagaacag ggtgaagcaa ttaaagaaga tctgcagggt     300
ctggcagatt tgttgaagg tcaggaaggc aaaattctgc agaacgaaac cagcatcaaa     360
aaaaacaccc agcgtaatct ggtgaatggc tttgaaattg aaaaaaacaa agatgccatt     420
gccaaaaaca cgaaagcat gaagatctg tatgattttg tcatgaagt tgccgaaagc       480 attggtgaaa ttcatgcaca taacgaagca cagaatgaaa ccctgaaagg tctgattacc     540
aacagcatcg aaaataccaa taacattacc aaaaacaaag cagatattca ggcgctggaa     600
aataatgttg tggaagaact gtttaatctg agcggtcgtc tgattgatca aaaagccgat     660
atcgataata acattaacaa catttatgaa ctggcacagc agcaggatca gcatagcagc     720
gatatcaaaa ccctgaaaaa aaacgttgaa gaaggtctgc tggaactgtc tggtcacctg     780
atcgatcaga aaactgatat tgcccagaat caggcaaata ttcaggatct ggccacctat     840
aatgaactgc aggatcagta tgcacagaaa cagaccgaag caattgatgc cctgaataaa     900
gcgagcagcg aaaacacccca gaatatcgaa gatctggcag catacaacga actgcaggat     960
gcctatgcaa acagcagac tgaagccatc gacgcactga caaggcaag ctctgaaaac      1020

-continued

```
acgcagaaca ttgaagatct ggctgcctat aatgaattac aggatgcgta tgccaaacag    1080
cagaccgaag cgattgatgc gctgaacaaa gcctcttctg aaaatacaca gaatatcgcc    1140
aaaaatcagg ccgatattgc caacaatatc aataatatct atgaactggc ccagcagcag    1200
gatcagcact cttctgatat caaaacactg gcaaaagcaa gcgcagcaaa taccgatcgt    1260
attgcgaaaa acaaagccga tgcagatgca agctttgaaa cactgacgaa aaaccagaac    1320
accctgattg aaaagataa agaacatgat aaactgatca ccgccaataa aaccgcaatt    1380
gatgcaaata aagccagcgc agataccaaa tttgcagcaa ccgcagatgc aattaccaaa    1440
aatggcaatg ccatcaccaa aaatgccaaa agcattaccg atctgggcac caaagttgat    1500
ggttttgata gccgtgtgac cgcactggat accaaagtta atgcatttga tggtcgtatt    1560
accgctctgg atagtaaagt tgaaaatggt atggcagcac aggcagcagc aagccatcat    1620
catcaccacc actaa                                                     1635
```

<210> SEQ ID NO 65
<211> LENGTH: 544
<212> TYPE: PRT
<213> ORGANISM: Artificial Sequence
<220> FEATURE:
<223> OTHER INFORMATION: Protein sequence for MC-007 construct

<400> SEQUENCE: 65

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
```

|       |       |       | 245   |       |       |       | 250   |       |       |       | 255   |       |       |
|-------|-------|-------|-------|-------|-------|-------|-------|-------|-------|-------|-------|-------|-------|

Ser Gly His Leu Ile Asp Gln Lys Thr Asp Ile Ala Gln Asn Gln Ala
              260                      265                    270

Asn Ile Gln Asp Leu Ala Thr Tyr Asn Glu Leu Gln Asp Gln Tyr Ala
        275                    280                    285

Gln Lys Gln Thr Glu Ala Ile Asp Ala Leu Asn Lys Ala Ser Ser Glu
290                    295                    300

Asn Thr Gln Asn Ile Glu Asp Leu Ala Ala Tyr Asn Glu Leu Gln Asp
305              310                315            320

Ala Tyr Ala Lys Gln Gln Thr Glu Ala Ile Asp Ala Leu Asn Lys Ala
              325                    330              335

Ser Ser Glu Asn Thr Gln Asn Ile Glu Asp Leu Ala Ala Tyr Asn Glu
        340                    345                  350

Leu Gln Asp Ala Tyr Ala Lys Gln Gln Thr Glu Ala Ile Asp Ala Leu
              355                    360            365

Asn Lys Ala Ser Ser Glu Asn Thr Gln Asn Ile Ala Lys Asn Gln Ala
        370                    375                  380

Asp Ile Ala Asn Asn Ile Asn Asn Ile Tyr Glu Leu Ala Gln Gln Gln
385              390                395            400

Asp Gln His Ser Ser Asp Ile Lys Thr Leu Ala Lys Ala Ser Ala Ala
              405                    410              415

Asn Thr Asp Arg Ile Ala Lys Asn Lys Ala Asp Ala Asp Ala Ser Phe
        420                    425                  430

Glu Thr Leu Thr Lys Asn Gln Asn Thr Leu Ile Glu Lys Asp Lys Glu
              435                    440                  445

His Asp Lys Leu Ile Thr Ala Asn Lys Thr Ala Ile Asp Ala Asn Lys
450              455                460

Ala Ser Ala Asp Thr Lys Phe Ala Ala Thr Ala Asp Ala Ile Thr Lys
465              470                475            480

Asn Gly Asn Ala Ile Thr Lys Asn Ala Lys Ser Ile Thr Asp Leu Gly
              485                    490            495

Thr Lys Val Asp Gly Phe Asp Ser Arg Val Thr Ala Leu Asp Thr Lys
        500                    505                  510

Val Asn Ala Phe Asp Gly Arg Ile Thr Ala Leu Asp Ser Lys Val Glu
              515                    520            525

Asn Gly Met Ala Ala Gln Ala Ala Ala Ser His His His His His His
        530                    535                  540

<210> SEQ ID NO 66
<211> LENGTH: 1617
<212> TYPE: DNA
<213> ORGANISM: Artificial Sequence
<220> FEATURE:
<223> OTHER INFORMATION: DNA sequence for MC-008 construct

<400> SEQUENCE: 66
atgcaggcca aaatgatat taccctggaa gatctgccgt atctgatcaa aaaaatcgat       60
cagaacgaac tggaagccga tattggtgat attaccgcac tggaaaaata tctggcactg      120
agccagtatg aaatattct ggccctggaa gaactgaata agctctgga gagctggat       180 gaagatgtgg gttggaatca gaatgatatc gccaatctgg aagatgatgt tgaaaccctg      240
accaaaaatc agaatgcact ggcagaacag ggtgaagcaa ttaaagaaga tctgcagggt      300
ctggcagatt tgttgaagg tcaggaaggc aaaattctgc agaacgaaac cagcatcaaa      360
aaaacacccc agcgtaatct ggtgaatggc tttgaaattg aaaaaaacaa agatgccatt      420

-continued

```
gccaaaaaca acgaaagcat tgaagatctg tatgattttg gtcatgaagt tgccgaaagc    480
attggtgaaa ttcatgcaca taacgaagca cagaatgaaa ccctgaaagg tctgattacc    540
aacagcatcg aaataccaa taacattacc aaaaacaaag cagatattca ggcgctggaa     600
aataatgttg tggaagaact gtttaatctg agcggtcgtc tgattgatca gaaagccgat    660
atcgataata acattaacaa catttatgaa ctggcacagc agcaggatca gcatagcagc    720
gatatcaaaa ccctgaaaaa aaacgttgaa gaaggtctgc tggaactgtc tggtcacctg    780
atcgatcaga aaactgatat tgcccagaat caggcaaata ttcaggatct ggccacctat    840
aatgaactgc aggatcagta tgcacagaaa cagaccgaag caattgatgc cctgaataaa    900
gcgagcagcg aaaacaccca gaatatcgaa gatctggcag catacaacga actgcaggat    960
gcctatgcaa acagcagac tgaagccatc gacgcactga caaggcaag ctctgaaaac     1020 acgcagaaca ttgaagatct ggctgcctat aatgaattac aggatgcgta tgccaaacag   1080
cagaccgaag cgattgatgc gctgaacaaa gcctcttctg aaaatacaca gaatatcgcc    1140
aaaaatcagg ccgatattgc caacaatatc aataatatct atgaactggc ccagcagcag   1200
gatcagcact cttctgatat caaaacactg gcaaaagcaa gcgcagcaaa taccgatcgt    1260
attgcgaaaa acaaagccga tgcagatgca agctttgaaa cactgacgaa aaaccagaac    1320
accctgattg aaaagataa agaacatgat aaactgatca ccgccaataa aaccgcaatt     1380
gatgcaaata agccagcgc agataccaaa tttgcagcaa ccgcagatgc aattaccaaa    1440
aatggcaatg ccatcaccaa aaatgccaaa agcattaccg atctgggcac caaagttgat    1500
ggttttgata gccgtgtgac cgcactggat accaaagtta atgcatttga tggtcgtatt    1560
accgctctgg atagtaaagt tgaaaatggt atggcagcac aggcagcaca ccactaa      1617
```

<210> SEQ ID NO 67
<211> LENGTH: 538
<212> TYPE: PRT
<213> ORGANISM: Artificial Sequence
<220> FEATURE:
<223> OTHER INFORMATION: Protein sequence for MC-008 construct

<400> SEQUENCE: 67

```
Met Gln Ala Lys Asn Asp Ile Thr Leu Glu Asp Leu Pro Tyr Leu Ile
1               5                  10                  15

Lys Lys Ile Asp Gln Asn Glu Leu Glu Ala Asp Ile Gly Asp Ile Thr
                20                  25                  30

Ala Leu Glu Lys Tyr Leu Ala Leu Ser Gln Tyr Gly Asn Ile Leu Ala
            35                  40                  45

Leu Glu Glu Leu Asn Lys Ala Leu Glu Glu Leu Asp Glu Asp Val Gly
        50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
```

```
            145                 150                 155                 160
        Ile Gly Glu Ile His Ala His Asn Glu Ala Gln Asn Glu Thr Leu Lys
                        165                 170                 175
        Gly Leu Ile Thr Asn Ser Ile Glu Asn Thr Asn Asn Ile Thr Lys Asn
                        180                 185                 190
        Lys Ala Asp Ile Gln Ala Leu Glu Asn Asn Val Val Glu Glu Leu Phe
                        195                 200                 205
        Asn Leu Ser Gly Arg Leu Ile Asp Gln Lys Ala Asp Ile Asp Asn Asn
                    210                 215                 220
        Ile Asn Asn Ile Tyr Glu Leu Ala Gln Gln Gln Asp Gln His Ser Ser
        225                 230                 235                 240
        Asp Ile Lys Thr Leu Lys Lys Asn Val Glu Glu Gly Leu Leu Glu Leu
                        245                 250                 255
        Ser Gly His Leu Ile Asp Gln Lys Thr Asp Ile Ala Gln Asn Gln Ala
                        260                 265                 270
        Asn Ile Gln Asp Leu Ala Thr Tyr Asn Glu Leu Gln Asp Gln Tyr Ala
                        275                 280                 285
        Gln Lys Gln Thr Glu Ala Ile Asp Ala Leu Asn Lys Ala Ser Ser Glu
                    290                 295                 300
        Asn Thr Gln Asn Ile Glu Asp Leu Ala Ala Tyr Asn Glu Leu Gln Asp
        305                 310                 315                 320
        Ala Tyr Ala Lys Gln Gln Thr Glu Ala Ile Asp Ala Leu Asn Lys Ala
                        325                 330                 335
        Ser Ser Glu Asn Thr Gln Asn Ile Glu Asp Leu Ala Ala Tyr Asn Glu
                        340                 345                 350
        Leu Gln Asp Ala Tyr Ala Lys Gln Gln Thr Glu Ala Ile Asp Ala Leu
                    355                 360                 365
        Asn Lys Ala Ser Ser Glu Asn Thr Gln Asn Ile Ala Lys Asn Gln Ala
                    370                 375                 380
        Asp Ile Ala Asn Asn Ile Asn Asn Ile Tyr Glu Leu Ala Gln Gln Gln
        385                 390                 395                 400
        Asp Gln His Ser Ser Asp Ile Lys Thr Leu Ala Lys Ala Ser Ala Ala
                        405                 410                 415
        Asn Thr Asp Arg Ile Ala Lys Asn Lys Ala Asp Ala Asp Ala Ser Phe
                        420                 425                 430
        Glu Thr Leu Thr Lys Asn Gln Asn Thr Leu Ile Glu Lys Asp Lys Glu
                        435                 440                 445
        His Asp Lys Leu Ile Thr Ala Asn Lys Thr Ala Ile Asp Ala Asn Lys
                    450                 455                 460
        Ala Ser Ala Asp Thr Lys Phe Ala Ala Thr Ala Asp Ala Ile Thr Lys
        465                 470                 475                 480
        Asn Gly Asn Ala Ile Thr Lys Asn Ala Lys Ser Ile Thr Asp Leu Gly
                        485                 490                 495
        Thr Lys Val Asp Gly Phe Asp Ser Arg Val Thr Ala Leu Asp Thr Lys
                        500                 505                 510
        Val Asn Ala Phe Asp Gly Arg Ile Thr Ala Leu Asp Ser Lys Val Glu
                        515                 520                 525
        Asn Gly Met Ala Ala Gln Ala Ala His His
                    530                 535

<210> SEQ ID NO 68
<211> LENGTH: 1614
<212> TYPE: DNA
<213> ORGANISM: Artificial Sequence
```

<220> FEATURE:
<223> OTHER INFORMATION: DNA sequence for MC-009 construct

<400> SEQUENCE: 68

| | |
|---|---|
| atggcgaaaa atgatattac cctggaagat ctgccgtatc tgatcaaaaa aatcgatcag | 60 |
| aacgaactgg aagccgatat tggtgatatt accgcactgg aaaaatatct ggcactgagc | 120 |
| cagtatggaa atattctggc cctggaagaa ctgaataaag ctctggaaga gctggatgaa | 180 |
| gatgtgggtt ggaatcagaa tgatatcgcc aatctggaag atgatgttga accctgacc | 240 |
| aaaaatcaga atgcactggc agaacagggt gaagcaatta agaagatctg cagggtctg | 300 |
| gcagattttg ttgaaggtca ggaaggcaaa attctgcaga cgaaaccag catcaaaaaa | 360 |
| aacacccagc gtaatctggt gaatggcttt gaaattgaaa aaacaaaga tgccattgcc | 420 |
| aaaaacaacg aaagcattga agatctgtat gattttggtc atgaagttgc cgaaagcatt | 480 |
| ggtgaaattc atgcacataa cgaagcacag aatgaaaccc tgaaaggtct gattaccaac | 540 |
| agcatcgaaa ataccaataa cattaccaaa aacaaagcag atattcaggc gctggaaaat | 600 |
| aatgttgtgg aagaactgtt taatctgagc ggtcgtctga ttgatcagaa agccgatatc | 660 |
| gataataaca ttaacaacat ttatgaactg gcacagcagc aggatcagca tagcagcgat | 720 |
| atcaaaaccc tgaaaaaaaa cgttgaagaa ggtctgctgg aactgtctgg tcacctgatc | 780 |
| gatcagaaaa ctgatattgc ccagaatcag gcaaatattc aggatctggc cacctataat | 840 |
| gaactgcagg atcagtatgc acagaaacag accgaagcaa ttgatgccct gaataaagcg | 900 |
| agcagcgaaa acacccagaa tatcgaagat ctggcagcat acaacgaact gcaggatgcc | 960 |
| tatgcaaaac agcagactga agccatcgac gcactgaaca aggcaagctc tgaaaacacg | 1020 |
| cagaacattg aagatctggc tgcctataat gaattacagg atgcgtatgc caaacagcag | 1080 |
| accgaagcga ttgatgcgct gaacaaagcc tcttctgaaa atacacagaa tatcgccaaa | 1140 |
| aatcaggccg atattgccaa caatatcaat aatatctatg aactggccca gcagcaggat | 1200 |
| cagcactctt ctgatatcaa aacactggca aaagcaagcg cagcaaatac cgatcgtatt | 1260 |
| gcgaaaaaca aagccgatgc agatgcaagc tttgaaacac tgacgaaaaa ccagaacacc | 1320 |
| ctgattgaaa aagataaaga acatgataaa ctgatcaccg ccaataaaac cgcaattgat | 1380 |
| gcaaataaag ccagcgcaga taccaaattt gcagcaaccg cagatgcaat taccaaaaat | 1440 |
| ggcaatgcca tcaccaaaaa tgccaaaagc attaccgatc tgggcaccaa agttgatggt | 1500 |
| tttgatagcc gtgtgaccgc actggatacc aaagttaatg catttgatgg tcgtattacc | 1560 |
| gctctggata gtaaagttga aaatggtatg gcagcacagg cagcacacca ctaa | 1614 |

<210> SEQ ID NO 69
<211> LENGTH: 537
<212> TYPE: PRT
<213> ORGANISM: Artificial Sequence
<220> FEATURE:
<223> OTHER INFORMATION: Protein sequence for MC-009 construct

<400> SEQUENCE: 69

Met Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
            20                  25                  30

Leu Glu Lys Tyr Leu Ala Leu Ser Gln Tyr Gly Asn Ile Leu Ala Leu
        35                  40                  45

Glu Glu Leu Asn Lys Ala Leu Glu Glu Leu Asp Glu Asp Val Gly Trp

```
            50                  55                  60
Asn Gln Asn Asp Ile Ala Asn Leu Glu Asp Asp Val Glu Thr Leu Thr
65                  70                  75                  80

Lys Asn Gln Asn Ala Leu Ala Glu Gln Gly Glu Ala Ile Lys Glu Asp
                    85                  90                  95

Leu Gln Gly Leu Ala Asp Phe Val Glu Gly Gln Glu Gly Lys Ile Leu
                100                 105                 110

Gln Asn Glu Thr Ser Ile Lys Lys Asn Thr Gln Arg Asn Leu Val Asn
                115                 120                 125

Gly Phe Glu Ile Glu Lys Asn Lys Asp Ala Ile Ala Lys Asn Asn Glu
                130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Ile Thr Lys Asn Lys
                180                 185                 190

Ala Asp Ile Gln Ala Leu Glu Asn Asn Val Val Glu Glu Leu Phe Asn
                195                 200                 205

Leu Ser Gly Arg Leu Ile Asp Gln Lys Ala Asp Ile Asp Asn Asn Ile
210                 215                 220

Asn Asn Ile Tyr Glu Leu Ala Gln Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Gly His Leu Ile Asp Gln Lys Thr Asp Ile Ala Gln Asn Gln Ala Asn
                260                 265                 270

Ile Gln Asp Leu Ala Thr Tyr Asn Glu Leu Gln Asp Gln Tyr Ala Gln
                275                 280                 285

Lys Gln Thr Glu Ala Ile Asp Ala Leu Asn Lys Ala Ser Ser Glu Asn
                290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                325                 330                 335

Ser Glu Asn Thr Gln Asn Ile Glu Asp Leu Ala Ala Tyr Asn Glu Leu
                340                 345                 350

Gln Asp Ala Tyr Ala Lys Gln Gln Thr Glu Ala Ile Asp Ala Leu Asn
                355                 360                 365

Lys Ala Ser Ser Glu Asn Thr Gln Asn Ile Ala Lys Asn Gln Ala Asp
                370                 375                 380

Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
                405                 410                 415

Thr Asp Arg Ile Ala Lys Asn Lys Ala Asp Ala Asp Ala Ser Phe Glu
                420                 425                 430

Thr Leu Thr Lys Asn Gln Asn Thr Leu Ile Glu Lys Asp Lys Glu His
                435                 440                 445

Asp Lys Leu Ile Thr Ala Asn Lys Thr Ala Ile Asp Ala Asn Lys Ala
                450                 455                 460

Ser Ala Asp Thr Lys Phe Ala Ala Thr Ala Asp Ala Ile Thr Lys Asn
465                 470                 475                 480
```

```
Gly Asn Ala Ile Thr Lys Asn Ala Lys Ser Ile Thr Asp Leu Gly Thr
                485                 490                 495

Lys Val Asp Gly Phe Asp Ser Arg Val Thr Ala Leu Asp Thr Lys Val
            500                 505                 510

Asn Ala Phe Asp Gly Arg Ile Thr Ala Leu Asp Ser Lys Val Glu Asn
        515                 520                 525

Gly Met Ala Ala Gln Ala Ala His His
    530                 535

<210> SEQ ID NO 70
<211> LENGTH: 1611
<212> TYPE: DNA
<213> ORGANISM: Artificial Sequence
<220> FEATURE:
<223> OTHER INFORMATION: DNA sequence for MC-010 construct

<400> SEQUENCE: 70
atgcaggcca aaaatgatat taccctggaa gatctgccgt atctgatcaa aaaaatcgat      60
cagaacgaac tggaagccga tattggtgat attaccgcac tggaaaaata tctggcactg     120
agccagtatg aaatattct ggccctggaa gaactgaata agctctgga agagctggat       180 gaagatgtgg gttggaatca gaatgatatc gccaatctgg aagatgatgt tgaaaccctg     240
accaaaaatc agaatgcact ggcagaacag ggtgaagcaa ttaaagaaga tctgcagggt     300
ctggcagatt ttgttgaagg tcaggaaggc aaaattctgc agaacgaaac cagcatcaaa    360
aaaaacaccc agcgtaatct ggtgaatggc tttgaaattg aaaaaaacaa agatgccatt    420
gccaaaaaca cgaaagcat tgaagatctg tatgattttg gtcatgaagt tgccgaaagc     480
attggtgaaa ttcatgcaca taacgaagca cagaatgaaa ccctgaaagg tctgattacc    540
aacagcatcg aaaataccaa taacattacc aaaaacaaag cagatattca ggcgctggaa    600 ataatgttg tggaagaact gtttaatctg agcggtcgtc tgattgatca gaaagccgat     660
atcgataata acattaacaa catttatgaa ctggcacagc agcaggatca gcatagcagc    720
gatatcaaaa ccctgaaaaa aaacgttgaa gaaggtctgc tggaactgtc tggtcacctg    780
atcgatcaga aaactgatat tgcccagaat caggcaaata ttcaggatct ggccaccta    840 aatgaactgc aggatcagta tgcacagaaa cagaccgaag caattgatgc cctgaataaa    900
gcgagcagcg aaaacaccca gaatatcgaa gatctggcag catacaacga actgcaggat   960
gcctatgcaa acagcagac tgaagccatc gacgcactga caaggcaag ctctgaaaac    1020 acgcagaaca ttgaagatct ggctgccta taatgaattac aggatgcgta tgccaaacag    1080
cagaccgaag cgattgatgc gctgaacaaa gcctcttctg aaaatacaca gaatatcgcc   1140
aaaaatcagg ccgatattgc caacaatatc aataatatct atgaactggc ccagcagcag   1200
gatcagcact ttctgatat caaaacactg gcaaagcaa gcgcagcaaa taccgatcgt    1260
attgcgaaaa acaaagccga tgcagatgca agctttgaaa cactgacgaa aaaccagaac   1320
accctgattg aaaaagataa agaacatgat aaactgatca ccgccaataa accgcaatt    1380 gatgcaaata agccagcgc agataccaaa tttgcagcaa ccgcagatgc aattaccaaa   1440
aatggcaatg ccatcaccaa aaatgccaaa agcattaccg atctgggcac caaagttgat  1500
ggttttgata gccgtgtgac cgcactggat accaaagtta tgcatttga tggtcgtatt    1560 accgctctgg atagtaaagt tgaaaatggt atggcagcac aggcagcata a            1611

<210> SEQ ID NO 71
```

<211> LENGTH: 536
<212> TYPE: PRT
<213> ORGANISM: Artificial Sequence
<220> FEATURE:
<223> OTHER INFORMATION: Protein sequence for MC-010 construct

<400> SEQUENCE: 71

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Ile Tyr Glu Leu Ala Gln Gln Gln
385                 390                 395                 400

Asp Gln His Ser Ser Asp Ile Lys Thr Leu Ala Lys Ala Ser Ala Ala
            405                 410                 415

Asn Thr Asp Arg Ile Ala Lys Asn Lys Ala Asp Ala Asp Ala Ser Phe
        420                 425                 430

Glu Thr Leu Thr Lys Asn Gln Asn Thr Leu Ile Glu Lys Asp Lys Glu
    435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
            485                 490                 495

Thr Lys Val Asp Gly Phe Asp Ser Arg Val Thr Ala Leu Asp Thr Lys
        500                 505                 510

Val Asn Ala Phe Asp Gly Arg Ile Thr Ala Leu Asp Ser Lys Val Glu
    515                 520                 525

Asn Gly Met Ala Ala Gln Ala Ala
    530                 535

<210> SEQ ID NO 72
<211> LENGTH: 1560
<212> TYPE: DNA
<213> ORGANISM: Artificial Sequence
<220> FEATURE:
<223> OTHER INFORMATION: DNA sequence for MC-011 construct

<400> SEQUENCE: 72
atggcgaaaa atgatattac cctggaagat ctgccgtatc tgatcaaaaa aatcgatcag    60
aacgaactgg aagccgatat tggtgatatt accgcactgg aaaaatatct ggcactgagc   120
cagtatggaa atattctggc cctggaagaa ctgaataaag ctctggaaga gctggatgaa   180
gatgtgggtt ggaatcagaa tgatatcgcc aatctggaag atgatgttga acccctgacc   240
aaaaatcaga atgcactggc agaacagggt gaagcaatta agaagatctg cagggtctg    300 gcagattttg ttgaaggtca ggaaggcaaa attctgcaga cgaaaccag catcaaaaaa    360 aacacccagc gtaatctggt gaatggcttt gaaattgaa aaaacaaaga tgccattgcc    420
aaaaacaacg aaagcattga agatctgtat gattttggtc atgaagttgc cgaaagcatt    480
ggtgaaattc atgcacataa cgaagcacag aatgaaaccc tgaaaggtct gattaccaac    540
agcatcgaaa ataccaataa cattaccaaa acaaagcag atattcaggc gctggaaaat    600
aatgttgtgg aagaactgtt taatctgagc ggtcgtctga ttgatcagaa agccgatatc    660
gataataaca ttaacaacat ttatgaactg gcacagcagc aggatcagca tagcagcgat    720
atcaaacccc tgaaaaaaaa cgttgaagaa ggtctgctgg aactgtctgg tcacctgatc    780
gatcagaaaa ctgatattgc ccagaatcag gcaaatattc aggatctggc cacctataat    840
gaactgcagg atcagtatgc acagaaacag accgaagcaa ttgatgccct gaataaagcg    900
agcagcgaaa cacccagaa tatcgaagat ctggcagcat acaacgaact gcaggatgcc    960
tatgcaaaac agcagactga agccatcgac gcactgaaca aggcaagctc tgaaaacacg   1020
cagaacattg aagatctggc tgcctataat gaattacagg atgcgtatgc caaacagcag   1080
accgaagcga ttgatgcgct gaacaaagcc tcttctgaaa atacacagaa tatcgccaaa   1140

```
aatcaggccg atattgccaa caatatcaat aatatctatg aactggccca gcagcaggat   1200
cagcactctt ctgatatcaa aacactggca aaagcaagcg cagcaaatac cgatcgtatt   1260
gcgaaaaaca aagccgatgc agatgcaagc tttgaaacac tgacgaaaaa ccagaacacc   1320
ctgattgaaa agataaaga acatgataaa ctgatcaccg ccaataaaac cgcaattgat   1380
gcaaataaag ccagcgcaga taccaaattt gcagcaaccg cagatgcaat taccaaaaat   1440
ggcaatgcca tcaccaaaaa tgccaaaagc attaccgatc tgggcaccaa agttgatggt   1500
tttgatagcc gtgtgaccgc actggatacc aaagcaagcc atcatcatca ccaccactaa   1560
```

<210> SEQ ID NO 73
<211> LENGTH: 519
<212> TYPE: PRT
<213> ORGANISM: Artificial Sequence
<220> FEATURE:
<223> OTHER INFORMATION: Protein sequence for MC-011 construct

<400> SEQUENCE: 73

```
Met Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
            20                  25                  30

Leu Glu Lys Tyr Leu Ala Leu Ser Gln Tyr Gly Asn Ile Leu Ala Leu
        35                  40                  45

Glu Glu Leu Asn Lys Ala Leu Glu Glu Leu Asp Glu Asp Val Gly Trp
    50                  55                  60

Asn Gln Asn Asp Ile Ala Asn Leu Glu Asp Asp Val Glu Thr Leu Thr
65                  70                  75                  80

Lys Asn Gln Asn Ala Leu Ala Glu Gln Gly Glu Ala Ile Lys Glu Asp
                85                  90                  95

Leu Gln Gly Leu Ala Asp Phe Val Glu Gly Gln Glu Gly Lys Ile Leu
            100                 105                 110

Gln Asn Glu Thr Ser Ile Lys Lys Asn Thr Gln Arg Asn Leu Val Asn
        115                 120                 125

Gly Phe Glu Ile Glu Lys Asn Lys Asp Ala Ile Ala Lys Asn Asn Glu
    130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Ile Thr Lys Asn Lys
            180                 185                 190

Ala Asp Ile Gln Ala Leu Glu Asn Asn Val Val Glu Glu Leu Phe Asn
        195                 200                 205

Leu Ser Gly Arg Leu Ile Asp Gln Lys Ala Asp Ile Asp Asn Asn Ile
    210                 215                 220

Asn Asn Ile Tyr Glu Leu Ala Gln Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Gly His Leu Ile Asp Gln Lys Thr Asp Ile Ala Gln Asn Gln Ala Asn
            260                 265                 270

Ile Gln Asp Leu Ala Thr Tyr Asn Glu Leu Gln Asp Gln Tyr Ala Gln
        275                 280                 285

Lys Gln Thr Glu Ala Ile Asp Ala Leu Asn Lys Ala Ser Ser Glu Asn
```

| | | | | | | | | | | | 290 | | | 295 | | | 300 | | |
|---|---|---|---|---|---|---|---|---|---|---|---|---|---|---|---|---|---|---|---|

Thr Gln Asn Ile Glu Asp Leu Ala Ala Tyr Asn Glu Leu Gln Asp Ala
305                     310                     315                     320

Tyr Ala Lys Gln Gln Thr Glu Ala Ile Asp Ala Leu Asn Lys Ala Ser
                325                     330                     335

Ser Glu Asn Thr Gln Asn Ile Glu Asp Leu Ala Ala Tyr Asn Glu Leu
                340                     345                     350

Gln Asp Ala Tyr Ala Lys Gln Gln Thr Glu Ala Ile Asp Ala Leu Asn
                355                     360                     365

Lys Ala Ser Ser Glu Asn Thr Gln Asn Ile Ala Lys Asn Gln Ala Asp
        370                     375                     380

Ile Ala Asn Asn Ile Asn Asn Ile Tyr Glu Leu Ala Gln Gln Gln Asp
385                     390                     395                     400

Gln His Ser Ser Asp Ile Lys Thr Leu Ala Lys Ala Ser Ala Ala Asn
                405                     410                     415

Thr Asp Arg Ile Ala Lys Asn Lys Ala Asp Ala Asp Ala Ser Phe Glu
                420                     425                     430

Thr Leu Thr Lys Asn Gln Asn Thr Leu Ile Glu Lys Asp Lys Glu His
                435                     440                     445

Asp Lys Leu Ile Thr Ala Asn Lys Thr Ala Ile Asp Ala Asn Lys Ala
        450                     455                     460

Ser Ala Asp Thr Lys Phe Ala Ala Thr Ala Asp Ala Ile Thr Lys Asn
465                     470                     475                     480

Gly Asn Ala Ile Thr Lys Asn Ala Lys Ser Ile Thr Asp Leu Gly Thr
                485                     490                     495

Lys Val Asp Gly Phe Asp Ser Arg Val Thr Ala Leu Asp Thr Lys Ala
                500                     505                     510

Ser His His His His His His
        515

<210> SEQ ID NO 74
<211> LENGTH: 1893
<212> TYPE: DNA
<213> ORGANISM: Moraxella catarrhalis

<400> SEQUENCE: 74

| | | |
|---|---|---|
| atgaaaacca tgaaacttct ccctctaaaa atcgctgtaa ccagtgccat gattattggc | 60 |
| ttgggtgcgg catctactgc gaatgcgcag gctaaaaatg atataacttt agaggattta | 120 |
| ccatatttaa taaaaaagat tgaccaaaat gaattggaag cagatatcgg agatattact | 180 |
| gctcttgaaa gtatctagc acttagccag tatggcaata ttttagctct agaagagctc | 240 |
| aacaaggctc tagaagagct cgacgaggat gttggatgga atcagaatga tattgcaaac | 300 |
| ttggaagatg atgttgaaac gctcaccaaa atcaaaatg ctttggctga acaaggtgag | 360 |
| gcaattaaag aagatcttca agggcttgca gattttgtag aagggcaaga gggtaaaatt | 420 |
| ctacaaaatg aaacttcaat taaaaaaat actcagagaa accttgtcaa tgggtttgag | 480 |
| attgagaaaa ataaagatgc tattgctaaa acaatgagt ctatcgaaga tctttatgat | 540 |
| tttggtcatg aggttgcaga aagtataggc gagatacatg ctcataatga agcgcaaaat | 600 |
| gaaactctta aaggcttgat aacaaacagt attgagaata ctaataatat taccaaaaac | 660 |
| aaagctgaca tccaagcact tgaaaacaat gtcgtagaag aactattcaa tctaagcggt | 720 |
| cgcctaattg atcaaaaagc agatattgat aataacatca caatatcta tgagctggca | 780 |
| caacagcaag atcagcatag ctctgatatc aaaacactta aaaaaaatgt cgaagaaggt | 840 |

```
ttgttggagc taagcggtca cctaattgat caaaaaacag atattgctca aaaccaagct    900
aacatccaag atctggccac ttacaacgag ctacaagacc agtatgctca aaagcaaacc    960
gaagcgattg acgctctaaa taaagcaagc tctgagaata cacaaaacat cgaagatctg   1020
gccgcttaca acgagctaca agatgcctat gccaaacagc aaaccgaagc aattgacgct   1080
ctaaataaag caagctctga gaatacacaa aacatcgaag atctggccgc ttacaacgag   1140
ctacaagatg cctatgccaa acagcaaacc gaagccattg acgctctaaa taaagcaagc   1200
tctgagaata cacaaaacat tgctaaaaac caagcggata ttgctaataa catcaacaat   1260
atctatgagc tggcacaaca gcaagatcag catagctctg atatcaaaac cttggcaaaa   1320
gcaagtgctg ccaatactga tcgtattgct aaaaacaaag ccgatgctga tgcaagtttt   1380
gaaacgctca ccaaaaatca aaatactttg attgaaaaag ataaagagca tgacaaatta   1440
attactgcaa acaaaactgc gattgatgcc aataaagcat ctgcggatac caagtttgca   1500
gcgacagcag acgccattac caaaaatgga atgctatca ctaaaaacgc aaaatctatc    1560
actgatttgg gcactaaagt ggatggtttt gacagtcgtg taactgcatt agacaccaaa   1620
gtcaatgcct ttgatggtcg tatcacagct ttagacagta agttgaaaaa cggtatggct   1680
gcccaagctg ccctaagtgg tctattccag ccttatagcg ttggtaagtt taatgcgacc   1740
gctgcacttg gtggctatgg ctcaaaatct gcggttgcta tcggtgctgg ctatcgtgtg   1800
aatccaaatc tggcgtttaa agctggtgcg gcgattaata ccagtggtaa taaaaaaggc   1860
tcttataaca tcggtgtgaa ttacgagttc taa                                 1893

<210> SEQ ID NO 75
<211> LENGTH: 44
<212> TYPE: DNA
<213> ORGANISM: Artificial Sequence
<220> FEATURE:
<223> OTHER INFORMATION: Primer sequence

<400> SEQUENCE: 75
gaattcttaa ttaacatatg caggccaaaa atgatattac cctg                       44

<210> SEQ ID NO 76
<211> LENGTH: 43
<212> TYPE: DNA
<213> ORGANISM: Artificial Sequence
<220> FEATURE:
<223> OTHER INFORMATION: Primer sequence

<400> SEQUENCE: 76
ggcgcgcctc gagttattat ttggtatcca gtgcggtcac acg                        43

<210> SEQ ID NO 77
<211> LENGTH: 43
<212> TYPE: DNA
<213> ORGANISM: Artificial Sequence
<220> FEATURE:
<223> OTHER INFORMATION: Primer sequence

<400> SEQUENCE: 77
ggcgcgcctc gagttagtgt ttggtatcca gtgcggtcac acg                        43

<210> SEQ ID NO 78
<211> LENGTH: 46
<212> TYPE: DNA
<213> ORGANISM: Artificial Sequence
<220> FEATURE:
```

<223> OTHER INFORMATION: Primer sequence

<400> SEQUENCE: 78
ggcgcgcctc gagttagtgg tgtttggtat ccagtgcggt cacacg    46

<210> SEQ ID NO 79
<211> LENGTH: 66
<212> TYPE: DNA
<213> ORGANISM: Artificial Sequence
<220> FEATURE:
<223> OTHER INFORMATION: Primer sequence

<400> SEQUENCE: 79
ggcgcgcctc gagttagtgg tggtgatgat gatggcttgc gcttttggca ttttggtga    60 tggcat    66

<210> SEQ ID NO 80
<211> LENGTH: 36
<212> TYPE: DNA
<213> ORGANISM: Artificial Sequence
<220> FEATURE:
<223> OTHER INFORMATION: Primer sequence

<400> SEQUENCE: 80
ccgctcgagc tagcttttgg cattttggt gatggc    36

<210> SEQ ID NO 81
<211> LENGTH: 43
<212> TYPE: DNA
<213> ORGANISM: Artificial Sequence
<220> FEATURE:
<223> OTHER INFORMATION: Primer sequence

<400> SEQUENCE: 81
ggaattccat atggcgaaaa atgatattac cctggaagat ctg    43

<210> SEQ ID NO 82
<211> LENGTH: 46
<212> TYPE: DNA
<213> ORGANISM: Artificial Sequence
<220> FEATURE:
<223> OTHER INFORMATION: Primer sequence

<400> SEQUENCE: 82
ggcgcgcctc gagttagtgg tgtgctgcct gtgctgccat accatt    46

<210> SEQ ID NO 83
<211> LENGTH: 40
<212> TYPE: DNA
<213> ORGANISM: Artificial Sequence
<220> FEATURE:
<223> OTHER INFORMATION: Primer sequence

<400> SEQUENCE: 83
ggcgcgcctc gagttatgct gcctgtgctg ccataccatt    40

<210> SEQ ID NO 84
<211> LENGTH: 27
<212> TYPE: DNA
<213> ORGANISM: Artificial Sequence
<220> FEATURE:
<223> OTHER INFORMATION: Primer sequence

<400> SEQUENCE: 84
cagttcatta taggtggcca gatcctg    27

```
<210> SEQ ID NO 85
<211> LENGTH: 4
<212> TYPE: PRT
<213> ORGANISM: Artificial Sequence
<220> FEATURE:
<223> OTHER INFORMATION: N terminal amino acids of MC-001

<400> SEQUENCE: 85

Met Gln Ala Lys
1

<210> SEQ ID NO 86
<211> LENGTH: 11
<212> TYPE: PRT
<213> ORGANISM: Artificial Sequence
<220> FEATURE:
<223> OTHER INFORMATION: N terminal amino acid sequence

<400> SEQUENCE: 86

Ala Lys Asn Asp Ile Thr Leu Glu Asp Leu Pro
1               5                   10

<210> SEQ ID NO 87
<211> LENGTH: 1542
<212> TYPE: DNA
<213> ORGANISM: Artificial Sequence
<220> FEATURE:
<223> OTHER INFORMATION: DNA sequence for MC-003 Construct

<400> SEQUENCE: 87
atgcaggcca aaaatgatat taccctggaa gatctgccgt atctgatcaa aaaaatcgat      60
cagaacgaac tggaagccga tattggtgat attaccgcac tggaaaaata tctggcactg     120
agccagtatg aaatattct ggccctggaa gaactgaata agctctgga agagctggat       180 gaagatgtgg gttggaatca gaatgatatc gccaatctgg aagatgatgt tgaaaccctg     240
accaaaaatc agaatgcact ggcagaacag ggtgaagcaa ttaaagaaga tctgcagggt     300
ctggcagatt ttgttgaagg tcaggaaggc aaaattctgc agaacgaaac cagcatcaaa     360
aaaaacaccc agcgtaatct ggtgaatggc tttgaaattg aaaaaaacaa agatgccatt     420
gccaaaaaca cgaaagcat tgaagatctg tatgattttg gtcatgaagt tgccgaaagc      480
attggtgaaa ttcatgcaca taacgaagca cagaatgaaa ccctgaaagg tctgattacc     540
aacagcatcg aaaataccaa taacattacc aaaaacaaag cagatattca ggcgctggaa     600
aataatgttg tggaagaact gtttaatctg agcggtcgtc tgattgatca gaaagccgat     660
atcgataata acattaacaa catttatgaa ctggcacagc agcaggatca gcatagcagc     720
gatatcaaaa ccctgaaaaa aacgttgaa gaaggtctgc tggaactgtc tggtcacctg      780
atcgatcaga aaactgatat tgcccagaat caggcaaata ttcaggatct ggccacctat     840
aatgaactgc aggatcagta tgcacagaaa cagaccgaag caattgatgc cctgaataaa     900
gcgagcagcg aaaacaccca gaatatcgaa gatctggcag catacaacga actgcaggat     960
gcctatgcaa acagcagac tgaagccatc gacgcactga caaggcaag ctctgaaaac     1020 acgcagaaca ttgaagatct ggctgcctat aatgaattac aggatgcgta tgccaaacag    1080
cagaccgaag cgattgatgc gctgaacaaa gcctcttctg aaaatacaca gaatatcgcc    1140
aaaaatcagg ccgatattgc caacaatatc aataatatct atgaactggc cagcagcag    1200 gatcagcact cttctgatat caaaacactg gcaaagcaa gcgcagcaaa taccgatcgt     1260
attgcgaaaa acaaagccga tgcagatgca agctttgaaa cactgacgaa aaaccagaac    1320
```

```
accctgattg aaaaagataa agaacatgat aaactgatca ccgccaataa aaccgcaatt   1380
gatgcaaata aagccagcgc agataccaaa tttgcagcaa ccgcagatgc aattaccaaa   1440
aatggcaatg ccatcaccaa aaatgccaaa agcattaccg atctgggcac caaagttgat   1500
ggttttgata gccgtgtgac cgcactggat accaaacact aa                     1542
```

```
<210> SEQ ID NO 88
<211> LENGTH: 513
<212> TYPE: PRT
<213> ORGANISM: Artificial Sequence
<220> FEATURE:
<223> OTHER INFORMATION: Protein sequence for MC-003 Construct

<400> SEQUENCE: 88
```

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320
```

```
Ala Tyr Ala Lys Gln Gln Thr Glu Ala Ile Asp Ala Leu Asn Lys Ala
                325                 330                335

Ser Ser Glu Asn Thr Gln Asn Ile Glu Asp Leu Ala Ala Tyr Asn Glu
            340                 345                350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
                420                 425                 430

Glu Thr Leu Thr Lys Asn Gln Asn Thr Leu Ile Glu Lys Asp Lys Glu
            435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
                485                 490                 495

Thr Lys Val Asp Gly Phe Asp Ser Arg Val Thr Ala Leu Asp Thr Lys
            500                 505                 510

His
```